(12) United States Patent
Demont et al.

(10) Patent No.: US 8,580,957 B2
(45) Date of Patent: Nov. 12, 2013

(54) THETRAHYDROQUINOLINES DERIVATIVES AS BROMODOMAIN INHIBITORS

(75) Inventors: Emmanuel Hubert Demont, Stevenage (GB); Romain Luc Marie Gosmini, Les Ulis (FR)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/503,947

(22) PCT Filed: Nov. 3, 2010

(86) PCT No.: PCT/EP2010/066701
§ 371 (c)(1),
(2), (4) Date: Apr. 25, 2012

(87) PCT Pub. No.: WO2011/054848
PCT Pub. Date: May 12, 2011

(65) Prior Publication Data
US 2012/0208814 A1    Aug. 16, 2012

(30) Foreign Application Priority Data
Nov. 5, 2009    (GB) .................................... 0919434.1

(51) Int. Cl.
C07D 401/10    (2006.01)
C07D 401/14    (2006.01)
C07D 413/10    (2006.01)

(52) U.S. Cl.
USPC ........... 544/128; 544/331; 544/363; 544/405; 546/159

(58) Field of Classification Search
None
See application file for complete search history.

(56) References Cited

FOREIGN PATENT DOCUMENTS

| | | | |
|---|---|---|---|
| EP | 1435356 A1 | 7/2004 |
| EP | 2199283 A1 | 6/2010 |
| WO | 03105849 A1 | 12/2003 |
| WO | 2006083692 A2 | 8/2006 |
| WO | WO 2009/041072 A1 * | 4/2009 |
| WO | 2010113498 A1 | 10/2010 |

\* cited by examiner

*Primary Examiner* — Janet Andres
*Assistant Examiner* — Timothy R Rozof
(74) *Attorney, Agent, or Firm* — Robert H. Brink

(57) ABSTRACT

Tetrahydroquinoline compounds of formula (I)

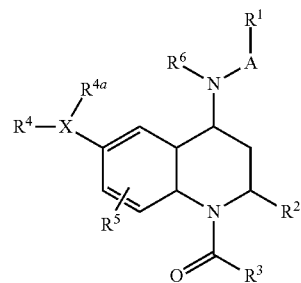

or a salt thereof, pharmaceutical compositions containing such compounds and their use in therapy, in particular in the treatment of diseases or conditions for which a bromodomain inhibitor is indicted.

19 Claims, No Drawings

TETRAHYDROQUINOLINES DERIVATIVES AS BROMODOMAIN INHIBITORS

CROSS-REFERENCE TO RELATED APPLICATIONS

This application is filed pursuant to 35 USC 371 as a United States National Phase Application of International Patent Application Serial No. PCT/EP2010/066701 filed on Nov. 3, 2010, which claims priority from 0919434.1 filed on Nov. 5, 2009 in the United Kingdom.

FIELD OF THE INVENTION

The present invention relates to tetrahydroquinoline derivatives, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009/084693 discloses a series of thienotriazolodiazepiene derivatives that are said to inhibit the binding between an acetylated histone and a bromodomain containing protein which are said to be useful as anti-cancer agents.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof.

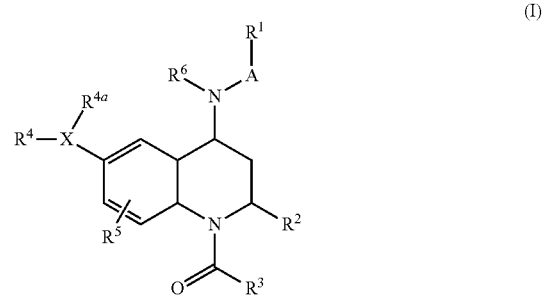

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof

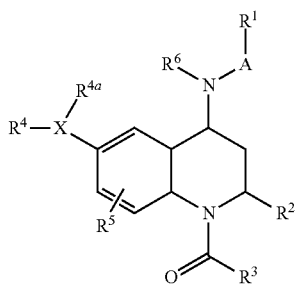

(I)

wherein:
A represents a bond or $C_{1-4}$ alkyl;
X represents:
  i) a 6 to 10 membered aromatic group, or
  ii) a 5 to 10 membered heteroaromatic comprising 1, 2 or 3 heteroatoms selected from the group consisting of O, N and S,
$R^1$ represents:
  i) phenyl optionally substituted by 1 or 2 substituents independently selected from halogen, cyano, $C_{1-6}$ alkyl, $C_{1-6}$ haloalkyl, $C_{1-6}$ alkoxy, $SO_2C_{1-6}$ alkyl and —$COR^7$,
  ii) a 5 to 10 membered heteroaromatic comprising 1, 2 or 3 heteroatoms selected from the group consisting of O, N and S optionally substituted by 1 or 2 substituents independently selected from halogen, cyano, $C_{1-6}$ alkyl, $C_{1-6}$ haloalkyl, $C_{1-6}$ alkoxy and —$COR^7$, or
  iii) cyclohexyl;
$R^2$ represents $C_{1-6}$ alkyl;
$R^3$ represents $C_{1-6}$ alkyl;
$R^4$ represents:
  i) H, halogen, cyano, $C_{1-6}$ alkyl, $C_{1-6}$ haloalkyl, $C_{1-6}$ alkoxy, $C_{0-6}$ hydroxyalkyl, $SO_2C_{1-6}$ alkyl, —C(O)$NR^8R^9$, $C(O)R^{10}$, —$C_{0-6}$ alkyl-$NR^{11}R^{12}$, or
  ii) —$O_mC_{0-6}$ alkyl substituted by a 5 or 6 membered heterocyclyl or heteroaromatic each comprising 1, 2 or 3 heteroatoms independently selected from the group consisting of N, O and S and wherein said heterocyclyl or heteroaromatic is optionally substituted by 1, 2 3 or 4 groups independently selected from halogen, cyano, $C_{1-6}$ alkyl, $C_{1-6}$ haloalkyl and $C_{1-6}$ alkoxy,
  wherein when the heterocyclyl or heteroatomic is linked through a heteroatom and m is 1, then the heteroatom and O are not directly linked if the resultant arrangement would be unstable,
$R^{4a}$ represents H, halogen, $C_{1-6}$ alkyl, $C_{1-6}$ haloalkyl, $C_{1-6}$ alkoxy or $C_{0-6}$ hydroxyalkyl;
$R^5$ represents H, halogen, —$C_{1-6}$ alkyl or —$C_{1-6}$ alkoxy;
$R^6$ represents H, —$C_{1-6}$ alkyl, —$C_{0-6}$ alkylcyano, —$C_{0-6}$ alkyl$C_{1-6}$ alkoxy or $C_{0-2}$ alkyl$COR^7$;

$R^7$ represents hydroxyl, $C_{1-6}$ alkoxy, —$NH_2$, —$NHC_{1-6}$ alkyl or $N(C_{1-6}$ alkyl$)_2$;
$R^8$ and $R^9$ independently represent:
  i) H, $C_{1-6}$ alkyl, —$C_{0-6}$ alkylphenyl, —$C_{0-6}$ alkylheteroaromatic, $C_{3-6}$ cycloalkyl, or
  ii) $R^8$ and $R^9$ together with the N to which they are attached form a 5 or 6 membered heterocyclyl or heteroaromatic wherein said heterocyclyl or heteroaromatic may comprise 1, 2 or 3 further heteroatoms independently selected from O, N and S;
$R^{10}$ represents hydroxyl, $C_{1-6}$ alkoxy or a 5 or 6 membered heterocyclyl or heteroaromatic comprising 1, 2, 3 or 4 heteroatoms selected from O, N and S;
$R^{11}$ and $R^{12}$ independently represent:
  (i) H or $C_{1-6}$ alkyl; or
  (ii) $R^{11}$ and $R^{12}$ together with the N to which they are attached form a 5 or 6 membered heterocyclyl or heteroaromatic wherein said heterocyclyl or heteroaromatic may comprise 1, 2 or 3 further heteroatoms independently selected from O, N and S; and m represents 0 or 1.

In one embodiment, the present invention relates to compounds of formula (I) or a salt thereof

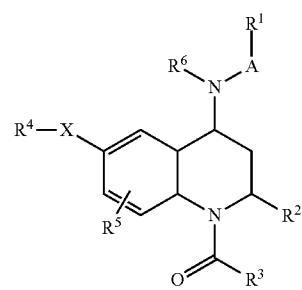

(I)

wherein:
A represents a bond or $C_{1-4}$ alkyl;
X represents:
  i) 6 to 10 membered aromatic group,
  ii) a 5 to 10 membered heteroaromatic comprising 1, 2 or 3 heteroatoms selected from the group consisting of O, N and S,
$R^1$ represents:
  i) phenyl optionally substituted by 1 or 2 substituents independently selected from halogen, cyano, $C_{1-6}$ alkyl, $C_{1-6}$ haloalkyl, $C_{1-6}$ alkoxy, $SO_2C_{1-6}$ alkyl and —$COR^7$,
  ii) a 5 to 10 membered heteroaromatic comprising 1, 2 or 3 heteroatoms selected from the group consisting of O, N and S optionally substituted by 1 or 2 substituents independently selected from halogen, cyano, $C_{1-6}$ alkyl, $C_{1-6}$ haloalkyl, $C_{1-6}$ alkoxy and —$COR^7$, or
  iii) cyclohexyl;
$R^2$ represent $C_{1-6}$ alkyl;
$R^3$ represent $C_{1-6}$ alkyl;
$R^4$ represents:
  i) H, halogen, cyano, $C_{1-6}$ alkyl, $C_{1-6}$ haloalkyl, $C_{1-6}$ alkoxy, $C_{0-6}$ hydroxyalkyl, $SO_2C_{1-6}$ alkyl, —C(O)$NR^8R^9$, $C(O)R^{10}$, —$C_{0-6}$ alkyl-$NR^{11}R^{12}$,
  ii) —$O_mC_{0-6}$ alkyl substituted by a 5 or 6 membered heterocyclyl or heteroaromatic each comprising 1, 2 or 3 heteroatoms independently selected from the group consisting of N, O and S and wherein said heterocyclyl or heteroaromatic is optionally substituted by 1, 2 or 3 groups independently selected from halogen, cyano, $C_{1-6}$ alkyl, $C_{1-6}$ haloalkyl, $C_{1-6}$ alkoxy, wherein the heterocyclyl or heteroatomic is linked through a heteroatom and m is 1 then the heteroatom and O is not directly linked if the resultant arrangement would be unstable, $R^5$ represents H, halogen, —$C_{1-6}$ alkyl or —$C_{1-6}$ alkoxy;

$R^6$ represent H, —$C_{1-6}$ alkyl, —$C_{0-6}$ alkylcyano, —$C_{0-6}$ alkyl$C_{1-6}$ alkoxy or $C_{0-2}$ alkylCOR$^7$;

$R^7$ represents hydroxyl, $C_{1-6}$ alkoxy, —$NH_2$, —$NHC_{1-6}$ alkyl or $N(C_{1-6}$ alkyl$)_2$;

$R^8$ and $R^9$ independently represent:

i) H, $C_{1-6}$ alkyl, —$C_{0-6}$ alkylphenyl, —$C_{0-6}$alkylheteroaromatic, $C_{3-6}$ cycloalkyl, or ii) $R^8$ and $R^9$ together with the N to which they are attached form a 5 or 6 membered heterocyclyl or heteroaromatic wherein said heterocyclyl or heteroaromatic may comprise 1, 2 or 3 further heteroatoms independently selected from O, N and S;

$R^{10}$ represents hydroxyl, $C_{1-6}$ alkoxy or a 5 or 6 membered heterocyclyl or heteroaromatic comprising 1, 2, 3 or 4 heteroatoms selected from O, N or S;

$R^{11}$ and $R^{12}$ independently represent H or $C_{1-6}$ alkyl; and m represents 0 or 1.

In one aspect of the invention the compound of formula (I) is not 4-quinolinamine, 1-acetyl-7-(3-fluorophenyl)-1,2,3,4-tetrahydro-2-methyl-N-(4-methylphenyl).

Representative examples of A include a bond or —$CH_2$—, more particularly a bond.

When X is a 5 to 10 membered heteroaromatic comprising 1, 2 or 3 heteroatoms selected from the group consisting of O, N and S, representative examples include indolyl, pyridinyl, pyrrolyl, thienyl or pyrazolyl, such as pyrazolyl or pyridinyl. In one embodiment X is selected from pyridinyl, imidazolyl, pyrazolyl and triazolyl. A more specific example of X is pyrazolyl.

In an alternative embodiment X represents phenyl.

Representative examples of optional $R^1$ substituents when $R^1$ is phenyl include methoxy, —$SO_2CH_3$, fluoro, chloro, cyano, —$CF_3$ or methyl such as methoxy, fluoro, chloro, cyano, —$CF_3$ or methyl. In one embodiment of the present invention, $R^1$ represents phenyl optionally substituted by fluoro, chloro, cyano, —$CF_3$, methyl —$COR^7$, or —$SO_2CH_3$.

Phenyl substituents may, for example be in the meta or para position.

In this general aspect of the invention then the phenyl may, for example, bear one substituent. In one embodiment the substituent is in the para position on the phenyl ring. In a more specific aspect the one substituent is chloro, for example in the para position.

When $R^1$ is a 5 to 10 membered heteroaromatic representative examples include 5 or 6 membered heteroaromatics such as pyridinyl.

When $R^1$ is a 5 to 10 membered heteroaromatic representative examples of optional substituents include methyl, —$OCF_3$ and cyano.

In one embodiment of the invention, $R^1$ represents pyridinyl, pyrazinyl or pyrimidinyl optionally substituted by fluoro, chloro, methyl or —$CF_3$. In another embodiment $R^1$ represents unsubstituted pyrazinyl or pyrimidinyl. In a further embodiment $R^1$ represents optionally substituted pyridinyl selected from:

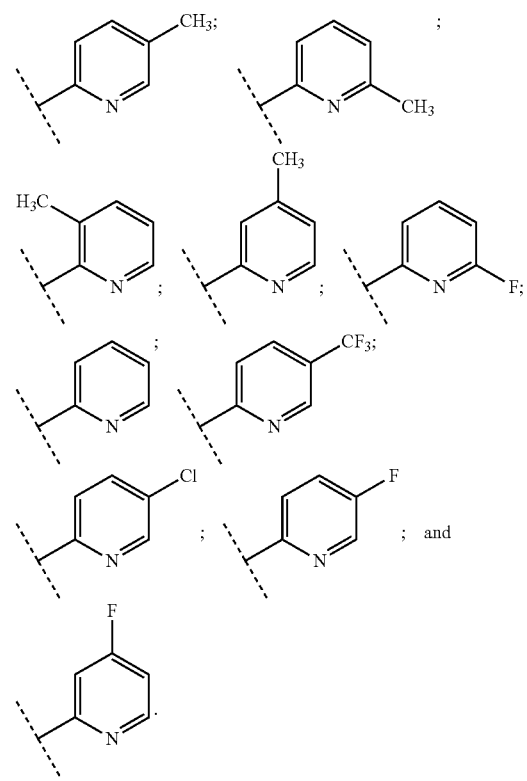

Representative examples of $R^2$ include —$C_{1-6}$ alkyl, for example —$C_{1-4}$ alkyl such as methyl.

Representative examples of $R^3$ include methyl.

In one embodiment $R^{4a}$ represents H.

Representative examples of $R^4$ include —C(O)NR$^8$R$^9$, methoxy, C(O)R$^{10}$ and $CF_3$.

In one embodiment $R^4$ is in the para position.

In one embodiment $R^4$ is selected from methyl, —C(O)R$^{10}$, C(O)NR$^8$R$^9$, —$C_{0-6}$alkyl-NR$^{11}$R$^{12}$ and —$C_{0-6}$hydroxyalkyl. In an alternative embodiment representative examples of $R^4$ include —$CH_2$-morpholinyl, —$CH_2$piperidinyl, —$CH_2$—N-methylpiperizinyl, —$CH_2$pyrrolidinyl, benzyl and —$OCH_2CH_2$pyrrolidinyl such as —$CH_2$piperidinyl.

Representative examples of $R^5$ include H, halogen, methoxy and methyl, such as H.

Representative examples of $R^6$ include H and —$C_{1-6}$ alkyl such as ethyl.

In one embodiment, $R^7$ represents hydroxyl or methoxy.

In one embodiment, $R^8$ and $R^9$ independently represent H or $C_{1-6}$alkyl. In another embodiment, $R^8$ and $R^9$ together with the N to which they are attached form a 6 membered heterocyclyl comprising 1 further heteroatom independently selected from O and N. When $R^8$ and $R^9$ together with the N to which they are attached form a 5 or 6 membered heterocyclyl or heteroaromatic a representative example includes morpholinyl.

In one embodiment $R^{10}$ represents hydroxyl or methoxy. In another embodiment $R^{10}$ represents hydroxyl.

In one embodiment, $R^{11}$ and $R^{12}$ independently represent H or $C_{1-6}$ alkyl. In another embodiment, $R^{11}$ and $R^{12}$ together with the N to which they are attached form a 6-membered heterocyclyl optionally comprising one further heteroatom selected from O and N, for example piperazinyl, morpholinyl and piperidinyl.

In one embodiment the invention provides a compound of formula (Ia)

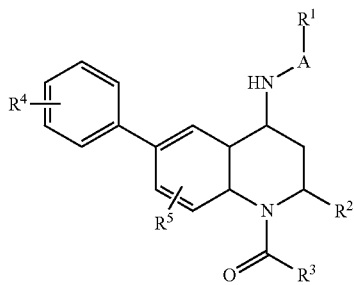

(Ia)

wherein A, R¹, R², R³, R⁴ and R⁵ are as defined above for compounds of formula (I).

In one embodiment there is provided a compound of formula (1a) in which R² represents methyl.

In one embodiment there is provided a compound of formula (1a) in which R³ represents methyl.

In one embodiment there is provided a compound of formula (1a) in which R⁴ is in the para-position.

In one embodiment there is provided a compound of formula (1a) in which R⁵ represents H.

In a further embodiment the invention provides a compound of formula (Ib)

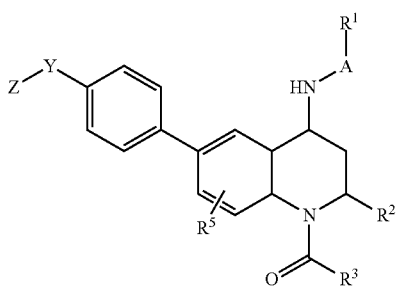

(Ib)

wherein:
A, R¹, R², R³ and R⁵ are as defined above for compounds of formula (I),
Y represents —CH₂— or —C(O)—, and
Z represents hydroxyl a 5 or 6 membered heterocyclyl or a 5 or 6 membered heteroaromatic.

In one embodiment there is provided a compound of formula (1b) in which R² represents methyl.

In one embodiment there is provided a compound of formula (1b) in which R³ represents methyl.

In one embodiment there is provided a compound of formula (1b) in which R⁵ represents H.

In one embodiment the invention provides compounds with cis relative stereochemistry across the tetrahydroquinoline ring in respect of the substituents in the 2 and 4 position on the ring. In one embodiment the compound of formula (I) or a salt thereof is the (2S,4R) enantiomer.

Specific compounds of formula (I) include Examples 1-191 as described herein or a salt thereof, in particular a pharmaceutically acceptable salt thereof.

In one embodiment the compound of formula (I) is selected from:
4-{-1-acetyl-4-[(4-chlorophenyl)amino]-2-methyl-1,2,3,4-tetrahydro-6-quinolinyl}benzoic acid;
4-1-acetyl-4-[(4-fluorophenyl)amino]-2-methyl-1,2,3,4-tetrahydro-6-quinolinyl}benzoic acid;
4-{-1-acetyl-2-methyl-4-[(4-methylphenyl)amino]-1,2,3,4-tetrahydro-6-quinolinyl}benzoic acid;
4-(-1-acetyl-2-methyl-4-{[4-(trifluoromethyl)phenyl]amino}-1,2,3,4-tetrahydro-6-quinolinyl)benzoic acid;
4-(-1-acetyl-2-methyl-4-{[3-(trifluoromethyl)phenyl]amino}-1,2,3,4-tetrahydro-6-quinolinyl)benzoic acid;
1-acetyl-2-methyl-6-[3-(4-morpholinylmethyl)phenyl]-N-phenyl-1,2,3,4-tetrahydro-4-quinolinamine;
methyl-4-{-1-acetyl-4-[(4-cyanophenyl)amino]-2-methyl-1,2,3,4-tetrahydro-6-quinolinyl}benzoate;
4-{-1-acetyl-4-[(4-cyanophenyl)amino]-2-methyl-1,2,3,4-tetrahydro-6-quinolinyl}benzoic acid;
1-acetyl-2-methyl-N-(4-methylphenyl)-6-[4-(4-morpholinylcarbonyl)phenyl]-1,2,3,4-tetrahydro-4-quinolinamine;
4-{-1-acetyl-4-[(4-chlorophenyl)(ethyl)amino]-2-methyl-1,2,3,4-tetrahydro-6-quinolinyl}-N-methylbenzamide;
2-(4-{-1-acetyl-2-methyl-4-[(5-methyl-2-pyridinyl)amino]-1,2,3,4-tetrahydro-6-quinolinyl}-1H-1,2,3-triazol-1-yl)ethanol;
2-(4-{-1-acetyl-2-methyl-4-[(6-methyl-2-pyridinyl)amino]-1,2,3,4-tetrahydro-6-quinolinyl}-1H-1,2,3-triazol-1-yl)ethanol;
2-(4-{-1-acetyl-2-methyl-4-[(3-methyl-2-pyridinyl)amino]-1,2,3,4-tetrahydro-6-quinolinyl}-1H-1,2,3-triazol-1-yl)ethanol;
2-(4-{-1-acetyl-2-methyl-4-[(4-methyl-2-pyridinyl)amino]-1,2,3,4-tetrahydro-6-quinolinyl}-1H-1,2,3-triazol-1-yl)ethanol;
4-{-1-acetyl-2-methyl-4-[(5-methyl-2-pyridinyl)amino]-1,2,3,4-tetrahydro-6-quinolinyl}benzoic acid;
2-{-4-[-1-acetyl-2-methyl-4-(2-pyridinylamino)-1,2,3,4-tetrahydro-6-quinolinyl]-1H-1,2,3-triazol-1-yl}ethanol;
1-acetyl-2-methyl-6-{1-[2-(methylamino)ethyl]-1H-pyrazol-4-yl}-N-phenyl-1,2,3,4-tetrahydro-4-quinolinamine;
1-acetyl-2-methyl-6-{1-[2-(methylamino)ethyl]-1H-pyrazol-4-yl}-N-2-pyridinyl-1,2,3,4-tetrahydro-4-quinolinamine;
(cis)-1-acetyl-6-(6-amino-3-pyridinyl)-2-methyl-N-phenyl-1,2,3,4-tetrahydro-4-quinolinamine;
(cis)-1-acetyl-2-methyl-6-[4-(1-piperidinylmethyl)phenyl]-N-2-pyridinyl-1,2,3,4-tetrahydro-4-quinolinamine;
(cis)-1-acetyl-2-methyl-6-[4-(1-piperidinylmethyl)phenyl]-N-[5-(trifluoromethyl)-2-pyridinyl]-1,2,3,4-tetrahydro-4-quinolinamine;
(cis)-1-acetyl-2-methyl-N-(5-methyl-2-pyridinyl)-6-[4-(1-piperidinylmethyl)phenyl]-1,2,3,4-tetrahydro-4-quinolinamine;
(cis)-1-acetyl-N-(5-chloro-2-pyridinyl)-2-methyl-6-[4-(1-piperidinylmethyl)phenyl]-1,2,3,4-tetrahydro-4-quinolinamine;
(cis)-1-acetyl-N-(5-fluoro-2-pyridinyl)-2-methyl-6-[4-(1-piperidinylmethyl)phenyl]-1,2,3,4-tetrahydro-4-quinolinamine;
methyl 4-{[(cis)-1-acetyl-2-methyl-6-(4-methyl-1H-imidazol-1-yl)-1,2,3,4-tetrahydro-4-quinolinyl]amino}benzoate;
(cis)-1-acetyl-N-(5-fluoro-2-pyridinyl)-2-methyl-6-(4-methyl-1H-imidazol-1-yl)-1,2,3,4-tetrahydro-4-quinolinamine;

1-acetyl-2-methyl-6-{1-[2-(methylamino)ethyl]-1H-pyrazol-4-yl}-N-(6-methyl-2-pyridinyl)-1,2,3,4-tetrahydro-4-quinolinamine;
1-acetyl-2-methyl-6-{1-[2-(methylamino)ethyl]-1H-pyrazol-4-yl}-N-(4-methyl-2-pyridinyl)-1,2,3,4-tetrahydro-4-quinolinamine;
1-acetyl-N-(6-fluoro-2-pyridinyl)-2-methyl-6-{1-[2-(methylamino)ethyl]-1H-pyrazol-4-yl}-1,2,3,4-tetrahydro-4-quinolinamine;
1-acetyl-2-methyl-6-{1-[2-(methylamino)ethyl]-1H-pyrazol-4-yl}-N-2-pyrazinyl-1,2,3,4-tetrahydro-4-quinolinamine;
1-acetyl-2-methyl-6-{-1-[2-(methylamino)ethyl]-1H-pyrazol-4-yl}-N-2-pyrimidinyl-1,2,3,4-tetrahydro-4-quinolinamine;
1-acetyl-N-(5-fluoro-2-pyridinyl)-2-methyl-6-{1-[2-(methylamino)ethyl]-1H-pyrazol-4-yl}-1,2,3,4-tetrahydro-4-quinolinamine;
1-acetyl-2-methyl-6-{-1-[2-(methylamino)ethyl]-1H-pyrazol-4-yl}-N-(5-methyl-2-pyridinyl)-1,2,3,4-tetrahydro-4-quinolinamine;
1-acetyl-N-(4-fluoro-2-pyridinyl)-2-methyl-6-{1-[2-(methylamino)ethyl]-1H-pyrazol-4-yl}-1,2,3,4-tetrahydro-4-quinolinamine;
1-acetyl-N-(5-fluoro-2-pyridinyl)-2-methyl-6-{4-[(methylamino)methyl]phenyl}-1,2,3,4-tetrahydro-4-quinolinamine;
1-acetyl-2-methyl-N-phenyl-6-[4-(1-piperidinylmethyl) phenyl]-1,2,3,4-tetrahydro-4-quinolinamine;
4-{-1-acetyl-2-methyl-4-[(4-methylphenyl)amino]-1,2,3,4-tetrahydro-6-quinolinyl}benzoic acid; and
4-(-1-acetyl-2-methyl-4-{[4-(methylsulfonyl)phenyl]amino}-1,2,3,4-tetrahydro-6-quinolinyl)benzoic acid;
or a salt thereof.

In one embodiment of the invention, there is provided a compound which is 4-(2S,4R)-{-1-acetyl-4-[(4-chlorophenyl)amino]-2-methyl-1,2,3,4-tetrahydro-6-quinolinyl}benzoic acid or a salt thereof. In another embodiment there is provided a compound which is 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof. In a further embodiment there is provided a compound which is 4-(2S,4R)-{-1-acetyl-4-[(4-chlorophenyl)amino]-2-methyl-1,2,3,4-tetrahydro-6-quinolinyl}benzoic acid.

As used herein, the term "alkyl" refers to straight or branched hydrocarbon chains containing the specified number of carbon atoms. For example, $C_{1-6}$ alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl. However, when a moiety is defined such that alkyl bears a substituent it will be clear to the skilled person from the context that alkyl may include alkylene.

As used herein, the term "alkoxy" refers to a straight or branched alkoxy group containing the specified number of carbon atoms. For example, $C_{1-6}$ alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "halogen" or "halo" refers to the elements fluorine, chlorine, bromine and iodine. Preferred halo groups are fluorine, chlorine and bromine.

Unless otherwise indicated, carbocyclyl as used herein refers to a cyclic group containing 3 to 10 carbon ring-atoms, and may be saturated (cycloalkyl) or unsaturated but may not be aromatic. Examples of saturated carbocyclyl groups include cyclopropyl, cyclopentyl or cyclohexyl. Unsaturated carbocyclyl groups may contain 2 double bonds or more provided the moiety remains non-aromatic. Examples of unsaturated carbocyclyl groups include cyclopentene or cyclopentene.

Examples of aromatic, aryl or "Ar" groups include naphthyl, anthryl, phenanthryl, indanyl, indenyl, azulenyl, azulanyl, fluorenyl, phenyl and napthyl, and more specifically phenyl.

Heteroaromatic as used in this specification refers to an aromatic cyclic group containing 5 to 10 ring-atoms 1, 2, 3 or 4 of which are hetero-atoms independently selected from nitrogen, oxygen and sulfur. This definition includes bicyclic structures at least a portion of which is aromatic.

Heterocyclyl as used in the specification refers to a cyclic group containing 5 to 10 ring-atoms 1, 2, 3 or 4 of which are hetero-atoms independently selected from nitrogen, oxygen and sulfur, and, wherein said cyclic group is saturated or unsaturated but, which is not aromatic. This definition includes bicyclic structures provided the moiety is non-aromatic.

Examples of heterocyclyl and heteroaromatic groups include: furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, homopiperazinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl may include fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl.

As used herein, the term "substituted" refers to substitution with the named substituent or substituents, multiple degrees of substitution being allowed unless otherwise stated.

For the avoidance of doubt, the term "independently" means that where more than one substituent is selected from a number of possible substituents, those substituents may be the same or different.

It will be appreciated that the present invention covers compounds of formula (I) as the free base and as salts thereof, for example as a pharmaceutically acceptable salt thereof.

In one embodiment the invention relates to compounds of formula (I) as the free base. In another embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compounds of formula (I) and pharmaceutically acceptable salts thereof, which upon administration to the recipient are capable of providing (directly or indirectly) a compound of formula (I) or a pharmaceutically acceptable salt thereof, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Compounds described herein contain chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures).

Similarly the invention also extends to conformational isomers of compounds of formula (I) and any geometric (cis and/or trans) isomers of said compounds.

An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) and pharmaceutically acceptable salts thereof may be made by a variety of methods, including standard chemistry. Any previously defined variable will continue to have the previously defined meaning unless otherwise indicated. Illustrative general synthetic methods are set out below and then specific compounds of formula (I) and pharmaceutically acceptable salts thereof are prepared in the working Examples. These processes form further aspects of the invention.

Throughout the specification, general formulae are designated by Roman numerals (I), (II), (III), (IV) etc.

In certain instances "final" compounds of formula (I) can be converted into other compounds of formula (I) by techniques known to those in the art, for example, carboxylic acid substituents can be converted to esters or amides by routine techniques.

In a general process, compounds of formula (I) may be prepared by the reaction of a compound of formula (II)

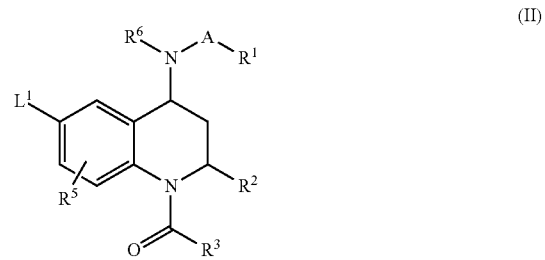

wherein:
A, $R^1$, $R^2$, $R^3$, $R^5$ and $R^6$ are as defined above for compounds of formula (I) and $L^1$ represents a leaving group, for example, halogen such as Br, with, 4) a boronic acid derivative of "R$^{4a}$R$^4$X" such as a compound of formula (III) below:

wherein:
R$^4$, R$^{4a}$ and X are as defined above for compounds of formula (I).

The reaction may be effected by stirring a compound of formula (II) with the boronic acid of formula (III) in the presence of a suitable catalyst such as Pd(PPh$_3$)$_4$, a base such as aqueous sodium carbonate, such as 2N sodium carbonate, and a suitable solvent, for example, DME or toluene such as DME, at a non-extreme temperature such as reflux, for example 85° C., for a period of, for example 5 to 24 hours such as about 12 hours.

Alternatively, compounds of formula (I) where A represents a bond may be prepared by reacting a compound of formula (IV):

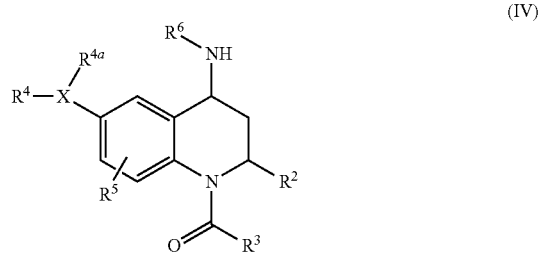

wherein:
X, R$^2$, R$^3$, R$^4$, R$^{4a}$, R$^5$, and R$^6$ are as defined above for compounds of formula (I), with:
  i) a boronic acid derivative of R$^1$ such as compound of formula (V)

wherein R$^1$ is as defined above for compounds of formula (I), or
  ii) a compound of formula (VI)

wherein R$^1$ is as defined above for compounds of formula (I) and L$^2$ represents a leaving group, for example a halogen such as bromo.

The reaction part i) may be effected by stirring a compound of formula (IV) with the boronic acid of formula (V) in the presence of a suitable catalyst such as cupric acetate, an organic base such as triethylamine, and a suitable solvent, for example, an aprotic polar solvent such as DCM, at a non-extreme temperature such as room temperature for a period of approximately 48 to 72 hour. The reaction is likely to be more efficient if anhydrous reagents are used and the reaction is performed under a nitrogen atmosphere.

The reaction in part ii) may be effected by, for example, reacting of a compound of formula (IV) with a compound of formula (VI) in the presence of Pd$_2$ dba$_3$, a base such a NaOtBu, and a suitable phosphine ligand such as a monophosphosphinobiphenyl ligand, for example 2'(dichlohexylphophanyl)-2-biphenyl]dimethylamine or 2'-biphenylyl[bis (1,1-dimethylethyl)]phosphane and a suitable solvent, for example toluene at a non-extreme temperature such as 80° C., for a period of approximately 1 to 4 such as about 2 hours.

Compounds of formula (I) wherein A represents C$_{1-4}$ alkyl can be prepared by reacting a compound of formula (IV) below:

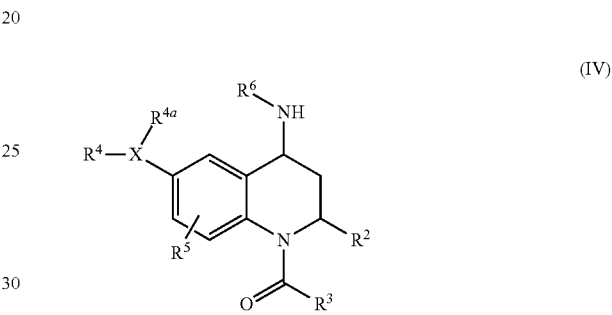

wherein:
X, R$^2$, R$^3$, R$^4$, R$^{4a}$, R$^5$, and R$^6$ are as defined above for compounds of formula (I), with an aldehyde of the following formula:

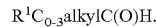

The above reaction may be effected in the presence of a reducing agent such as a suitable hydride eg tri-acetoxysodiumborohydride, in a suitable solvent, for example, 1,2-dichloroethane or THF such as 1,2-dichoroethane at, for example, room temperature for a period of approximately 10 to 15 such as about 12 hours.

Thus compounds of formula (I) wherein R$^6$ represents H, A is a bond and X is an aromatic or heteroaromatic group can be prepared as shown by one or more of the routes shown in scheme 1a, 1b and 1c below.

Scheme 1a

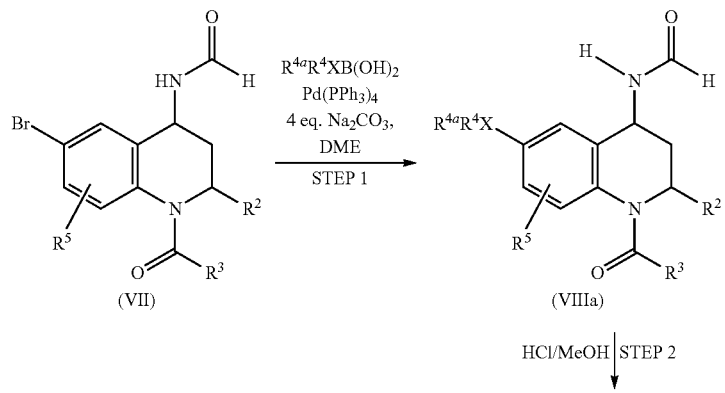

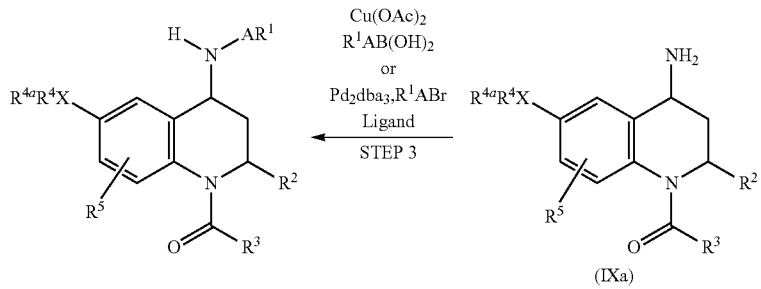

wherein:

Ligand represents a monophosphosphinobiphenyl ligand such as 2'(dichlohexylphophanyl)-2-biphenyl]dimethylamine or 2'-biphenylyl[bis(1,1-dimethylethyl)]phosphane.

Step 1 in scheme 1a may be effected by stirring the reagents in a suitable solvent, for example DME at an elevated temperature, for example above 50° C. such as refluxing at 85° C. for a period of between 5 and 24 hours such as approximately 10 hours.

Step 2 in scheme 1a may be effected by stirring at an elevated temperature such as reflux for less than 6 hours such as for a period of about 4 hours.

Step 3 in scheme 1a, may be effected by stirring the copper (II) acetate and boronic derivative in a suitable solvent such as DCM at a non-extreme temperature, such as room temperature, for a prolonged period, for example approximately 1 week such as about 5 days.

Alternatively, step 3 in scheme 1a above may be effected by stirring the compound of formula (Ixa) with the ligand and the palladium and the bromo compound in a suitable solvent, for example toluene at an elevated temperature, example above 50° C. such as 80° C. for less than 12 hours, such as for a period of approximately 7 hours.

Compounds of formula (I) wherein $R^6$ represents H, A is a bond and X is an aromatic or heteroaromatic group can be prepared as shown in Scheme 1b below:

Scheme 1b

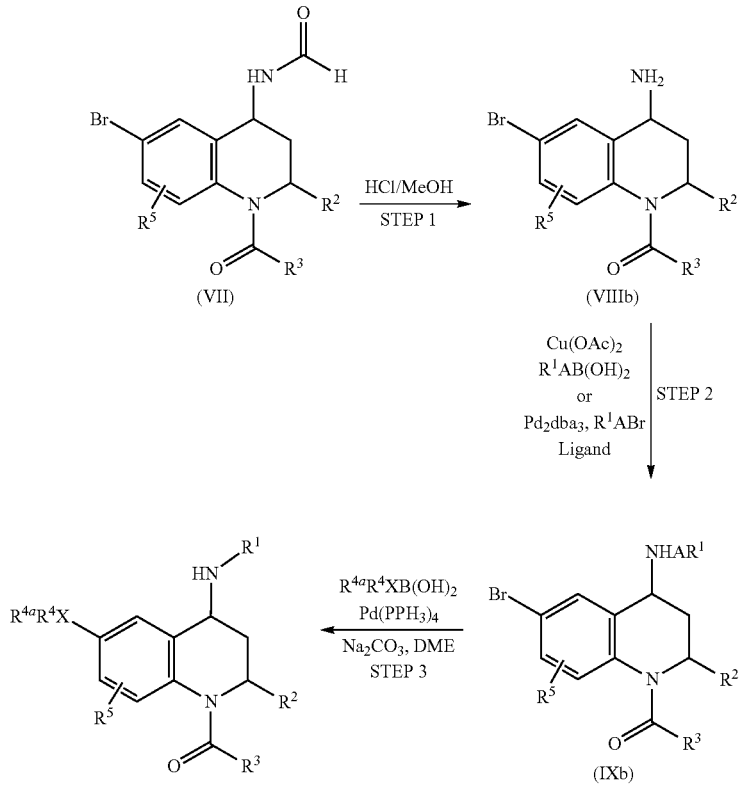

Step 1 in scheme 1b may be effected as described for step 2 in scheme 1a above.

Step 2 in scheme 1b may be effected by treatment with the boronic acid in the presence of a suitable catalyst, such a cupric acetate, in a suitable solvent such as DCM, in the presence of an organic base, such as triethylamine, at room temperature for between 48 to 72 hours.

The alternative process for step 2 is described as the alternative step 3 in scheme 1a above.

Step 3 in scheme 1b may be effected as described for step 1 in scheme 1a above.

Compounds of formula (I) wherein $R^6$ represents H, A is a bond and X is an aromatic or heteroaromatic group can be prepared as shown in Scheme 1c below:

Scheme 1c

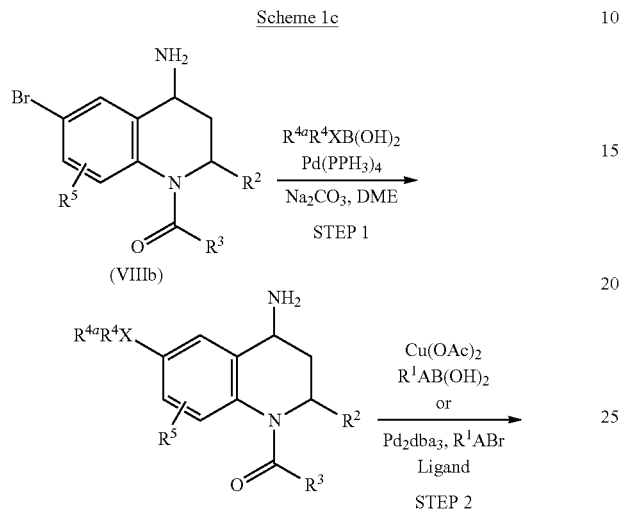

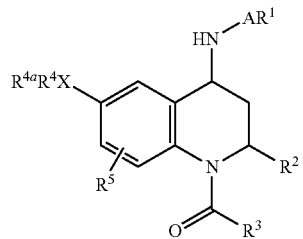

Step 1 in scheme 1c may be effected as described for step 1 in scheme 1a above.

Step 2 in scheme 1c may be effected as described for step 3 in scheme 1a above.

Compounds of formula (I) wherein A represents a bond, $R^4$ represents —$CH_2NR^{11}R^{12}$ and X represents phenyl, can be prepared by the reductive amination process described in Scheme 1d below:

Scheme 1d

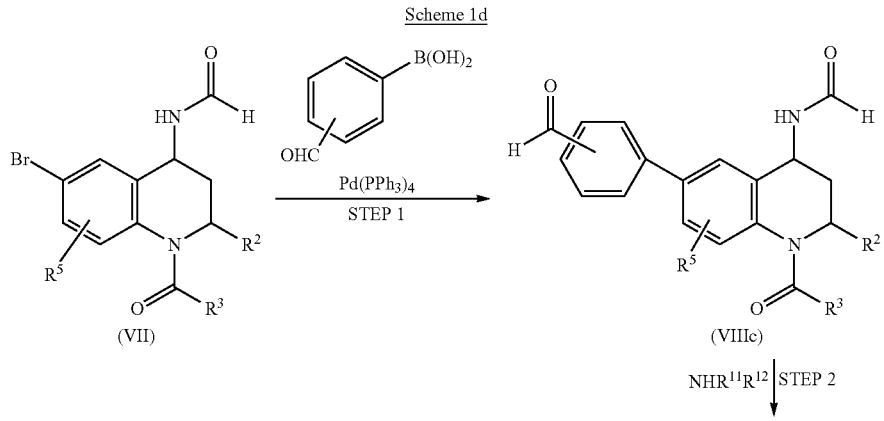

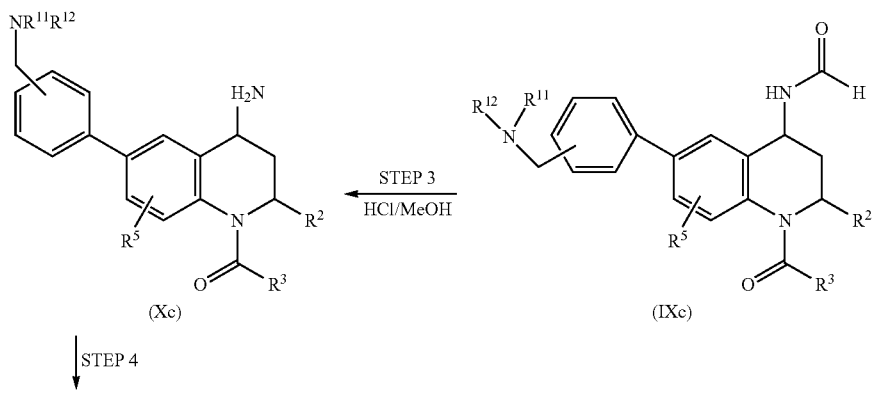

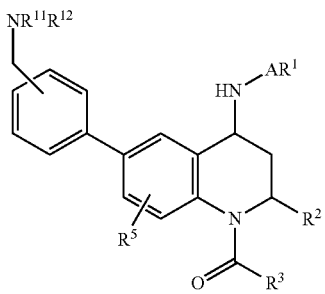

Step 1 in scheme 1d above can be performed as described for step 3 in scheme 1b above.

Step 2 in scheme 1d above can be effected by stirring the compound of formula (VIIIc) with the amine reagent in the presence of a reducing agent such as a hydride, for example tri-acetoxysodium borohydride, and a catalytic amount of acetic acid in a suitable solvent, such as DCM at a non-extreme temperature, for example room temperature for 1 to 4 hours such as about 2 hours.

Step 3 in scheme 1d can be performed as described for step 1 in scheme 1b above.

Step 4 may be performed as described for step 2 in scheme 1b above.

Compounds of formula (I) wherein $R^4$ represent $C_{2-6}$alkylNR$^{11}$R$^{12}$ can be prepared, for example by employing a modified boronic acid reagent, in step 1 of scheme 1d, wherein the aldehyde is linked to the phenyl ring by a $C_{1-5}$ alkyl chain.

An analogous method to that described in Scheme 1d above can be used to prepare compounds of formula (I) wherein $R^4$ represents —CH$_2$NR$^{11}$R$^{12}$ and X represents heteroaromatic, by employing the appropriate starting materials.

The methodology in Scheme 1d can also be used to prepare compounds of formula (I) wherein $R^4$ represents —C$_{1-6}$alkylNR$^8$R$^9$ and $R^8$ and $R^9$ together with the nitrogen to which they are attached form a 5 or 6 membered heteroaromatic or heterocyclyl.

Compounds of formula (I) wherein A is a bond and X is an aromatic or heteroaromatic group can be prepared as shown in Scheme 1e below:

Scheme e:

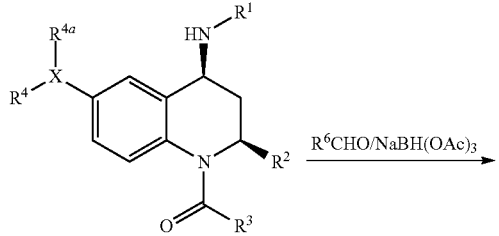

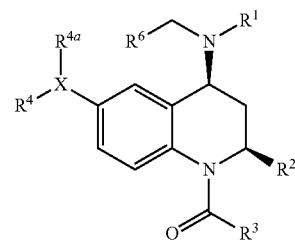

The reaction may be carried out by stirring the compounds with an aldehyde and a reducing agent such as triacetoxysodiumborohydride in a suitable solvent, for example AcOH at room temperature, for a period of several days such as approximately 2 days.

Compounds of formula (I) wherein A is a bond and X is an aromatic or heteroaromatic group can be prepared as shown in Scheme 1f below:

Scheme 1f:

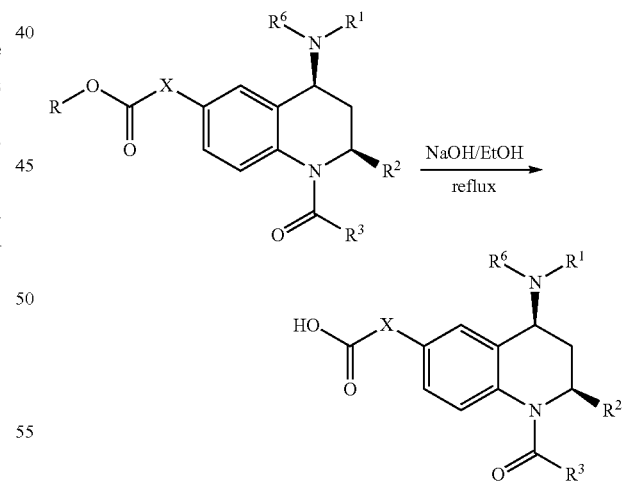

The reaction may be carried out by stirring the esters derivatives in a suitable solvent, for example EtOH at an elevated temperature, for example above 50° C. such as refluxing for a period of between 0.5 and 12 hours such as approximately 2 hours.

Compounds of formula (I) wherein A is a bond, X is an aromatic or heteroaromatic group and $R^4$ a carboxylic group can be prepared as shown in Scheme 1g below:

Scheme 1g:

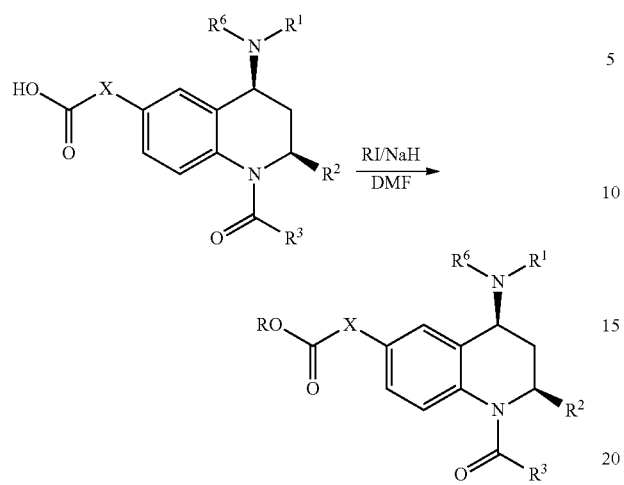

The reaction may be carried out by stirring the acid derivatives, a base, for example sodium hydride, and an alkylating agent such as ethyl iodide in a suitable solvent, for example DMF at room temperature, for a period of between 5 and 48 hours such as approximately 14 hours.

Compounds of formula (I) wherein A is a bond and X is an aromatic or heteroaromatic group can be prepared as shown in Scheme 1h below:

Scheme 1 h:

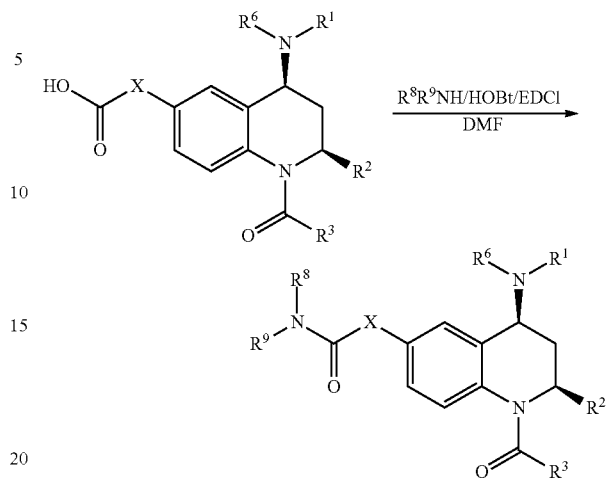

The reaction may be carried out by reacting compounds of formula (I) where $R^4$ is COOH, with $R^8R^9NH$ in the presence of HOBt, EDCl and $Et_3N$ at room temperature.

Compounds of formula (VII) can be prepared by the methods described in Scheme 2 below:

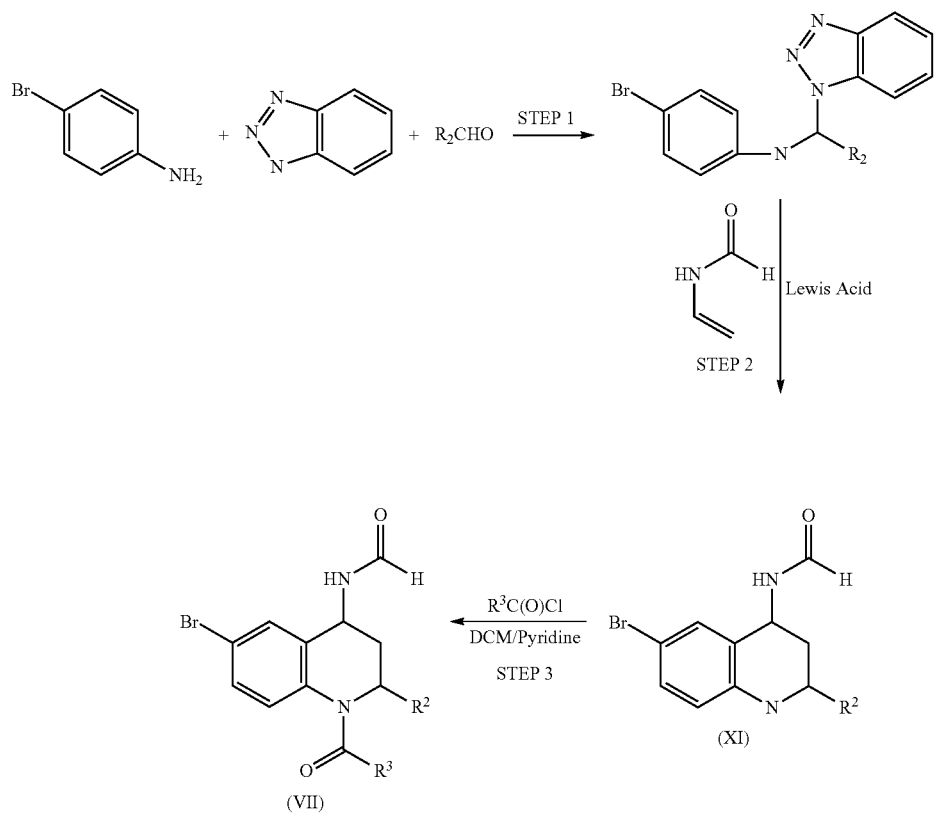

Step 1 in scheme 2 may be effected by stirring a reagents in a suitable solvent, such toluene at room temperature for a period of, for example 10 to 24 hours such as about 12 hours.

Step 2 may be performed in a suitable solvent, such as THF, at a reduced temperature, for example −5° C., in the presence of a lewis acid, such as $BF_3$, $Et_2O$, for less than 4 hours such as a period of about 2 hours.

Step 3 in scheme 2 above may be performed by stirring compound of formula (XI) with an acid chloride $R_3COCl$ in the presence of pyridine in a suitable solvent, such as DCM, at a reduced temperature such as 0° C., for less than 4 hours such as about 2 hours.

Compounds of formula (III), (V) and (VI) are commercially available or can be readily synthesised by known methods, for example as reported by Suzuki in Chem. Rev., 1995, vol. 95, p2457-2483.

Further details for the preparation of compounds of formula (I) are found in the examples section hereinafter.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. In one embodiment there is provided 4-(2S, 4R)-{-1-acetyl-4-[(4-chlorophenyl)amino]-2-methyl-1,2,3,4-tetrahydro-6-quinolinyl}benzoic acid or a pharmaceutically acceptable salt thereof for use in therapy. The compounds of formula (I) and pharmaceutically salts thereof can be used in the treatment of diseases or conditions for which a bromodomain inhibitor is indicated.

In one embodiment there is provided a compound of formula (I) or a pharmaceutically acceptable salt thereof for use in the treatment of diseases or conditions for which a bromodomain inhibitor is indicated. In another embodiment, there is provided a compound or a pharmaceutically acceptable salt thereof for use in the treatment of a chronic autoimmune and/or inflammatory condition. In a further embodiment, there is provided a compound or a pharmaceutically acceptable salt thereof for use in the treatment of cancer.

In one embodiment there is provided 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof for use in the treatment of diseases or conditions for which a bromodomain inhibitor is indicated. In another embodiment, there is provided 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof for use in the treatment of a chronic autoimmune and/or inflammatory condition. In a further embodiment, there is provided 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof for use in the treatment of cancer.

In one embodiment there is provided the use of a compound of formula (I) or a pharmaceutically acceptable salt thereof in the manufacture of a medicament for the treatment of diseases or conditions for which a bromodomain inhibitor is indicated. In another embodiment, there is provided the use of a compound of formula (I) or a pharmaceutically acceptable salt thereof in the manufacture of a medicament for the treatment of a chronic autoimmune and/or inflammatory condition. In a further embodiment, there is provided the use of a compound of formula (I) or a pharmaceutically acceptable salt thereof in the manufacture of a medicament for the treatment of cancer.

In one embodiment there is provided the use of 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof in the manufacture of a medicament for the treatment of diseases or conditions for which a bromodomain inhibitor is indicated. In another embodiment, there is provided the use of 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof in the manufacture of a medicament for the treatment of a chronic autoimmune and/or inflammatory condition. In a further embodiment, there is provided the use of 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof in the manufacture of a medicament for the treatment of cancer.

In one embodiment there is provided a method for the treatment of a disease or condition, for which a bromodomain inhibitor is indicated in a subject in need thereof which comprises administering a therapeutically effective amount of compound of formula (I) or a pharmaceutically acceptable salt thereof. In another embodiment there is provided a method for treatment of a chronic autoimmune and/or inflammatory condition, in a subject in need thereof which comprises administering a therapeutically effective amount of compound of formula (I) or a pharmaceutically acceptable salt thereof. In a further embodiment there is provided a method for treatment of cancer, in a subject in need thereof which comprises administering a therapeutically effective amount of compound of formula (I) or a pharmaceutically acceptable salt thereof.

In one embodiment there is provided a method for treatment of a disease or condition, for which a bromodomain inhibitor is indicated, in a subject in need thereof which comprises administering a therapeutically effective amount of 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof. In another embodiment there is provided a method for treatment of a chronic autoimmune and/or inflammatory condition, in a subject in need thereof which comprises administering a therapeutically effective amount of 4-(2S, 4R)-{-1-acetyl-4-[(4-chlorophenyl)amino]-2-methyl-1,2,3,4-tetrahydro-6-quinolinyl}benzoic acid or a pharmaceutically acceptable salt thereof. In a further embodiment there is provided a method for treatment of cancer, in a subject in need thereof which comprises administering a therapeutically effective amount of 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock or endotoxaemia. In another embodiment, the bromodomain inhibitor is indicated for the treatment of acute or chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include any of or all of the above disease states.

In one embodiment, there is provided a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of formula (I) and pharmaceutically acceptable salts thereof, are as described above. In one embodiment there is provided a pharmaceutical composition comprising 4-(2S,4R)-{-1-acetyl-4-[(4-chlorophenyl)amino]-2-methyl-1,2,3,4-tetrahydro-6-quinolinyl}benzoic acid or a pharmaceutically acceptable salt thereof and one or more pharmaceutically acceptable carriers, diluents or excipients. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be for use in the treatment of any of the conditions described herein.

Since the compounds of formula (I) and pharmaceutically acceptable salts thereof are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO2005/044354A1.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof and may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof and the other pharmaceutically active agent(s) and the relative timings of administration will be selected in order to achieve the desired combined therapeutic effect. Thus in a further aspect, there is provided a combination comprising a compound of formula (I) or a pharmaceutically acceptable salt thereof and at least one other pharmaceutically active agent.

Thus in one aspect, the compound of formula (I) and pharmaceutically acceptable salts thereof and pharmaceutical compositions comprising said compounds of formula (I) and pharmaceutically acceptable salts thereof may be used in combination with or include one or more other therapeutic agents, for example selected from antibiotics, anti-virals, glucocorticosteroids, muscarinic antagonists and beta-2 agonists.

It will be appreciated that when the compound of formula (I) or a pharmaceutically acceptable salt thereof is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and salts thereof may be prepared by the methods described below or by similar methods. Thus the following Intermediates and Examples serve to illustrate the preparation of the compounds of formula (I) and salts thereof, and are not to be considered as limiting the scope of the invention in any way.

INTERMEDIATES AND EXAMPLES

The following non-limiting Examples illustrate the present invention.
Abbreviations
TLC—thin layer chromatography
AcOH—acetic acid
$BF_3.Et_2O$—boron trifluoride diethyletherate
BuLi—butyl lithium
DCM—dichloromethane
DME—1,2-Dimethoxyethane
DMF—N,N-dimethylformamide
EDCl—1-[3-(dimethylamino)propyl]-3-ethylcarbodiimide hydrochloride
$Et_2O$—diethyl ether
$Et_3N$—triethylamine
EtOH—ethanol
EtOAc—ethyl acetate
HOBt—1H-1,2,3-benzotriazol-1-ol
MeCN—acetonitrile
MeOH—methanol
NaOtBu—Sodium terbutylate
$Pd(PPh_3)_4$— palladium tetrakistriphenylphosphine
$Pd_2 dba_3$—tris(dibenzylideneacetone)dipalladium(0)
Py—pyridine
Rt—retention time
THF—tetrahydrofuran
RT—room temperature LC/MS refers to analyses by analytical HPLC which were conducted on the following kinds of apparatus:
a) On a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 ml/minute. The mass spectra (MS) were recorded on a Fisons VG Platform mass spectrometer using electrospray positive ionisation [(ES+ve to give $[M+H]^+$ and $[M+NH_4]^+$ molecular ions] or electrospray negative ionisation [(ES−ve to give $[M-H]^-$ molecular ion] modes. Analytical data from this apparatus are given with the following format: $[M+H]^+$ or $[M-H]^-$.
b) On a Chromolith Performance RP 18 column (100×4.6 mm id) eluting with 0.01M ammonium acetate in water (solvent A) and 100% acetonitrile (solvent B), using the following elution gradient 0-4 minutes 0→100% B, 4-5 minutes 100% B at a flow rate of 5 ml/minute. The mass spectra (MS) were recorded on a micromass Platform-LC mass spectrometer using atmospheric pressure chemical positive ionisation [AP+ve to give MH⁺ molecular ions] or atmospheric pressure chemical negative ionisation [AP-ve to give $(M-H)^-$ molecular ions] modes. Analytical data from this apparatus are given with the following format: [M+H]+ or [M−H]− preceded by the acronym APCI to specify between both mass spectrometry analyses sources.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 ml/minute. The mass spectra (MS) were recorded on a micromass LCT mass spectrometer using electrospray positive ionisation [ES+ve to give MH⁺ molecular ions] or electrospray negative ionisation [ES−ve to give $(M-H)^-$ molecular ions] modes.

Biotage™ chromatography refers to purification carried out using equipment sold by Dyax Corporation (either the Flash 40i or Flash 150i) and cartridges pre-packed with KP-Sil™ silica.

Mass directed auto-prep HPLC refers to the method where the material was purified by high performance liquid chromatography on a HPLCABZ+ 5 μm column (5 cm×10 mm i.d.) with 0.1% $HCO_2H$ in water and 95% MeCN, 5% water (0.5% $HCO_2H$) using the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 ml/minute. The Gilson 202-fraction collector was triggered by a VG Platform Mass Spectrometer on detecting the mass of interest.

SPE (solid phase extraction) refers to the use of cartridges sold by International Sorbent Technology Ltd. SCX is a benzene sulfonic acid stationary phase.

TLC (thin layer chromatography) refers to the use of TLC plates sold by Merck coated with silica gel 60 F254.

LCMS c) Method Formate

LC Conditions

The HPLC analysis was conducted on an Acquity HPLC BEH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.

MS Conditions
MS Waters: ZQ
Ionisation mode: Alternate-scan positive and negative electrospray
Scan range: 100 to 1000 AMU
Scan time: 0.27 sec
Inter scan delay: 0.10 sec d) Method HpH LC Conditions The UPLC analysis was conducted on an Acquity UPLC BEH C18 column (50 mm×2.1 mm, i.d. 1.7 μm packing diameter) at 40° C.

The solvents employed were:
A=10 mM ammonium hydrogen carbonate in water adjusted to pH10 with ammonia solution
B=acetonitrile The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.

MS Conditions
MS Waters: ZQ
Ionisation mode: Alternate-scan positive and negative electrospray
Scan range: 100 to 1000 AMU
Scan time: 0.27 sec
Inter scan delay: 0.10 sec MDAP Methodology e) Method Formate LC Conditions The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.

The solvents employed were:
A=0.1% v/v solution of formic acid in water
B=0.1% v/v solution of formic acid in acetonitrile Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).

The UV detection was a summed signal from wavelength of 210 nm to 350 nm.

MS Conditions
MS Waters: ZQ
Ionisation mode: Alternate-scan positive and negative electrospray
Scan range: 100 to 1000 AMU
Scan time: 0.50 sec
Inter scan delay: 0.20 sec f) Method HpH LC Conditions The HPLC analysis was conducted on either an Xbridge C18 column (100 mm×19 mm, i.d 5 μm packing diameter) or a Xbridge C18 column (100 mm×30 mm, i.d. 5 μm packing diameter) at ambient temperature.

The solvents employed were:
A=10 mM ammonium bicarbonate in water, adjusted to pH10 with ammonia solution
B=acetonitrile Run as a gradient over either 15 or 25 min (extended run) with a flow rate of 20 ml/min (100 mm×19 mm, i.d 5 μm packing diameter) or 40 ml/min (100 mm×30 mm, i.d 5 μm packing diameter).

The UV detection was a summed signal from wavelength of 210 nm to 350 nm.

MS Conditions
MS Waters: ZQ
Ionisation mode: Alternate-scan positive and negative electrospray
Scan range: 100 to 1000 AMU
Scan time: 0.50 sec
Inter scan delay: 0.20 sec g) Method TFA LC Conditions The HPLC analysis was conducted on either a Sunfire C18 column (100 mm×19 mm, i.d. 5 μm packing diameter) or Sunfire C18 column (150 mm×30 mm, i.d. 5 μm packing diameter) at ambient temperature.

The solvents employed were:
A=0.1% v/v solution of trifluoroacetic acid in water
B=0.1% v/v solution of trifluoroacetic in acetonitrile Run as a gradient over either 15 or 25 min (extended run) with a flow rate of 20 ml/min (100 mm×19 mm, i.d 5 μm packing diameter) or 40 ml/min (150 mm×30 mm, i.d 5 μm packing diameter).

The UV detection was a summed signal from wavelength of 210 nm to 350 nm.

MS Conditions
MS Waters: ZQ
Ionisation mode: Positive electrospray
Scan range: 100 to 1000 AMU
Scan time: 0.50 sec
Inter scan delay: 0.20 sec In the procedures that follow, after each starting material, reference to an Intermediate by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Intermediate 1

(6-Bromo-2-methyl-1,2,3,4-tetrahydro-4-quinolinyl)formamide

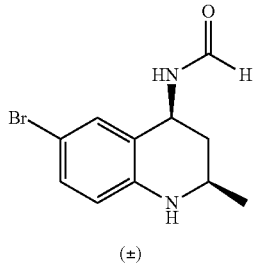

(±)

A 3 L, four neck flask under nitrogen atmosphere was charged with N-vinyl formamide (66.2 g, 0.946 mol) and dry THF (400 mL). BF$_3$Et$_2$O (239 mL, 1.9 mol) were added dropwise at −5° C. to the milky mixture. After 15 minutes Intermediate 8 (150 g, 0.473 mol) in solution in THF (1 L) was added at −5° C. After 2 h, the mixture was slowly and carefully poured in a NaHCO$_3$ saturated solution (5 L). Ethyl acetate (2 L) was added and the mixture was transferred to a separatory funnel. The organic layer was separated and was washed 1×200 mL H$_2$O, 1×200 mL brine and dried (Na$_2$SO$_4$). The mixture was filtered and the solids washed 1×50 mL ethyl acetate. The filtrate was concentrated progressively until a precipitate appeared and the mixture cooled in an ice bath during 2 h. The precipitate was filtered through a Buchner funnel, and washed with 2×100 mL iPr$_2$O to deliver the title compound as a solid (71 g, 56%). LC/MS: APCI, m/z 269 and 271 [M+H]$^+$, Rt=2.29 min; 1H NMR (300 MHz, CHLOROFORM-d) δ ppm 0.98 (d, 3 H) 1.24 (q, 1 H) 2.04 (ddd, 1 H) 3.33 (m, 1 H) 5.17 (m, 1 H) 5.45 (m, 1 H) 6.15 (d, 1 H) 6.88 (dd, 1 H) 7.00 (d, 1 H) 8.11 (s, 1 H)

Intermediate 2

(6-Bromo-2-ethyl-1,2,3,4-tetrahydro-4-quinolinyl)formamide

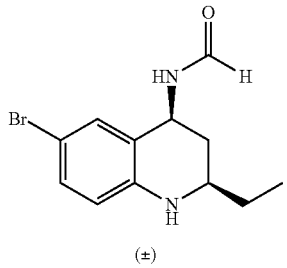 [SMILES: CC[C@@H]1C[C@H](NC=O)c2cc(Br)ccc2N1]

(±)

Intermediate 2 was prepared by similar methods to that described for Intermediate 1 using intermediate 9. LC/MS: APCI, m/z 284.98 [M+H]$^+$, Rt=2.6 min Intermediate 3

[1-Acetyl-6-bromo-2-methyl-1,2,3,4-tetrahydro-4-quinolinyl]formamide

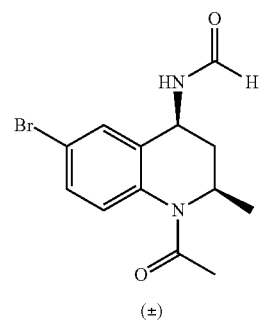 [SMILES: CC(=O)N1c2ccc(Br)cc2[C@@H](NC=O)C[C@H]1C]

(±)

Acetyl chloride (21 mL, 0.29 mol) is added dropwise at 0° C. to a solution of intermediate 1 (71 g, 0.26 mol) in a mixture of DCM (1 L) and pyridine (350 mL). After stirring 2 hours at 0° C. the mixture is poured into a mixture of crushed ice (2 kg) and concentrated HCl (450 mL). The product is extracted with DCM (1 L) washed with brine and dried over Na$_2$SO$_4$. Concentration under vacuo afforded the expected product as an off white solid (82 g, 100%). 1H NMR (300 MHz, CHLOROFORM-d) δ ppm 0.98 (d, 3 H) 1.15 (m, 1 H) 1.95 (s, 3 H) 2.4 (m, 1 H) 4.7 (m, 1 H) 4.85 (m, 1 H) 5.8 (bra d, 1H) 6.85 (d, 1 H) 7.15 (s, 1 H) 7.25 (d, 1 H) 8.2 (s, 1 H)

Intermediate 4

[1-Acetyl-6-bromo-2-ethyl-1,2,3,4-tetrahydro-4-quinolinyl]formamide

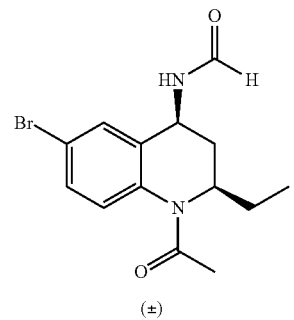 [SMILES: CC[C@@H]1C[C@H](NC=O)c2cc(Br)ccc2N1C(C)=O]

(±)

Intermediate 4 was prepared by similar methods to that described for Intermediate 3 using intermediate 2. LC/MS: APCI, m/z 324.94 [M−H]⁻, Rt=2.38 min Intermediate 5

[6-Bromo-2-methyl-1-profanely-1,2,3,4-tetrahydro-4-quinolinyl]formamide

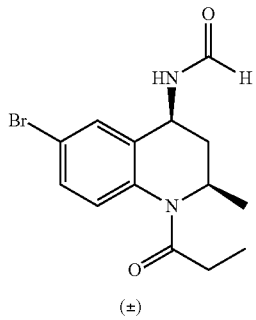 [SMILES: CCC(=O)N1c2ccc(Br)cc2[C@@H](NC=O)C[C@H]1C]

(±)

Intermediate 5 was prepared by similar methods to that described for Intermediate 3 using profanely chloride instead of acetyl chloride. 1H NMR (300 MHz, CHLOROFORM-d) δ ppm 1.15 (m, 6H) 1.25 (m, 1H) 2.3 (m, 1H) 2.45 (m, 1 H) 2.55 (m, 1H) 4.9 (m, 1 H) 5.0 (m, 1 H) 5.75 (br d, 1H) 7.0 (d, 1 H) 7.35 (d, 1 H) 7.55 (d, 1 H) 8.45 (s, 1 H)

Intermediate 6

1-Acetyl-6-bromo-2-methyl-1,2,3,4-tetrahydro-4-quinolinamine

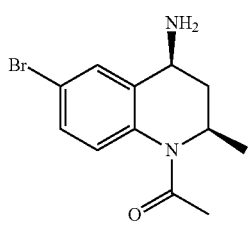 [SMILES: CC(=O)N1c2ccc(Br)cc2[C@@H](N)C[C@H]1C]

To a suspension of Intermediate 3 (4 g, 12.9 mol) in MeOH (50 mL) was added 6N HCl (6.5 mL, 38.6 mmol). The resulting mixture was stirred at reflux for 3 hours and the medium was made basic by the addition of 2N NaOH. The MeOH was evaporated under reduced pressure and the organic material extracted with EtOAc (250 mL). The organic phase was washed with brine, dried over Na₂SO₄ and concentrated to dryness to afford the title compound as an oil (3.3 g, 91%); LC/MS: APCI, m/z 284 [M+H]⁺, Rt=2.18 min Intermediate 7

6-Bromo-2-methyl-1-profanely-1,2,3,4-tetrahydro-4-quinolinamine

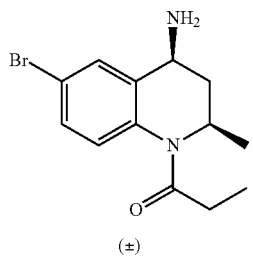 [SMILES: CCC(=O)N1c2ccc(Br)cc2[C@@H](N)C[C@H]1C]

(±)

Intermediate 7 was prepared by similar methods to that described for Intermediate 6 using intermediate 5.1H NMR (300 MHz, CHLOROFORM-d) δ ppm 1.1 (m, 7H) 1.75 (bra s, 2H) 2.25 (m, 1H) 2.5 (m, 2 H) 3.7 (dd, 1H) 4.85 (m, 1 H) 7.0 (d, 1 H) 7.4 (d, 1 H) 7.65 (s, 1 H)

Intermediate 8

[1-(1H-1,2,3-Benzotriazol-1-yl)ethyl](4-bromophenyl)amine

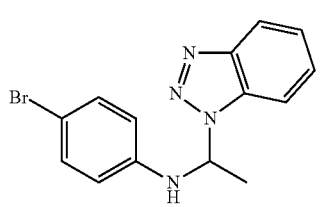 [SMILES: CC(Nc1ccc(Br)cc1)n1nnc2ccccc21]

To a suspension of benzotriazole (139 g, 1.16 mol) in toluene (2 L) in a 3 L, four neck flask under nitrogen atmosphere was added at room temperature a solution of 4-bromoaniline (200 g, 1.16 mol) in toluene (300 mL). Then, via an addition funnel was added drop wise acetaldehyde (64.7 ml, 1.17 mol) in solution in toluene (200 mL). The reaction mixture becomes progressively homogenous and then gives a precipitate. The resulting mixture is stirred 12 hours under nitrogen atmosphere and then filtered. The precipitate is recrystallised in toluene to afford the title compound as a white solid (304 g, 82%).

1H NMR (300 MHz, CHLOROFORM-d) δ ppm 2.1 (m, 3 H) 4.9 (m, 0.66 H) 5.15 (m, 0.33 H) 6.5-6.9 (m, 3 H) 7.2-8.2 (m, 7H)

Intermediate 9

[1-(1H-1,2,3-Benzotriazol-1-yl)propyl](4-bromophenyl)amine

Intermediate 9 was prepared by similar methods to that described for Intermediate 8 using propionaldehyde and was isolated as a white powder.

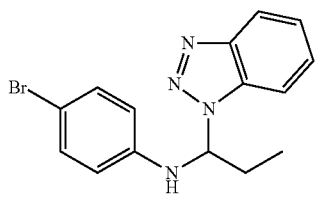 [SMILES: CCC(Nc1ccc(Br)cc1)n1nnc2ccccc21]

MP: 132° C.

Intermediate 10

[1-Acetyl-6-(4-formylphenyl)-2-methyl-1,2,3,4-tetrahydro-4-quinolinyl]formamide

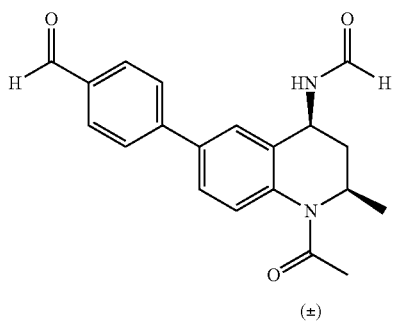 [SMILES: CC(=O)N1c2ccc(-c3ccc(C=O)cc3)cc2[C@@H](NC=O)C[C@H]1C]

(±)

To a solution of Intermediate 3 (82 g, 0.263 mol) in DME (2 L) are added (4-formylphenyl)boronic acid (51.4 g, 0.34 mol) at room temperature. A 2N solution of $Na_2CO_3$ (527 mL, 1.05 mol) and palladium tetrakis (8.2 g, 10% w/w) are added and the mixture is heated to reflux under a nitrogen atmosphere. Monitoring of the reaction progression is carried out by LC/MS (the starting material and the product display a similar Rf in various solvent combinations). After 2 hours, the reaction is complete and the mixture is concentrated under reduced pressure. The residue is taken up in water (1 L) and the darkened mixture is diluted with EtOAC (1 L) and transferred to a separatory funnel. A dark precipitate has formed and is isolated by filtration after separation of the organic phase. The organic layer is dried over $Na_2SO_4$ and delivers the title compound (37.5 g) as a yellow solid after concentration under reduced pressure and precipitation of the organic residue in a DCM/hexane mixture. The dark solid is taken up in a DCM/MeOH mixture and purified by flash chromatography on silica gel eluting with a DCM/MeOH 80/2. to afford the title compound (45 g) as a yellow brown solid.

Mp: 85.6° C.

Intermediates 11 to 14 below were prepared by similar methods to that described for Intermediate 10 using the appropriate boronic acid derivative and suitable precipitation or recrystallisation conditions (see Table 1):

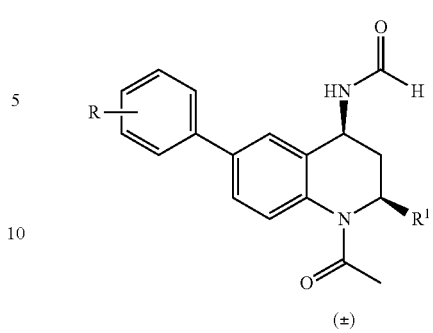

(±)

TABLE 1

| Intermediate | R | R1 | From intermediate | Physical data |
|---|---|---|---|---|
| 11 | meta-CHO | $CH_3$ | 3 | LC/MS: m/z 337 $[M + H]^+$, Rt = 2.38 min |
| 12 | para-COOMe | $CH_3$ | 3 | LC/MS: m/z 337 $[M + H]^+$, Rt = 2.38 min |
| 13 | para-OH | $CH_3$ | 3 | LC/MS: m/z 325 $[M + H]^+$, Rt = 2.22 min |
| 14 | Para-OMe | $CH_2CH_3$ | 4 | HRMS $[M + H]^+$: calculated for $C_{21}H_{24}N_2O_3$ Theo: 353.1865 Found: 353.1817 Rt: 2.41 min |

Intermediate 15 Procedure 2

{(cis)-1-Acetyl-2-methyl-6-[4-(1-piperidinylmethyl)phenyl]-1,2,3,4-tetrahydro-4-quinolinyl}formamide

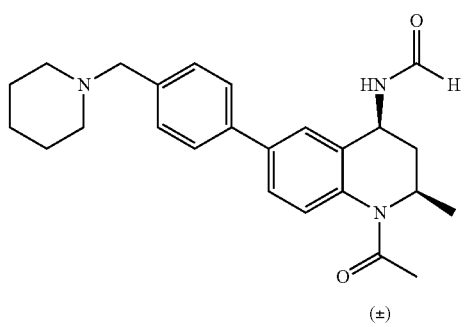 [SMILES: CC(=O)N1c2ccc(-c3ccc(CN4CCCCC4)cc3)cc2[C@@H](NC=O)C[C@H]1C]

(±)

To a solution of intermediate 10 (95 g, 0.25 mol) and piperidine (31 g, 0.3 mol) in solution in dichloroethane (2 L) were added at room temperature triacetoxysodiumborohydride (70 g, 0.33 mol) and acetic acid (33 g). After stirring 2 hours a t.l.c monitoring indicated the completion of the reaction and the mixture was poured into a saturated solution of $NaHCO_3$. The organic phase was extracted after addition of DCM (500 mL) and washed with brine (100 mL), dried over $Na_2SO_4$, filtered and evaporated to dryness. Trituration of the residue in a mixture of DCM/hexane afforded the title compound (109 g, 95.6%) as an off white solid; LC/MS: APCI, m/z 406 $[M+H]^+$, Rt=2.22 min;

Intermediate 15 Procedure 2

{(cis)-1-Acetyl-2-methyl-6-[4-(1-piperidinylmethyl)phenyl]-1,2,3,4-tetrahydro-4-quinolinyl}formamide 1-Acetyl-6-(4-formylphenyl)-2-methyl-1,2,3,4-tetrahydro-4-quinolinyl]formamide (for a preparation see Intermediate 10) (5 g, 14.86 mmol) was dissolved in dichloromethane (DCM) (100 mL), mixed with acetic acid (1.702 mL, 29.7 mmol) and piperidine (1.762 mL, 17.84 mmol), then stirred under nitrogen for 1 h. Sodium triacetoxyborohydride (3.78 g, 17.84 mmol) was added to the reaction mixture after this time and the resulting mixture was stirred under nitrogen for 24 h then was concentrated in vacuo. The residue was partitioned between a 1:1 saturated $NaHCO_3$ aqueous solution/water (200 mL) and AcOEt (100 mL) and the layers were separated. The aqueous layer was extracted with AcOEt (2×50 mL) and the combined organic phases were dried over $Na_2SO_4$ and concentrated in vacuo. The residue was loaded on a SCX column then eluted with MeOH followed by a 2N $NH_3$ in MeOH. The ammonia phases were collected and concentrated in vacuo to give {(cis)-1-acetyl-2-methyl-6-[4-(1-piperidinylmethyl)phenyl]-1,2,3,4-tetrahydro-4-quinolinyl}formamide (4.784 g, 11.74 mmol, 79%) as a white solid.

LCMS (Method A): Retention time 0.61 min, $[M+H]^+$ =406.0

Intermediates 16 to 18 (see Table 2) were prepared by methods similar to that described for Intermediate 10 using the Intermediates indicated in the table and the appropriate amine.

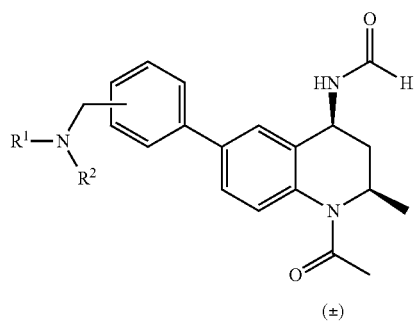

(±)

TABLE 2

| Intermediate | $NR^1R^2$ | From intermediate | Physical data |
|---|---|---|---|
| 16 | 4-morpholino | 10 | LC/MS: m/z 408 $[M + H]^+$, Rt = 2.39 min |
| 17 | 4-N-Methyl piperazine | 10 | LC/MS: m/z 421 $[M + H]^+$, Rt = 2.08 min |
| 18 | 4-pyrrolidine | 10 | LC/MS: m/z 392 $[M + H]^+$, Rt = 2.00 min |
| 19 | 3-N-Methylpiperazine | 11 | LC/MS: m/z 421 $[M + H]^+$, Rt = 1.91 min |
| 20 | 3-Pyrrolidine | 11 | LC/MS: m/z 392 $[M + H]^+$, Rt = 1.85 min |
| 21 | 3-Piperidine | 11 | LC/MS: m/z 406 $[M + H]^+$, Rt = 2.24 min |
| 22 | 3-Morpholino | 11 | LC/MS: m/z 408 $[M + H]^+$, Rt = 2.40 min |
| 23 | $3-NMe_2$ | 11 | LC/MS: m/z 366 $[M + H]^+$, Rt = 1.82 min |

Intermediate 24

[1-Acetyl-2-methyl-6-(4-{[2-(1-pyrrolidinyl)ethyl]oxy}phenyl)-1,2,3,4-tetrahydro-4-quinolinyl]formamide

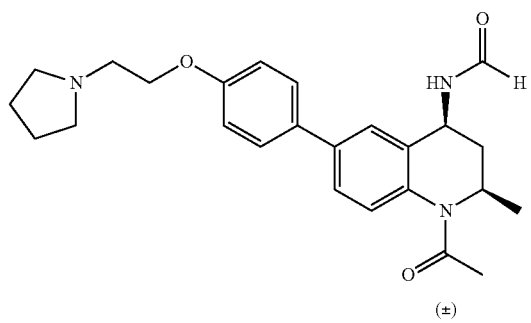 [SMILES: CC(=O)N1c2ccc(-c3ccc(OCCN4CCCC4)cc3)cc2[C@@H](NC=O)C[C@H]1C]

(±)

To a solution of Intermediate 13 (2.5 g, 7.7 mmol) in acetone (100 mL) was added finely divided $K_2CO_3$ (4.28 g, 31 mmol) and 1-(2-chloroethyl)pyrrolidine chlorohydrate (1.96 g, 11.5 mmol). The resulting mixture was stirred at reflux for 48 hours and concentrated under vacuo. The residue was taken up in water (100 mL) and the organic materials were extracted with DCM (2×0.25 L) dried over $Na_2SO_4$ and concentrated to dryness. The title compound was obtained as a crude product (3.2 g, 97%); LC/MS: APCI, m/z 422 $[M+H]^+$, Rt=2.13 min.

Intermediate 25 Procedure 1

1-Acetyl-2-methyl-6-[4-(1-piperidinylmethyl)phenyl]-1,2,3,4-tetrahydro-4-quinolinamine

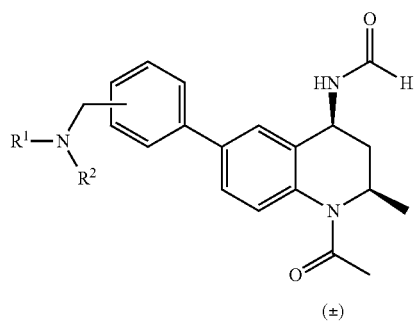

(±)

To a suspension of Intermediate 15 (109 g, 0.27 mol) in MeOH (1 L) was added 6N HCl (136 mL, 0.8 mol). The resulting homogenous mixture was stirred at reflux for 2 hours and concentrated under vacuo. The residue was taken up in water (1 L) and washed with DCM (100 mL). The aqueous phase was basified with $NaHCO_3$ and the organic materials were extracted with DCM (2×0.5 L) dried over $Na_2SO_4$ and concentrated to dryness. After heating of the residue in DCM (100 mL) and $iPr_2O$ (1 L) and filtration the title compound was obtained as a white precipitate (70 g, 70%); LC/MS: APCI, m/z 378 $[M+H]^+$, Rt=2.19 min.

Intermediate 25 Procedure 2

(cis)-1-Acetyl-2-methyl-6-[4-(1-piperidinylmethyl)phenyl]-1,2,3,4-tetrahydro-4-quinolinamine {1-Acetyl-2-methyl-6-[4-(1-piperidinylmethyl)phenyl]-1,2,3,4-tetrahydro-4-quinolinyl}formamide (for a preparation see Intermediate 15) (4.784 g, 11.80 mmol) was dissolved in ethanol (115 mL) and treated with HCl (5N in water, 7.08 ml, 35.4 mmol). The resulting mixture was stirred at 85° C. for 16 h, at room temperature for 16 h then most of the ethanol was removed in vacuo. The aqueous residue was basified to pH 9 with a saturated NaHCO$_3$ aqueous solution (100 mL) then partitioned between water (150 mL) and AcOEt (200 mL). The layers were separated and the aqueous layer was extracted with AcOEt (5×100 mL). The combined organic phases were dried over Na$_2$SO$_4$ and concentrated in vacuo to give (cis)-1-acetyl-2-methyl-6-[4-(1-piperidinylmethyl)phenyl]-1,2,3,4-tetrahydro-4-quinolinamine (4.36 g, 10.62 mmol, 90%) as a pale yellow solid which was used in the next step without further purification.

LCMS (Method A): Retention time 0.51 min, [M+H]+=378.0

Intermediates 26 to 36 (see Table 3) were prepared by methods similar to that described for intermediate 25 Procedure 1 using the intermediates indicated in the table.

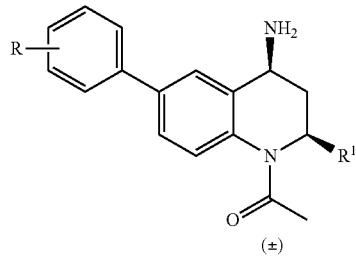

TABLE 3

| Int. | R | R1 | From Intermediate | Physical data |
|---|---|---|---|---|
| 26 | 4-CH$_2$-morpholino | CH$_3$ | 16 | LC/MS: m/z 380 [M + H]+, Rt = 2.29 min |
| 27 | 4-CH$_2$—N-Methyl piperazine | CH$_3$ | 17 | LC/MS: m/z 393 [M + H]+, Rt = 2.09 min |
| 28 | 4-CH$_2$-pyrrolidine | CH$_3$ | 18 | LC/MS: m/z 364 [M + H]+, Rt = 1.99 min |
| 29 | 3-CH$_2$—N-Methylpiperazine | CH$_3$ | 19 | LC/MS: m/z 393 [M + H]+, Rt = 2.16 min |
| 30 | 3-CH$_2$-pyrrolidine | CH$_3$ | 20 | LC/MS: m/z 364 [M + H]+, Rt = 1.91 min |
| 31 | 3-CH$_2$-piperidine | CH$_3$ | 21 | LC/MS: m/z 378 [M + H]+, Rt = 2.21 min |
| 32 | 3-CH$_2$-morpholino | CH$_3$ | 22 | LC/MS: m/z 380 [M + H]+, Rt = 2.34 min |
| 33 | 3-CH$_2$—NMe$_2$ | CH$_3$ | 23 | LC/MS: m/z 338 [M + H]+, Rt = 1.87 min |
| 34 | 4-COOMe | CH$_3$ | 12 | LC/MS: m/z 339 [M + H]+, Rt = 2.50 min Mp: 250.3 1H NMR (300 MHz, DMSO-d6) δ ppm 1.05 (d, 3 H) 1.35 (m, 1H) 2.05 (s, 3 H) 2.75 (m, 1H) 3.85 (s, 3H) 4.25 (m, 1 H) 4.65 (m, 1H) 7.55 (d, 1 H) 7.75 (d, 1H) 7.8 (s, 1 H), 7.95 (d, 2H) 8.1 (d, 2H) 9.05 (broad s, 2H) |
| 35 | para- pyrrolidinyl-CH$_2$CH$_2$O- | CH$_3$ | 24 | LC/MS: m/z 394 [M + H]+, Rt = 2.15 min |
| 36 | 4-OMe | CH$_2$CH$_3$ | 14 | 1H NMR (300 MHz, CDCl$_3$) δ ppm 0.9 (t, 3 H) 1.2 (m, 1H) 1.4 (m, 1H) 1.55 (m, 1H) 2.15 (s, 3 H) 2.55 (m, 1H) 3.85 (m, 4H) 4.80 (m, 1 H) 6.95 (d, 2H) 7.15 (m, 1H) 7.45 (dd, 1 H) 7.55 (d, 2H) 7.65 (s, 1 H), |

Intermediate 37

(2S,3S)-2,3-bis[(phenylcarbonyl)oxy]butanedioic acid-methyl 4-(1-acetyl-4-amino-2-methyl-1,2,3,4-tetrahydro-6-quinolinyl)benzoate (1:2)

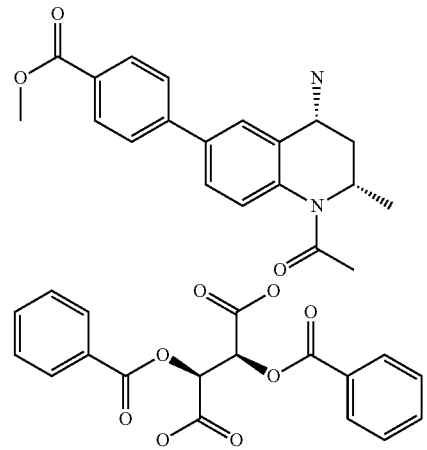

A mixture of the racemic amine intermediate 34 (185 g,) in EtOH (600 mL) and L-(+)-lactic acid (20% in water, 450 mL) was heated to reflux during 30 minutes. After concentration under reduced pressure hexane (300 mL) was added to the residue and the resulting mixture heated to reflux 10 min. The mixture was allowed to settle and the hexane phase was discarded. The remaining paste was taken up with Et$_2$O (300 mL), heated to reflux during 10 minutes and allowed to settle. The Et$_2$O phase was discarded and the resulting paste once again was treated with hexane (200 mL), heated to reflux and allowed to settle. The hexane phase was discarded and EtOAc (2.3 L) was added to the remaining paste. The mixture was heated to reflux and allowed to stand at room temperature for 16 hours. The precipitate was filtered and washed with EtOAc (200 mL). The filtrate was made basic with addition of Na$_2$CO$_3$ and the resulting free amino was extracted with EtOAc (3×1000 mL), washed with water, dried over Na$_2$SO$_4$ and concentrated under reduced pressure. The resulting free amino (95 g) in solution in THF (950 mL) was treated with L(−)-dibenzoyltartaric acid (50.3 g, 0.14 mol) and heated to reflux 30 minutes. The resulting precipitate was allowed to stand at room temperature during 16 hours and then was filtered and washed with THF (200 ml). An HPLC monitoring of a neutralised aliquot indicated a 95.6% ee of the expected amine enantiomer. Recrystallisation of the tartaric salt in EtOH (1 L) afforded the title compound (95 g) as a single diastereomer salt.

mp: 196° C.

1H NMR (300 MHz, DMSO-d6) δ ppm 0.95 (d, 3 H) 1.15 (m, 1H) 2.05 (s, 3 H) 2.55 (m, 1H) 3.85 (s, 3H) 4.0 (m, 1 H) 4.55 (m, 1H) 5.7 (s, 1H, CH tartaric) 7.4 (m, 3 H) 7.6 (m, 2H) 7.85 (m, 3 H), 7.95 (m, 4H)

Intermediate 38

Methyl 4-[1-acetyl-4-amino-2-methyl-1,2,3,4-tetrahydro-6-quinolinyl]benzoate

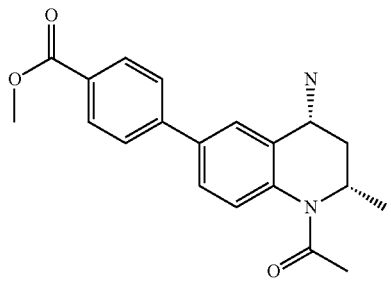 [SMILES: COC(=O)c1ccc(-c2ccc3c(c2)[C@H](N)C[C@H](C)N3C(C)=O)cc1]

A mixture of intermediate 37 (121 g) in DCM (3 L) was made basic with addition of Na$_2$CO$_3$. The resulting free amine was extracted with DCM (2 L) washed with water and dried over Na$_2$SO$_4$ to deliver the title compound as an off white solid (79 g). 1H NMR (300 MHz, CHLOROFORM-d) δ ppm 1.15 (m, 4 H) 1.7 (m, 2 H) 2.15 (s, 3 H) 2.6 (m, 1 H) 3.8 (dd, 1H), 3.95 (s, 3H) 4.85 (m, 1 H) 7.2 (d, 1 H) 7.55 (d, 1 H) 7.7 (d, 2 H), 7.8 (s, 1H) 8.1 (d, 2H) [α]$_D$=+333.8 (c=0.985 g/cl, EtOH).

The title compound eluted at 18.57 min by HPLC as the second peak using a CHIRACEL OD (250×4.6 mm 10 μm) column with hexane/ethanol 80/20 as the mobile phase. A 1 ml/mn flow rate was applied and 10 μL of sample prepared with the dilution of 1 mg of the title compound in 1 ml of eluent was injected. Detection of the compound was carried out with both 210 and 254 nM UV wavelengths. The other enantiomer came off at 12.8 min.

Intermediate 39 Procedure 1

1-Acetyl-6-bromo-2-methyl-N-phenyl-1,2,3,4-tetrahydro-4-quinolinamine

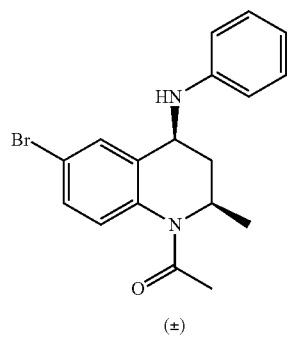 [SMILES: CC(=O)N1c2ccc(Br)cc2[C@@H](Nc2ccccc2)C[C@H]1C]

The resulting dark-blue to turquoise mixture of the intermediate 6 (4 g, 14 mmol), phenyl boronic acid (5.12 g, 42 mmol), anhydrous cupric acetate (3.8 g, 21 mmol), triethylamine (5.8 ml, 42 mmol) in dry DCM (50 ml) was stirred at room temperature for 48-72 hr. Progression of the reaction was monitored by tlc and if necessary an additional equivalent of phenyl boronic acid and triethylamine was added and the mixture allowed to stir at room temperature for further 12 hr. This operation was repeated until the amount of the expected product exceeded the remaining proportion of the starting intermediate. The resulting mixture was poured into water (15 ml) and the organic phase was extracted with DCM (250 mL), dried over Na$_2$SO$_4$, filtered and evaporated to dryness. The resulting residue was purified by flash column chromatography on silica gel eluting with DCM to give the title compound as a brown powder (1.16 g, 22%), LC/MS: m/z 360 [M+H]$^+$, Rt=3.36 min Intermediate 39 Procedure 2

(cis)-1-Acetyl-6-bromo-2-methyl-N-phenyl-1,2,3,4-tetrahydro-4-quinolinamine

A flask was charged with myristic acid (100 mg, 0.438 mmol), copper(II) acetate (29.2 mg, 0.161 mmol), phenylboronic acid (294 mg, 2.410 mmol), 2,6-lutidine (0.25 mL, 2.146 mmol), and (cis)-1-acetyl-6-bromo-2-methyl-1,2,3,4-tetrahydro-4-quinolinamine (for a preparation see intermediate 6) (455 mg, 1.607 mmol) then filled with toluene (20 mL) and the resulting mixture was stirred vigorously in air for 72 h then partitioned between AcOEt (50 mL) and a saturated NaHCO$_3$ aqueous solution (50 mL). The layers were separated and the organic phase was washed with brine, dried over Na$_2$SO$_4$ and concentrated in vacuo. Purification of the residue by SP4 using a 40 G silica cartridge (gradient:0 to 100% AcOEt in Hexanes) gave (cis)-1-acetyl-6-bromo-2-methyl-N-phenyl-1,2,3,4-tetrahydro-4-quinolinamine (218 mg, 0.607 mmol, 38%) as a colourless oil.

LCMS (Method B): Retention time 1.22 min, [M+H]$^+$=359.1

Intermediates 40 to 41 (see Table 4) were prepared by methods similar to that described for intermediate 39 Procedure 1 using the intermediates indicated in the table.

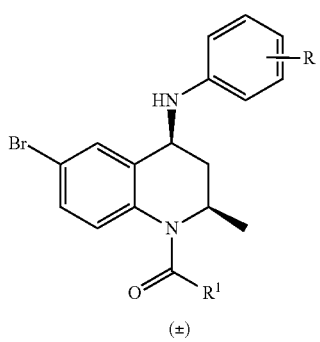

(±)

TABLE 4

| Intermediate | R1 | R | From Intermediate | Physical data |
|---|---|---|---|---|
| 40 | CH₃ | 4-Cl | 6 | LC/MS: m/z 395 [M + H]⁺, Rt = 3.62 min |
| 41 | CH₂CH₃ | H | 7 | 1H NMR (300 MHz, CHLOROFORM-d) δ ppm 1.1 (t, 6H) 1.3 (m, 1H) 2.35(m, 1H) 2.55 (m, 1H) 2.7 (m, 1H) 4.15(dd, 1H) 4.9 (m, 1H) 6.65 (m, 2H) 6.8 (m, 1H) 7.05 (d, 1H) 7.2 (m, 2H) 7.4(d, 1H) 7.5 (s, 1H) |

Intermediate 42

1-Acetyl-2-methyl-6-phenyl-1,2,3,4-tetrahydro-4-quinolinamine

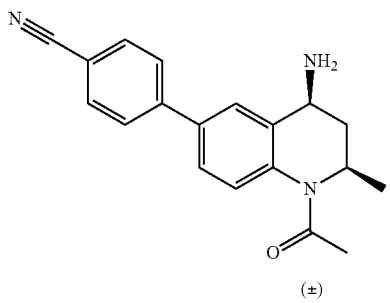 [SMILES: CC(=O)N1c2ccc(-c3ccc(C#N)cc3)cc2[C@@H](N)C[C@H]1C]

(±)

To a solution of Intermediate 6 (10 g, 0.263 mol) in DME (140) are added 4-cyanoboronic acid (6.23 g, 42 mmol) at room temperature. A 2N solution of Na₂CO₃ (70 mL, 0.14 mol) and palladium tetrakis (1 g, 10% w/w) are added and the mixture is heated to reflux under a nitrogen atmosphere. Monitoring of the reaction progression is carried out by LC/MS (the starting material and the product display a similar Rf in various solvent combinations). After 4 hours, the reaction is complete and the mixture is concentrated under reduced pressure. The residue is taken up in water (250 mL) and the darkened mixture is diluted with EtOAC (300 mL) and transferred to a separatory funnel. The organic layer is dried over Na₂SO₄ and delivers the title compound (8 g) after concentration under reduced pressure and purification by flashchromatografy on silicagel eluting with a DCM/MeOH 95/5, %), LC/MS: m/z 306 [M+H]⁺, Rt=2.40 min Intermediate 43

(2S,4R)-1-Acetyl-6-[1-(2-{[(1,1-dimethylethyl)(dimethyl)silyl]oxy}ethyl)-1H-1,2,3-triazol-4-yl]-2-methyl-N-(5-methyl-2-pyridinyl)-1,2,3,4-tetrahydro-4-quinolinamine

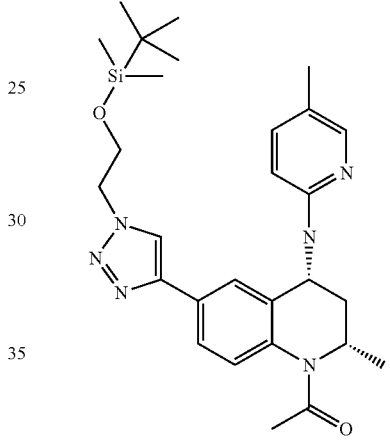

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (for a preparation see intermediate 44) (48 mg, 0.112 mmol) and 2-bromo-5-methylpyridine (57.7 mg, 0.335 mmol) in toluene (2.5 mL) were successively added sodium tert-butoxide (107 mg, 1.117 mmol), tris(dibenzylideneacetone)dipalladium(0) (20.46 mg, 0.022 mmol) and 2'-(dicyclohexylphosphino)-N,N-dimethylbiphenyl-2-amine (DavePhos) (17.59 mg, 0.045 mmol). The reaction mixture was stirred at 75° C. for 5 h then cooled to room temperature, and filtered through Celite. The insoluble material was washed with 5% MeOH in DCM. The combined filtrate and washings were concentrated in vacuo. Purification of the residue on SP4 using a 10 G silica cartridge (gradient:10 to 80% AcOEt in Hexanes) gave (2S,4R)-1-acetyl-6-[1-(2-{[(1,1-dimethylethyl)(dimethyl)silyl]oxy}ethyl)-1H-1,2,3-triazol-4-yl]-2-methyl-N-(5-methyl-2-pyridinyl)-1,2,3,4-tetrahydro-4-quinolinamine (34 mg, 0.065 mmol, 58%) as a colourless oil.

LCMS (Method A): Retention time 0.93 min, [M+H]+=521.5

Intermediate 44

(2S,4R)-1-Acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine

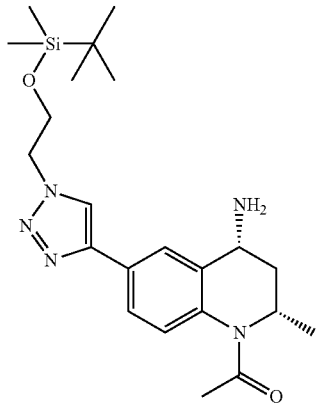

To 2-{4-[(2S,4R)-1-acetyl-4-amino-2-methyl-1,2,3,4-tetrahydro-6-quinolinyl]-1H-1,2,3-triazol-1-yl}ethanol (for a preparation see intermediate 45) (358 mg, 0.834 mmol) and imidazole (114 mg, 1.667 mmol) in N,N-dimethylformamide (DMF) (15 mL), was added chloro(1,1-dimethylethyl)dimethylsilane (151 mg, 1.0 mmol) and the resulting reaction mixture was stirred at room temperature for 16 h. Another equivalent of imidazole (114 mg, 1.667 mmol) and chloro(1,1-dimethylethyl)dimethylsilane (151 mg, 1.000 mmol) were then added and after 15 min the resulting mixture was partitioned between EtOAc and water. The layers were separated and the aqueous phase was extracted three times with EtOAc. The combined organic layers were washed twice with brine, dried over MgSO$_4$ and concentrated in vacuovacuo. Purification of the residue on SP4 using a 25 G silica cartridge (gradient:0 to 10% MeOH in DCM) gave (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (202 mg, 0.451 mmol, 54.1% yield) as a yellow oil.

LCMS (Method A): Retention time 0.84 min, [M+H]+=430.4

Intermediate 45

2-{4-[(2S,4R)-1-Acetyl-4-amino-2-methyl-1,2,3,4-tetrahydro-6-quinolinyl]-1H-1,2,3-triazol-1-yl}ethanol

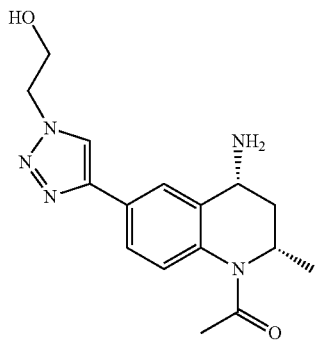 [SMILES: CC(=O)N1c2ccc(-c3cn(CCO)nn3)cc2[C@H](N)C[C@@H]1C]

A solution of 1,1-dimethylethyl {(2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinyl}carbamate (for a preparation see intermediate 46) (599 mg, 1.131 mmol) in dichloromethane (DCM) (20 mL) was treated with trifluoroacetic acid (TFA) (5.00 mL) and the resulting reaction mixture was stirred for 1 h at room temperature then concentrated in vacuovacuo. Purification of the residue on SP4 using a 50 G silica cartridge (gradient:0 to 12% MeOH in DCM) gave 2-{4-[(2S,4R)-1-acetyl-4-amino-2-methyl-1,2,3,4-tetrahydro-6-quinolinyl]-1H-1,2,3-triazol-1-yl}ethanol (396 mg, 0.885 mmol, 78% yield) as a yellow solid.

LCMS (Method A): Retention time 0.39 min, [M+H]+=316.12

Intermediate 46

1,1-Dimethylethyl {(2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinyl}carbamate

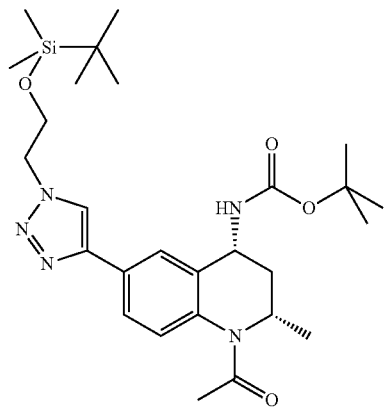 [SMILES: CC(=O)N1c2ccc(-c3cn(CCO[Si](C)(C)C(C)(C)C)nn3)cc2[C@H](NC(=O)OC(C)(C)C)C[C@@H]1C]

A solution of 1,1-dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate (for a preparation see intermediate 47) (659 mg, 1.586 mmol) and imidazole (216 mg, 3.17 mmol) in N,N-dimethylformamide (DMF) (20.0 mL) was treated with chloro(1,1-dimethylethyl)dimethylsilane (0.330 mL, 1.903 mmol) and the resulting reaction mixture was stirred at room temperature for 16 h. Another equivalent of imidazole (216 mg, 3.17 mmol) and chloro(1,1-dimethylethyl)dimethylsilane (0.330 mL, 1.903 mmol) were then added to the reaction which was stirred at room temperature for 1 h then partitioned between water and EtOAc. The layers were separated and the aqueous phase was extracted three times with EtOAc. The combined organic layers were washed twice with brine, dried over MgSO$_4$, and concentrated in vacuovacuo. Purification of the residue on SP4 using a 50 G silica cartridge (gradient:10 to 50% AcOEt in Hexanes) gave 1,1-dimethylethyl {(2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinyl}carbamate (599 mg, 1.085 mmol, 68.4% yield).

LCMS (Method B): Retention time 1.31 min, [M+H]+=530.30

Intermediate 47

1,1-Dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate

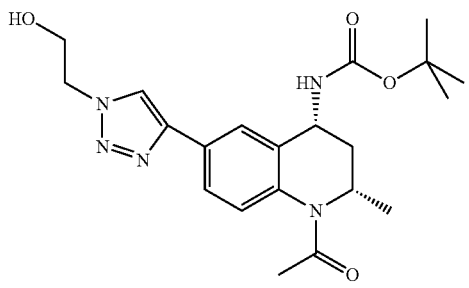 [SMILES: CC(=O)N1c2ccc(-c3cn(CCO)nn3)cc2[C@H](NC(=O)OC(C)(C)C)C[C@@H]1C]

A flask was charged with 2-azidoethanol (318 mg, 3.65 mmol) and copper(I) iodide (17.40 mg, 0.091 mmol) then filled with N,N-dimethylformamide (DMF) (13 mL) and methanol (1.5 mL). This mixture was treated with 1,1-dimethylethyl[(2S,4R)-1-acetyl-6-ethynyl-2-methyl-1,2,3,4-tetrahydro-4-quinolinyl]carbamate (for a preparation see Intermediate 48) (600 mg, 1.827 mmol) and the resulting mixture was stirred at 100° C. for 2 h under microwave irradiation then cooled to room temperature and partitioned between EtOAc and water. The layers were separated and the aqueous phase was extracted three times with EtOAc. The combined organic layers were washed twice with brine, and then dried over MgSO$_4$ and concentrated in vacuovacuo. Purification of the residue by flash chromatography on silica gel (gradient:0 to 5% MeOH in DCM) gave 1,1-dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate (659 mg, 1.523 mmol, 83% yield).

LCMS (Method A): Retention time 0.76 min, [M+H]+=416.3

Intermediate 48

1,1-Dimethylethyl[(2S,4R)-1-acetyl-6-ethynyl-2-methyl-1,2,3,4-tetrahydro-4-quinolinyl]carbamate

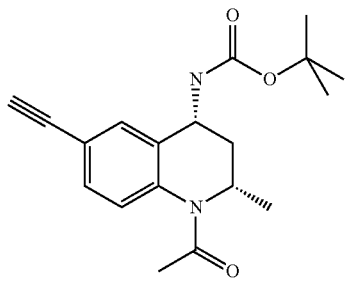 [SMILES: C#Cc1ccc2c(c1)[C@H](NC(=O)OC(C)(C)C)C[C@H](C)N2C(C)=O]

To a solution of 1,1-dimethylethyl {(2S,4R)-1-acetyl-2-methyl-6-[(trimethylsilyl)ethynyl]-1,2,3,4-tetrahydro-4-quinolinyl}carbamate (for a preparation see Intermediate 49) (3.4 g, 8.49 mmol) in tetrahydrofuran (THF) (50 mL) at room temperature was added TBAF (1M in THF, 8.49 mL, 8.49 mmol) and the resulting mixture was stirred at this temperature for 30 min then most of the solvent was removed in vacuovacuo. The residue was partitioned between AcOEt and water/brine (1/1) and the layers were separated. The aqueous phase was extracted three times with AcOEt and the combined organic phases were washed with water/brine (1/1) which when combined were extracted twice with AcOEt. All organic phases were combined and dried over MgSO$_4$ then concentrated in vacuovacuo. Purification of this residue by SP4 using a 50 G silica cartridge (gradient:10 to 50% AcOEt in Hexanes) gave 1,1-dimethylethyl[(2S,4R)-1-acetyl-6-ethynyl-2-methyl-1,2,3,4-tetrahydro-4-quinolinyl]carbamate (2.75 g, 8.37 mmol, 99% yield) as a yellow foam.

LCMS (Method B): Retention time 1.06 min, [M+H]+=329.15

Intermediate 49

1,1-Dimethylethyl {(2S,4R)-1-acetyl-2-methyl-6-[(trimethylsilyl)ethynyl]-1,2,3,4-tetrahydro-4-quinolinyl}carbamate

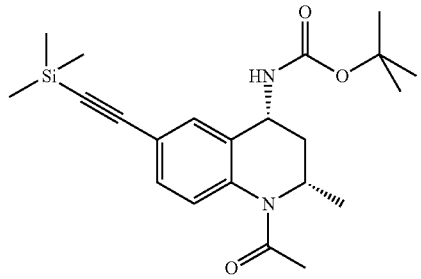 [SMILES: CC(=O)N1c2ccc(C#C[Si](C)(C)C)cc2[C@H](NC(=O)OC(C)(C)C)C[C@@H]1C]

A flask was charged with 1,1-dimethylethyl[(2S,4R)-1-acetyl-6-bromo-2-methyl-1,2,3,4-tetrahydro-4-quinolinyl]carbamate (for a preparation see Intermediate 50) (4 g, 10.44 mmol), copper(I) iodide (0.199 g, 1.044 mmol) and bis(triphenylphosphine)palladium(II) chloride (0.733 g, 1.044 mmol) then filled with N,N-dimethylformamide (DMF) (60 mL). Triethylamine (58.2 mL, 417 mmol) and ethynyl(trimethyl)silane (29.7 mL, 209 mmol) were added and the resulting mixture was stirred for 20 h at 90° C. under nitrogen then cooled to room temperature. Most of the solvent was removed in vacuo and the residue was partitioned between AcOEt and water/brine (1/1). The layers were separated and the aqueous phase was extracted with AcOEt. The combined organic phases were washed three times with water/brine (1/1), dried over MgSO$_4$ and concentrated in vacuovacuo. Purification of this residue by SP4 using a 100 G silica cartridge (gradient:10 to 50% AcOEt in Hexanes) gave 1,1-dimethylethyl {(2S,4R)-1-acetyl-2-methyl-6-[(trimethylsilyl)ethynyl]-1,2,3,4-tetrahydro-4-quinolinyl}carbamate (3.4 g, 8.49 mmol, 81% yield) as a black foam.

LCMS (Method B): Retention time 1.39 min, [M+H]+=401.19

Intermediate 50

1,1-Dimethylethyl[(2S,4R)-1-acetyl-6-bromo-2-methyl-1,2,3,4-tetrahydro-4-quinolinyl]carbamate

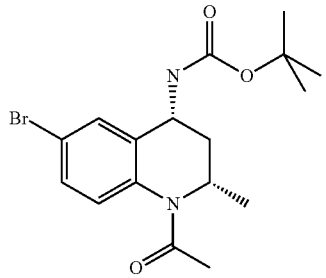 [SMILES: CC(=O)N1c2ccc(Br)cc2[C@H](NC(=O)OC(C)(C)C)C[C@@H]1C]

To a solution of (2S,4R)-1-acetyl-6-bromo-2-methyl-1,2,3,4-tetrahydro-4-quinolinamine hydrochloride (for a preparation, see Intermediate 57) (5.36 g, 16.77 mmol) in dichloromethane (DCM) (100 mL) at room temperature was added triethylamine (7.01 mL, 50.3 mmol) then bis(1,1-dimethylethyl) dicarbonate (4.28 mL, 18.45 mmol). After 90 min, triethylamine (1.75 mL, 12.6 mmol) then bis(1,1-dimethylethyl) dicarbonate (1.07 mL, 4.61 mmol) were added and the resulting mixture was stirred at room temperature for another 30 min. The reaction mixture was then washed with water. The aqueous phase was extracted with DCM and the combined organic phases were washed with water then dried using a phase separator and concentrated in vacuovacuo. Purification of the residue by SP4 using a 100 G silica cartridge (gradient:13 to 63% AcOEt in Hexanes) gave 1,1-dimethylethyl[(2S,4R)-1-acetyl-6-bromo-2-methyl-1,2,3,4-tetrahydro-4-quinolinyl]carbamate (5.27 g, 13.75 mmol, 82% yield) as a white foam.

LCMS (Method B): Retention time 1.14 min, [M−H]−=383.09 (1 Br)

Intermediate 51

(2S,4R)-1-Acetyl-6-bromo-2-methyl-1,2,3,4-tetrahydro-4-quinolinamine

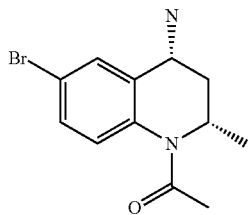 [SMILES: CC(=O)N1c2ccc(Br)cc2[C@H](N)C[C@@H]1C]

To a suspension of aluminium chloride (6.97 g, 52.3 mmol) in dichloromethane (DCM) (80 mL) at 0° C. under nitrogen was added 1-methylethyl[(2S,4R)-1-acetyl-6-bromo-2-methyl-1,2,3,4-tetrahydro-4-quinolinyl]carbamate (for a preparation see Intermediate 100) (5.08 g, 13.76 mmol) in DCM (10 mL). The resulting mixture was stirred for 30 min then triethylamine (23.01 mL, 165 mmol) in methanol (8 mL) was slowly added to the mixture. AcOEt (200 mL) was added and the resulting mixture was stirred at room temperature for 15 min. The precipitate formed was filtered off and rinsed with AcOEt then partitioned between a saturated NaHCO₃ aqueous solution and DCM (200 mL each). The biphasic mixture was vigorously stirred for 2 h. The two layers were separated and the organic phase was dried using a phase separator then concentrated in vacuo to give a first batch of (2S,4R)-1-acetyl-6-bromo-2-methyl-1,2,3,4-tetrahydro-4-quinolinamine. The aqueous layer was treated with another 200 mL of DCM and the resulting biphasic mixture was vigorously stirred for 20 min. The two layers were separated and the organic phase was dried using a phase separator then concentrated in vacuo to give a second batch of (2S,4R)-1-acetyl-6-bromo-2-methyl-1,2,3,4-tetrahydro-4-quinolinamine. Both batches were combined to give (2S,4R)-1-acetyl-6-bromo-2-methyl-1,2,3,4-tetrahydro-4-quinolinamine (3.65 g, 12.7 mmol, 93%) as white solid which was used in the next step without further purification.

LCMS (Method B): Retention time 0.78 min, [M−H]−=281.21 (1 Br)

Intermediate 52

Ethyl 4-[(2S,4R)-1-acetyl-4-amino-2-methyl-1,2,3,4-tetrahydro-6-quinolinyl]benzoate

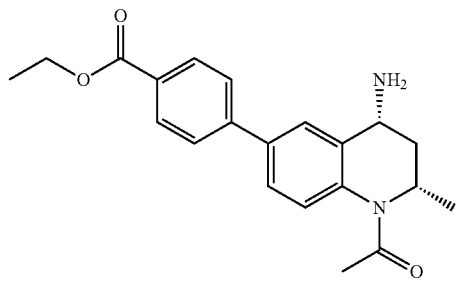 [SMILES: CCOC(=O)c1ccc(-c2ccc3c(c2)[C@H](N)C[C@H](C)N3C(C)=O)cc1]

Ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see intermediate 53) (25.33 g, 57.8 mmol) was added to a cold (ice/water bath) suspension of aluminum chloride (29.24 g, 219 mmol) in DCM (450 mL). The resulting solution was stirred at approximately 0° C. for 35 min then a solution of triethylamine (96 mL, 693 mmol) and methanol (50 mL) was added over 30 s. The resulting mixture was stirred for approximately 1 h in the ice bath, and then partitioned between AcOEt and a saturated NaHCO₃ aqueous solution. The mixture was filtered through Celite, and the residue washed with AcOEt and a saturated NaHCO₃ aqueous solution (several times each). The layers were separated and the aqueous phase was extracted with AcOEt (×2). The combined organic phases were washed with brine, dried using a hydrophobic frit and concentrated in vacuovacuo. The solid obtained was dissolved, with warming, in AcOEt, filtered through Celite in order to remove remaining inorganics and the insoluble material was washed with warm AcOEt. The combined filtrate and washings were concentrated in vacuo to give a first batch of ethyl 4-[(2S,4R)-1-acetyl-4-amino-2-methyl-1,2,3,4-tetrahydro-6-quinolinyl]benzoate (15.0 g, 42.6 mmol, 74%) as a cream solid The solid residue on celite was further washed with acetone, and the filtrate concentrated in vacuovacuo. The residue was partially dissolved in AcOEt, filtered through a hydrophobic frit and the filtrate was concentrated vacuo to give a second batch of ethyl 4-[(2S,4R)-1-acetyl-4-amino-2-methyl-1,2,3,4-tetrahydro-6-quinolinyl]benzoate (2.78 g, 7.9 mmol, 14%) as a cream foam.

LCMS (Method A): Retention time 0.74 min, [M+H₂]+=336.4

Intermediate 53

Ethyl 4-[(2S,4R)-1-acetyl-2-methyl-4-({[(1-methylethyl)oxy]carbonyl}amino)-1,2,3,4-tetrahydro-6-quinolinyl]benzoate

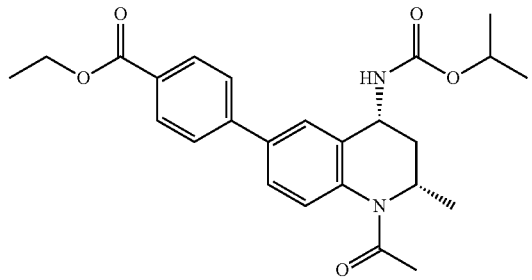 [SMILES: CCOC(=O)c1ccc(-c2ccc3c(c2)[C@H](NC(=O)OC(C)C)C[C@H](C)N3C(C)=O)cc1]

1-Methylethyl[(2S,4R)-1-acetyl-6-bromo-2-methyl-1,2,3,4-tetrahydro-4-quinolinyl]carbamate (for a preparation see intermediate 100) (39.0 g, 106 mmol), {4-[(ethyloxy)carbonyl]phenyl}boronic acid (22.5 g, 116 mmol) and tetrakis(triphenylphosphine)palladium(0) (1.83 g, 1.584 mmol) were mixed in DME (430 mL) and the mixture treated with a 2M Na$_2$CO$_3$ aqueous solution (210 mL, 420 mmol). The resulting mixture was degassed under house vacuo with several quenches with nitrogen, stirred at 105° C. under nitrogen for approximately 6 h and then cooled to room temperature and partitioned between AcOEt and water. The two layers were separated and the aqueous phase was extracted with AcOEt. The combined organic phases were washed brine then were filtered through a 70 g silica cartridge, washing the cartridge with AcOEt. The combined filtrate and washings were concentrated in vacuovacuo. The residue was triturated with Et$_2$O then filtered off to give ethyl 4-[(2S,4R)-1-acetyl-2-methyl-4-({[(1-methylethyl)oxy]carbonyl}amino)-1,2,3,4-tetrahydro-6-quinolinyl]benzoate (35.2 g, 80.56 mmol, 76%) as a grey solid. The mother liquors were concentrated in vacuo and the residue obtained triturated with Et$_2$O. The solid formed was filtered off to give ethyl 4-[(2S,4R)-1-acetyl-2-methyl-4-({[(1-methylethyl)oxy]carbonyl}amino)-1,2,3,4-tetrahydro-6-quinolinyl]benzoate (5.96 g, 13.64 mmol, 13%) as a grey solid.

LCMS (Method B): Retention time 1.16 min, [M+H]+=439.16

Intermediate 54

1,1-Dimethylethyl (2-{4-[(2S,4R)-1-acetyl-2-methyl-4-(phenylamino)-1,2,3,4-tetrahydro-6-quinolinyl]-1H-pyrazol-1-yl}ethyl)methylcarbamate

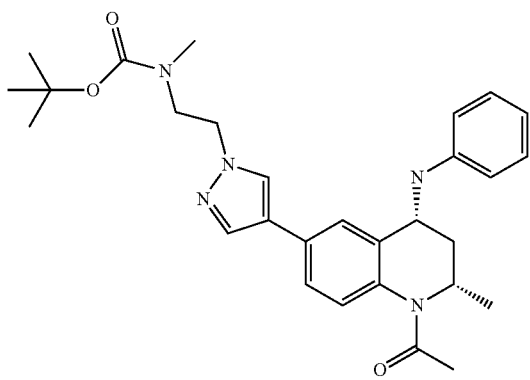 [SMILES: CC(=O)N1c2ccc(-c3cnn(CCN(C)C(=O)OC(C)(C)C)c3)cc2[C@H](Nc2ccccc2)C[C@@H]1C]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (150 mg, 0.351 mmol), iodobenzene (0.078 mL, 0.702 mmol), 2'-(dicyclohexylphosphino)-N,N-dimethylbiphenyl-2-amine (DavePhos) (27.6 mg, 0.070 mmol), tris(dibenzylideneacetone)dipalladium(0) (32.1 mg, 0.035 mmol) and sodium tert-butoxide (67.4 mg, 0.702 mmol) were dissolved in 1,4-dioxane (4 mL). The resulting mixture was stirred at 100° C. under nitrogen for 20 h, at 120° C. for 16 h then cooled to room temperature and partitioned between DCM and a saturated NaHCO$_3$ aqueous solution. The layers were separated using an hydrophobic frit and the organic phase concentrated in vacuovacuo. Purification of the residue on SP4 using a 10 G silica cartridge (gradient:20 to 100% AcOEt in hexanes) gave 1,1-dimethylethyl (2-{4-[(2S,4R)-1-acetyl-2-methyl-4-(phenylamino)-1,2,3,4-tetrahydro-6-quinolinyl]-1H-pyrazol-1-yl}ethyl)methylcarbamate (104 mg, 0.206 mmol, 58.9% yield) as a yellow oil.

LCMS (Method A): retention time 1.12 min, [M+H]+=504.21

Intermediate 55

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate

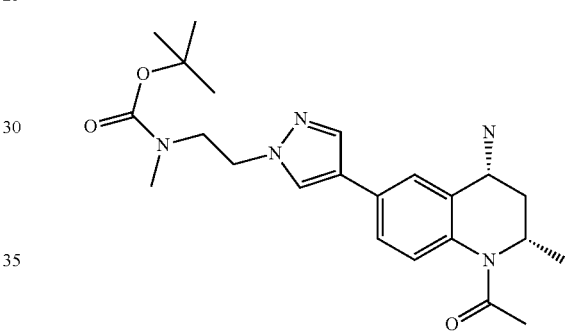

(2S,4R)-1-Acetyl-6-bromo-2-methyl-1,2,3,4-tetrahydro-4-quinolinamine hydrochloride (for a preparation see intermediate 57) (1.219 g, 3.81 mmol) and 1,1-dimethylethyl methyl{2-[4-(4,4,5,5-tetramethyl-1,3,2-dioxaborolan-2-yl)-1H-pyrazol-1-yl]ethyl}carbamate (for a preparation see intermediate 56) (1.608 g, 4.58 mmol) were combined in 1,4-dioxane (15 mL) and water (5.00 mL) under nitrogen to give a clear yellow solution. Potassium carbonate (1.212 g, 8.77 mmol) then [1,1-bis(diphenylphosphino)ferrocene]dichloropalladium(II) (0.419 g, 0.572 mmol) were added and the resulting red mixture was stirred at 110° C. for 16 h then was cooled to room temperature and concentrated in vacuovacuo. The brown residue was suspended in DCM (20 mL) and filtered through a pad of celite (2 g). The insoluble material was washed with DCM (30 mL) and the combined filtrate and washings were concentrated in vacuovacuo. Purification of the residue on SP4 using a 10 G silica cartridge (gradient:1 to 10% MeOH in DCM) gave 1,1-dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (1.195 g, 2.66 mmol, 69.6% yield) as a brown foam.

LCMS (Method B): Retention time 0.68 min, [M+H]+=428.20

Intermediate 56

1,1-Dimethylethyl methyl{2-[4-(4,4,5,5-tetramethyl-1,3,2-dioxaborolan-2-yl)-1H-pyrazol-1-yl]ethyl}carbamate

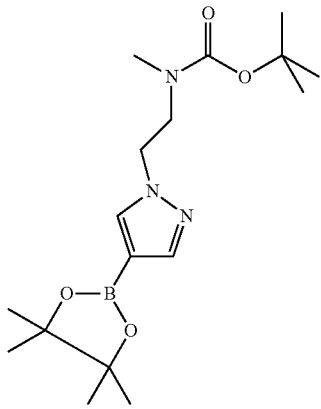 [SMILES: CN(CCn1cc(B2OC(C)(C)C(C)(C)O2)cn1)C(=O)OC(C)(C)C]

4-(4,4,5,5-Tetramethyl-1,3,2-dioxaborolan-2-yl)-1H-pyrazole (5 g, 25.8 mmol), bis(1-methylethyl) (E)-1,2-diazenedicarboxylate (5.73 g, 28.3 mmol), triphenylphosphine (7.43 g, 28.3 mmol) and 1,1-dimethylethyl (2-hydroxyethyl)methylcarbamate (4.52 g, 25.8 mmol) were dissolved in THF at 0° C. under nitrogen and the resulting mixture was stirred at this temperature for 4 h, then evaporated in vacuo and the residue triturated with MTBE. The precipitated solid was removed by filtration and the filtrate evaporated in vacuo, then purified by chromatography on silica gel (gradient:0-100% EtOAc in Hexanes) to give 1,1-dimethylethyl methyl{2-[4-(4,4,5,5-tetramethyl-1,3,2-dioxaborolan-2-yl)-1H-pyrazol-1-yl]ethyl}carbamate (4.85 g, 13.81 mmol, 53.6% yield) as a colourless oil.

Intermediate 57

(2S,4R)-1-Acetyl-6-bromo-2-methyl-1,2,3,4-tetrahydro-4-quinolinamine hydrochloride

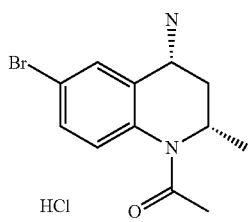 [SMILES: CC(=O)N1c2ccc(Br)cc2[C@H](N)C[C@@H]1C ; Cl]

(2S,4R)-1-Acetyl-6-bromo-2-methyl-1,2,3,4-tetrahydro-4-quinolinamine (for a preparation see intermediate 51) (4.24 g, 14.98 mmol) was dissolved in MeOH (20 mL) and the solution treated with HCl (1M in MeOH, 16.47 mL, 16.47 mmol). The resulting mixture was concentrated in vacuovacuo. The reside was co-evaporated with Et$_2$O to give (2S,4R)-1-acetyl-6-bromo-2-methyl-1,2,3,4-tetrahydro-4-quinolinamine hydrochloride (4.255 g, 12.65 mmol, 84% yield) as a light brown solid.

LCMS (Method B): Retention time 0.49 min, [M+H]+=284.96 (1 Br)

Intermediate 58

1,1-Dimethylethyl (2-{4-[(2S,4R)-1-acetyl-2-methyl-4-(3-pyridinylamino)-1,2,3,4-tetrahydro-6-quinolinyl]-1H-pyrazol-1-yl}ethyl)methylcarbamate

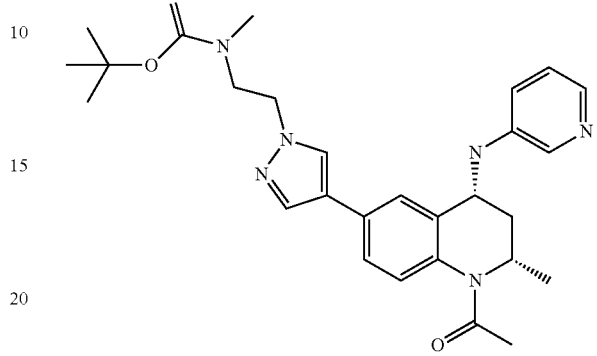

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (150 mg, 0.351 mmol), 3-iodopyridine (144 mg, 0.702 mmol), 2'-(dicyclohexylphosphino)-N,N-dimethylbiphenyl-2-amine (DavePhos) (27.6 mg, 0.070 mmol), tris(dibenzylideneacetone)dipalladium(0) (32.1 mg, 0.035 mmol) and sodium tert-butoxide (67.4 mg, 0.702 mmol) were dissolved in 1,4-dioxane (4 mL) and the resulting mixture was stirred at 100° C. under nitrogen for 20 h, at 120° C. for 16 h, then cooled to room temperature and concentrated in vacuovacuo. The residue was partitioned between DCM and a saturated NaHCO$_3$ aqueous solution and the layers were separated using a hydrophobic frit. The organic phase was concentrated in vacuovacuo. Purification of the residue by SP4 using a 50 G silica cartridge (gradient:0.5 to 10% (2M NH$_3$ in MeOH) in DCM) gave 1,1-dimethylethyl (2-{4-[(2S,4R)-1-acetyl-2-methyl-4-(3-pyridinylamino)-1,2,3,4-tetrahydro-6-quinolinyl]-1H-pyrazol-1-yl}ethyl)methylcarbamate (84 mg, 0.166 mmol, 47.4% yield).

LCMS (Method B): Retention time 0.75 min, [M+H]+=505.25

Intermediate 59

1,1-Dimethylethyl (2-{4-[(2S,4R)-1-acetyl-2-methyl-4-(4-pyridinylamino)-1,2,3,4-tetrahydro-6-quinolinyl]-1H-pyrazol-1-yl}ethyl)methylcarbamate

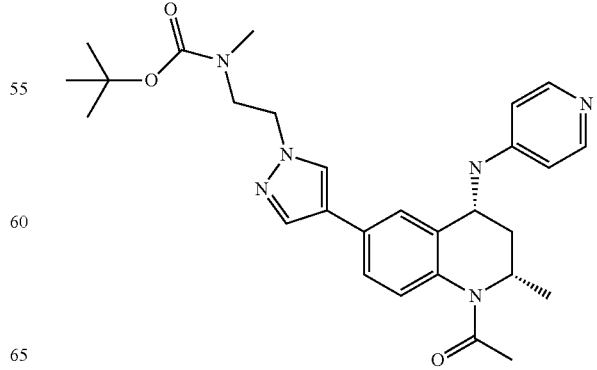

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (159 mg, 0.372 mmol), 4-bromopyridine (0.071 mL, 0.744 mmol), 2'-(dicyclohexylphosphino)-N,N-dimethylbiphenyl-2-amine (DavePhos) (58.5 mg, 0.149 mmol), tris(dibenzylideneacetone)dipalladium(0) (68.1 mg, 0.074 mmol) and sodium tert-butoxide (107 mg, 1.116 mmol) were dissolved in 1,4-dioxane (4 mL) and the resulting mixture was stirred at 120° C. under nitrogen for 16 h then cooled to room temperature and partitioned between EtOAc and a saturated NaHCO₃ aqueous solution. The layers were separated and the aqueous phase was extracted with EtOAc. The combined organic phases were washed with brine, dried over MgSO₄ and concentrated in vacuovacuo. Purification of the residue by SP4 using a 50 G silica cartridge (gradient:5 to 20% (2M NH₃ in MeOH) in DCM) gave 1,1-dimethylethyl (2-{4-[(2S,4R)-1-acetyl-2-methyl-4-(4-pyridinylamino)-1,2,3,4-tetrahydro-6-quinolinyl]-1H-pyrazol-1-yl}ethyl)methylcarbamate (147 mg, 0.29 mmol, 78%).

LCMS (Method B): Retention time 0.75 min, [M+H]+=505.18

Intermediate 60

1,1-Dimethylethyl (2-{4-[(2S,4R)-1-acetyl-2-methyl-4-(2-pyridinylamino)-1,2,3,4-tetrahydro-6-quinolinyl]-1H-pyrazol-1-yl}ethyl)methylcarbamate formate

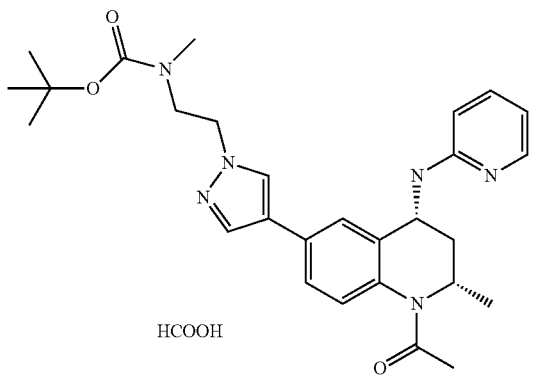 [SMILES: CC(=O)N1c2ccc(-c3cnn(CCN(C)C(=O)OC(C)(C)C)c3)cc2[C@H](Nc2ccccn2)C[C@@H]1C ; "HCOOH"]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (159 mg, 0.372 mmol), 2-bromopyridine (0.071 mL, 0.744 mmol), 2'-(dicyclohexylphosphino)-N,N-dimethylbiphenyl-2-amine (DavePhos) (58.5 mg, 0.149 mmol), tris(dibenzylideneacetone)dipalladium(0) (68.1 mg, 0.074 mmol) and sodium tert-butoxide (107 mg, 1.116 mmol) were dissolved in 1,4-dioxane (4 mL) and the resulting mixture was stirred at 120° C. under nitrogen for 16 h then cooled to room temperature and concentrated in vacuovacuo. The residue was partitioned between EtOAc and a saturated NaHCO₃ aqueous solution and the layers were separated. The aqueous phase was extracted with EtOAc and the combined organic phases were washed with brine, dried over MgSO₄ and concentrated in vacuovacuo. The residue was dissolved in 1:1 MeOH:DMSO (0.6 mL ×3) and purified by MDAP (modifier: formic acid). The desired fractions were combined and the solvent was removed under vacuo to give 1,1-dimethylethyl (2-{4-[(2S,4R)-1-acetyl-2-methyl-4-(2-pyridinylamino)-1,2,3,4-tetrahydro-6-quinolinyl]-1H-pyrazol-1-yl}ethyl)methylcarbamate formate (126 mg, 0.250 mmol, 67.1% yield).

LCMS (Method A): Retention time 0.73 min, [M+H]+=505.4

Intermediate 61

(cis)-1-Acetyl-2-methyl-6-(4-methyl-1H-imidazol-1-yl)-1,2,3,4-tetrahydro-4-quinolinamine di-hydrochloride

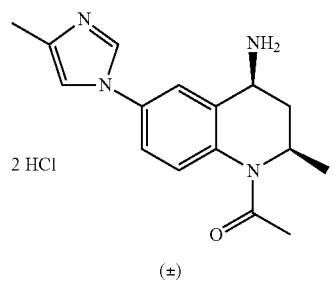

A solution of 1,1-dimethylethyl[1-acetyl-2-methyl-6-(4-methyl-1H-imidazol-1-yl)-1,2,3,4-tetrahydro-4-quinolinyl]carbamate (for a preparation see Intermediate 62) (5.7 g, 14.83 mmol) in dichloromethane (DCM) (40 mL) was treated at room temperature with HCl (4N in 1,4-dioxane, 20 ml, 80 mmol). An ice bath was used during the addition to keep the temperature below 30° C. Once the addition was completed, DCM (20 mL) was added and the resulting mixture was stirred at room temperature for 2 h then concentrated in vacuo to give (cis)-1-acetyl-2-methyl-6-(4-methyl-1H-imidazol-1-yl)-1,2,3,4-tetrahydro-4-quinolinamine di-hydrochloride as (5.12 g, 14.33 mmol, 97%) as a white solid.

LCMS (Method B): Retention time 0.63 min, [M−H]−=282.04

Intermediate 62

1,1-Dimethylethyl[(cis)-2-methyl-6-(4-methyl-1H-imidazol-1-yl)-1,2,3,4-tetrahydro-4-quinolinyl]carbamate

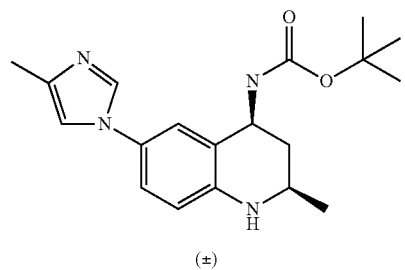 [SMILES: Cc1cn(-c2ccc3c(c2)[C@@H](NC(=O)OC(C)(C)C)C[C@@H](C)N3)cn1]

Sodium borohydride (29 mg, 0.767 mmol) was added to a solution of 1,1-dimethylethyl (3-{[4-(4-methyl-1H-imidazol-1-yl)phenyl]amino}butanoyl)carbamate (for a preparation see intermediate 63) (340 mg, 0.949 mmol) in ethanol (6 mL) cooled at −15° C. (cold bath: ethanol/card ice). Magnesium chloride hexahydrate (202 mg, 0.996 mmol) in water (1 mL) was then slowly added keeping the temperature below 10° C.). The mixture was then stirred at 0° C. for 45 min and at room temperature for 45 min before being poured onto a stirred mixture of citric acid (456 mg, 2.371 mmol), HCl (1M in water, 10 mL) and DCM (5 mL). The resulting mixture was stirred for 30 min at room temperature then the layers were separated. The aqueous phase was basified with solid $K_2CO_3$ and extracted twice with AcOEt (25 mL). The combined organic phases were washed with water then brine, dried over $MgSO_4$ and concentrated in vacuovacuo. Purification of the residue by flash chromatography on silica gel (gradient:4 to 8% MeOH in DCM) gave 1,1-dimethylethyl [(cis)-2-methyl-6-(4-methyl-1H-imidazol-1-yl)-1,2,3,4-tetrahydro-4-quinolinyl]carbamate (273 mg, 0.797 mmol, 84%) as a white solid.

LCMS (Method B): Retention time 1.02 min, [M+H]+=343.19

Intermediate 63

1,1-Dimethylethyl (3-{[4-(4-methyl-1H-imidazol-1-yl)phenyl]amino}butanoyl)carbamate

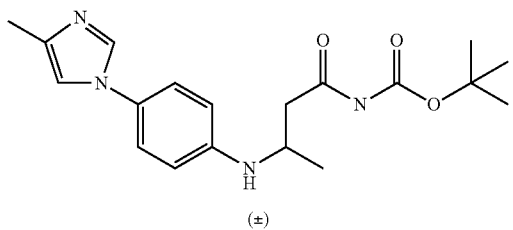 [SMILES: Cc1cn(-c2ccc(NC(C)CC(=O)NC(=O)OC(C)(C)C)cc2)cn1]

(±)

A mixture of 4-(4-methyl-1H-imidazol-1-yl)aniline (for a preparation see intermediate 64) (500 mg, 2.89 mmol), 1,1-dimethylethyl (2E)-2-butenoylcarbamate (for a preparation see intermediate 65) (615 mg, 3.32 mmol) and Yttrium(III) Nitrate hexahydrate (111 mg, 0.289 mmol) in acetonitrile (2 mL) was heated at 50° C. for 15 h. An extra portion of Yttrium(III) Nitrate hexahydrate (111 mg, 0.289 mmol) was added to the mixture which was stirred for 7 more hours before being cooled to room temperature. Half of the solvent was removed in vacuo and the residue was partitioned between AcOEt (40 mL) and a saturated $NaHCO_3$ aqueous solution (20 mL). The layers were separated and the organic phase was washed with brine (15 mL). The combined aqueous phases were extracted with AcOEt (35 mL) and the combined organic were dried over $MgSO_4$ and concentrated in vacuovacuo. Purification of the residue by flash chromatography on silica gel (gradient:4 to 8% MeOH in DCM) gave a residue which was further purified by flash chromatography on silica gel (gradient:60-95% AcOEt in Hexanes) to give 1,1-dimethylethyl (3-{[4-(4-methyl-1H-imidazol-1-yl)phenyl]amino}butanoyl)carbamate (343 mg, 0.956 mmol, 33%) as a colourless sticky solid.

LCMS (Method B): Retention time 0.94 min, [M+H]+=359.12

Intermediate 64

4-(4-Methyl-1H-imidazol-1-yl)aniline

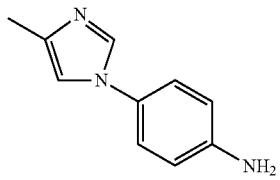

Ammonium formate (2.202 g, 34.9 mmol) and palladium (10% w/w on carbon, 50% wet, 0.473 g, 4.44 mmol) were added to a solution of 4-methyl-1-(4-nitrophenyl)-1H-imidazole (for a preparation see intermediate 93) (4.73 g, 23.28 mmol) in ethanol (150 mL) and the resulting mixture was refluxed under nitrogen for 1 h then cooled to room temperature. An extra portion of ammonium formate (2.202 g, 34.9 mmol) was then added and the resulting mixture was refluxed for a further hour then cooled to room temperature and filtered through celite. Most of the solvent was removed in vacuo and the residue was loaded on a 50 g SCX column which was eluted with MeOH (5 CV) then with 2N $NH_3$ in MeOH (5 CV). The ammonia fractions were combined and concentrated in vacuo to give 4-(4-methyl-1H-imidazol-1-yl)aniline (3.92 g, 21.06 mmol, 90%) as a yellow solid.

LCMS (Method A): Retention time 0.61 min, [M+H]+=174.08

Intermediate 65

1,1-Dimethylethyl (2E)-2-butenoylcarbamate

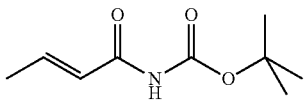

1,1-Dimethylethyl carbamate (5 g, 42.7 mmol) was dissolved in tetrahydrofuran (THF) (100 mL) in a 500 mL 3 necks round bottom flask and cooled at −78° C. under nitrogen. n-Butyl lithium (1.6 M in THF, 26.7 mL, 42.7 mmol) and (2E)-2-butenoyl chloride (4.55 mL, 42.7 mmol) were added in slow successive additions as follow: 1) n-Butyl lithium: 13.4 mL and (2E)-2-butenoyl chloride 2.28 mL; 2) n-Butyl lithium:6.8 mL and (2E)-2-butenoyl chloride 1.14 mL; 3) n-Butyl lithium:3.34 mL and (2E)-2-butenoyl chloride 0.57 mL; 4) n-Butyl lithium: 1.67 mL and (2E)-2-butenoyl chloride 0.28 mL (2×). A five to ten minutes waiting time was observed between each double addition, and the final mixture was stirred for an extra 30 minutes period at −78° C. The temperature was kept below −60° C. during the additions. The reaction mixture was then slowly poured into a stirred saturated $NaHCO_3$ aqueous solution (250 mL). The aqueous layer was extracted with AcOEt (2×250 mL). The combined organic phases were washed with brine (150 mL), dried over $MgSO_4$ and concentrated in vacuovacuo. Purification of the residue by flash chromatography on silica gel (gradient:50 to 100% AcOEt in Hexanes) gave 1,1-dimethylethyl (2E)-2-butenoylcarbamate (2.21 g, 11.93 mmol, 28%) as a white solid.

LCMS (Method A): Retention time 0.61 min, [M+H]+=164.03

Intermediate 66

(2S,4R)-1-Acetyl-2-methyl-6-[4-(1-piperidinylmethyl)phenyl]-1,2,3,4-tetrahydro-4-quinolinamine

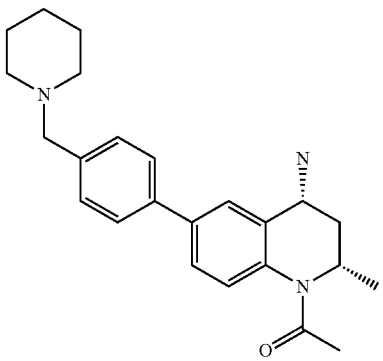 [SMILES: CC(=O)N1c2ccc(-c3ccc(CN4CCCCC4)cc3)cc2[C@H](N)C[C@@H]1C]

A suspension of aluminium chloride (1.053 g, 7.89 mmol) in DCM (10 mL) at room temperature under nitrogen was treated with 1-methylethyl {(2S,4R)-1-acetyl-2-methyl-6-[4-(1-piperidinylmethyl)phenyl]-1,2,3,4-tetrahydro-4-quinolinyl}carbamate (for a preparation see intermediate 67) (0.915 g, 1.974 mmol) as a solution in DCM (2.5 mL) and the resulting mixture was stirred at room temperature for 1 h then cooled using an ice bath and treated with triethylamine (3.30 ml, 23.68 mmol) in methanol (2 mL) producing a thick precipitate. AcOEt (25 mL) was added to the thick precipitate formed and the mixture was stirred for 30 min. The precipitate was filtered off and partitioned between a saturated NaHCO$_3$ aqueous solution (50 mL) and AcOEt (50 mL). The resulting biphasic mixture was stirred at room temperature for 30 min and then the layers were separated. The aqueous layer was stirred with 1:1 DCM:AcOEt (50 mL) and the organic layer was collected using a hydrophobic frit. This was repeated twice. The first AcOEt phase was also eluted through the hydrophobic frit and the combined organics concentrated in vacuovacuo. Purification of the residue by flash chromatography on silica gel using a 100 G silica cartridge (gradient:1 to 10% (2N NH$_3$ in MeOH) in DCM) gave (2S,4R)-1-acetyl-2-methyl-6-[4-(1-piperidinylmethyl)phenyl]-1,2,3,4-tetrahydro-4-quinolinamine (150 mg, 0.358 mmol, 18.12% yield) as a yellow oil.

LCMS (Method B): Retention time 0.45 min, [M+H]+=378.22

Intermediate 67

1-Methylethyl {(2S,4R)-1-acetyl-2-methyl-6-[4-(1-piperidinylmethyl)phenyl]-1,2,3,4-tetrahydro-4-quinolinyl}carbamate

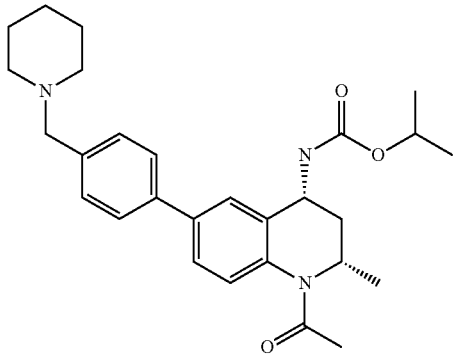 [SMILES: CC(=O)N1c2ccc(-c3ccc(CN4CCCCC4)cc3)cc2[C@H](NC(=O)OC(C)C)C[C@@H]1C]

A suspension of 1-methylethyl[(2S,4R)-1-acetyl-6-(4-formylphenyl)-2-methyl-1,2,3,4-tetrahydro-4-quinolinyl]carbamate (for a preparation see Intermediate 68) (1.078 g, 2.73 mmol) in dichloromethane (DCM) (20 mL) under nitrogen was treated with acetic acid (0.313 mL, 5.47 mmol) and piperidine (0.279 g, 3.28 mmol). The resulting mixture was stirred at room temperature for 1 h then sodium triacetoxyborohydride (0.695 g, 3.28 mmol) was added and the reaction left to stir at room temperature over 60 h then concentrated in vacuovacuo. The residue was partitioned between a saturated NaHCO$_3$ aqueous solution (25 mL) and AcOEt (40 mL) and the layers were separated. The aqueous phase was extracted with AcOEt (25 mL) and the combined organic phases were washed with brine, dried over Na$_2$SO$_4$ and concentrated in vacuovacuo. The residue was loaded on a 20 g SCX cartridge and eluted with MeOH (45 mL) then with 2M NH$_3$ in MeOH (2×45 mL). The ammonia fractions were combined and concentrated in vacuo to give a first residue. The methanol fractions were concentrated and the residue obtained was loaded on a 20 g SCX cartridge and eluted with MeOH (45 mL) then with 2M NH$_3$ in MeOH (2×45 mL). The ammonia fractions were combined and concentrated in vacuo to give a second residue. The two residues were combined and purified by flash chromatography on silica gel using an SP4 and a 100 G cartridge (gradient:1 to 5% (2M NH$_3$ in MeOH) in DCM) to give 1-methylethyl {(2S,4R)-1-acetyl-2-methyl-6-[4-(1-piperidinylmethyl)phenyl]-1,2,3,4-tetrahydro-4-quinolinyl}carbamate (0.9195 g, 1.884 mmol, 68.9% yield) as a yellow oil.

LCMS (Method B): Retention time 0.73 min, [M+H]+=464.18

Intermediate 68

1-Methylethyl[(2S,4R)-1-acetyl-6-(4-formylphenyl)-2-methyl-1,2,3,4-tetrahydro-4-quinolinyl]carbamate

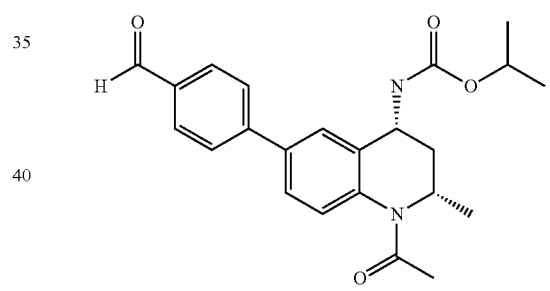

A mixture of 1-methylethyl[(2S,4R)-1-acetyl-6-bromo-2-methyl-1,2,3,4-tetrahydro-4-quinolinyl]carbamate (for a preparation see intermediate 100) (1 g, 2.71 mmol) and 4-formylbenzeneboronic acid (0.487 g, 3.25 mmol) in ethanol (4.7 mL) and toluene (4.70 mL) was treated with K$_2$CO$_3$ (0.449 g, 3.25 mmol) and tetrakis(triphenylphosphine)palladium(0) (0.156 g, 0.135 mmol). The resulting mixture was stirred under nitrogen at 90° C. for 16 h then was cooled to room temperature and concentrated in vacuovacuo. The residue was partitioned between water (8.5 mL) and EtOAc (3 mL) and the resulting biphasic mixture was stirred at room temperature for 30 min then the insoluble residue was filtered off and dried under house vacuo at 40° C. for 1 hr to give 1-methylethyl[(2S,4R)-1-acetyl-6-(4-formylphenyl)-2-methyl-1,2,3,4-tetrahydro-4-quinolinyl]carbamate (1.0759 g, 2.59 mmol, 96% yield) as a light yellow solid.

LCMS (Method B): Retention time 1.00 min, [M+H]+=395.09

Intermediate 69

1,1-Dimethylethyl[2-(4-{(2S,4R)-1-acetyl-2-methyl-4-[(6-methyl-2-pyridinyl)amino]-1,2,3,4-tetrahydro-6-quinolinyl}-1H-pyrazol-1-yl)ethyl]methylcarbamate

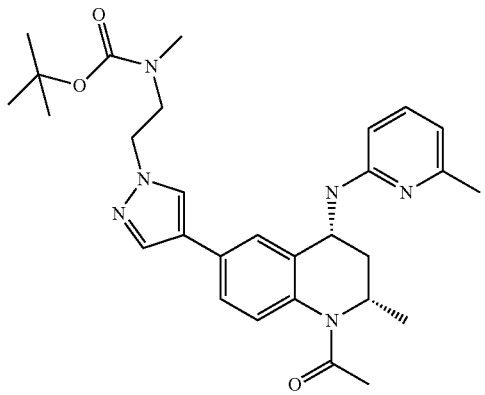 [SMILES: CC(=O)N1c2ccc(-c3cnn(CCN(C)C(=O)OC(C)(C)C)c3)cc2[C@H](Nc2cccc(C)n2)C[C@@H]1C]

A flask was charged with 2-chloro-6-methylpyridine (141 mg, 1.103 mmol) and treated at room temperature under nitrogen with 1,1-dimethylethyl[2-(4-{(2S,4R)-1-acetyl-2-methyl-4-amino-1,2,3,4-tetrahydro-6-quinolinyl}-1H-pyrazol-1-yl)ethyl]methylcarbamate (for a preparation see intermediate 55) (228 mg, 0.551 mmol) in 1,4-dioxane (5 mL). 2'-(dicyclohexylphosphino)-N,N-dimethylbiphenyl-2-amine (DavePhos) (43.4 mg, 0.110 mmol), sodium tert-butoxide (106 mg, 1.103 mmol) and tris(dibenzylideneacetone)dipalladium(0) (50.5 mg, 0.055 mmol) were added and the resulting mixture was stirred at 110° C. for 16 h then cooled to room temperature and partitioned between AcOEt (25 mL) and water (25 mL). The layers were separated and the organic phase was washed with water (25 mL) then dried over Na$_2$SO$_4$ and concentrated in vacuovacuo. Purification of the residue on SP4 using a 50 G silica cartridge (gradient:1 to 5% MeOH in DCM) gave 1,1-dimethylethyl[2-(4-{(2S,4R)-1-acetyl-2-methyl-4-[(6-methyl-2-pyridinyl)amino]-1,2,3,4-tetrahydro-6-quinolinyl}-1H-pyrazol-1-yl)ethyl]methylcarbamate (107.9 mg, 0.198 mmol, 35.8% yield) as a brown oil.

LCMS (Method B): Retention time 0.79 min, [M+H]+=519.20

Intermediate 70

1,1-Dimethylethyl[2-(4-{(2S,4R)-1-acetyl-2-methyl-4-[(3-methyl-2-pyridinyl)amino]-1-1,2,3,4-tetrahydro-6-quinolinyl}-1H-pyrazol-1-yl)ethyl]methylcarbamate

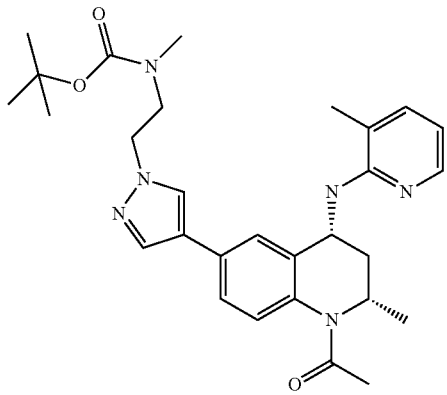 [SMILES: CC(=O)N1c2ccc(-c3cnn(CCN(C)C(=O)OC(C)(C)C)c3)cc2[C@H](Nc2ncccc2C)C[C@@H]1C]

A flask was charged with 2-chloro-3-methylpyridine (141 mg, 1.103 mmol) and treated at room temperature under nitrogen with 1,1-dimethylethyl[2-(4-{(2S,4R)-1-acetyl-2-methyl-4-amino-1,2,3,4-tetrahydro-6-quinolinyl}-1H-pyrazol-1-yl)ethyl]methylcarbamate (for a preparation see intermediate 55) (228 mg, 0.551 mmol) in 1,4-dioxane (5 mL). 2'-(dicyclohexylphosphino)-N,N-dimethylbiphenyl-2-amine (DavePhos) (43.4 mg, 0.110 mmol), sodium tert-butoxide (106 mg, 1.103 mmol) and tris(dibenzylideneacetone)dipalladium(0) (50.5 mg, 0.055 mmol) were added and the resulting mixture was stirred at 110° C. for 16 h then cooled to room temperature and partitioned between AcOEt (25 mL) and water (25 mL). The layers were separated and the organic phase was washed with water (25 mL) then dried over Na$_2$SO$_4$ and concentrated in vacuovacuo. Purification of the residue on SP4 using a 50 G silica cartridge (gradient:1 to 5% MeOH in DCM) gave 1,1-dimethylethyl[2-(4-{(2S,4R)-1-acetyl-2-methyl-4-[(3-methyl-2-pyridinyl)amino]-1,2,3,4-tetrahydro-6-quinolinyl}-1H-pyrazol-1-yl)ethyl]methylcarbamate (161 mg, 0.295 mmol, 53.5% yield) as a brown oil.

LCMS (Method B): Retention time 0.77 min, [M+H]+=519.21

Intermediate 71

1,1-Dimethylethyl[2-(4-{(2S,4R)-1-acetyl-2-methyl-4-[(4-methyl-2-pyridinyl)amino]-1,2,3,4-tetrahydro-6-quinolinyl}-1H-pyrazol-1-yl)ethyl]methylcarbamate

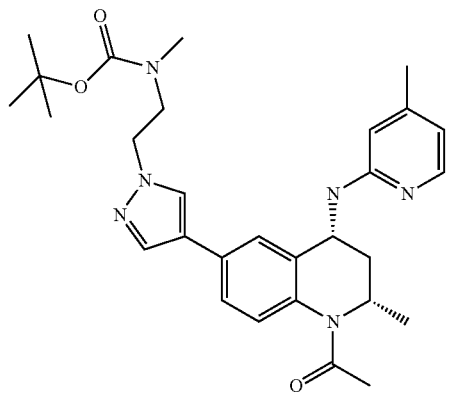 [SMILES: CC(=O)N1c2ccc(-c3cnn(CCN(C)C(=O)OC(C)(C)C)c3)cc2[C@H](Nc2cc(C)ccn2)C[C@@H]1C]

A flask was charged with 2-chloro-4-methylpyridine (141 mg, 1.103 mmol) and treated at room temperature under nitrogen with 1,1-dimethylethyl[2-(4-{(2S,4R)-1-acetyl-2-methyl-4-amino-1,2,3,4-tetrahydro-6-quinolinyl}-1H-pyrazol-1-yl)ethyl]methylcarbamate (for a preparation see intermediate 55) (228 mg, 0.551 mmol) in 1,4-dioxane (5 mL). 2'-(dicyclohexylphosphino)-N,N-dimethylbiphenyl-2-amine (DavePhos) (43.4 mg, 0.110 mmol), sodium tert-butoxide (106 mg, 1.103 mmol) and tris(dibenzylideneacetone)dipalladium(0) (50.5 mg, 0.055 mmol) were added and the resulting mixture was stirred at 110° C. for 16 h then cooled to room temperature and partitioned between AcOEt (25 mL) and water (25 mL). The layers were separated and the organic phase was washed with water (25 mL) then dried over Na$_2$SO$_4$ and concentrated in vacuovacuo. Purification of the residue on SP4 using a 50 G silica cartridge (gradient:1 to 5% MeOH in DCM) gave 1,1-dimethylethyl[2-(4-{(2S,4R)-1-acetyl-2-methyl-4-[(4-methyl-2-pyridinyl)amino]-1,2,3,4-tetrahydro-6-quinolinyl}-1H-pyrazol-1-yl)ethyl]methylcarbamate (192.2 mg, 0.296 mmol, 53.8% yield) as a brown oil.

LCMS (Method B): Retention time 0.78 min, [M+H]+=519.23

Intermediate 72

1,1-Dimethylethyl[2-(4-{(2S,4R)-1-acetyl-4-[(3-fluoro-2-pyridinyl)amino]-2-methyl-1,2,3,4-tetrahydro-6-quinolinyl}-1H-pyrazol-1-yl)ethyl]methylcarbamate

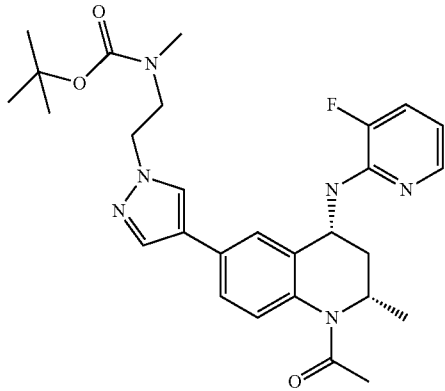 [SMILES: CC(=O)N1c2ccc(-c3cnn(CCN(C)C(=O)OC(C)(C)C)c3)cc2[C@H](Nc2ncccc2F)C[C@@H]1C]

A solution of 1,1-dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (250 mg, 0.585 mmol) in 1,4-dioxane (5 mL) under nitrogen was treated with 2-chloro-3-fluoropyridine (154 mg, 1.169 mmol), sodium tert-butoxide (112 mg, 1.169 mmol), 2'-(dicyclohexylphosphino)-N,N-dimethylbiphenyl-2-amine (DavePhos) (46.0 mg, 0.117 mmol) and then tris(dibenzylideneacetone)dipalladium(0) (53.5 mg, 0.058 mmol) and the resulting mixture was stirred at 110° C. for 16 h then cooled to room temperature and partitioned between EtOAc (25 mL) and water (25 mL). The layers were separated and the aqueous phase was extracted with EtOAc (25 mL). The combined organic phases were washed with brine (50 mL), dried over $Na_2SO_4$ and concentrated in vacuovacuo. Purification of the residue on SP4 using a 50 G silica cartridge (gradient:1 to 10% MeOH in DCM) gave 1,1-dimethylethyl [2-(4-{(2S,4R)-1-acetyl-4-[(3-fluoro-2-pyridinyl)amino]-2-methyl-1,2,3,4-tetrahydro-6-quinolinyl}-1H-pyrazol-1-yl)ethyl]methylcarbamate (111.6 mg, 0.203 mmol, 34.7% yield) as an orange oil.

LCMS (Method B): Retention time 0.99 min, [M+H]+=523.25

Intermediate 73

1,1-Dimethylethyl[2-(4-{(2S,4R)-1-acetyl-4-[(6-fluoro-2-pyridinyl)amino]-2-methyl-1,2,3,4-tetrahydro-6-quinolinyl}-1H-pyrazol-1-yl)ethyl]methylcarbamate

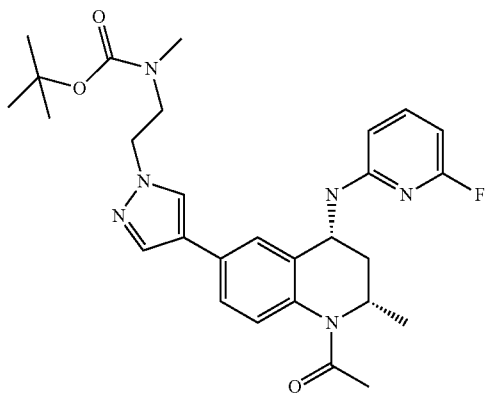 [SMILES: CC(=O)N1c2ccc(-c3cnn(CCN(C)C(=O)OC(C)(C)C)c3)cc2[C@H](Nc2cccc(F)n2)C[C@@H]1C]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (250 mg, 0.585 mmol) was taken up in 1,4-dioxane (5 mL) under nitrogen and 2-chloro-6-fluoropyridine (154 mg, 1.169 mmol) added followed by sodium tert-butoxide (112 mg, 1.169 mmol), 2'-(dicyclohexylphosphino)-N,N-dimethylbiphenyl-2-amine (DavePhos) (46.0 mg, 0.117 mmol) then tris(dibenzylideneacetone)dipalladium(0) (53.5 mg, 0.058 mmol) and the resulting mixture was stirred at 110° C. for 16 h then cooled to room temperature and partitioned between EtOAc (25 mL) and water (25 mL). The layers were separated and the aqueous phase was extracted with EtOAc (25 mL). The combined organic phases were washed with brine (50 mL), dried over $Na_2SO_4$ and concentrated in vacuovacuo. Purification of the residue on SP4 using a 100 G silica cartridge (gradient:1 to 10% MeOH in DCM) gave 1,1-dimethylethyl[2-(4-{(2S,4R)-1-acetyl-4-[(6-fluoro-2-pyridinyl)amino]-2-methyl-1,2,3,4-tetrahydro-6-quinolinyl}-1H-pyrazol-1-yl)ethyl]methylcarbamate (260.2 mg, 0.423 mmol, 72.4% yield) as an orange oil.

LCMS (Method B): Retention time 1.06 min, [M+H]+=523.25

Intermediate 74

1,1-Dimethylethyl (2-{4-[(2S,4R)-1-acetyl-2-methyl-4-(2-pyrazinylamino)-1,2,3,4-tetrahydro-6-quinolinyl]-1H-pyrazol-1-yl}ethyl)methylcarbamate

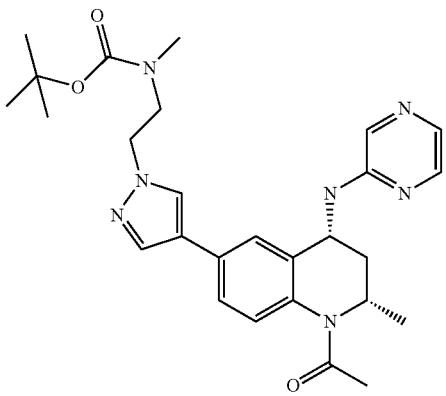 [SMILES: CC(=O)N1c2ccc(-c3cnn(CCN(C)C(=O)OC(C)(C)C)c3)cc2[C@H](Nc2cnccn2)C[C@@H]1C]

A flask was charged with 2-chloropyrazine (138 mg, 1.209 mmol) and treated at room temperature under nitrogen with a solution of 1,1-dimethylethyl[2-(4-{(2S,4R)-1-acetyl-2-methyl-4-amino-1,2,3,4-tetrahydro-6-quinolinyl}-1H-pyrazol-1-yl)ethyl]methylcarbamate (for a preparation see intermediate 55) (250 mg, 0.605 mmol) in 1,4-dioxane (5 mL). 2'-(dicyclohexylphosphino)-N,N-dimethylbiphenyl-2-amine (DavePhos) (47.6 mg, 0.121 mmol), sodium tert-butoxide (116 mg, 1.209 mmol) and tris(dibenzylideneacetone)dipalladium(0) (55.4 mg, 0.060 mmol) were added and the resulting mixture was stirred under nitrogen at 110° C. for 16 h then cooled to room temperature and partitioned between EtOAc (25 mL) and water (25 mL). The layers were separated and the aqueous phase was extracted with EtOAc (25 mL). The combined organic phases were washed with brine (50 mL), dried over $Na_2SO_4$ and concentrated in vacuovacuo. Purification of this residue on SP4 using a 25 G silica cartridge (gradient:1 to 5% MeOH in DCM) gave 1,1-dimethylethyl (2-{4-[(2S,4R)-1-acetyl-2-methyl-4-(2-pyrazinylamino)-1,2,3,4-tetrahydro-6-quinolinyl]-1H-pyrazol-1-yl}ethyl)methylcarbamate (204.6 mg, 0.344 mmol, 56.9% yield) as an orange oil.

LCMS (Method B): Retention time 0.89 min, [M+H]+=506.23

Intermediate 75

1,1-Dimethylethyl (2-{4-[(2S,4R)-1-acetyl-2-methyl-4-(2-pyrimidinylamino)-1,2,3,4-tetrahydro-6-quinolinyl]-1H-pyrazol-1-yl}ethyl)methylcarbamate

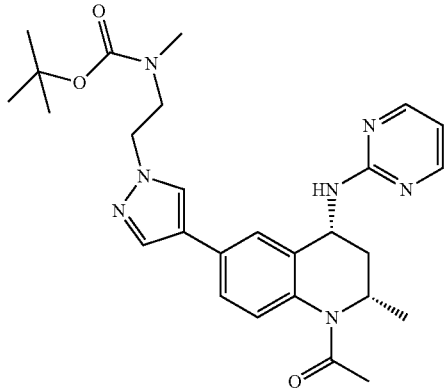 [SMILES: CC(=O)N1c2ccc(-c3cnn(CCN(C)C(=O)OC(C)(C)C)c3)cc2[C@H](Nc2ncccn2)C[C@@H]1C]

A flask was charged with 1,1-dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (250 mg, 0.585 mmol), 2-bromopyrimidine (186 mg, 1.169 mmol), sodium tert-butoxide (112 mg, 1.169 mmol), 2'-(dicyclohexylphosphino)-N,N-dimethylbiphenyl-2-amine (DavePhos) (46.0 mg, 0.117 mmol) and then tris(dibenzylideneacetone)dipalladium(0) (53.5 mg, 0.058 mmol) then filled with 1,4-dioxane (5 mL) and the resulting mixture was stirred at 110° C. for 16 h then cooled to room temperature and partitioned between EtOAc (25 mL) and water (25 mL). The layers were separated and the aqueous phase was extracted with EtOAc (25 mL). The combined organic phases were washed with brine (50 mL), dried over $Na_2SO_4$ and concentrated in vacuovacuo. Purification of this residue on SP4 using a 50 G silica cartridge (gradient:1 to 5% MeOH in DCM) gave 1,1-dimethylethyl (2-{4-[(2S,4R)-1-acetyl-2-methyl-4-(2-pyrimidinylamino)-1,2,3,4-tetrahydro-6-quinolinyl]-1H-pyrazol-1-yl}ethyl)methylcarbamate (68.5 mg, 0.122 mmol, 20.85% yield) as an orange oil.

LCMS (Method A): Retention time 0.90 min, [M+H]+=506.2

Intermediate 76

1,1-Dimethylethyl[2-(4-{(2S,4R)-1-acetyl-4-[(5-fluoro-2-pyridinyl)amino]-2-methyl-1,2,3,4-tetrahydro-6-quinolinyl}-1H-pyrazol-1-yl)ethyl]methylcarbamate

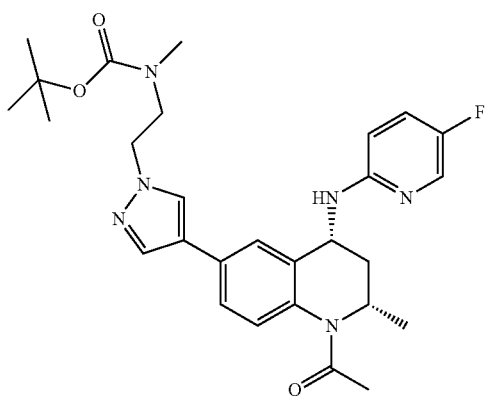 [SMILES: CC(=O)N1c2ccc(-c3cnn(CCN(C)C(=O)OC(C)(C)C)c3)cc2[C@H](Nc2ccc(F)cn2)C[C@@H]1C]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (80 mg, 0.187 mmol), 2-bromo-5-fluoropyridine (65.9 mg, 0.374 mmol), 2'-(dicyclohexylphosphino)-N,N-dimethylbiphenyl-2-amine (DavePhos) (14.73 mg, 0.037 mmol), tris(dibenzylideneacetone)dipalladium(0) (17.13 mg, 0.019 mmol) and sodium tert-butoxide (36.0 mg, 0.374 mmol) were combined in dry 1,4-dioxane (2 mL). The resulting mixture was degased under house vacuo for 20 min with several quenches with nitrogen then stirred at 120° C. for 15 min under microwave irradiation, cooled to room temperature and partitioned between AcOEt and water. The layers were separated and the organic phase was washed with water, dried over $Na_2SO_4$ and concentrated in vacuo. Purification of this residue on SP4 using a 10 G silica cartridge (gradient:20 to 100% AcOEt in Hexanes) gave 1,1-dimethylethyl[2-(4-{(2S,4R)-1-acetyl-4-[(5-fluoro-2-pyridinyl)amino]-2-methyl-1,2,3,4-tetrahydro-6-quinolinyl}-1H-pyrazol-1-yl)ethyl]methylcarbamate (51 mg, 0.088 mmol, 47%) as an orange oil.

LCMS (Method A): Retention time 0.86 min, [M+H]+=523.2

Intermediate 77

1,1-Dimethylethyl[2-(4-{(2S,4R)-1-acetyl-2-methyl-4-[(5-methyl-2-pyridinyl)amino]-1,2,3,4-tetrahydro-6-quinolinyl}-1H-pyrazol-1-yl)ethyl]methylcarbamate

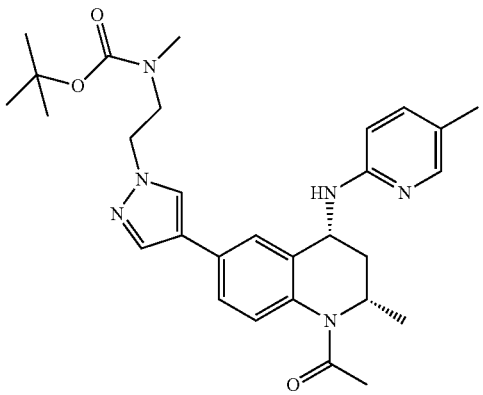 [SMILES: CC(=O)N1c2ccc(-c3cnn(CCN(C)C(=O)OC(C)(C)C)c3)cc2[C@H](Nc2ccc(C)cn2)C[C@@H]1C]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see Intermediate 55) (50 mg, 0.117 mmol), 2-bromo-5-methylpyridine (40.2 mg, 0.234 mmol), 2'-(dicyclohexylphosphino)-N,N-dimethylbiphenyl-2-amine (DavePhos) (9.21 mg, 0.023 mmol), tris(dibenzylideneacetone)dipalladium(0) (10.71 mg, 0.012 mmol) and sodium tert-butoxide (22.48 mg, 0.234 mmol) were combined in dry 1,4-dioxane (2 ml). The resulting mixture was degased under house vacuo for 20 min with several quenches with nitrogen then stirred at 120° C. for 30 min under microwave irradiation, cooled to room temperature and partitioned between AcOEt and water. The layers were separated and the organic phase was washed with water, dried over Na$_2$SO$_4$ and concentrated in vacuo. Purification of this residue on SP4 using a 10 G silica cartridge (gradient:20 to 100% AcOEt in Hexanes) gave 1,1-dimethylethyl[2-(4-{(2S,4R)-1-acetyl-2-methyl-4-[(5-methyl-2-pyridinyl)amino]-1,2,3,4-tetrahydro-6-quinolinyl}-1H-pyrazol-1-yl)ethyl]methylcarbamate (40 mg, 0.066 mmol, 56%) as a pale orange oil.

LCMS (Method B): Retention time 0.76 min, [M+H]+=519.2

Intermediate 78

1,1-Dimethylethyl[2-(4-{(2S,4R)-1-acetyl-4-[(4-fluoro-2-pyridinyl)amino]-2-methyl-1,2,3,4-tetrahydro-6-quinolinyl}-1H-pyrazol-1-yl)ethyl]methylcarbamate

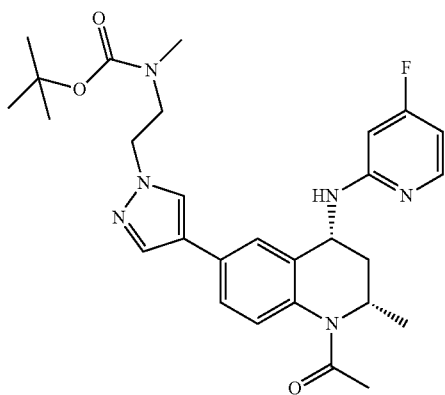 [SMILES: CC(=O)N1c2ccc(-c3cnn(CCN(C)C(=O)OC(C)(C)C)c3)cc2[C@H](Nc2cc(F)ccn2)C[C@@H]1C]

1,1-Dimethylethyl (2-{4-[(2S,4R)-1-acetyl-4-amino-2-methyl-1,2,3,4-tetrahydro-6-quinolinyl]-1H-pyrazol-1-yl}ethyl)methylcarbamate (for a preparation see intermediate 55) (50 mg, 0.117 mmol), 2-chloro-4-fluoropyridine (0.021 ml, 0.234 mmol), 2'-(dicyclohexylphosphino)-N,N-dimethylbiphenyl-2-amine (DavePhos) (9.21 mg, 0.023 mmol), tris(dibenzylideneacetone)dipalladium(0) (10.71 mg, 0.012 mmol) and sodium tert-butoxide (22.48 mg, 0.234 mmol) were combined in dry 1,4-dioxane (2 mL). The resulting mixture was degased under house vacuo for 20 min with several quenches with nitrogen then stirred at 120° C. for 5.5 h under microwave irradiation then cooled to room temperature. Further portions of 2-chloro-4-fluoropyridine (0.021 ml, 0.234 mmol), DavePhos (9.21 mg, 0.023 mmol), tris(dibenzylideneacetone)dipalladium(0) (10.71 mg, 0.012 mmol) and sodium tert-butoxide (22.48 mg, 0.234 mmol) were added and reaction mixture was heated for a further 3 h at 120° C. under microwave irradiation then cooled to room temperature and partitioned between AcOEt and water. The layers were separated and the organic phase was washed with water, dried over Na$_2$SO$_4$ and concentrated in vacuovacuo. Purification of this residue on SP4 using a 25 G silica cartridge (gradient:20 to 100% AcOEt in Hexanes) gave 1,1-dimethylethyl[2-(4-{(2S,4R)-1-acetyl-4-[(4-fluoro-2-pyridinyl)amino]-2-methyl-1,2,3,4-tetrahydro-6-quinolinyl}-1H-pyrazol-1-yl)ethyl]methylcarbamate (36 mg, 0.055 mmol, 47%) as a yellow oil.

LCMS (Method A): Retention time 0.83 min, [M+H]+=523.14

Intermediate 79

Phenylmethyl[(4-{(2S,4R)-1-acetyl-4-[(5-fluoro-2-pyridinyl)amino]-2-methyl-1,2,3,4-tetrahydro-6-quinolinyl}phenyl)methyl]methylcarbamate

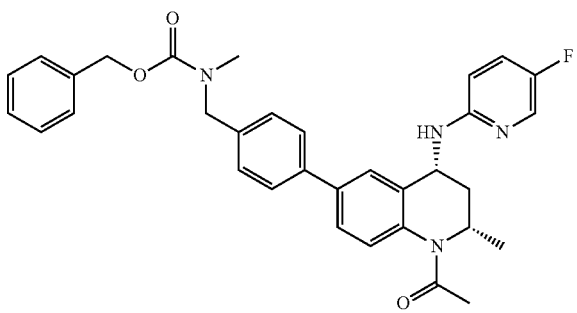 [SMILES: CC(=O)N1c2ccc(-c3ccc(CN(C)C(=O)OCc4ccccc4)cc3)cc2[C@H](Nc2ccc(F)cn2)C[C@@H]1C]

A flask was charged with phenylmethyl({4-[(2S,4R)-1-acetyl-4-amino-2-methyl-1,2,3,4-tetrahydro-6-quinolinyl]phenyl}methyl)methylcarbamate (for a preparation see intermediate 80) (100 mg, 0.219 mmol), sodium tert-butoxide (31.5 mg, 0.328 mmol), racemic BINAP (6.80 mg, 10.93 μmol), tris(dibenzylideneacetone)dipalladium(0) (10.01 mg, 10.93 μmol) and 2-chloro-5-fluoropyridine (0.033 mL, 0.328 mmol), then filled with toluene (2 mL) and the resulting mixture was stirred at 110° C. for 22 h then cooled to room temperature and partitioned between water (20 mL) and EtOAc (60 mL). The layers were separated and the aqueous phase was extracted with EtOAc (30 mL). The combined organic phases were washed with brine (30 mL), dried over MgSO$_4$ and concentrated in vacuovacuo. Purification of this residue on SP4 using a 25 G silica cartridge (gradient:10 to 50% AcOEt in Hexanes) following by another purification using a 12 G silica cartridge (gradient:10 to 50% AcOEt in Hexanes) gave phenylmethyl[(4-{(2S,4R)-1-acetyl-4-[(5-fluoro-2-pyridinyl)amino]-2-methyl-1,2,3,4-tetrahydro-6-quinolinyl}phenyl)methyl]methylcarbamate (60 mg, 35%)

LCMS (Method A): Retention time 1.04 min, [M+H]+=553.1

Intermediate 80

Phenylmethyl({4-[(2S,4R)-1-acetyl-4-amino-2-methyl-1,2,3,4-tetrahydro-6-quinolinyl]phenyl}methyl)methylcarbamate

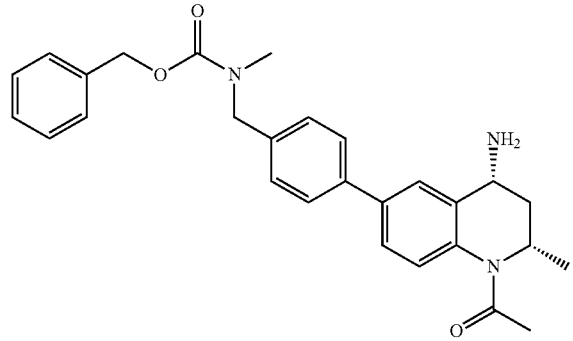 [SMILES: CC(=O)N1c2ccc(-c3ccc(CN(C)C(=O)OCc4ccccc4)cc3)cc2[C@H](N)C[C@@H]1C]

To a solution of phenylmethyl({4-[(2S,4R)-1-acetyl-4-({[(1,1-dimethylethyl)oxy]carbonyl}amino)-2-methyl-1,2,3,4-tetrahydro-6-quinolinyl]phenyl}methyl)methylcarbamate (for a preparation see intermediate 81) (1 g, 1.793 mmol) in methanol (50 mL) was added acetyl chloride (2 mL, 28.1 mmol). The resulting mixture was stirred at room temperature for 3 h then concentrated in vacuovacuo. The residue was loaded on a 50 g SCX column, then eluted with MeOH (3 column volume (CV)) followed by 2N $NH_3$ in methanol (4 CV). The ammonia fractions were combined and evaporated in vacuovacuo. Purification of the residue obtained by flash chromatography on silica gel (40 g column, gradient:0 to 5% (2N $NH_3$ in MeOH) in DCM) gave phenylmethyl ({4-[(2S,4R)-1-acetyl-4-amino-2-methyl-1,2,3,4-tetrahydro-6-quinolinyl]phenyl}methyl)methylcarbamate (581 mg, 1.27 mmol, 71%) as a colourless oil which solidified on standing.

LCMS (Method A): Retention time 0.84 min, $[M+H_2]+=441.0$

Intermediate 81

Phenylmethyl({4-[(2S,4R)-1-acetyl-4-({[(1,1-dimethylethyl)oxy]carbonyl}amino)-2-methyl-1,2,3,4-tetrahydro-6-quinolinyl]phenyl}methyl)methylcarbamate

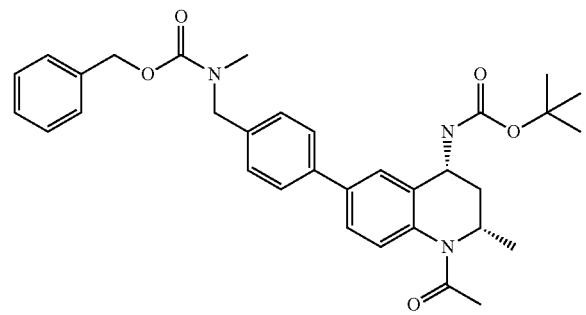 [SMILES: CC(=O)N1c2ccc(-c3ccc(CN(C)C(=O)OCc4ccccc4)cc3)cc2[C@H](NC(=O)OC(C)(C)C)C[C@@H]1C]

A flask was charged with 1,1-dimethylethyl[(2S,4R)-1-acetyl-6-bromo-2-methyl-1,2,3,4-tetrahydro-4-quinolinyl]carbamate (for a preparation see intermediate 50) (1 g, 2.61 mmol), phenylmethyl methyl{[4-(4,4,5,5-tetramethyl-1,3,2-dioxaborolan-2-yl)phenyl]methyl}carbamate (for a preparation see intermediate 82) (1.194 g, 3.13 mmol), tetrakis(triphenylphosphine)palladium(0) (0.151 g, 0.130 mmol) and potassium carbonate (0.541 g, 3.91 mmol) then filled with ethanol (10 mL) and toluene (10 mL). The resulting mixture was degassed under house vacuo for 30 min with several quenches with nitrogen, heated to reflux for 45 min then cooled to room temperature. The insoluble material was filtered off and most of the solvent was concentrated in vacuovacuo. The residue was partitioned between DCM (100 mL) and water (100 mL). The layers were separated and the organic phase was dried through a hydrophobic frit and concentrated in vacuovacuo. Purification of the residue by SP4 using a 40 G silica cartridge (gradient:0 to 50% AcOEt in Hexanes) gave phenylmethyl({4-[(2S,4R)-1-acetyl-4-({[(1,1-dimethylethyl)oxy]carbonyl}amino)-2-methyl-1,2,3,4-tetrahydro-6-quinolinyl]phenyl}methyl)methylcarbamate (1 g, 1.7 mmol, 69%) as a white solid.

LCMS (Method A): Retention time 1.26 min, $[M+H]+=558.1$

Intermediate 82

Phenylmethyl methyl{[4-(4,4,5,5-tetramethyl-1,3,2-dioxaborolan-2-yl)phenyl]methyl}carbamate

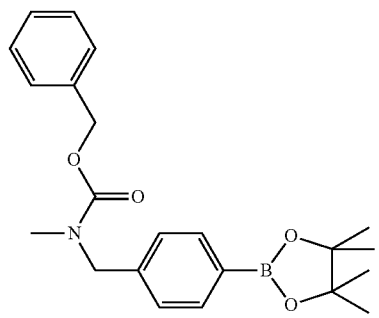 [SMILES: CN(Cc1ccc(B2OC(C)(C)C(C)(C)O2)cc1)C(=O)OCc1ccccc1]

A mixture of phenylmethyl[(4-bromophenyl)methyl]methylcarbamate (for a preparation see intermediate 83) (8.6 g, 25.7 mmol) was mixed with bis(pinacolato)diboron (16.99 g, 66.9 mmol), potassium acetate (4.90 g, 49.9 mmol) and bis(diphenylphosphino)ferrocene]dichloropalladium(II) (1.224 g, 1.673 mmol in dimethyl sulfoxide (DMSO) (100 mL) was stirred under nitrogen at 80° C. for 16 h then cooled to room temperature and partitioned between water (50 mL) and DCM (100 mL). The layers were separated and the aqueous phase was extracted with DCM (50 mL). The combined organic phases were washed with brine (40 mL), dried over $MgSO_4$ and concentrated in vacuovacuo. The residue was dissolved in AcOEt (500 mL) and the organic phase was washed with water (3×100 mL), dried over $MgSO_4$ and concentrated in vacuovacuo. Purification of the residue by flash chromatography on silica gel (gradient:0 to 20% AcOEt in Hexanes) gave phenylmethyl methyl{[4-(4,4,5,5-tetramethyl-1,3,2-dioxaborolan-2-yl)phenyl]methyl}carbamate (4.65 g, 12.1 mmol, 44%) as a colourless oil.

LCMS (Method A): Retention time 1.39 min, $[M+H]+=382.0$

Intermediate 83

Phenylmethyl[(4-bromophenyl)methyl]methylcarbamate

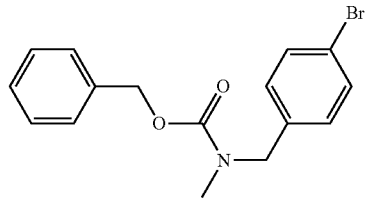 [SMILES: CN(Cc1ccc(Br)cc1)C(=O)OCc1ccccc1]

A mixture of [(4-bromophenyl)methyl]methylamine (5.09 mL, 25.4 mmol) and DIPEA (6.22 mL, 35.6 mmol), in dichloromethane (DCM) (120 mL) was treated with phenylmethyl chloridocarbonate (3.98 mL, 28.0 mmol). The resulting mixture was stirred at room temperature under nitrogen for 30 min then was partitioned between water (20 mL) and DCM (60 mL). The layers were separated and the organic phase was washed with 2M HCl in water (20 mL), a saturated NaHCO₃ aqueous solution (20 mL) and brine (20 mL), dried over MgSO₄ and concentrated in vacuo to give phenylmethyl[(4-bromophenyl)methyl]methylcarbamate (8.66 g, 25.9 mmol, 92%) as a pale yellow liquid which was used in the next step without further purification.

LCMS (Method A): Retention time 1.36 min, [M+H2]+=335.9

Intermediate 84

Ethyl 4-[(2S,4R)-1-acetyl-4-amino-2-methyl-1,2,3,4-tetrahydro-6-quinolinyl]benzoate

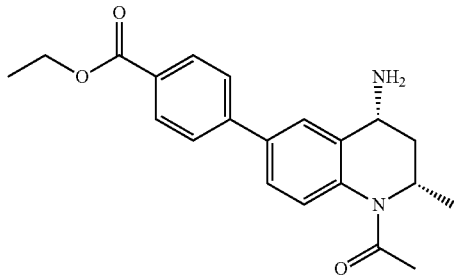 [SMILES: CCOC(=O)c1ccc(-c2ccc3c(c2)[C@H](N)C[C@H](C)N3C(C)=O)cc1]

Ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see intermediate 85) (8.90 g, 20.30 mmol) was added to a suspension of aluminium chloride (10.3 g, 77 mmol) in DCM (160 mL) cooled with an ice/water bath. The temperature rose from 0° C. to approximately 6° C. after the addition. The resulting mixture was stirred at approximately 0° C. for 20 min, and then treated with a solution of methanol (18 mL) and triethylamine (34 mL, 245 mmol) over approximately 30 sec. The resulting mixture was stirred at 0° C. for approximately 30 min, and then partitioned between AcOEt and a saturated NaHCO₃ aqueous solution. The same reaction was done in parallel, using 0.89 g (2.030 mmol) of ethyl 4-[(2S,4R)-1-acetyl-2-methyl-4-({[(1-methylethyl)oxy]carbonyl}amino)-1,2,3,4-tetrahydro-6-quinolinyl]benzoate (for a preparation see intermediate 85), 1.03 g (7.72 mmol) of aluminium chloride, 3.4 mL (24.53 mmol) of triethylamine, 16 mL of DCM and 1.3 mL of MeOH. The products of both reactions were combined at this stage and the resulting mixture was stirred at room temperature for approximately 10 min (total volume: approximately 1 L). The mixture was filtered through celite, the insoluble residue was washed with AcOEt and a saturated NaHCO₃ aqueous solution and the layers were separated. The aqueous phase was extracted with AcOEt and the combined organic phases were washed with brine, dried using an hydrophobic frit and concentrated in vacuo to give ethyl 4-[(2S,4R)-1-acetyl-4-amino-2-methyl-1,2,3,4-tetrahydro-6-quinolinyl]benzoate (6.6 g, 84%—allowing for the addition of the parallel experiment) as a cream solid.

LCMS (Method A): Retention time 0.73 min, [M+H₂]+=336.2

Intermediate 85

Ethyl 4-[(2S,4R)-1-acetyl-2-methyl-4-({[(1-methylethyl)oxy]carbonyl}amino)-1,2,3,4-tetrahydro-6-quinolinyl]benzoate

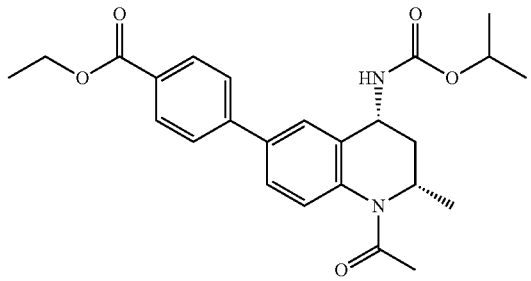 [SMILES: CCOC(=O)c1ccc(-c2ccc3c(c2)[C@H](NC(=O)OC(C)C)C[C@H](C)N3C(C)=O)cc1]

1-methylethyl[(2S,4R)-1-acetyl-6-bromo-2-methyl-1,2,3,4-tetrahydro-4-quinolinyl]carbamate (for a preparation see intermediate 100), (39.0 g, 106 mmol), {4-[(ethyloxy)carbonyl]phenyl}boronic acid (22.5 g, 116 mmol) and tetrakis(triphenylphosphine)palladium(0) (1.83 g, 1.58 mmol) were mixed in DME (430 mL) and the resulting mixture was treated with 2N aqueous Na₂CO₃ (210 mL, 420 mmol). The mixture was degassed under house vacuum with several quenches with nitrogen and then stirred at 105° C. under nitrogen for approximately 6 h before being allowed to cool to room temperature. The mixture was partitioned between AcOEt and water and the layers were separated. The aqueous phase was extracted with AcOEt and the combined organic phases were washed with brine. The organic phase was then filtered through a 70 g silica cartridge, washing the cartridge with AcOEt. The combined filtrate and washings were concentrated in vacuovacuo. The residue was triturated with Et₂O then filtered off. The solid obtained was air dried to give ethyl 4-[(2S,4R)-1-acetyl-2-methyl-4-({[(1-methylethyl)oxy]carbonyl}amino)-1,2,3,4-tetrahydro-6-quinolinyl]benzoate (35.2 g, 80.2 mmol, 76%) as a grey solid. The filtrate was concentrated in vacuo and the residue obtained triturated with Et₂O (approximately 30 mL). The solid formed was isolated by filtration and air dried, to give ethyl 4-[(2S,4R)-1-acetyl-2-methyl-4-({[(1-methylethyl)oxy]carbonyl}amino)-1,2,3,4-tetrahydro-6-quinolinyl]benzoate as a grey solid (5.96 g, 13.5 mmol, 13%).

LCMS (Method B): Retention time 1.16 min, [M+H]+=439.15

Intermediate 86

(cis)-1-Acetyl-6-bromo-N-phenyl-2-propyl-1,2,3,4-tetrahydro-4-quinolinamine

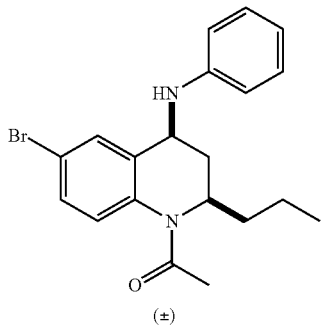 [SMILES: CCC[C@@H]1C[C@H](Nc2ccccc2)c2cc(Br)ccc2N1C(C)=O]

A mixture of myristic acid (88 mg, 0.385 mmol), copper (II) acetate (23.29 mg, 0.128 mmol) and (cis)-1-acetyl-6-bromo-2-propyl-1,2,3,4-tetrahydro-4-quinolinamine (for a preparation see intermediate 87) (399 mg, 1.282 mmol) and phenylboronic acid (234 mg, 1.923 mmol) in toluene (12 mL) was treated with 2,6-lutidine (0.209 mL, 1.795 mmol) and the resulting mixture was stirred vigorously in air for 72 h then was partitioned between AcOEt (50 mL) and a saturated NaHCO$_3$ aqueous solution (25 mL). The layers were separated and the organic phase dried over Na$_2$SO$_4$ and concentrated in vacuovacuo. Purification of the residue by SP4 using a 25 G silica cartridge (gradient:0 to 100% AcOEt in Hexanes) gave (cis)-1-acetyl-6-bromo-N-phenyl-2-propyl-1,2,3,4-tetrahydro-4-quinolinamine (155 mg, 0.40 mmol, 31%) as a yellow oil which solidified on standing.

LCMS (Method A): Retention time 1.34 min, [M+H]+=389.1 (1 Br)

Intermediate 87

(cis)-1-Acetyl-6-bromo-2-propyl-1,2,3,4-tetrahydro-4-quinolinamine

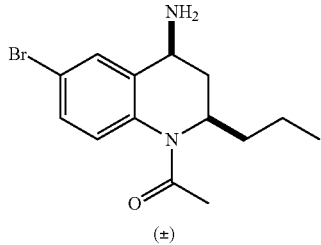 [SMILES: CCC[C@@H]1C[C@H](N)c2cc(Br)ccc2N1C(C)=O]

(±)

(1-acetyl-6-bromo-2-propyl-1,2,3,4-tetrahydro-4-quinolinyl)formamide (for a preparation see intermediate 88) (0.5 g, 1.474 mmol) was suspended in ethanol (4 mL) and treated with HCl (5N in water, 1 ml, 5.00 mmol). The resulting mixture was stirred at 75° C. for 40 min under microwave irradiation then cooled to room temperature. The reaction mixture was basified with a saturated NaHCO$_3$ aqueous solution (50 mL), and the aqueous phase was extracted with AcOEt (3×50 mL). The combined organic phases were dried over MgSO$_4$ then concentrated in vacuo to give (cis)-1-acetyl-6-bromo-2-propyl-1,2,3,4-tetrahydro-4-quinolinamine (399 mg, 1.28 mmol, 87%)

LCMS (Method A): Retention time 0.61 min, [M+H]+=311.07 (1 Br)

Intermediate 88

[(cis)-1-Acetyl-6-bromo-2-propyl-1,2,3,4-tetrahydro-4-quinolinyl]formamide

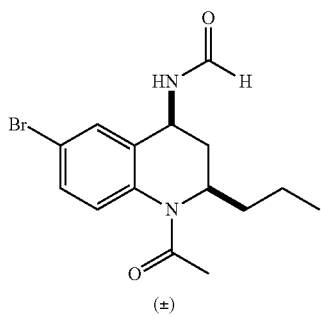 [SMILES: CCC[C@@H]1C[C@H](NC=O)c2cc(Br)ccc2N1C(C)=O]

(±)

[(cis)-6-Bromo-2-propyl-1,2,3,4-tetrahydro-4-quinolinyl]formamide (for a preparation see intermediate 89) (8.0 g, 26.9 mmol) in DCM (100 mL) was added dropwise at room temperature to a mixture of acetyl chloride (6.7 mL, 94.28 mmol) and pyridine (10.85 mL, 134.7 mmol) in DCM (150 mL). The resulting mixture was stirred at this temperature for 1 h then was washed with 1M NaOH aqueous solution, 1M HCl aqueous solution, a saturated NaHCO$_3$ aqueous solution then brine, was dried over MgSO$_4$ and concentrated in vacuovacuo. Purification of the residue by flash chromatography on silica gel (20:1 DCM/MeOH) gave [(cis)-1-acetyl-6-bromo-2-propyl-1,2,3,4-tetrahydro-4-quinolinyl]formamide (6.29 g, 18.5 mmol, 68%) as a light orange solid.

LCMS (Method A): Retention time 1.62 min, [M+H]+=341.0 (1 Br)

Intermediate 89

[(cis)-6-Bromo-2-propyl-1,2,3,4-tetrahydro-4-quinolinyl]formamide

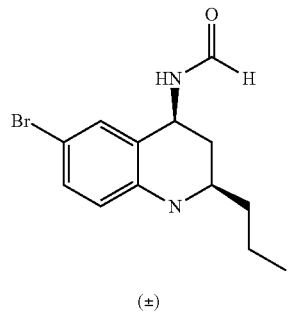 [SMILES: CCC[C@@H]1C[C@H](NC=O)c2cc(Br)ccc2N1]

(±)

To a suspension of 1H-1,2,3-benzotriazole (3.46 g, 29.1 mmol) in toluene (38 mL) was added 4-bromoaniline (5.09 g, 29.1 mmol) in toluene (4.7 mL) and the reaction mixture was bubbled with Argon gas then cooled to 0° C. Butanal (2.88 mL, 32 mmol) in toluene (4.7 mL) was added dropwise and the resulting mixture was allowed to warm to room temperature and stirred for 16 h before being treated with ethenylformamide (2.03 mL, 29.1 mmol), 4-methylbenzenesulfonic acid monohydrate (55.3 mg, 0.29 mmol). The resulting mixture was stirred at 72° C. for 3 h then cooled to room temperature and diluted with AcOEt (50 mL). The organic phase was washed with a 1M NaOH aqueous solution (20 mL), water (50 mL) then brine (50 mL), dried over MgSO$_4$ and concentrated in vacuovacuo. The residue was recrystallised from petroleum/Et$_2$O (1:10, 3×30 mL) to give [(cis)-6-bromo-2-propyl-1,2,3,4-tetrahydro-4-quinolinyl]formamide (2.59 g, 29%) as a white solid.

LCMS (Method A): Retention time 1.35 min, [M+H]+=299.1 (1 Br)

Intermediate 90

(cis)-1-Acetyl-6-bromo-2-ethyl-N-phenyl-1,2,3,4-tetrahydro-4-quinolinamine

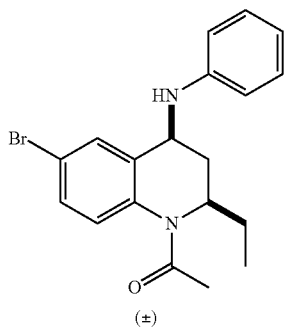

(±)

A mixture of myristic acid (87 mg, 0.381 mmol), copper (II) acetate (23.04 mg, 0.127 mmol) and (cis)-1-acetyl-6-bromo-2-ethyl-1,2,3,4-tetrahydro-4-quinolinamine (for a preparation see intermediate 91) (377 mg, 1.269 mmol), phenylboronic acid (232 mg, 1.903 mmol) in toluene (12 mL) was treated with 2,6-lutidine (0.207 mL, 1.776 mmol). The resulting mixture was stirred vigorously in air for 72 h then was partitioned between AcOEt (50 mL) and a saturated NaHCO$_3$ aqueous solution (25 mL). The layers were separated and the organic phase was dried over Na$_2$SO$_4$ and concentrated in vacuovacuo. Purification of the residue by SP4 using a 25 G silica cartridge (gradient:0 to 100% AcOEt in Hexanes) gave (cis)-1-acetyl-6-bromo-2-ethyl-N-phenyl-1,2,3,4-tetrahydro-4-quinolinamine (139 mg, 0.37 mmol, 29%) as a pale yellow oil which solidified on standing.

LCMS (Method A): Retention time 1.29 min, [M+H]+=373.1 (1 Br)

Intermediate 91

(cis)-1-Acetyl-6-bromo-2-ethyl-1,2,3,4-tetrahydro-4-quinolinamine

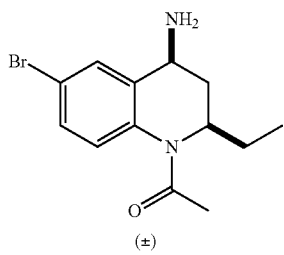 [SMILES: CC[C@@H]1C[C@H](N)c2cc(Br)ccc2N1C(C)=O]

(±)

A suspension of (1-acetyl-6-bromo-2-ethyl-1,2,3,4-tetrahydro-4-quinolinyl)formamide (for a preparation see intermediate 4) (0.5 g, 1.538 mmol) in ethanol (4 mL) was treated with HCl (5N in water, 1 mL, 5.00 mmol) and the resulting mixture was stirred at 75° C. for 40 min under microwave irradiation then cooled to room temperature and basified with a saturated NaHCO$_3$ aqueous solution (50 mL). The aqueous phase was extracted with AcOEt (3×50 mL). The combined organic phases were dried over MgSO$_4$ then concentrated in vacuo to give (cis)-1-acetyl-6-bromo-2-ethyl-1,2,3,4-tetrahydro-4-quinolinamine (377 mg, 1.27 mmol, 83%).

LCMS (Method A): Retention time 0.55 min, [M+H]+=297.05 (1 Br)

Intermediate 92

4-[(cis)-1-Acetyl-2-ethyl-4-(phenylamino)-1,2,3,4-tetrahydro-6-quinolinyl]benzaldehyde

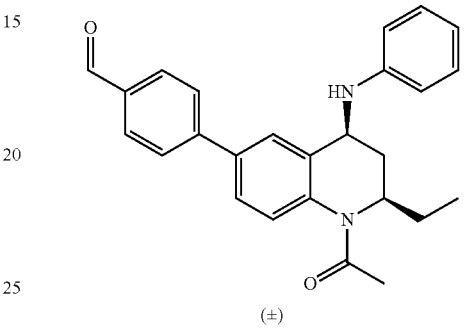

(±)

A mixture of (4-formylphenyl)boronic acid (31.7 mg, 0.212 mmol), (cis)-1-acetyl-6-bromo-2-ethyl-N-phenyl-1,2,3,4-tetrahydro-4-quinolinamine (for a preparation see intermediate 90) (79 mg, 0.212 mmol) and tetrakis(triphenylphosphine)palladium(0) (15 mg, 0.013 mmol) in 1,4-dioxane (1 mL) and water (0.5 mL) was treated with potassium carbonate (45 mg, 0.326 mmol) and the resulting mixture was stirred at 130° C. for 15 min under microwave irradiation then cooled to room temperature and concentrated in vacuovacuo. Purification of the residue by SP4 using a 25 G silica cartridge (gradient:0 to 100% AcOEt in Hexanes) gave 4-[(cis)-1-acetyl-2-ethyl-4-(phenylamino)-1,2,3,4-tetrahydro-6-quinolinyl]benzaldehyde (67.8 mg, 0.17 mmol, 80%) as a yellow oil.

LCMS (Method A): Retention time 1.23 min, [M−NHC$_6$H$_6$]+=306.2

Intermediate 93

4-Methyl-1-(4-nitrophenyl)-1H-imidazole

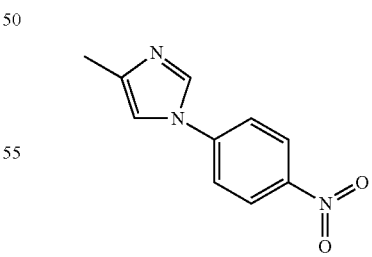

A mixture of 4-methyl-1H-imidazole (10 g, 119 mmol), 1-fluoro-4-nitrobenzene (12.79 mL, 119 mmol) and potassium carbonate (18.15 g, 131 mmol) in acetonitrile (200 mL) was stirred under nitrogen at 60° C. over 70 h then cooled to room temperature and concentrated in vacuovacuo. The residue was partitioned between AcOEt (250 mL) and water (150 mL) and the layers were separated. The aqueous layer was extracted with AcOEt (200 mL) and the combined organic phases were washed with brine (150 mL), dried overn MgSO₄, and concentrated in vacuovacuo. Purification of the residue on Biotage Companion XL using a 330 g silica cartridge (gradient:65 to 95% AcOEt in hexanes) gave a 4:1 mixture of 4-methyl-1-(4-nitrophenyl)-1H-imidazole and 5-methyl-1-(4-nitrophenyl)-1H-imidazole (7.2 g). A second purification of this mixture on Biotage Companion XL using a 330 g silica cartridge (gradient:65 to 95% AcOEt in Hexanes) gave 4-methyl-1-(4-nitrophenyl)-1H-imidazole (4.73 g, 22.11 mmol, 19%) as a white solid.

Intermediate 94

(2S,4R)-1-acetyl-6-[3,4-bis(methyloxy)phenyl]-2-methyl-1,2,3,4-tetrahydro-4-quinolinamine

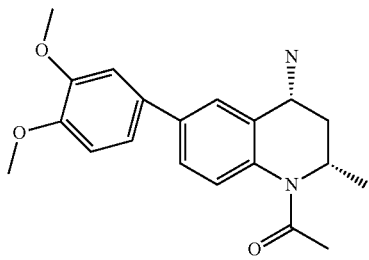

1-Methylethyl {(2S,4R)-1-acetyl-6-[3,4-bis(methyloxy)phenyl]-2-methyl-1,2,3,4-tetrahydro-4-quinolinyl}carbamate (for a preparation see intermediate 95) (327 mg, 0.767 mmol) was added to a cold (ice bath) suspension of aluminium chloride (388 mg, 2.91 mmol) in dichloromethane (DCM) (4 mL). The reaction was stirred at approximately 0° C. for 30 min then an extra amount of aluminium chloride (102 mg, 0.767 mmol) was added and the resulting mixture was stirred at approximately 0° C. for 30 min. Aluminium chloride (102 mg, 0.767 mmol) was further added and the resulting mixture was stirred at approximately 0° C. for 30 min. Further Aluminium chloride (102 mg, 0.767 mmol) was added and the resulting mixture was stirred at approximately 0° C. for 30 min. The reaction mixture was then treated with a solution of methanol (0.884 mL) and triethylamine (2.312 mL, 16.59 mmol) and the resulting mixture was stirred further at approximately 0° C. for 20 min then was partitioned between EtOAc (35 mL) and a saturated NaHCO₃ aqueous solution (35 mL). The reaction mixture was then filtered through celite and the insoluble were washed with EtOAc (25 mL) and NaHCO₃ (25 mL). The filtered aluminum residues were suspended in MeOH and sonicated. The resulting suspension was filtered and the filtrate was concentrated in vacuovacuo. The white solid residue was loaded onto a 10 g SCX cartridge and eluted with MeOH and then with 2M NH₃ in MeOH. The methanol fractions were combined and concentrated in vacuo to give (2S,4R)-1-acetyl-6-[3,4-bis(methyloxy)phenyl]-2-methyl-1,2,3,4-tetrahydro-4-quinolinamine (103 mg, 39%) and the combined ammonia fractions were combined to give (2S,4R)-1-acetyl-6-[3,4-bis(methyloxy)phenyl]-2-methyl-1,2,3,4-tetrahydro-4-quinolinamine (71 mg, 27%).

LCMS (Method A): Retention time 0.60 min, [M+H2]+=324.13

Intermediate 95

1-Methylethyl {(2S,4R)-1-acetyl-6-[3,4-bis(methyloxy)phenyl]-2-methyl-1,2,3,4-tetrahydro-4-quinolinyl}carbamate

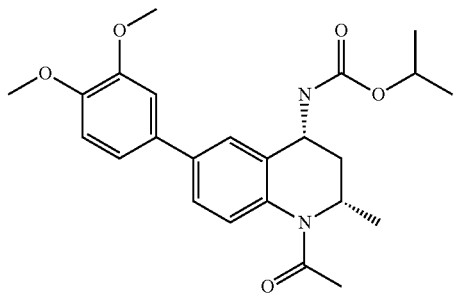 [SMILES: COc1ccc(-c2ccc3c(c2)[C@H](NC(=O)OC(C)C)C[C@H](C)N3C(C)=O)cc1OC]

A flask was charged with 2-[3,4-bis(methyloxy)phenyl]-4,4,5,5-tetramethyl-1,3,2-dioxaborolane (0.429 g, 1.625 mmol), 1-methylethyl[(2S,4R)-1-acetyl-6-bromo-2-methyl-1,2,3,4-tetrahydro-4-quinolinyl]carbamate (for a preparation see Intermediate 100) (0.5 g, 1.354 mmol), a saturated NaHCO₃ aqueous solution (1.5 mL, 1.354 mmol) and bis (diphenylphosphino)ferrocene]dichloropalladium(II)-DCM adduct (0.111 g, 0.135 mmol) then filled with 1,4-dioxane (7 mL). The resulting mixture was degassed by bubbling nitrogen in to it, stirred at 100° C. for 1 hr under microwave irradiation then cooled to room temperature. The reaction mixture was filtered through celite and concentrated in vacuovacuo. The residue was partitioned between EtOAC (30 mL) and water (30 mL) and the layers were separated. The organic phase was washed with brine (25 mL) dried over MgSO₄ and concentrated in vacuovacuo. Purification of the residue by flash chromatography on silica gel (gradient:0 to 60% AcOEt in Hexanes) gave 1-methylethyl {(2S,4R)-1-acetyl-6-[3,4-bis(methyloxy)phenyl]-2-methyl-1,2,3,4-tetrahydro-4-quinolinyl}carbamate (327 mg, 0.766 mmol, 56.6%).

LCMS (Method B): Retention time 1.02 min, [M+H]+=427.18

Intermediate 96

Methyl 4-[(2S,4R)-1-acetyl-4-amino-2-methyl-1,2,3,4-tetrahydro-6-quinolinyl]-3-methylbenzoate

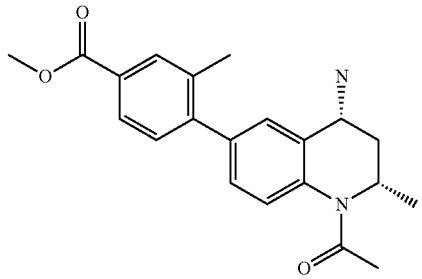

Methyl 4-[(2S,4R)-1-acetyl-2-methyl-4-({[(1-methylethyl)oxy]carbonyl}amino)-1,2,3,4-tetrahydro-6-quinolinyl]-3-methylbenzoate (for a preparation see Intermediate 97) (320 mg, 0.730 mmol) was added to a cold (ice bath) suspension of aluminium chloride (370 mg, 2.77 mmol) in dichloromethane (DCM) (4 mL). The reaction was stirred at approximately 0° C. for 30 min, then treated with a solution of methanol (0.320 mL) and triethylamine (1.230 mL, 8.82 mmol). The resulting mixture was stirred further at approximately 0° C. for 20 min then was diluted with EtOAc (25 mL) and a saturated NaHCO₃ aqueous solution (25 mL). The reaction mixture was then filtered through celite and the insoluble residues were washed with EtOAc (15 mL) and a saturated NaHCO₃ aqueous solution (15 ml). The filtered aluminum residues were suspended in MeOH and sonicated. The resulting suspension was filtered and the filtrate was concentrated in vacuo to give a white solid. This solid was loaded onto a 20 G SCX cartridge and eluted with MeOH then with 2M NH₃ in MeOH. The ammonia fractions were combined and concentrated in vacuo to give methyl 4-[(2S,4R)-1-acetyl-4-amino-2-methyl-1,2,3,4-tetrahydro-6-quinolinyl]-3-methylbenzoate (145 mg, 56%).

LCMS (Method A): Retention time 0.72 min, [M+H]+=336.13

Intermediate 97

Methyl 4-[(2S,4R)-1-acetyl-2-methyl-4-({[(1-methylethyl)oxy]carbonyl}amino)-1,2,3,4-tetrahydro-6-quinolinyl]-3-methylbenzoate

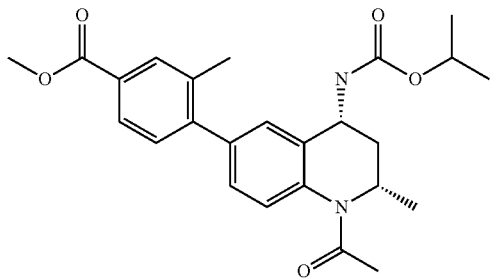 [SMILES: COC(=O)c1ccc(-c2ccc3c(c2)[C@H](NC(=O)OC(C)C)C[C@H](C)N3C(C)=O)c(C)c1]

A flask was charged with methyl 3-methyl-4-(4,4,5,5-tetramethyl-1,3,2-dioxaborolan-2-yl)benzoate (0.449 g, 1.625 mmol), 1-methylethyl[(2S,4R)-1-acetyl-6-bromo-2-methyl-1,2,3,4-tetrahydro-4-quinolinyl]carbamate (for a preparation see Intermediate 100) (0.5 g, 1.354 mmol), sodium bicarbonate (saturated solution) (1.5 mL, 1.354 mmol) and bis(diphenylphosphino)ferrocene]dichloropalladium(II)-DCM adduct (0.111 g, 0.135 mmol) then filled with 1,4-dioxane (7 mL). The resulting mixture was degassed by bubbling nitrogen in to it, stirred at 100° C. for 1 hr under microwave irradiation then cooled to room temperature. The reaction mixture was filtered through celite and concentrated in vacuovacuo. The residue was partitioned between EtOAC (30 mL) and water (30 mL) and the layers were separated. The organic phase was washed with brine (25 mL) dried over MgSO₄ and concentrated in vacuovacuo. Purification of the residue by flash chromatography on silica gel (gradient:0 to 60% AcOEt in Hexanes) gave methyl 4-[(2S,4R)-1-acetyl-2-methyl-4-({[(1-methylethyl)oxy]carbonyl}amino)-1,2,3,4-tetrahydro-6-quinolinyl]-3-methylbenzoate (337 mg, 0.769 mmol, 56.8%) as a light yellow solid.

LCMS (Method B): Retention time 1.12 min, [M+H]+=439.17

Intermediate 98

Methyl 3-[(2S,4R)-1-acetyl-4-amino-2-methyl-1,2,3,4-tetrahydro-6-quinolinyl]benzoate

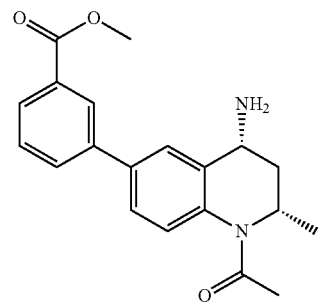 [SMILES: COC(=O)c1cccc(-c2ccc3c(c2)[C@H](N)C[C@H](C)N3C(C)=O)c1]

Methyl 3-[(2S,4R)-1-acetyl-2-methyl-4-({[(1-methylethyl)oxy]carbonyl}amino)-1,2,3,4-tetrahydro-6-quinolinyl]benzoate (for a preparation see Intermediate 99) (319 mg, 0.751 mmol) was added to a cold (ice bath) suspension of aluminium chloride (381 mg, 2.86 mmol) in dichloromethane (DCM) (5 mL). The resulting mixture was stirred at approximately 0° C. for 30 min then was treated with a solution of methanol (0.400 mL) and triethylamine (1.266 mL, 9.09 mmol). The reaction was stirred further at approximately 0° C. for 20 min then was diluted with EtOAc (35 mL) and a saturated NaHCO₃ aqueous solution (35 ml). The reaction mixture was then filtered through celite and the insoluble residues were washed with EtOAc (25 mL) and NaHCO₃ (25 mL. The filtered aluminum residues were suspended in MeOH and sonicated. The resulting suspension was filtered and the filtrate was concentrated in vacuo to yield a white solid which was loaded onto a 20 g SCX cartridge and eluted with MeOH and then with 2M NH₃ in MeOH. The ammonia fractions were combined and concentrated in vacuo to give methyl 3-[(2S,4R)-1-acetyl-4-amino-2-methyl-1,2,3,4-tetrahydro-6-quinolinyl]benzoate (50 mg, 20%).

LCMS (Method A): Retention time 0.68 min, [M+H2]+=322.11

Intermediate 99

Methyl 3-[(2S,4R)-1-acetyl-2-methyl-4-({[(1-methylethyl)oxy]carbonyl}amino)-1,2,3,4-tetrahydro-6-quinolinyl]benzoate

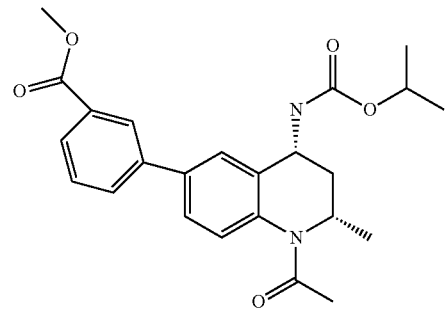 [SMILES: COC(=O)c1cccc(-c2ccc3c(c2)[C@H](NC(=O)OC(C)C)C[C@H](C)N3C(C)=O)c1]

A flask was charged with methyl 3-(4,4,5,5-tetramethyl-1,3,2-dioxaborolan-2-yl)benzoate (0.355 g, 1.354 mmol), 1-methylethyl[(2S,4R)-1-acetyl-6-bromo-2-methyl-1,2,3,4-tetrahydro-4-quinolinyl]carbamate (for a preparation see Intermediate 100) (0.5 g, 1.354 mmol), a saturated NaHCO$_3$ aqueous solution (1.5 mL, 1.354 mmol) and PdCl2(dppf)-CH$_2$Cl$_2$ adduct (0.111 g, 0.135 mmol) then filled with 1,4-dioxane (7 mL) and the resulting mixture was degassed by bubbling nitrogen into it then stirred at 100° C. for 1 h under microwave irradiation before being cooled to room temperature, filtered through celite and concentrated in vacuo. The residue was partioned between EtOAC (30 mL) and water (30 mL) and the layers were separated. The organic phase was washed with brine (30 mL), dried under MgSO$_4$ and concentrated in vacuo. Purification of the residue on Sp4 using a 50 G silica cartridge (gradient:20 to 80% AcOEt in Hexanes) gave methyl 3-[(2S,4R)-1-acetyl-2-methyl-4-({[(1-methylethyl)oxy]carbonyl}amino)-1,2,3,4-tetrahydro-6-quinolinyl]benzoate (319 mg, 55%).

LCMS (Method A): Retention time 1.10 min, [M+H2]+=425.27

Intermediate 100

1-Methylethyl[(2S,4R)-1-acetyl-6-bromo-2-methyl-1,2,3,4-tetrahydro-4-quinolinyl]carbamate

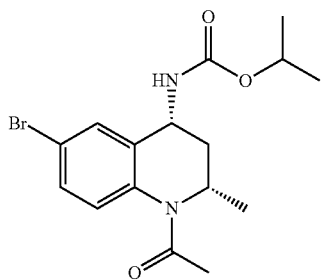 [SMILES: CC(=O)N1c2ccc(Br)cc2[C@H](NC(=O)OC(C)C)C[C@@H]1C]

1-Methylethyl[(2S,4R)-6-bromo-2-methyl-1,2,3,4-tetrahydro-4-quinolinyl]carbamate (for a preparation see Intermediate 101) (14.1 g, 43.1 mmol) was taken up in dichloromethane (DCM) (400 mL) under nitrogen at room temperature. Pyridine (10.46 mL, 129 mmol), then acetyl chloride (4.60 mL, 64.6 mmol), were added and the reaction stirred at room temperature for 16 h, then partitioned between EtOAc (2000 mL) and a saturated NaHCO$_3$ aqueous solution (800 mL). The layers were separated and the organic phase was washed with water then brine (1500 mL each) and then dried with Na$_2$SO$_4$ and concentrated in vacuo to yield a purple solid. The crude product was taken up in the minimum of DCM and applied to a 330 g Companion XL column and eluted with a gradient of 12-63% Ethyl Acetate in cyclohexane to give the product as an off-white solid (12.37 g).

LCMS (Method B): Rt=1.03, MH+=369

[alpha]D=+281.1025° (T=20.7° C., 10 mm cell, c=0.508 g/100 ml, ethanol).

Intermediate 101

1-Methylethyl[(2S,4R)-6-bromo-2-methyl-1,2,3,4-tetrahydro-4-quinolinyl]carbamate

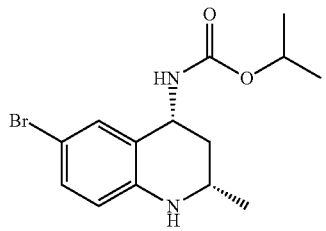 [SMILES: CC(C)OC(=O)N[C@@H]1C[C@H](C)Nc2ccc(Br)cc21]

1-Methylethyl {(3S)-3-[(4-bromophenyl)amino]butanoyl}carbamate (for a preparation see Intermediate 102) (17.9 g, 52.2 mmol) was taken up in ethanol (150 mL) and cooled to below −10° C. (internal temperature) in a CO$_2$/acetone bath. NaBH$_4$ (1.381 g, 36.5 mmol) was added followed by magnesium chloride hexahydrate (11.35 g, 55.8 mmol) in water (25 mL) keeping the temperature below −5° C. The mixture was allowed to stir at <0° C. for 1 h then warmed to room temperature and stirred for an hour. The resulting thick suspension was poured into a mixture of citric acid (25.05 g, 130 mmol), HCl (1M in water, 205 mL, 205 mmol) and dichloromethane (DCM) (205 mL). The biphasic mixture was stirred at room temperature for 1 h. LCMS showed no remaining starting material so the layers were separated and the organic layer dried with Na$_2$SO$_4$, filtered and concentrated to yield the product as a light brown solid (14.1 g).

LCMS (Method B): Rt=1.13, MH+=327

Intermediate 102

1-Methylethyl {(3S)-3-[(4-bromophenyl)amino]butanoyl}carbamate

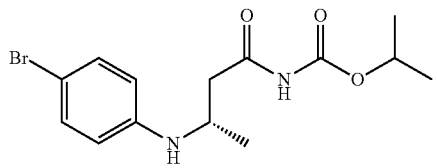 [SMILES: CC(C)OC(=O)NC(=O)C[C@H](C)Nc1ccc(Br)cc1]

(3S)-3-[(4-Bromophenyl)amino]butanamide (for a preparation see Intermediate 103, 24.9 g, 97 mmol) was taken up in ethyl acetate (850 mL) and cooled to <−9° C. (internal temperature). Isopropyl chloroformate (116 mL, 116 mmol, Aldrich) was added followed by slow addition of lithium tert-butoxide (18.61 g, 232 mmol) in tetrahydrofuran (THF) (232 mL) keeping the temperature below 0° C. The reaction was stirred for 30 min then checked by LCMS which showed a complete reaction. The mixture was partitioned between EtOAc (1000 mL) and 2N HCl (2000 mL) and the layers were separated. The organic layer was washed with brine (2000 mL) and then dried with Na$_2$SO$_4$, filtered and concentrated to yield the product as a brown oil (17.9 g)

LCMS (Method B): Rt=1.09, MH+=343

Alternative Method

1-Methylethyl (2E)-2-butenoylcarbamate (Intermediate 106, 9.38 g, 54.8 mmol) was stirred in toluene (281 mL) under nitrogen and (R-BINAP)ditriflatebis(acetonitrile)palladium (II) (Intermediate 50, 3.35 g, 3.01 mmol) added. The catalyst formed a gummy ball, the solution turned to an opaque yellow mixture and was stirred for 20 min. 4-Bromoaniline (14.14 g, 82 mmol) was added, the solution turned to a clear light brown and the gummy catalyst dissolved further. The mixture was stirred for 16 h.

Similarly a second batch of 1-methylethyl (2E)-2-butenoylcarbamate (Intermediate 106, 8.51 g, 49.7 mmol) was stirred in toluene (255 mL) under nitrogen and (R-BINAP)ditriflatebis(acetonitrile)palladium(II) (3.04 g, 2.73 mmol) added. The catalyst formed a gummy ball, the solution turned to an opaque yellow mixture and was stirred for 20 min. 4-Bromoaniline (12.83 g, 74.6 mmol) was added, the solution turned to a clear light brown and the gummy catalyst dissolved further. The mixture was stirred for 16 h. The two reaction mixtures were combined and loaded on to a 1.5 kg Isco silica Redisep column. The column was eluted with DCM:MeOH (0%->0.5%, 19 CV). The clean, product containing fractions were evaporated to a pale brown oil. The mixture was dried in a vacuum oven overnight at 40° C. to give a white solid (24.2 g, 67% overall).

LCMS (Method C): Rt=0.91, MH+=343. ee=92%.

Intermediate 103

(3S)-3-[(4-Bromophenyl)amino]butanamide

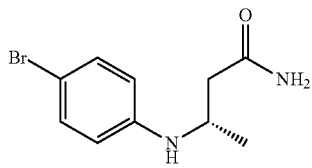

(3S)-3-[(4-Bromophenyl)amino]butanenitrile (for a preparation see Intermediate 104) (17.3 g, 72.4 mmol) was taken up in toluene (500 ml) and $H_2SO_4$ (19.28 ml, 362 mmol) added. The biphasic mixture was stirred at 60° C. After two hours, only a small amount of starting material remained by LCMS so the reaction was diluted with water (500 mL) and the phases separated. The aqueous phase was basified with 10N NaOH and extracted with EtOAc (2×750 mL). The combined organics were dried with $Na_2SO_4$, filtered and concentrated to yield the product as a cream solid (17.5 g).

LCMS (Method B): Rt=0.77, MH+=257

Intermediate 104

(3S)-3-[(4-Bromophenyl)amino]butanenitrile

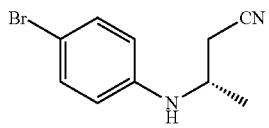

(3S)-3-(Phenylamino)butanenitrile (for a preparation see Intermediate 105) (11.3526 g, 70.9 mmol) was taken up in N,N-dimethylformamide (DMF) (200 mL) under nitrogen and cooled in an ice-bath. NBS (12.61 g, 70.9 mmol) was added and the reaction stirred. After 20 min, the reaction was partitioned between EtOAc (1000 mL) and water (500 mL). The organic layer was washed with 2M NaOH×2, water and brine (500 mL each) and then dried with $Na_2SO_4$, filtered and concentrated to yield the product as a cream solid (17.3 g).

LCMS (Method B): Rt=1.05, MH+=239

Intermediate 105

(3S)-3-(Phenylamino)butanenitrile

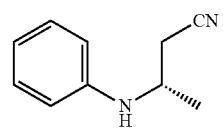

(3S)-3-Aminobutanenitrile (8.6 g, 102 mmol, may be prepared as described in PCT Int. Appl., 2005100321), bromobenzene (16.16 ml, 153 mmol) and cesium carbonate (50.0 g, 153 mmol) were combined in toluene (100 mL) under nitrogen were stirred for 45 min. Phenylboronic acid (0.187 g, 1.534 mmol, Aldrich), palladium(II) acetate (0.188 g, 0.837 mmol, available from Aldrich) and 2-dicyclohexylphosphino-2'-(N,N-dimethylamino)biphenyl (0.443 g, 1.125 mmol, available from Aldrich) were combined in tetrahydrofuran (THF) (6.67 ml) under nitrogen and stirred for 45 min. The THF solution was added to the toluene solution and the reaction heated to 80° C. for 16 h. The reaction mixture was cooled and partitioned between EtOAc (500 mL) and water (300 mL). The aqueous layer was reextracted with EtOAc (200 mL). The combined organic layers were washed with water and brine (500 mL each) and then dried with $Na_2SO_4$, filtered and concentrated to yield orange oil. The crude product was taken up in the minimum of DCM, applied to a 330 g Companion XL column and eluted with 5% ethyl acetate in cyclohexane for 1 CV then 5-30% ethyl acetate over 12 CV then held at 30% for 3CV; UV collection; 450 mL fractions. The product was isolated as an off-white solid (11.3526 g).

LCMS (Method B): Rt=0.87, MH+=161

Intermediate 106

1-Methylethyl (2E)-2-butenoylcarbamate

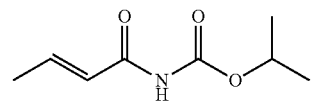

Isopropyl carbamate (30 g, 291 mmol, available from TCI) was charged to a 3 L Lara vessel and dry tetrahydrofuran (THF) (150 ml) added. (2E)-2-Butenoyl chloride (31.2 ml, 326 mmol, available from Aldrich) was added under nitrogen and the jacket cooled to −30° C. When the solution temperature reached −17° C. 1M Lithium tert-butoxide (655 mL, 655 mmol) was added by peristaltic pump over 2 hours, keeping the reaction temperature between −10° C. and −18° C. Once the addition was complete the mixture was complete the mixture was stirred for 30 mins and brought to 0° C. Diethyl ether (450 ml) and 1M HCl (375 mL) were added and the mixture brought to 20° C. with vigorous stirring. The stirring was stopped, the layers allowed to separate and the aqueous layer run off. Brine (375 mLl) was added and the mixture stirred vigorously. The stirring was stopped, the layers allowed to separate and the aqueous layer run off. The organic layer was dried (magnesium sulfate), filtered and evaporated to a brown oil (60 g). The mixture was loaded on to a 40+M Biotage silica column and eluted with DCM:ethyl acetate (1:1 to 0:1, 10CV). The product containing fractions were evaporated to dryness and loaded on to a 1500 g Redisep Isco silica column and eluted with a gradient of 0 to 40% ethyl acetate in cyclohexane. The clean, product containing fractions were evaporated to an off white solid (15.41 g). LCMS (Method C): Rt=0.68, MH+=172

Intermediate 107

1,1-Dimethylethyl((2S,4R)-1-acetyl-2-methyl-6-{[tris(1-methylethyl)silyl]ethynyl}-1,2,3,4-tetrahydro-4-quinolinyl)carbamate

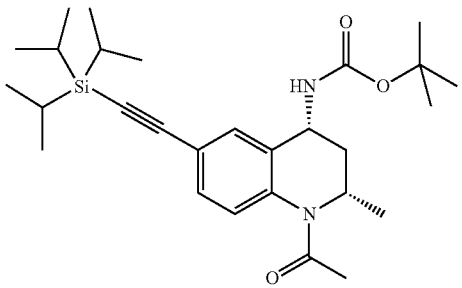 [SMILES: CC(=O)N1c2ccc(C#C[Si](C(C)C)(C(C)C)C(C)C)cc2[C@H](NC(=O)OC(C)(C)C)C[C@@H]1C]

A flask was charged with 1,1-dimethylethyl[(2S,4R)-1-acetyl-6-bromo-2-methyl-1,2,3,4-tetrahydro-4-quinolinyl]carbamate (for a preparation see Intermediate 50) (2 g, 5.22 mmol), copper(I) iodide (0.099 g, 0.522 mmol) and bis(triphenylphosphine)palladium(II) chloride (0.366 g, 0.522 mmol) then filled with N,N-dimethylformamide (DMF) (30 mL), ethynyl[tris(1-methylethyl)]silane (25 mL, 113 mmol) and triethylamine (29.1 mL, 209 mmol) and the resulting mixture was stirred at 90° C. under nitrogen for 16 h then cooled to room temperature. Ethynyl[tris(1-methylethyl)]silane (5 ml, 22.6 mmol) and triethylamine (5 mL, 35.9 mmol) were then added and the resulting mixture stirred again for 4 h at 90° C. under nitrogen then cooled to room temperature. Most of the volatiles were removed in vacuo. The residue was partitioned between AcOEt and 1:1 water/brine and the layers were separated. The aqueous layer was extracted three times with AcOEt and the combined organic phases were washed twice with 1:1 water/brine, dried over MgSO$_4$ and concentrated in vacuo. Purification of the residue by SP4 using a 220 G silica cartridge, (gradient:10 to 50% AcOEt in Hexanes) gave 1,1-dimethylethyl((2S,4R)-1-acetyl-2-methyl-6-{[tris(1-methylethyl)silyl]ethynyl}-1,2,3,4-tetrahydro-4-quinolinyl)carbamate (2.19 g, 4.52 mmol, 87% yield) as a brown foam.

LCMS (Method B): Retention time 1.72 min, [M−H]−=483.40

Intermediate 108

(2S,4R)-1-Acetyl-2-methyl-6-{[tris(1-methylethyl)silyl]ethynyl}-1,2,3,4-tetrahydro-4-quinolinamine hydrochloride

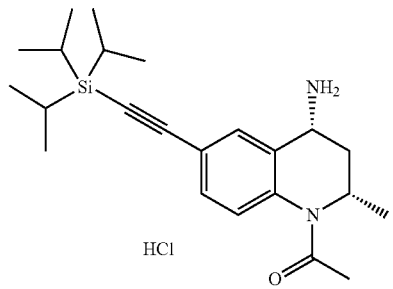 [SMILES: CC(=O)N1c2ccc(C#C[Si](C(C)C)(C(C)C)C(C)C)cc2[C@H](N)C[C@@H]1C ; Cl]

A solution of 1,1-dimethylethyl((2S,4R)-1-acetyl-2-methyl-6-{[tris(1-methylethyl)silyl]ethynyl}-1,2,3,4-tetrahydro-4-quinolinyl)carbamate (for a preparation see Intermediate 107) (1.96 g, 4.04 mmol) in 1,4-dioxane (10 mL) at room temperature was treated with HCl (4N in dioxane, 20 mL, 80 mmol) and the resulting mixture was stirred at this temperature for 7 h then the solvent was removed in vacuo. The residue was triturated with Et$_2$O then filtered off and dried under house vacuum to give (2S,4R)-1-acetyl-2-methyl-6-{[tris(1-methylethyl)silyl]ethynyl}-1,2,3,4-tetrahydro-4-quinolinamine hydrochloride (1.28 g, 3.04 mmol, 75% yield) as a white solid. The mother liquors were concentrated in vacuo to give (2S,4R)-1-acetyl-2-methyl-6-{[tris(1-methylethyl)silyl]ethynyl}-1,2,3,4-tetrahydro-4-quinolinamine hydrochloride (396 mg, 0.940 mmol, 23.26% yield) as a very pale yellow foam.

LCMS (Method B): Retention time 1.57 min, [M+H$_2$]+=368.23

Intermediate 109

(2S,4R)-1-Acetyl-2-methyl-N-(5-methyl-2-pyridinyl)-6-{[tris(1-methylethyl)silyl]ethynyl}-1,2,3,4-tetrahydro-4-quinolinamine

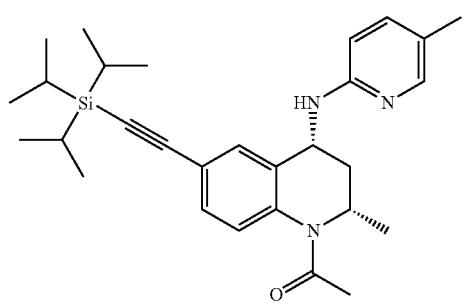 [SMILES: CC(=O)N1c2ccc(C#C[Si](C(C)C)(C(C)C)C(C)C)cc2[C@H](Nc2ccc(C)cn2)C[C@@H]1C]

A quantity of toluene was degassed under house vacuum over 10 min with several quenches with nitrogen.

A flask was charged with (2S,4R)-1-acetyl-2-methyl-6-{[tris(1-methylethyl)silyl]ethynyl}-1,2,3,4-tetrahydro-4-quinolinamine hydrochloride (for a preparation see Intermediate 108) (130 mg, 0.309 mmol), 2-bromo-5-methylpyridine (159 mg, 0.926 mmol), sodium tert-butoxide (148 mg, 1.544 mmol), 2-(dimethylamino)-2'-(dicyclohexylphosphino)biphenyl (DavePhos) (243 mg, 0.617 mmol) and tris(dibenzylideneacetone)dipalladium(0) (283 mg, 0.309 mmol) then flushed with nitrogen and filled with degassed toluene (3 mL). The resulting mixture was stirred at 100° C. for 1.5 h then cooled to room temperature and filtered through celite. The insoluble material was washed with AcOEt and the combined filtrate and washings were concentrated in vacuo. The residue was partitioned between water and AcOEt and the layers were separated. The aqueous phase was extracted with AcOEt and the combined organic phases were washed with water then brine, dried over MgSO$_4$ and concentrated in vacuo. Purification of the residue by SP4 using a 25 G silica cartridge (gradient:13 to 63% AcOEt in Hexanes) gave (2S,4R)-1-acetyl-2-methyl-N-(5-methyl-2-pyridinyl)-6-{[tris(1-methylethyl)silyl]ethynyl}-1,2,3,4-tetrahydro-4-quinolinamine (120 mg, 0.252 mmol, 82% yield) as a yellow foam which was used in the next step without further purification.

LCMS (Method B): Retention time 1.71 min, [M+H]+=476.27

Intermediate 110

(2S,4R)-1-Acetyl-6-ethynyl-2-methyl-N-(5-methyl-2-pyridinyl)-1,2,3,4-tetrahydro-4-quinolinamine

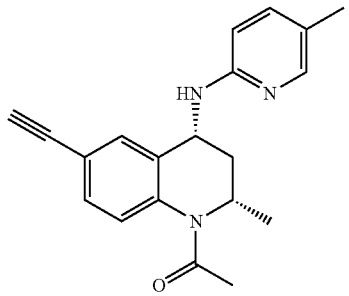 [SMILES: C#Cc1ccc2c(c1)[C@H](Nc1ccc(C)cn1)C[C@H](C)N2C(C)=O]

A solution of (2S,4R)-1-acetyl-2-methyl-N-(5-methyl-2-pyridinyl)-6-{[tris(1-methylethyl)silyl]ethynyl}-1,2,3,4-tetrahydro-4-quinolinamine (for a preparation see Intermediate 109) (135 mg, 0.284 mmol) in tetrahydrofuran (THF) (3 mL) at room temperature was treated with TBAF (1N in THF, 0.341 mL, 0.341 mmol) and the resulting mixture was stirred at this temperature for 30 min then most of the solvent was removed in vacuo. The residue was partitioned between AcOEt and water and the layers were separated. The organic phase was washed with water then brine, dried over MgSO$_4$ and concentrated in vacuo. Purification of the residue by SP4 using a 10 G silica cartridge (gradient:5 to 25% (20% MeOH in DCM) in DCM) gave (2S,4R)-1-acetyl-6-ethynyl-2-methyl-N-(5-methyl-2-pyridinyl)-1,2,3,4-tetrahydro-4-quinolinamine (70 mg, 0.219 mmol, 77% yield) as an orange foam.

LCMS (Method B): Retention time 1.03 min, [M+H]+=320.16

Intermediate 111

(2S,4R)-1-Acetyl-2-methyl-N-(6-methyl-2-pyridinyl)-6-{[tris(1-methylethyl)silyl]ethynyl}-1,2,3,4-tetrahydro-4-quinolinamine

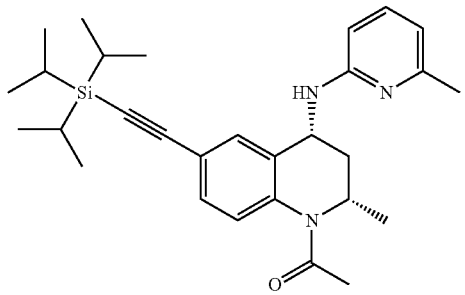 [SMILES: CC(=O)N1c2ccc(C#C[Si](C(C)C)(C(C)C)C(C)C)cc2[C@H](Nc2cccc(C)n2)C[C@@H]1C]

Toluene was degassed on its own under house vacuum for 10 min with several quenches with nitrogen.

A flask was charged with (2S,4R)-1-acetyl-2-methyl-6-{[tris(1-methylethyl)silyl]ethynyl}-1,2,3,4-tetrahydro-4-quinolinamine hydrochloride (for a preparation see Intermediate 108) (200 mg, 0.475 mmol), sodium tert-butoxide (228 mg, 2.375 mmol), tris(dibenzylideneacetone)dipalladium(0) (435 mg, 0.475 mmol) and 2-(dimethylamino)-2'-(dicyclohexylphosphino)biphenyl (DavePhos) (374 mg, 0.950 mmol) then filled with degassed toluene (6 mL) and the resulting mixture was treated with 2-bromo-6-methylpyridine (0.162 mL, 1.425 mmol) then stirred at 100° C. under nitrogen for 1.5 h then cooled to room temperature and partitioned between water and AcOEt. The two layers were filtered through celite then separated. The aqueous phase was extracted with AcOEt and the combined organic phases were washed with water then brine, dried over MgSO$_4$ and concentrated in vacuo. Purification of the residue by SP4 using a 25 G silica cartridge (gradient:13 to 63% AcOEt in Hexanes) gave (2S,4R)-1-acetyl-2-methyl-N-(6-methyl-2-pyridinyl)-6-{[tris(1-methylethyl)silyl]ethynyl}-1,2,3,4-tetrahydro-4-quinolinamine (280 mg, 0.589 mmol, 124% yield) contaminated with palladium ligand residues as a brown foam which was used in the next step without further purification.

LCMS (Method B): Retention time 1.26 min, [M+H]+=476.3

Intermediate 112

(2S,4R)-1-Acetyl-6-ethynyl-2-methyl-N-(6-methyl-2-pyridinyl)-1,2,3,4-tetrahydro-4-quinolinamine

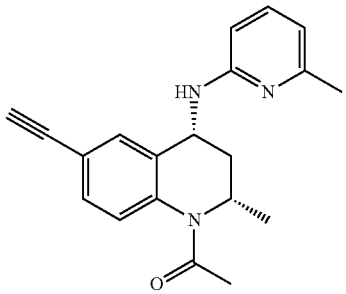 [SMILES: C#Cc1ccc2c(c1)[C@H](Nc1cccc(C)n1)C[C@H](C)N2C(C)=O]

A solution of (2S,4R)-1-acetyl-2-methyl-N-(6-methyl-2-pyridinyl)-6-{[tris(1-methylethyl)silyl]ethynyl}-1,2,3,4-tetrahydro-4-quinolinamine (for a preparation see Intermediate 111) (0.226 g, 0.475 mmol) in tetrahydrofuran (THF) (5 mL) at room temperature was treated with TBAF (1N in THF, 0.570 mL, 0.570 mmol) and the resulting mixture was stirred at this temperature for 30 min then most of the solvent was removed in vacuo. The residue was partitioned between AcOEt and water and the layers were separated. The organic phase was washed with water then brine, dried over MgSO$_4$ and concentrated in vacuo. Purification of the residue by SP4 using a 10 G silica cartridge (gradient:5 to 25% (20% MeOH in DCM) in DCM) gave (2S,4R)-1-acetyl-6-ethynyl-2-methyl-N-(6-methyl-2-pyridinyl)-1,2,3,4-tetrahydro-4-quinolinamine as an orange foam.

LCMS (Method B): Retention time 1.05 min, [M+H]+=320.17

Intermediate 113

(2S,4R)-1-Acetyl-2-methyl-N-2-pyrimidinyl-6-{[tris(1-methylethyl)silyl]ethynyl}-1,2,3,4-tetrahydro-4-quinolinamine

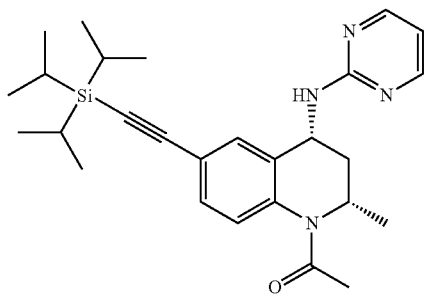 [SMILES: CC(=O)N1c2ccc(C#C[Si](C(C)C)(C(C)C)C(C)C)cc2[C@H](Nc2ncccn2)C[C@@H]1C]

Toluene was degassed on its own under house vacuum for 10 min with several quenches with nitrogen.

A flask was charged with (2S,4R)-1-acetyl-2-methyl-6-{[tris(1-methylethyl)silyl]ethynyl}-1,2,3,4-tetrahydro-4-quinolinamine hydrochloride (for a preparation see Intermediate 108) (295 mg, 0.7 mmol), 2-bromopyrimidine (334 mg, 2.100 mmol), sodium tert-butoxide (336 mg, 3.50 mmol), tris(dibenzylideneacetone)dipalladium(0) (641 mg, 0.700 mmol) and 2-(dimethylamino)-2'-(dicyclohexylphosphino)biphenyl (DavePhos) (551 mg, 1.400 mmol) then filled with toluene (10 mL) and the resulting mixture was stirred at 100° C. under nitrogen for 1.5 h then cooled to room temperature and partitioned between water and AcOEt, The two layers were filtered through celite then separated. The aqueous phase was extracted with AcOEt and the combined organic were washed with water then brine, dried over MgSO$_4$ and concentrated in vacuo. Purification of the residue by SP4 using a 25 G silica cartridge (gradient:13 to 63% AcOEt in Hexanes) gave (2S,4R)-1-acetyl-2-methyl-N-2-pyrimidinyl-6-{[tris(1-methylethyl)silyl]ethynyl}-1,2,3,4-tetrahydro-4-quinolinamine (220 mg, 0.475 mmol, 67.9% yield) as a brown foam.

LCMS (Method B): Retention time 1.58 min, [M+H]+=463.3

Intermediate 114

(2S,4R)-1-Acetyl-6-ethynyl-2-methyl-N-2-pyrimidinyl-1,2,3,4-tetrahydro-4-quinolinamine

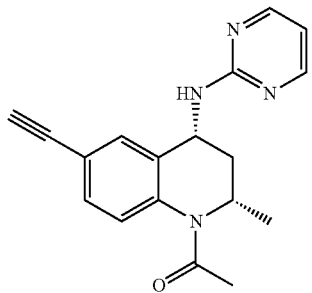 [SMILES: C#Cc1ccc2c(c1)[C@H](Nc1ncccn1)C[C@H](C)N2C(C)=O]

A solution of (2S,4R)-1-acetyl-2-methyl-N-2-pyrimidinyl-6-{[tris(1-methylethyl)silyl]ethynyl}-1,2,3,4-tetrahydro-4-quinolinamine (for a preparation see Intermediate 113) (220 mg, 0.475 mmol) in tetrahydrofuran (THF) (5 mL) at room temperature was treated with TBAF (1N in THF, 0.571 mL, 0.571 mmol) and the resulting mixture was stirred at this temperature for 30 min then most of the solvent was removed in vacuo. The residue was partitioned between AcOEt and water and the layers were separated. The organic phase was washed with water then brine, dried over MgSO$_4$ and concentrated in vacuo. Purification of the residue by SP4 using a 10 G column (gradient:5 to 25% (20% MeOH in DCM) in DCM) gave (2S,4R)-1-acetyl-6-ethynyl-2-methyl-N-2-pyrimidinyl-1,2,3,4-tetrahydro-4-quinolinamine as an orange foam.

LCMS (Method B): Retention time 0.85 min, [M+H]+=307.13

Example 1

Methyl-4-{1-acetyl-4-[(4-chlorophenyl)amino]-2-methyl-1,2,3,4-tetrahydro-6-quinolinyl}benzoate

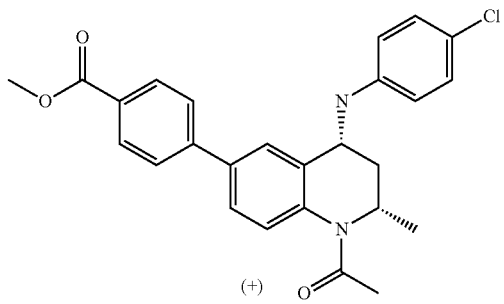 [SMILES: COC(=O)c1ccc(-c2ccc3c(c2)[C@H](Nc2ccc(Cl)cc2)C[C@H](C)N3C(C)=O)cc1]

To a flask charged with the intermediate 38 (800 mg, 2.4 mmol) in toluene (20 mL) was added 4-chlorobromobenzene (501 mg, 2.6 mmol), Pd$_2$(dba)$_3$ (87 mg, 0.09 mmol), NaO$^t$Bu (319 mg, 3.3 mmol) and 2'-(dicyclohexylphosphanyl)-N,N-dimethyl-2-biphenylamine (74 mg, 0.19 mmol). The resulting mixture was stirred to 80° C. during 16 hours and 3 additional hours at reflux. The mixture was poured into water and was made acidic upon addition of 1N HCl. Extraction was carried out with EtOAc (2×75 ml) and the organic layers were washed with water and dried over Na$_2$SO$_4$. After filtration, concentration under reduced pressure and purification by column chromatography eluting with C$_6$H$_{12}$/EtOAc:80/20 the title compound was obtained as a white solid (350 mg).

1H NMR (300 MHz, CHLOROFORM-d) δ ppm 1.2 (d, 3 H) 1.35 (m, 1 H) 2.25 (s, 3 H) 2.7 (m, 1 H) 3.95 (s, 3H), 4.25 (m, 1 H) 4.95 (m, 1 H) 6.6 (d, 2 H) 7.15 (d, 2 H) 7.25 (s, 1 H) 7.55 (m, 4 H), 8.1 (d, 2H)

LC/MS: m/z 449 [M+H]$^+$ and 447 [M−H]$^−$ Rt=3.67 min. [α]$_D$=+326 (c=0.98 g/cl, EtOH)

The title compound eluted at 22.58 min by HPLC as the second peak using a CHIRACEL OD (250×4.6 mm 10 μm) column with hexane/ethanol 90/10 as the mobile phase. A 1 ml/mn flow rate was applied and 10 μL of sample prepared with the dilution of 1 mg of the title compound in 1 ml of eluent was injected. Detection of the compound was carried out with both 210 and 254 nM UV wavelengths. The other enantiomer came off at 15.46 min Examples 2 to 5 were prepared by similar methods to that described for Example 1 using the appropriate aryl bromide derivative and suitable precipitation or recrystallisation conditions (see Table 5):

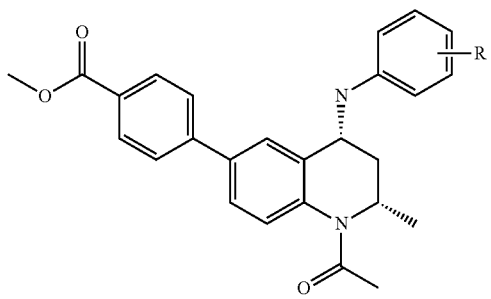

TABLE 5

| Ex | R | Physical data |
|----|------|---------------|
| 2 | 4-F | LC/MS: m/z 431 [M − H]⁻, Rt = 4.09 min |
| 3 | 4-CH₃ | LC/MS: m/z 429 [M + H]⁺, Rt = 3.58 min |
| 4 | 4-CF₃ | LC/MS: m/z 481 [M − H]⁻, Rt = 3.62 min |
| 5 | 3-CF₃ | LC/MS: m/z 481 [M − H]⁻, Rt = 3.64 min |

Example 6

Procedure 1

4-(2S,4R)-{-1-Acetyl-4-[(4-chlorophenyl)amino]-2-methyl-1,2,3,4-tetrahydro-6-quinolinyl}benzoic acid

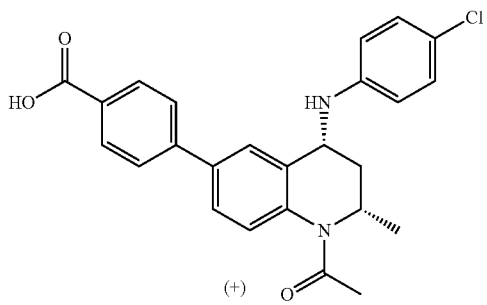 [SMILES: CC(=O)N1c2ccc(-c3ccc(C(=O)O)cc3)cc2[C@H](Nc2ccc(Cl)cc2)C[C@@H]1C]

A solution of example 1 (320 mg, 0.73 mmol) in EtOH (10 ml) and 1N NaOH (1.5 ml, 1.5 mmol) was heated to reflux. After 1 hour a tlc monitoring indicated the completion of the reaction. The crude mixture was evaporated to dryness and the residue taken up in water (10 mL). Acidification of the mixture at pH=3 was carried out by addition of a 1N HCl solution. The organic materials were extracted with EtOAc (3×25 mL) and the organic phase combined and washed with brine and dried over Na₂SO₄. After concentration under vacuo the residue was taken up in a DCM/hexane mixture to give a red solid after filtration. The compound was recrystallised in EtOAC, filtered and washed with iPr₂O. The resulting white powder was solubilised in MeOH/H₂O, concentrated to dryness and taken up with H₂O. Finally filtration of the precipitate afforded the title compound as a white powder (147 mg), mp: 275° C.

HRMS calculated for C₂₅H₂₃N₂O₃Cl (M−H)⁻ 433.1319. Found: 433.1299. Rt: 2.21 min

1H NMR (300 MHz, CHLOROFORM-d) δ ppm 1.2 (d, 3 H) 1.35 (m, 1 H) 2.3 (s, 3 H) 2.7 (m, 1 H) 4.25 (dd, 1 H) 4.95 (m, 1 H) 6.65 (d, 2 H) 7.15 (d, 2 H) 7.25 (s, 1 H) 7.55 (m, 4 H), 8.15 (d, 2H)

[α]$_D$=+395 (c=0.96 g/cl, EtOH) measured at the EtOAc recrystallisation stage.

The title compound eluted at 4.51 min by HPLC as the first peak using a Chiralpak IA (250×4.6 mm 5 µm) column with tert-butyl methyl oxide (MTBE)+0.1% TFA/Ethanol:90/10 as the mobile phase. A 1 ml/mn flow rate was applied and 10 µL of sample prepared with the dilution of 1 mg of the title compound in 1 ml of eluent was injected. Detection of the compound was carried out with both 210 and 254 nM UV wavelengths. The other enantiomer came off at 5.92 min Example 6

Procedure 2

4-{(2S,4R)-1-Acetyl-4-[(4-chlorophenyl)amino]-2-methyl-1,2,3,4-tetrahydro-6-quinolinyl}benzoic acid

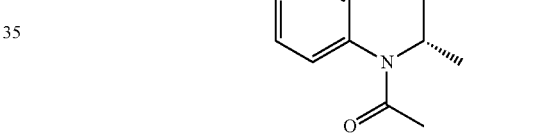

Ethyl 4-{(2S,4R)-1-acetyl-4-[(4-chlorophenyl)amino]-2-methyl-1,2,3,4-tetrahydro-6-quinolinyl}benzoate (for a preparation see Example 158) (5.41 g, 11.69 mmol) was dissolved in ethanol (100 mL) and the solution was treated with 2M NaOH aqueous solution (50 mL, 100 mmol). The resulting mixture was stirred at room temperature (air atmosphere) for approximately 2 h then most of the ethanol was removed in vacuo. The resulting yellow solution was diluted with water (resulting in the formation of an oily yellow precipitate). The aqueous phase was washed twice with DCM (which didn't dissolve the precipitate previously formed) then was acidified with a 2N hydrochloric acid aqueous solution to pH 1 and extracted twice with AcOEt. The combined AcOEt phases were washed with brine, dried using a hydrophobic frit and concentrated in vacuo. The residual yellow foam was triturated with Et₂O over approximately 1 h. The resulting solid was isolated by filtration, washed with Et₂O and air-dried to give 4-{(2S,4R)-1-acetyl-4-[(4-chlorophenyl)amino]-2-methyl-1,2,3,4-tetrahydro-6-quinolinyl}benzoic acid (4.41 g, 10.1 mmol, 87%) as a cream solid.

LCMS (high pH): Retention time 1.08 min, [M−H]−=433.16

Examples 7 to 10 were prepared by similar methods to that described for Example 6 Process 1 (see Table 6):

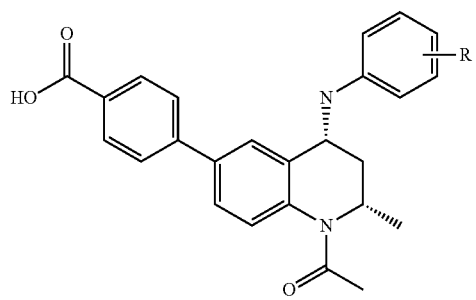

TABLE 6

| Ex | R | From Example | Physical data |
|---|---|---|---|
| 7 | 4-F | 2 | HRMS (M + H)⁺: calculated for C$_{25}$H$_{23}$FN$_2$O$_3$<br>Theo: 419.1771<br>Found: 419.1756<br>Rt: 2.10 min<br>ee = 97.2% |
| 8 | 4-CH$_3$ | 3 | HRMS (M + H)⁺: calculated for C$_{26}$H$_{26}$N$_2$O$_3$<br>Theo: 415.2021<br>Found: 415.2042<br>Rt: 2.14 min<br>ee > 99% |
| 9 | 4-CF$_3$ | 4 | HRMS (M + H)⁺: calculated for C$_{26}$H$_{23}$F$_3$N$_2$O$_3$<br>Theo: 469.1739<br>Found: 469.1754<br>Rt: 2.28 min<br>ee > 99% |
| 10 | 3-CF$_3$ | 5 | HRMS (M + H)⁺: calculated for C$_{26}$H$_{23}$F$_3$N$_2$O$_3$<br>Theo: 469.1739<br>Found: 469.1772<br>Rt: 2.24 min<br>ee = 95.4% |

Example 11

1-Acetyl-2-methyl-N-(4-fluorophenyl)-6-[4-(1-piperidinylmethyl)phenyl]-1,2,3,4-tetrahydro-4-quinolinamine

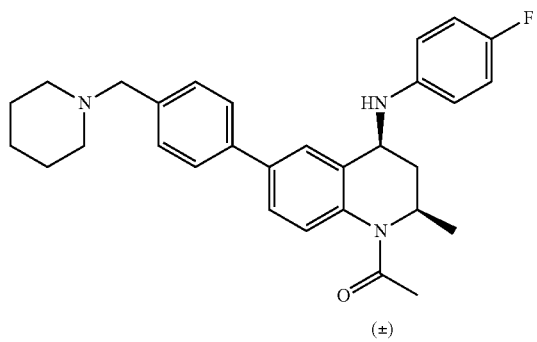 [SMILES: CC(=O)N1c2ccc(-c3ccc(CN4CCCCC4)cc3)cc2[C@@H](Nc2ccc(F)cc2)C[C@H]1C]

The resulting dark-blue to turquoise mixture of the intermediate 25 (188 mg, 0.5 mmol), 4-fluoro-phenyl boronic acid (210 mg, 1.5 mmol), anhydrous cupric acetate (135 mg, 0.75 mmol), triethylamine (156 mg, 1.5 mmol) in dry DCM (10 ml) was stirred at room temperature for 48-72 hr. Progression of the reaction was monitored by tlc and if necessary an additional equivalent of boronic acid and triethylamine was added and the mixture allowed to stir at room temperature for further 12 hr. This operation was repeated until the amount of the expected product exceeded the remaining proportion of the starting intermediate. The resulting mixture was poured into water (15 ml) and the organic phase was extracted with DCM (100 mL), dried over Na$_2$SO$_4$, filtered and evaporated to dryness. The resulting residue was purified by flash column chromatography on silica gel eluting with a mixture of toluene/isopropylamine 95/5 and precipitated from DCM/hexane to give the title compound as a pale yellow powder (53 mg, 22%), mp: 106° C.

HRMS calculated for C$_{30}$H$_{34}$FN$_3$O (M+H)⁺472.2764. Found: 472.2786. Rt: 3.04 min Examples 12 to 34 were prepared by similar methods to that described for Example 11 using the appropriate boronic acid derivative and suitable precipitation or recrystallisation conditions (see Table 7):

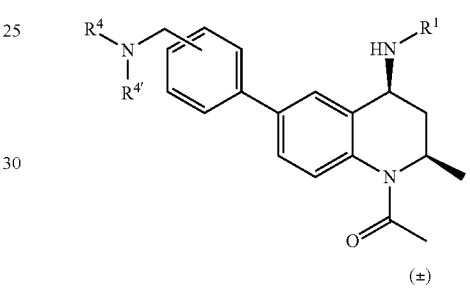

TABLE 7

| Ex | R$^1$ | R$^4$NR$^{4'}$ | From intermediate | Physical data |
|---|---|---|---|---|
| 12 | 4-CF$_3$—Ph | 4-piperidinyl | 25 | HRMS (M + H)⁺:<br>calculated for<br>C$_{31}$H$_{34}$F$_3$N$_3$O<br>Theo: 522.2732<br>Found: 522.2692<br>Rt: 3.18 min<br>MP: 104° C. |
| 13 | 4-OMe—Ph | 4-piperidinyl | 25 | HRMS (M + H)⁺:<br>calculated for<br>C$_{31}$H$_{37}$N$_3$O$_2$<br>Theo: 484.2964<br>Found: 484.2929<br>Rt: 2.78 min<br>MP: 80° C. |
| 14 | 4-Cl—Ph | 4-piperidinyl | 25 | HRMS (M + H)⁺:<br>calculated for<br>C$_{30}$H$_{34}$ClN$_3$O<br>Theo: 488.2469<br>Found: 488.2491<br>Rt: 3.34 min<br>MP: 128° C. |
| 15 | 4-CH$_3$—Ph | 4-piperidinyl | 25 | HRMS (M + H)⁺:<br>calculated for<br>C$_{31}$H$_{37}$N$_3$O<br>Theo: 468.3015<br>Found: 468.2986<br>Rt: 3.15 min<br>MP: 90° C. |

TABLE 7-continued

| Ex | R¹ | R⁴NR⁴' | | From intermediate | Physical data |
|---|---|---|---|---|---|
| 16 | 4-CO₂CH₃—Ph | 4- |  | 25 | HRMS (M + H)⁺: calculated for $C_{31}H_{37}N_3O$ Theo: 512.2913 Found: 512.2862 Rt: 2.77 min MP: 109° C. |
| 17 | Ph | 4- |  | 25 | HRMS (M + H)⁺: calculated for $C_{30}H_{35}N_3O$ Theo: 454.2858 Found: 454.2832 Rt: 2.92 min MP: 100° C. |
| 18 | 3-Cl—Ph | 4- |  | 25 | HRMS (M + H)⁺: calculated for $C_{30}H_{34}ClN_3O$ Theo: 488.2469 Found: 488.2467 Rt: 3.13 min MP: 150° C. |
| 19 | 3-CH₃—Ph | 4- |  | 25 | HRMS (M + H)⁺: calculated for $C_{31}H_{37}N_3O$ Theo: 468.3015 Found: 468.3008 Rt: 3.08 min MP: 140° C. |
| 20 | 3-F—Ph | 4- |  | 25 | HRMS (M + H)⁺: calculated for $C_{30}H_{34}FN_3O$ Theo: 472.2764 Found: 472.2770 Rt: 3.13 min MP: 172° C. |
| 21 | 3-CF₃—Ph | 4- |  | 25 | HRMS (M + H)⁺: calculated for $C_{31}H_{34}F_3N_3O$ Theo: 522.2732 Found: 522.2747 Rt: 3.41 min MP: 196° C. |
| 22 | 4F,3CH₃—Ph | 4- |  | 25 | HRMS (M + H)⁺: calculated for $C_{31}H_{36}FN_3O$ Theo: 486.2921 Found: 486.2935 Rt: 3.18 min MP: 140° C. |
| 23 | 3Cl,4OMe—Ph | 4- |  | 25 | HRMS (M + H)⁺: calculated for $C_{31}H_{36}ClN_3O_2$ Theo: 518.2574 Found: 518.2596 Rt: 2.98 min MP: 89° C. |
| 24 | 3Cl,4-Cl—Ph | 4- |  | 25 | HRMS (M + H)⁺: calculated for $C_{30}H_{33}Cl_2N_3O$ Theo: 522.2079 Found: 522.2032 Rt: 3.37 min MP: 164° C. |
| 25 | 3-Cl,5-Cl—Ph | 4- |  | 25 | HRMS (M + H)⁺: calculated for $C_{30}H_{33}Cl_2N_3O$ Theo: 522.2079 Found: 522.2024 Rt: 3.46 min MP: 203° C. |
| 26 | 3-Py | 4- |  | 25 | HRMS (M + H)⁺: calculated for $C_{29}H_3N_4O$ Theo: 455.2811 Found: 455.2788 Rt: 2.35 min MP: 170° C. |
| 27 | Ph | 4- |  | 28 | HRMS (M + H)⁺: calculated for $C_{29}H_{33}N_3O$ Theo: 440.2702 Found: 440.2664 Rt: 2.63 min MP: 96° C. |
| 28 | Ph | 4- |  | 26 | HRMS (M + H)⁺: calculated for $C_{29}H_{33}N_3O_2$ Theo: 456.2652 Found: 456.2619 Rt: 2.98 min MP: 80° C. |
| 29 | Ph | 4- |  | 27 | HRMS (M + H)⁺: calculated for $C_{30}H_{36}N_4O$ Theo: 469.2967 Found: 469.2939 Rt: 2.91 min MP: 110° C. |
| 30 | Ph | 3- |  | 31 | HRMS (M + H)⁺: calculated for $C_{30}H_{35}N_3O$ Theo: 454.2858 Found: 454.2867 Rt: 3.05 min |
| 31 | Ph | 3- |  | 32 | HRMS (M + H)⁺: calculated for $C_{29}H_{33}N_3O_2$ Theo: 456.2652 Found: 456.2620 Rt: 3.02 min |
| 32 | Ph | 3-N(Me)₂ | | 33 | HRMS (M + H)⁺: calculated for $C_{27}H_{31}N_3O$ Theo: 414.2545 Found: 414.2565 Rt: 2.8 min 72° C. |
| 33 | Ph | 3- |  | 29 | HRMS (M + H)⁺: calculated for $C_{30}H_{36}N_4O$ Theo: 469.2967 Found: 469.2982 Rt: 2.92 min |
| 34 | Ph | 3- |  | 30 | HRMS (M + H)⁺: calculated for $C_{29}H_{33}N_3O$ Theo: 440.2702 Found: 440.2640 Rt: 2.71 min | where Ph represents phenyl, Me represents methyl and Py represents pyridinyl

Examples 35 to 61 were prepared using the general methodology in the scheme below

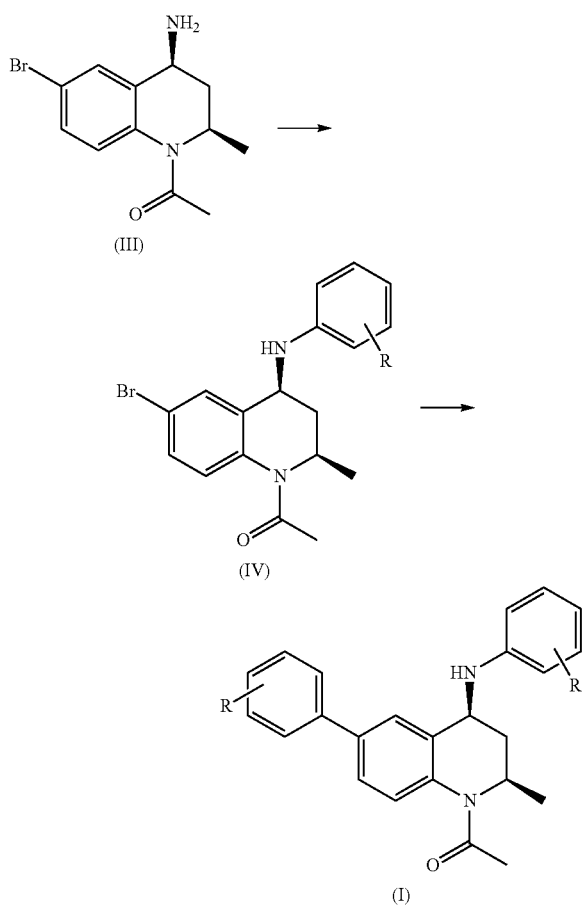

wherein the R groups fall within the general definitions given for the relevant substituent in compounds of formula (I).

Example 35

1-acetyl-6-{4-[(dimethylamino)methyl]phenyl}-2-methyl-N-phenyl-1,2,3,4-tetrahydro-4-quinolinamine

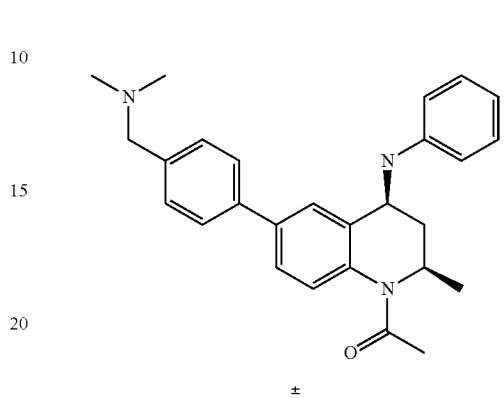

To a solution of intermediate 39 (100 m g, 0.28 mmol) in 1,2-dimethoxyethane (4 mL), was added N,N-dimethyl-1-[4-(4,4,5,5-tetramethyl-1,3,2-dioxaborolan-2-yl)phenyl]methan-amine (100 mg, 0.41 mmol), sodium carbonate (0.8 mL, 2N solution in water)) and Pd(PPh$_3$)$_4$ (20 mg) and the mixture was stirred under reflux for 20 hours. The solvent was then removed under reduced pressure and EtOAC (100 mL) was added to the residue. The organic phase was washed with brine, dried over Na$_2$SO$_4$, filtered and evaporated to dryness. The solid was purified by flash column chromatography eluting with CH$_2$Cl$_2$/MeOH: 90/10 to give the title compound as a white powder after trituration in DCM/hexane (38 mg, 33%), mp: 90° C.

HRMS calculated for C$_{27}$H$_{31}$N$_3$O (M+H)$^+$ 414.2545 found: 414.2554. Rt=2.81 min.

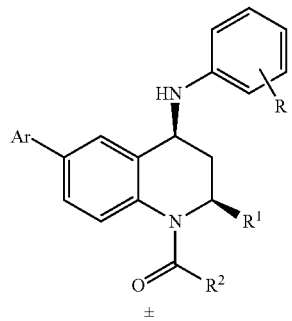

| Ex | Ar | R | R1 | R$^2$ | From intermediate | Physical data |
|---|---|---|---|---|---|---|
| 36 | 4-Ph—CH$_2$OH | H | CH$_3$ | CH$_3$ | 39 | HRMS (M + Na)$^+$: calculated for C$_{25}$H$_{26}$N$_2$NaO$_2$ Theo: 409.1892 Found: 409.1899 Rt: 2.63 min MP: 101.6° C. |

-continued

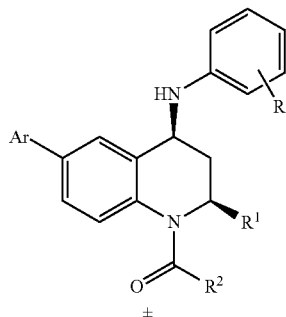

±

| Ex | Ar | R | R1 | R² | From intermediate | Physical data |
|---|---|---|---|---|---|---|
| 37 | 4-Ph—CN | H | $CH_3$ | $CH_3$ | 39 | HRMS (M − H)⁻: calculated for $C_{25}H_{23}N_3O$<br>Theo: 380.1763<br>Found: 380.1734<br>Rt: 2.63 min<br>MP: 104° C. |
| 38 | 4-Ph—CO₂Me | H | $CH_3$ | $CH_3$ | 39 | HRMS (2M + H)⁺: calculated for $C_{52}H_{52}N_4O_6$<br>Direct injection<br>Theo: 829.3964<br>Found: 829.3978<br>MP: 90° C. |
| 39 | Ph | H | $CH_3$ | $CH_3$ | 39 | HRMS (2M + H)⁺: calculated for $C_{48}H_{48}N_4O_2$<br>Direct injection<br>Theo: 713.3756<br>Found: 713.3691<br>MP: 186° C. |
| 40 | 4-Ph—CF₃ | H | $CH_3$ | $CH_3$ | 39 | HRMS (M + H)⁺: calculated for $C_{25}H_{23}F_3N_2O$<br>Theo: 425.1841<br>Found: 425.1817<br>Rt: 3.44 min<br>MP: 85° C. |
| 41 | 4-Ph—OMe | H | $CH_3$ | $CH_3$ | 39 | HRMS (M + H)⁺: calculated for $C_{25}H_{23}F_3N_2O$<br>Theo: 387.2072<br>Found: 387.2088<br>Rt: 3.22 min<br>MP: 86° C. gummy |
| 42 | ![pyrrole-Boc] | H | $CH_3$ | $CH_3$ | 39 | HRMS (M + Na)⁺: calculated for $C_{27}H_{31}N_3NaO_3$<br>Theo: 468.2264<br>Found: 468.2257<br>Rt: 3.34 min<br>MP: 94° C. |
| 43 | 2-Ph—OMe | 4-Cl | $CH_3$ | $CH_3$ | 40 | HRMS (M + H)⁺: calculated for $C_{25}H_{25}N_2O_2Cl$<br>Theo: 421.1683<br>Found: 421.1378<br>Rt: 3.40 min<br>MP: 173° C. |

-continued

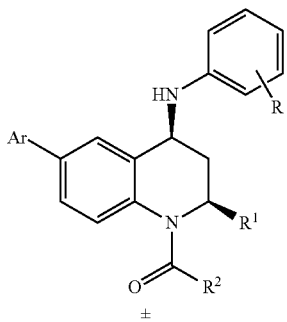

| Ex | Ar | R | R1 | R² | From intermediate | Physical data |
|---|---|---|---|---|---|---|
| 44 | 4-Ph—OMe | 4-Cl | CH₃ | CH₃ | 40 | HRMS (M + H)⁺: calculated for $C_{25}H_{25}N_2O_2Cl$ Theo: 421.1683 Found: 421.1711 Rt: 3.40 min MP: 180° C. |
| 45 | 3-Pyr | H | CH₃ | CH₃ | 39 | HRMS (M + H)⁺: calculated for $C_{23}H_{23}N_3O$ Theo: 358.1919 Found: 358.1913 Rt: 2.64 min MP: 181° C. |
| 46 | 3-Ph—F | 4-Cl | CH₃ | CH₃ | 40 | HRMS (M + Na)⁺: calculated for $C_{24}H_{22}ClFN_2O$ Theo: 409.1483 Found: 409.1457 Rt: 3.46 min MP: 165° C. |
| 47 | ![1-methylpyrazole] | 4-Cl | CH₃ | CH₃ | 40 | HRMS (M + H)⁺: calculated for $C_{22}H_{23}ClN_4O$ Theo: 395.1638 Found: 395.1642 Rt: 2.71 min MP: 181° C. gummy |
| 48 | ![2-methoxypyridine] | 4-Cl | CH₃ | CH₃ | 40 | HRMS (M + H)⁺: calculated for $C_{24}H_{24}ClN_3O_2$ Theo: 422.1635 Found: 42.1627 Rt: 3.20 min MP: 92.8° C. |
| 49 | ![cyanothiophene] | 4-Cl | CH₃ | CH₃ | 40 | HRMS (M + Na)⁺: calculated for $C_{46}H_{40}Cl_2N_6O_2S_2$ Theo: 843.2110 Found: 843.2108 Rt: 3.28 min MP: 97.2° C. |
| 50 | ![thiophene] | 4-Cl | CH₃ | CH₃ | 40 | HRMS (M + H)⁺: calculated for $C_{22}H_{21}ClN_2OS$ Theo: 397.1141 Found: 397.1175 Rt: 3.37 min MP: 173.9° C. gummy |

-continued

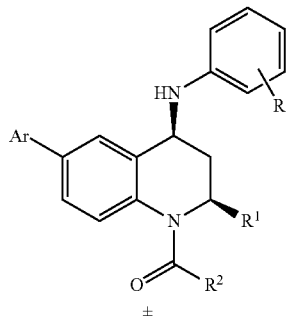

±

| Ex | Ar | R | R1 | R² | From intermediate | Physical data |
|---|---|---|---|---|---|---|
| 51 | ![1-methylindol-5-yl] | 4-Cl | $CH_3$ | $CH_3$ | 40 | HRMS $(2M + H)^+$: calculated for $C_{54}H_{52}Cl_2N_6O_2$ Theo: 887.3608 Found: 887.3567 Rt: 3.40 min MP: 156° C. gummy |
| 52 | ![furan-3-yl] | 4-Cl | $CH_3$ | $CH_3$ | 40 | HRMS $(M + H)^+$: calculated for $C_{22}H_{21}ClN_2O_2$ Theo: 381.1370 Found: 381.1361 Rt: 3.21 min |
| 53 | 4-Ph—$CH_3$ | 4-Cl | $CH_3$ | $CH_3$ | 40 | HRMS $(M + H)^+$: calculated for $C_{25}H_{25}ClN_2O_2$ Theo: 405.1733 Found: 405.1703 Rt: 3.59 min MP: 153° C. |
| 54 | 4-Ph—$^tBu$ | 4-Cl | $CH_3$ | $CH_3$ | 40 | HRMS $(M + H)^+$: calculated for $C_{28}H_{31}ClN_2O$ Theo: 447.2203 Found: 447.2238 Rt: 3.96 min MP: 194° C. |
| 55 | 4-Ph—$CF_3$ | 4-Cl | $CH_3$ | $CH_3$ | 40 | HRMS $(M + H)^+$: calculated for $C_{25}H_{22}ClF_3N_2O$ Theo: 459.1451 Found: 459.1407 Rt: 3.65 min MP: 164° C. |
| 56 | ![2-fluoropyridin-5-yl] | 4-Cl | $CH_3$ | $CH_3$ | 40 | HRMS $(M + H)^+$: calculated for $C_{23}H_{21}ClN_3O$ Theo: 410.1435 Found: 410.1458 Rt: 3.11 min MP: 165° C. |

-continued

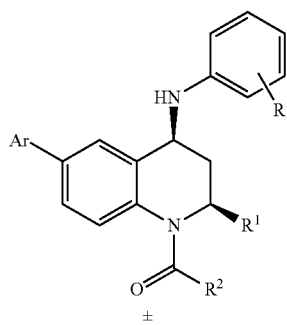

| Ex | Ar | R | R1 | R² | From intermediate | Physical data |
|---|---|---|---|---|---|---|
| 57 | (3-pyridyl) | 4-Cl | CH₃ | CH₃ | 40 | HRMS (M + H)⁺: calculated for C₂₃H₂₂ClN₃O Theo: 392.1529 Found: 392.1530 Rt: 2.87 min MP: 168° C. |
| 58 | 3-Ph—CH₃ | 4-Cl | CH₃ | CH₃ | 40 | HRMS (M + H)⁺: calculated for C₂₅H₂₅ClN₂O Theo: 405.1733 Found: 404.1764 Rt: 3.58 min MP: 87.7° C. |
| 59 | 3-(methyl benzoate) | 4-Cl | CH₃ | CH₃ | 40 | HRMS (M + H)⁺: calculated for C₂₆H₂₅ClN₂O₃ Theo: 449.1632 Found: 449.1638 Rt: 3.36 min MP: 98° C. |
| 60 | 4-Ph—F | 4-Cl | CH₃ | CH₃ | 40 | HRMS (M + H)⁺: calculated for C₂₄H₂₂ClFN₂O Theo: 409.1483 Found: 409.1493 Rt: 3.39 min |
| 61 | 4-OMe—Ph | H | CH₃ | CH₂CH₃ | 41 | HRMS (M + H)⁺: calculated for C₂₆H₂₇ClN₂O₂ Theo: 401.2229 Found: 401.2231 Rt: 3.37 min MP: 90.5° C. |

Examples 62 to 85 were prepared using the general methodology in the scheme below

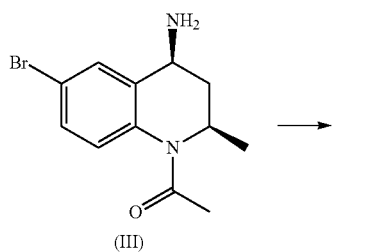
(III)

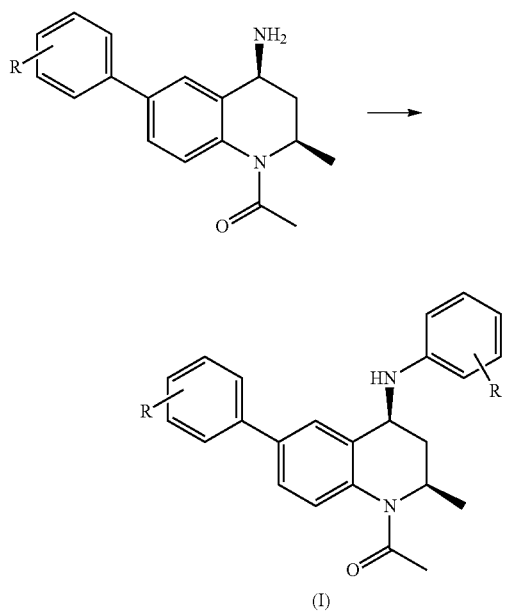
(I)

wherein the R groups fall within the general definitions given for the relevant substituent in compounds of formula (I).

Example 62

4-{1-acetyl-4-[(4-fluorophenyl)amino]-2-methyl-1,2,3,4-tetrahydro-6-quinolinyl}benzonitrile

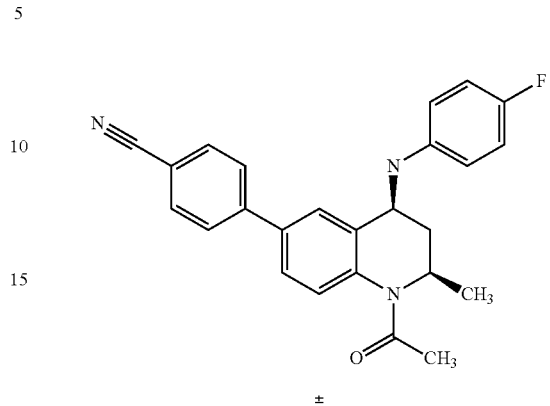

The resulting dark-blue to turquoise mixture of the intermediate 42 (305 mg, 1 mmol), 4-fluoro-phenyl boronic acid (420 mg, 3 mmol), anhydrous cupric acetate (271 mg, 1.5 mmol), triethylamine (156 mg, 1.5 mmol) in dry DCM (10 ml) was stirred at room temperature for 48-72 hr. Progression of the reaction was monitored by tlc and if necessary an additional equivalent of phenyl boronic acid and triethylamine was added and the mixture allowed to stir at room temperature for further 12 hr. This operation was repeated until the amount of the expected product exceeded the remaining proportion of the starting intermediate. The resulting mixture was poured into water (15 ml) and the organic phase was extracted with DCM (100 mL). After washing with aqueous ammonia (25 mL), 1N HCL (25 mL) and water (25 mL) drying over $Na_2SO_4$ the organic layer was filtered and evaporated to dryness. The resulting residue was flashchromatographied on silica gel eluting with a mixture of DCM/MeOH 90/10. The gummy residue was taken up in hot hexane and after filtration and evaporation to dryness the title compound was obtained (253 mg), mp: 140° C. HRMS calculated for $C_{25}H_{23}FN_3O$ $(M+H)^+$ 400.1825 found: 400.1828 Rt=3.09 min.

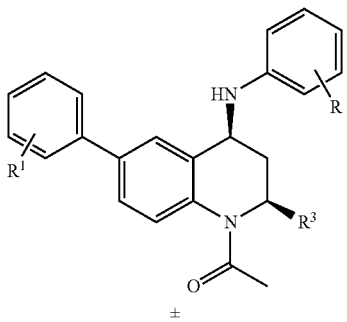

| Ex | $R^1$ | $R^2$ | $R^3$ | From Intermediate | Physical data |
|---|---|---|---|---|---|
| 63 | 4-CN | 4-Cl | $CH_3$ | 42 | HRMS calculated for $C_{25}H_{22}ClN_3O$ $(M + H)^+$ Theo: 416.1530 found: 416.1500 Rt: 3.23 min MP: 126° C. |

-continued

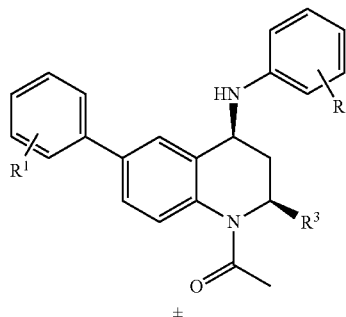

±

| Ex | R¹ | R² | R³ | From Intermediate | Physical data |
|---|---|---|---|---|---|
| 64 | 4-CN | 3-F | $CH_3$ | 42 | HRMS calculated for $C_{25}H_{22}FN_3O$ $(M - H)^-$ Theo: 398.1669 found: 398.1712. Rt: 2.98 min MP: 124° C. |
| 65 | 4-CN | 4-$CF_3$ | $CH_3$ | 42 | HRMS calculated for $C_{26}H_{22}F_3N_3O$ $(M - H)^-$ Theo: 448.1637 found: 448.1675 Rt: 3.17 min MP: 139° C. |
| 66 | 4-CN | 3-Cl | $CH_3$ | 42 | HRMS calculated for $C_{25}H_{22}ClN_3O$ $(M + CH3COOH - H)^-$ Theo: 474.1897 found: 474.1853 Rt: 3.10 min MP: 142° C. |
| 67 | 4-CN | 3-OMe | $CH_3$ | 42 | HRMS calculated for $C_{26}H_{25}N_3O_2$ $(M + H)^+$: Theo: 412.2025 found: 412.2035 Rt: 3.03 min MP: 104° C. |
| 68 | 4-$CO_2CH_3$ | 4-Cl | $CH_3$ | 34 | HRMS calculated for $C_{26}H_{25}N_3O_2$ $(M + H)^+$: Theo: 449.1632 found: 449.1644 Rt: 3.57 min MP: 84° C. |
| 69 | 4-CN | 4-$CH_3$ | $CH_3$ | 42 | HRMS calculated for $C_{25}H_{25}N_3O$ $(M + CH3COOH)^+$ Theo: 454.2131 found: 454.2155 Rt: 3.17 min MP: 168° C. |
| 70 | 4-CN | 2-$OCH_3$ | $CH_3$ | 42 | HRMS calculated for $C_{26}H_{25}N_3O_2$ $(M + H)^+$: Theo: 412.2025 found: 412.2055 Rt: 3.20 min MP: 192° C. |
| 71 | 4-CN | 4-$SO_2CH_3$ | $CH_3$ | 42 | HRMS calculated for $C_{26}H_{25}N_3NaO_3S$ $(M + Na)+$ Theo: 482.1514 found: 482.1506 Rt: 2.61 min MP: 130° C. |

-continued

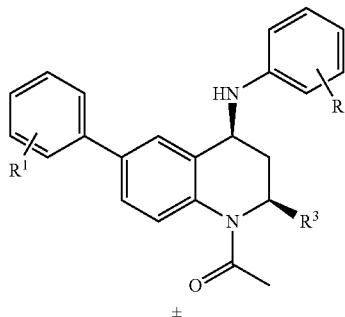

| Ex | R¹ | R² | R³ | From Intermediate | Physical data |
|---|---|---|---|---|---|
| 72 | 4-CN | 3-CF₃ | CH₃ | 42 | HRMS calculated for $C_{26}H_{22}F_3N_3O$ $(M + H)^+$: Theo: 450.1793 found: 450.1833 Rt: 3.28 min MP: 108° C. |
| 73 | para- pyrrolidinyl-ethoxy | meta-Cl | CH₃ | 35 | HRMS calculated for $(M + H)^+$ $C_{30}H_{39}ClN_3O_2$ Theo: 504.2418 found: 504.2472 Rt: 2.9 min MP: 108° C. |
| 74 | para- pyrrolidinyl-ethoxy | para-CF₃ | CH₃ | 35 | HRMS calculated for $(M + H)^+$ $C_{31}H_{34}F_2N_3O_2$ Theo: 538.2681 found: 538.2717 Rt: 3.01 min MP: 155° C. |
| 75 | para- pyrrolidinyl-ethoxy | para-Cl | CH₃ | 35 | HRMS calculated for $(M + H)^+$ $C_{30}H_{34}ClN_3O_2$ Theo: 504.2418 found: 504.2467 Rt: 2.94 min MP: 140° C. |
| 76 | para- pyrrolidinyl-ethoxy | meta-OCH₃ | CH₃ | 35 | HRMS calculated for $(M + H)^+$ $C_{31}H_{37}N_3O_3$ Theo: 500.2913 found: 500.2905 Rt: 2.65 min MP: 104° C. |
| 77 | para- pyrrolidinyl-ethoxy | para-F | CH₃ | 35 | HRMS calculated for $(M + H)^+$ $C_{30}H_{34}N_3O_2F$ Theo: 488.2713 found: 488.2677 Rt: 2.73 min MP: 94° C. |
| 78 | para- pyrrolidinyl-ethoxy | para-SO₂CH₃ | CH₃ | 35 | HRMS calculated for $(M + H)^+$ $C_{31}H_{37}N_3O_4S$ Theo: 548.2583 found: 548.2597 Rt: 2.28 min MP: 115° C. |

-continued

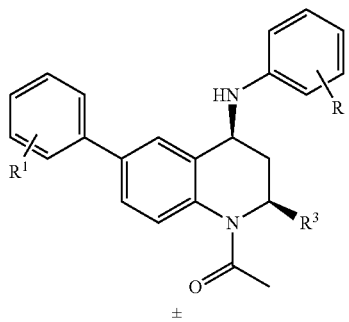

| Ex | R¹ | R² | R³ | From Intermediate | Physical data |
|---|---|---|---|---|---|
| 79 | para- pyrrolidin-1-yl-ethoxy | meta-F | CH₃ | 35 | HRMS calculated for (M + H)⁺ $C_{30}H_{34}FN_3O_2$ Theo: 488.2713 found: 488.2708 Rt: 2.76 min MP: 132° C. |
| 80 | 4-CO₂CH₃ | para-F | CH₃ | 34 | HRMS calculated for (M + H)⁺ $C_{26}H_{25}FN_2O_3$ Theo: 433.1927 found: 433.1967 Rt: 3.17 min MP: 95° C. |
| 81 | 4-CO₂CH₃ | meta-OCH₃ | CH₃ | 34 | HRMS calculated for (M + H)⁺ $C_{27}H_{28}N_2O_4$ Theo: 445.2127 found: 445.2116 Rt: 3.07 min MP: 68° C. |
| 82 | 4-CO₂CH₃ | para-CN | CH₃ | 34 | HRMS calculated for (M + H)⁺ $C_{27}H_{25}N_3O_3$ Theo: 438.1818 found: 438.1815 Rt: 2.96 min MP: 252° C. |
| 83 | 4-CO₂CH₃ | 3,4-OCH₂O | CH₃ | 34 | HRMS calculated for (M + H)⁺ $C_{27}H_{26}N_2O_5$ Theo: 459.1926 found: 459.1942 Rt: 3.08 min MP: 154° C. |
| 84 | 4-CO₂CH₃ | para-ᵗBu | CH₃ | 34 | HRMS calculated for (M + H)⁺ $C_{30}H_{34}N_2O_3$ Theo: 471.2648 found: 416.2683 Rt: 3.73 min MP: 144° C. |
| 85 | 4-CO₂CH₃ | 2-OMe | CH₃ | 34 | LC/MS: m/z 445 [M + H]⁺, Rt = 3.51 min |
| 86 | 4-OMe | 4-Cl | CH₂CH₃ | 36 | HRMS calculated for $C_{26}H_{27}ClN_2O_2$ (M + H)⁺: Theo: 435.1839 Found: 435.1861 Rt: 3.49 min MP: 108° C. |

Example 87

1-acetyl-N-ethyl-2-methyl-N,6-diphenyl-1,2,3,4-tetrahydro-4-quinolinamine

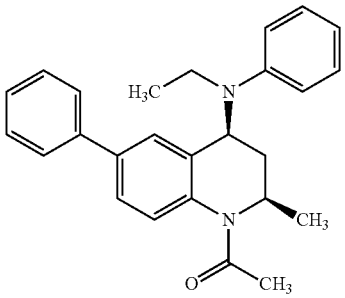 [SMILES: CCN(c1ccccc1)[C@H]1C[C@@H](C)N(C(C)=O)c2ccc(-c3ccccc3)cc21]

To a solution of example 39 (96 mg, 0.27 mmol) in 1,2-dichloroethane (2 mL) was added acetaldehyde (20 µL, 0.35 mmol), NaHB(OAc)$_3$ and acetic acid (30 µL, 0.54 mmol). The mixture was stirred at room temperature under a nitrogen atmosphere for 48 hours. The reaction progression was monitored by LC/MS and additional portions of aldehyde, NaHB(OAc)$_3$ and acetic acid were added until total completion of the reaction. After total consumption of the starting amine the mixture was poured in a saturated NaHCO$_3$ solution. The organics were extracted with DCM, washed with water and brine and dried over Na$_2$SO$_4$. After concentration under reduced pressure the residue was flash chromatographied eluting with DCM and recristallised in hexane to afford the title compound as an off-white powder (85 mg, 82%), mp: 121° C.

HRMS calculated for C$_{26}$H$_{28}$N$_2$O (M+H)$^+$ 385.2280 found: 385.2298 Rt=3.70 min.

Examples 88 to 90 were prepared by similar methods to that described for Example 87

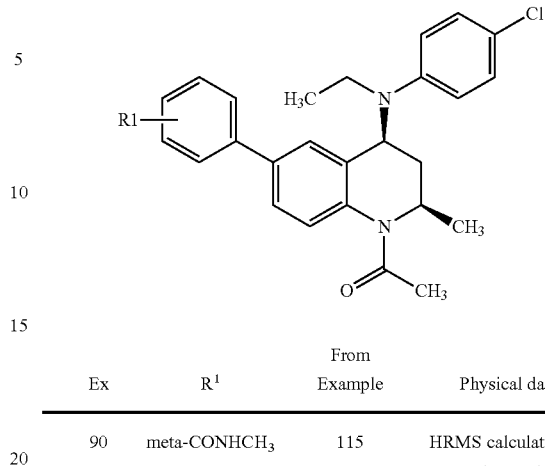

| Ex | R$^1$ | From Example | Physical data |
|----|-------|--------------|---------------|
| 88 | Para-CO$_2$CH$_2$CH$_3$ | 119 | HRMS calculated for C$_{29}$H$_{31}$ClN$_2$O$_3$ (M + H)$^+$ Theo: 491.2101 found: 491.2125 Rt: 3.88 min MP: 84° C. |
| 89 | Para-CO$_2$CH$_3$ | 68 | HRMS calculated for C$_{28}$H$_{29}$ClN$_2$O$_3$ (M + H)$^+$ Theo: 477.1945 found: 477.1988 Rt: 3.74 min |
| 90 | meta-CONHCH$_3$ | 115 | HRMS calculated for C$_{28}$H$_{30}$ClN$_3$O$_2$ (M + H)$^+$ Theo: 476.2105 found: 476.2115 Rt: 3.10 min MP: 145° C. |

Example 91

4-[1-Acetyl-2-methyl-4-(phenylamino)-1,2,3,4-tetrahydro-6-quinolinyl]benzoic acid

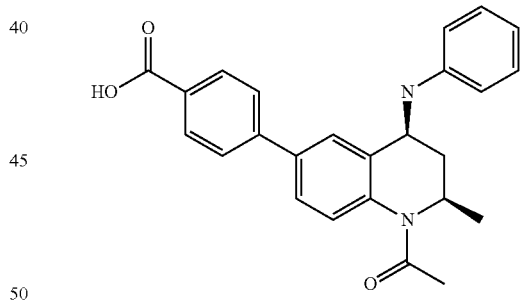

A solution of example 38 (200 mg, 0.48 mmol) in EtOH (4 ml) and 1N NaOH (1 ml, 1 mmol) was heated to 60° C. After 1 hour a tlc monitoring indicated the completion of the reaction. The crude mixture was evaporated to dryness and the residue taken up in water (20 mL). AcOH was added until PH 4-5. The organic materials were extracted with DCM (2×75 mL) and the organic phase combined and washed with brine and dried over Na2SO4. After concentration under vacuo the title compound was obtained as a white powder (150 mg, 78%), mp: 246° C. HRMS calculated for C$_{25}$H$_{24}$N$_2$O$_3$ (M−H)$^−$ 399.1709. Found: 399.1691. Rt: 2.02 min Examples 92 to 100 were prepared by similar methods to that described for Example 91

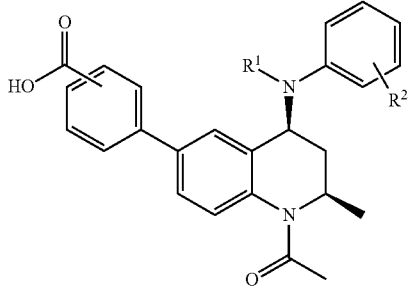
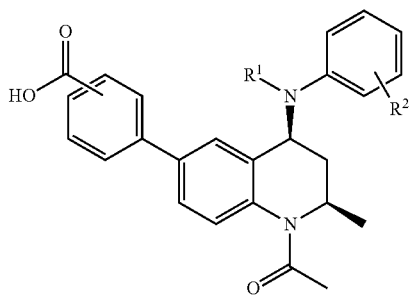

| Ex | Acid position | R¹ | R² | From Example | Physical data |
|---|---|---|---|---|---|
| 92 | para | H | 4-Cl | 68 | HRMS calculated for $C_{25}H_{23}N_2O_3Cl$ (M − H)⁻<br>Theo: 433.1319<br>found: 433.1309<br>Rt: 2.08 min<br>MP: 166° C. |
| 93 | para | H | 4-F | 80 | HRMS calculated for $C_{25}H_{23}N_2O_3F$ (M + H)⁺<br>Theo: 419.1771<br>found: 419.1793<br>Rt: 2.5 min<br>MP: 148° C. |
| 94 | meta | H | 4-Cl | 59 | HRMS calculated for $C_{25}H_{23}N_2O_3Cl$ (M + H)⁺<br>Theo: 435.1475<br>found: 435.1502<br>Rt: 2.19 min<br>MP: 152° C. |
| 95 | para | H | 3-OCH₃ | 81 | HRMS calculated for $C_{26}H_{26}N_2O_4$ (M + H)⁺<br>Theo: 431.1937<br>found: 431.1994<br>Rt: 2.0 min<br>MP: 146° C. |
| 96 | para | H | 4-CN | 82 | HRMS calculated for $C_{26}H_{23}N_3O_3$ (M + H)⁺<br>Theo: 443.2084<br>found: 443.2090<br>Rt: 1.98 min |
| 97 | para | H | 4-tBu | 84 | HRMS calculated for $C_{29}H_{32}N_3O_3$ (M + H)⁺<br>Theo: 457.2491<br>found: 457.2515<br>Rt: 2.49 min<br>MP: 168° C. |
| 98 | para | H | 3,4-OCH₂O | 83 | HRMS calculated for $C_{26}H_{24}N_2O_5$ (M + H)⁺<br>Theo: 445.1763<br>found: 445.1797<br>Rt: 2.29 min<br>MP: 184° C. |
| 99 | para | H | 2-OCH₃ | 85 | HRMS calculated for $C_{26}H_{26}N_2O_4$ (M + H)⁺<br>Theo: 431.2032<br>found: 431.2028<br>Rt: 2.15 min |
| 100 | para | CH₂CH₃ | 4-Cl | 86 | HRMS calculated for $C_{27}H_{27}ClN_2O_3$ (M + H)⁺<br>Theo: 463.1788<br>found: 463.1779<br>Rt: 2.42 min<br>MP: 140° C. |

Example 101

4-{1-Acetyl-4-[(4-chlorophenyl)amino]-2-methyl-1,2,3,4-tetrahydro-6-quinolinyl}-N-ethylbenzamide

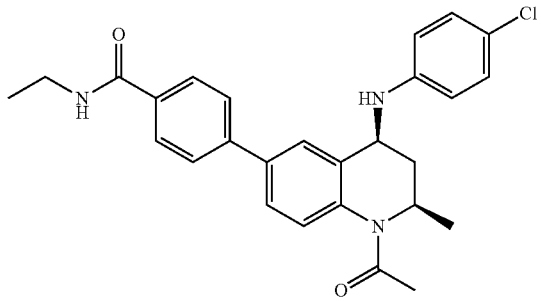 [SMILES: CCNC(=O)c1ccc(-c2ccc3c(c2)[C@@H](Nc2ccc(Cl)cc2)C[C@@H](C)N3C(C)=O)cc1]

To a solution of example 92 (217 mg, 0.5 mmol) in DCM (10 mL) at RT was added HOBt (90 mg, 0.65 mmol), EDCl (124 mg, 0.65 mmol), Et₃N (152 mg, 1.5 mmol) followed by the addition of ethylamine (375 μL, 2M in THF, 0.75 mmol). The mixture was solubilised by adding few drops of DMF, heated to reflux 48 hours and poured in water. The aqueous layer was extracted with DCM and organics were washed with 1N NaOH and brine. After drying over Na₂SO₄, filtration and concentrated in vacuo the crude product was purified by flash chromatography on silica gel ($C_6H_{12}$/EtOAc: 80/20 then DCM/MeOH: 98/2). Trituration of the residue in hexane afforded the title compound (103 mg, 44%) as a white solid. mp: 134° C. HRMS calculated for $C_{27}H_{28}ClN_3O_2$ (M+H)⁺ 462.1948 found: 462.1902. Rt=2.84 min.

Examples 102 to 114 were prepared by similar methods to that described for Example 101:

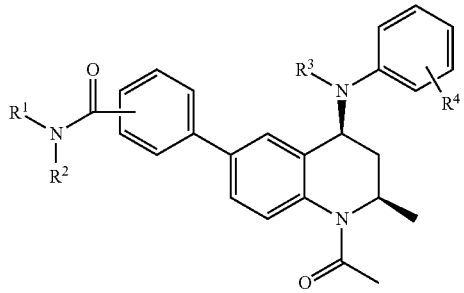

| Ex | Amide position | $R^1$ | $R^2$ | $R^3$ | $R^4$ | From Example | Physical data |
|---|---|---|---|---|---|---|---|
| 102 | para | $CH_3$ | H | H | 4-Cl | 92 | HRMS calculated for $C_{26}H_{26}N_3O_2Cl$ $(M + H)^+$ Theo: 448.1792 found: 448.1786 Rt: 2.70 min MP: 140° C. |
| 103 | para | $CH(CH_3)_2$ | H | H | 4-Cl | 92 | HRMS calculated for $C_{28}H_{30}ClN_3O_2$ $(M + H)^+$ Theo: 476.2105 found: 476.2105 Rt: 2.98 min MP: 134° C. |
| 104 | para | CyPent | H | H | 4-Cl | 92 | HRMS calculated for $C_{30}H_{32}ClN_3O_2$ $(M + H)^+$ Theo: 502.2261 found: 502.2216 Rt: 3.17 min MP: 122° C. |
| 105 | para | $CH_2Ph$ | H | H | 4-Cl | 92 | HRMS calculated for $C_{32}H_{30}ClN_3O_2$ $(M + H)^+$ Theo: 524.2104 found: 524.2058 Rt: 3.17 min MP: 99° C. |
| 106 | para | $CH_2CH_3$ | $CH_2CH_3$ | H | 4-Cl | 92 | HRMS calculated for $C_{29}H_{32}ClN_3O_2$ $(M + H)^+$ Theo: 490.2261 found: 490.2208 Rt: 3.09 min MP: 134° C. |
| 107 | para | $CH_2CH_2CH_3$ | H | H | 4-Cl | 92 | HRMS calculated for $C_{28}H_{30}ClN_3O_2$ $(M + H)^+$ Theo: 476.2105 found: 476.2109 Rt: 2.96 min MP: 135° C. |
| 108 | para | —$CH_2CH_2CH_2CH_2$— | | H | 4-Cl | 92 | HRMS calculated for $C_{28}H_{30}ClN_3O_2$ $(M + H)^+$ Theo: 488.2105 found: 488.2118 Rt: 2.92 min MP: 144° C. |
| 109 | para | —$CH_2CH_2OCH_2CH_2$— | | H | 4-Cl | 92 | HRMS calculated for $C_{29}H_{30}ClN_3O_3$ $(M + H)^+$ Theo: 504.2054 found: 504.2046 Rt: 2.75 min MP: 146° C. |

-continued

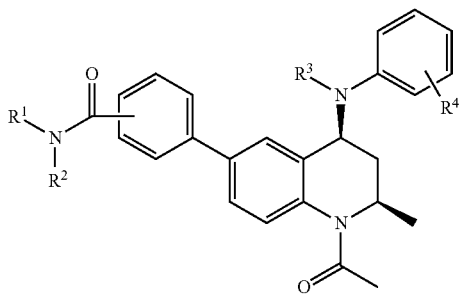

| Ex | Amide position | R¹ | R² | R³ | R⁴ | From Example | Physical data |
|---|---|---|---|---|---|---|---|
| 110 | para | Ph | H | H | 4-Cl | 92 | HRMS calculated for $C_{31}H_{28}ClN_3O_2$ $(M+H)^+$ Theo: 510.1948 found: 510.1929 Rt: 3.31 min MP: 163° C. |
| 111 | para | $CH_3$ | $CH_3$ | H | 4-Cl | 92 | HRMS calculated for $C_{27}H_{28}ClN_3O_2$ $(M+H)^+$ Theo: 462.1948 found: 462.1922 Rt: 2.85 min MP: 209° C. |
| 112 | para | H | H | H | 4-Cl | 92 | HRMS calculated for $C_{25}H_{24}ClN_3O_2$ $(M+H)^+$ Theo: 432.1479 found: 432.1455 Rt: 2.59 min MP: 235° C. |
| 113 | para | piperidin-1-yl | | H | 4-Cl | 92 | HRMS calculated for $C_{30}H_{33}ClN_4O_2$ $(M+H)^+$ Theo: 517.2370 found: 517.2406 Rt: 2.91 min MP: 274.1° C. |
| 114 | para | $CH_2CN$ | H | H | 4-Cl | 92 | HRMS calculated for $C_{27}H_{25}ClN_4O_2$ $(M+H)^+$ Theo: 473.1744 found: 473.1739 Rt: 2.8 min |
| 115 | meta | $CH_3$ | H | H | 4-Cl | 94 | HRMS calculated for $C_{26}H_{26}ClN_3O_2$ $(M+H)^+$ Theo: 448.1792 found: 448.1807 Rt: 2.78 min MP: 170° C. |
| 116 | para | —$CH_2CH_2OCH_2CH_2$— | | Et | 4-Cl | 100 | HRMS calculated for $C_{31}H_{34}ClN_3O_3$ $(M+H)^+$ Theo: 532.2367 found: 532.2404 Rt: 3.14 min |
| 117 | para | $CH_2CH_3$ | H | Et | 4-Cl | 100 | HRMS calculated for $C_{29}H_{32}ClN_3O_2$ $(M+H)^+$ Theo: 490.2261 found: 490.2309 Rt: 3.18 min |
| 118 | para | $CH_3$ | H | Et | 4-Cl | 100 | HRMS calculated for $C_{28}H_{30}ClN_3O_2$ $(M+H)^+$ Theo: 476.2105 found: 476.2151 Rt: 3.03 min |

Example 119

Ethyl 4-{1-acetyl-4-[(4-chlorophenyl)amino]-2-methyl-1,2,3,4-tetrahydro-6-quinolinyl}benzoate

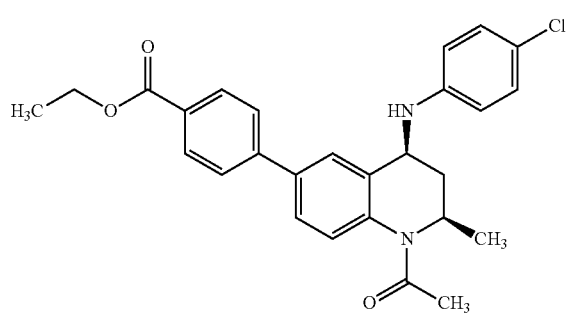 [SMILES: CCOC(=O)c1ccc(-c2ccc3c(c2)[C@@H](Nc2ccc(Cl)cc2)C[C@@H](C)N3C(C)=O)cc1]

To a solution of example 92 (434 mg, 1 mmol) in DMF (5 mL) are added at room temperature ethyl iodide (, 3 mmol) and sodium hydride (60%, 6 mmol). The reaction mixture was allowed to stir at room temperature for 14 hours and then poured in water (150 mL). EtOAC was added (200 mL) and the organic layer was separated and dried over $Na_2SO_4$. After filtration and concentration under reduced pressure the title compound was obtained as a yellow solid (250 mg, 54%), mp: 114° C. HRMS calculated for $C_{27}H_{27}ClN_2O_3$ $(M+H)^+$ 463.1788 found: 463.1805 Rt=3.51 min.

Example 120

1-Acetyl-N-(4-chlorophenyl)-2-methyl-6-(1H-pyrrol-2-yl)-1,2,3,4-tetrahydro-4-quinolinamine

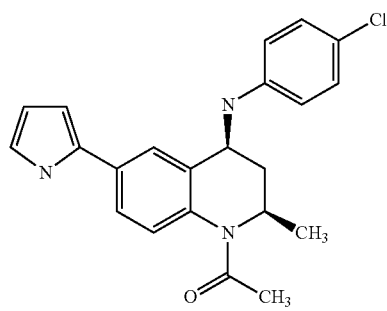 [SMILES: CC(=O)N1c2ccc(-c3ccc[nH]3)cc2[C@@H](Nc2ccc(Cl)cc2)C[C@H]1C]

HCl gas was bubbled through a solution of example 42 (100 mg, 0.2 mmol) in EtOAC (3 mL). After stirring overnight at room temperature and concentration to dryness the residue was flash chromatographied to deliver the title compound as a pale yellow powder (8 mg, 10%). HRMS calculated for $C_{22}H_{22}ClN_3O$ $(M+H)^+$380.1530 found: 380.1542 Rt=3.02 min

Example 121

1-Acetyl-N-(4-chlorophenyl)-2-methyl-6-[4-(1H-tetrazol-5-yl)phenyl]-1,2,3,4-tetrahydro-4-quinolinamine

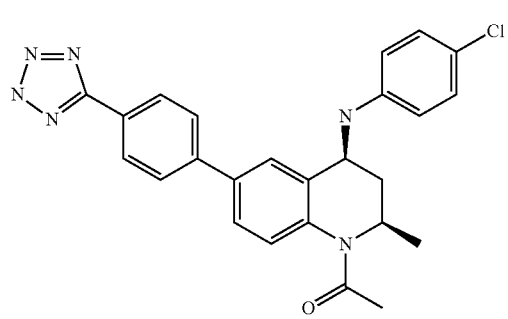 [SMILES: CC(=O)N1c2ccc(-c3ccc(-c4nn[nH]n4)cc3)cc2[C@@H](Nc2ccc(Cl)cc2)C[C@H]1C]

A mixture of example 63 (183 mg, 0.44 mmol), $NH_4Cl$ (30 mg, 0.57 mmol), $NaN_3$ (40 mg, 0.617 mmol) in DMF (3 mL) was heated for 14 hours to 120° C. and an additional 2 hours to 140° C. After concentration under vacuum the residue was taken up with DCM (150 mL) and washed with 1N HCl. Insoluble materials were collected and mixed with the organic layer in a MeOH/DCM mixture and filtered on silica gel eluting with DCM/MeOH 99:1 then 80:20. The title compound was obtained as a yellow solid (84, 42%) after precipitation in a EtOH/iPr$_2$O mixture, mp: 250° C. HRMS calculated for $C_{25}H_{23}ClN_6O$ $(M+H)^+$457.1544 found: 457.1553 Rt=2.17 min

Example 122

2-(4-{(2S,4R)-1-Acetyl-2-methyl-4-[(5-methyl-2-pyridinyl)amino]-1,2,3,4-tetrahydro-6-quinolinyl}-1H-1,2,3-triazol-1-yl)ethanol

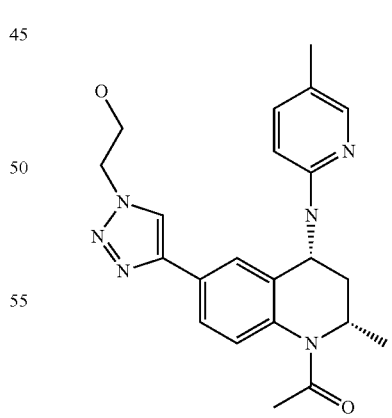

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-N-(5-methyl-2-pyridinyl)-1,2,3,4-tetrahydro-4-quinolinamine (for a preparation see intermediate 43) (34 mg, 0.065 mmol) in tetrahydrofuran (THF) (3 mL) was added TBAF (1M in THF, 0.085 mL, 0.085 mmol). The resulting mixture was stirred at room temperature for 30 min, and then was concentrated in vacuo. The residue was dissolved in a 1:1 (MeOH/DMSO) mixture (1 mL) and purified via MDAP (modifier: formic acid). The appropriate fractions were combined and concentrated under reduced pressure to give 2-(4-{(2S,4R)-1-acetyl-2-methyl-4-[(5-methyl-2-pyridinyl)amino]-1,2,3,4-tetrahydro-6-quinolinyl}-1H-1,2,3-triazol-1-yl)ethanol (19 mg, 0.045 mmol, 69%) as a colourless oil LCMS (formic): Retention time 0.49 min, [M+H]+=407.3

Example 123

2-(4-{(2S,4R)-1-Acetyl-2-methyl-4-[(6-methyl-2-pyridinyl)amino]-1,2,3,4-tetrahydro-6-quinolinyl}-1H-1,2,3-triazol-1-yl)ethanol

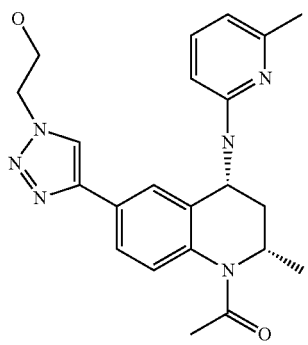 [SMILES: CC(=O)N1c2ccc(-c3cn(CCO)nn3)cc2[C@H](Nc2cccc(C)n2)C[C@@H]1C]

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (for a preparation, see Intermediate 44) (59 mg, 0.137 mmol) and 2-bromo-6-methylpyridine (70.9 mg, 0.412 mmol) in toluene (2.5 mL) were successively added sodium tert-butoxide (132 mg, 1.373 mmol), tris(dibenzylideneacetone)dipalladium(0) (25.2 mg, 0.027 mmol) and 2'-(dicyclohexylphosphino)-N,N-dimethylbiphenyl-2-amine (DavePhos) (21.62 mg, 0.055 mmol). The reaction mixture was stirred at 75° C. for 5 h then cooled to room temperature and filtered through Celite. The insoluble material was washed with 5% MeOH in DCM and the combined filtrate and washings were concentrated in vacuo. The residue was dissolved in a 1:1 MeOH/DMSO mixture and was purified by MDAP (modifier: formic acid). The appropriate fractions were combined and the solvents evaporated using a blow down apparatus (nitrogen inlet) to give 2-(4-{(2S,4R)-1-acetyl-2-methyl-4-[(6-methyl-2-pyridinyl)amino]-1,2,3,4-tetrahydro-6-quinolinyl}-1H-1,2,3-triazol-1-yl)ethanol (12.5 mg, 0.031 mmol, 22%) as a viscous yellow oil.

LCMS (formic): Retention time 0.49 min, [M+H]+=407.3

Example 124

2-(4-{(2S,4R)-1-Acetyl-2-methyl-4-[(3-methyl-2-pyridinyl)amino]-1,2,3,4-tetrahydro-6-quinolinyl}-1H-1,2,3-triazol-1-yl)ethanol

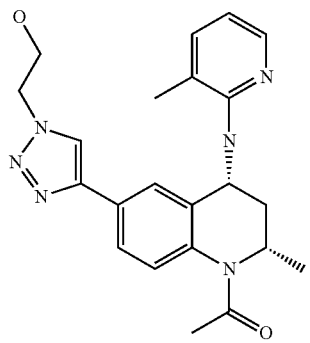 [SMILES: CC(=O)N1c2ccc(-c3cn(CCO)nn3)cc2[C@H](Nc2ncccc2C)C[C@@H]1C]

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (for a preparation, see Intermediate 44) (31 mg, 0.072 mmol) and 2-chloro-3-methylpyridine (27.6 mg, 0.216 mmol) in toluene (2.5 mL) were successively added sodium tert-butoxide (69.3 mg, 0.722 mmol), tris(dibenzylideneacetone)dipalladium(0) (66.1 mg, 0.072 mmol) and 2'-(dicyclohexylphosphino)-N,N-dimethylbiphenyl-2-amine (DavePhos) (56.8 mg, 0.144 mmol). The resulting mixture was stirred at 100° C. for 5 h then cooled to room temperature and filtered through Celite. The insoluble material was washed with 5% MeOH in DCM. The combined filtrate and washings were concentrated in vacuo and the residue was dissolved in a 1:1 (DMSO/MeOH) mixture and purified via MDAP (modifier: formic acid). The appropriate fractions were combined and were concentrated using a blow down apparatus (45° C.) to give 2-(4-{(2S,4R)-1-acetyl-2-methyl-4-[(3-methyl-2-pyridinyl)amino]-1,2,3,4-tetrahydro-6-quinolinyl}-1H-1,2,3-triazol-1-yl)ethanol (4.5 mg, 10.63 µmol, 15%) as viscous colourless oil.

LCMS (formic): Retention time 0.48 min, [M+H]+=407.28

Example 125

2-(4-{(2S,4R)-1-Acetyl-2-methyl-4-[(4-methyl-2-pyridinyl)amino]-1,2,3,4-tetrahydro-6-quinolinyl}-1H-1,2,3-triazol-1-yl)ethanol

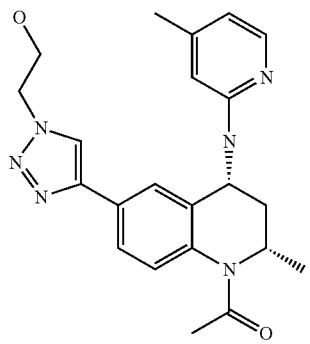 [SMILES: CC(=O)N1c2ccc(-c3cn(CCO)nn3)cc2[C@H](Nc2cc(C)ccn2)C[C@@H]1C]

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (for a preparation, see Intermediate 44) (115 mg, 0.268 mmol) and 2-chloro-4-methylpyridine (102 mg, 0.803 mmol) in toluene (2.5 mL) were successively added sodium tert-butoxide (129 mg, 1.338 mmol), tris(dibenzylideneacetone)dipalladium(0) (245 mg, 0.268 mmol) and 2'-(dicyclohexylphosphino)-N,N-dimethylbiphenyl-2-amine (DavePhos) (211 mg, 0.535 mmol). The resulting mixture was stirred at 100° C. for 1 h then cooled to room temperature. The insoluble material was washed with 5% MeOH in DCM. The combined filtrate and washings were concentrated in vacuo and the residue was dissolved in a 1:1 MeOH/DMSO mixture and purified via MDAP (modifier; formic acid). The appropriate fractions were combined and the solvents evaporated using a blow down apparatus to give 2-(4-{(2S,4R)-1-acetyl-2-methyl-4-[(4-methyl-2-pyridinyl)amino]-1,2,3,4-tetrahydro-6-quinolinyl}-1H-1,2,3-triazol-1-yl)ethanol (18.5 mg, 0.046 mmol, 17%) as a colourless oil.

LCMS (formic): Retention time 0.51 min, [M+H]+=407.15

Example 126

4-{(2S,4R)-1-Acetyl-2-methyl-4-[(5-methyl-2-pyridinyl)amino]-1,2,3,4-tetrahydro-6-quinolinyl}benzoic acid

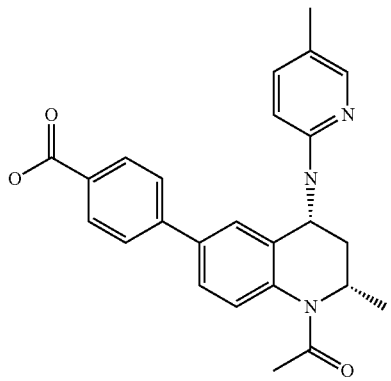 [SMILES: CC(=O)N1c2ccc(-c3ccc(C(=O)O)cc3)cc2[C@H](Nc2ccc(C)cn2)C[C@@H]1C]

To a solution of ethyl 4-[(2S,4R)-1-acetyl-4-amino-2-methyl-1,2,3,4-tetrahydro-6-quinolinyl]benzoate (for a preparation, see Intermediate 52) (153 mg, 0.434 mmol) and 2-bromo-5-methylpyridine (224 mg, 1.302 mmol) in toluene (10 mL) were successively added sodium tert-butoxide (417 mg, 4.34 mmol), tris(dibenzylideneacetone)dipalladium(0) (398 mg, 0.434 mmol) and 2'-(dicyclohexylphosphino)-N,N-dimethylbiphenyl-2-amine (DavePhos) (342 mg, 0.868 mmol). The resulting mixture was stirred at 100° C. for 3 h then cooled to room temperature. The insoluble material was washed with 5% MeOH in DCM. The combined filtrate and washings were concentrated in vacuo and the residue was dissolved in a 1:1 MeOH/DMSO mixture and purified via MDAP (modifier: formic acid). The appropriate fractions were combined and the solvents evaporated using a blow down apparatus to give 4-{(2S,4R)-1-acetyl-2-methyl-4-[(5-methyl-2-pyridinyl)amino]-1,2,3,4-tetrahydro-6-quinolinyl}benzoic acid (27.5 mg, 0.066 mmol, 15%) as an off white solid.

LCMS (formic): Retention time 0.66 min, [M+H]+=416.30

Example 127

2-{4-[(2S,4R)-1-Acetyl-2-methyl-4-(2-pyridinylamino)-1,2,3,4-tetrahydro-6-quinolinyl]-1H-1,2,3-triazol-1-yl}ethanol

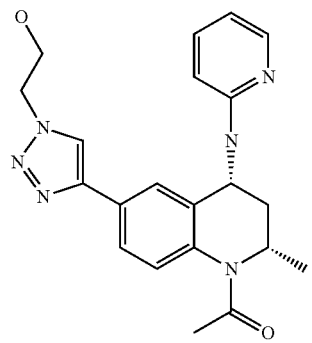 [SMILES: CC(=O)N1c2ccc(-c3cn(CCO)nn3)cc2[C@H](Nc2ccccn2)C[C@@H]1C]

To a solution of (2S,4R)-1-acetyl-6-[1-(2-{[(1,1-dimethylethyl)(dimethyl)silyl]oxy}ethyl)-1H-1,2,3-triazol-4-yl]-2-methyl-1,2,3,4-tetrahydro-4-quinolinamine (for a preparation see intermediate 44) (100 mg, 0.233 mmol) and 2-bromo pyridine (110 mg, 0.698 mmol) in toluene (2.5 mL) were successively added sodium tert-butoxide (224 mg, 2.328 mmol), tris(dibenzylideneacetone)dipalladium(0) (213 mg, 0.233 mmol) and 2'-(dicyclohexylphosphino)-N,N-dimethylbiphenyl-2-amine (DavePhos) (183 mg, 0.466 mmol). The resulting mixture was stirred at 100° C. for 2 h then cooled to room temperature and filtered through Celite. The insoluble material was washed with 5% MeOH in DCM and the combined filtrate and washings were concentrated in vacuo. The residue was dissolved in a 1:1 MeOH/DMSO mixture and purified via MDAP (modifier: formic acid). The appropriate fractions were combined and concentrated using a blow down apparatus (45° C.) to give 2-{4-[(2S,4R)-1-acetyl-2-methyl-4-(2-pyridinylamino)-1,2,3,4-tetrahydro-6-quinolinyl]-1H-1,2,3-triazol-1-yl}ethanol as a colourless oil.

LCMS (formic): Retention time 0.52 min, [M−H]−=391.11

Example 128

(2S,4R)-1-Acetyl-2-methyl-6-{1-[2-(methylamino)ethyl]-1H-pyrazol-4-yl}-N-phenyl-1,2,3,4-tetrahydro-4-quinolinamine trifluoroacetate

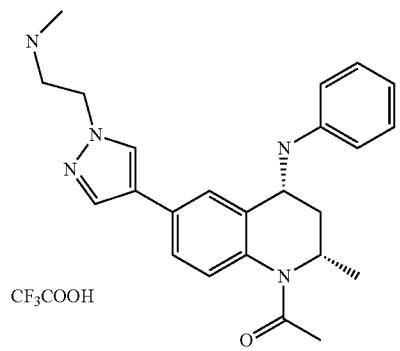 [SMILES: "CF3COOH" ; CNCCn1cc(-c2ccc3c(c2)[C@H](Nc2ccccc2)C[C@H](C)N3C(C)=O)cn1]

CF₃COOH

A solution of 1,1-dimethylethyl (2-{4-[(2S,4R)-1-acetyl-2-methyl-4-(phenylamino)-1,2,3,4-tetrahydro-6-quinolinyl]-1H-pyrazol-1-yl}ethyl)methylcarbamate (for a preparation see intermediate 54) (104 mg, 0.206 mmol) in dichloromethane (DCM) (3 mL) at room temperature under nitrogen was treated with trifluoroacetic acid (TFA) (0.5 mL, 6.49 mmol) and the resulting mixture was stirred at this temperature for 1 h then concentrated in vacuo to give (2S,4R)-1-acetyl-2-methyl-6-{1-[2-(methylamino)ethyl]-1H-pyrazol-4-yl}-N-phenyl-1,2,3,4-tetrahydro-4-quinolinamine trifluoroacetate (99 mg, 0.191 mmol, 93% yield) as a brown solid.

LCMS (high pH): Retention time 0.71 min, [M+H]+=404.15

Example 129

(2S,4R)-1-Acetyl-2-methyl-6-{1-[2-(methylamino)ethyl]-1H-pyrazol-4-yl}-N-3-pyridinyl-1,2,3,4-tetrahydro-4-quinolinamine

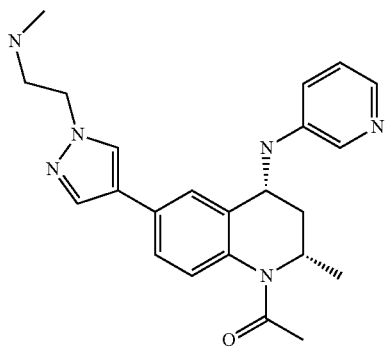 [SMILES: CNCCn1cc(-c2ccc3c(c2)[C@H](Nc2cccnc2)C[C@H](C)N3C(C)=O)cn1]

A solution of 1,1-dimethylethyl (2-{4-[(2S,4R)-1-acetyl-2-methyl-4-(3-pyridinylamino)-1,2,3,4-tetrahydro-6-quinolinyl]-1H-pyrazol-1-yl}ethyl)methylcarbamate (for a preparation see intermediate 58) (84 mg, 0.166 mmol) in dichloromethane (DCM) (3 mL) at room temperature under nitrogen was treated with trifluoroacteic acid TFA (0.5 mL, 6.49 mmol) and the resulting mixture was stirred at this temperature for 1 h then concentrated in vacuo. The residue was loaded onto a 10 G SCX cartridge and eluted with MeOH (2×20 mL) then with a 2N NH3 in MeOH (20 mL). The ammonia fractions were collected and concentrated in vacuo to give (2S,4R)-1-acetyl-2-methyl-6-{1-[2-(methylamino)ethyl]-1H-pyrazol-4-yl}-N-3-pyridinyl-1,2,3,4-tetrahydro-4-quinolinamine (61 mg, 0.151 mmol, 91%) as a brown oil.

LCMS (high pH): Retention time 0.42 min, [M+H]+=405.18

Example 130

(2S,4R)-1-Acetyl-2-methyl-6-{1-[2-(methylamino)ethyl]-1H-pyrazol-4-yl}-N-4-pyridinyl-1,2,3,4-tetrahydro-4-quinolinamine formate salt

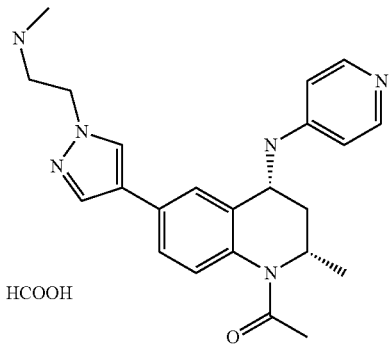 [SMILES: "HCOOH" ; CNCCn1cc(-c2ccc3c(c2)[C@H](Nc2ccncc2)C[C@H](C)N3C(C)=O)cn1]

A solution of 1,1-dimethylethyl (2-{4-[(2S,4R)-1-acetyl-2-methyl-4-(4-pyridinylamino)-1,2,3,4-tetrahydro-6-quinolinyl]-1H-pyrazol-1-yl}ethyl)methylcarbamate (for a preparation see intermediate 59) (147 mg, 0.291 mmol) in dichloromethane (DCM) (3 mL) at room temperature under nitrogen was treated with trifluoroacetic acid (TFA) (0.449 mL, 5.83 mmol). The resulting mixture was stirred at this temperature for 2 h then concentrated in vacuo. The residue was co-evaporated with DCM then was dissolved in 1:1 MeOH:DMSO (1 ml×2) and purified by MDAP (modifier: formic acid). The desired fractions were combined and the solvent was removed under vacuo to give (2S,4R)-1-acetyl-2-methyl-6-{1-[2-(methylamino)ethyl]-1H-pyrazol-4-yl}-N-4-pyridinyl-1,2,3,4-tetrahydro-4-quinolinamine formate salt (60 mg, 0.133 mmol, 45.7% yield).

LCMS (high pH): Retention time 0.40 min, [M+H]+=405.20

Example 131

(2S,4R)-1-Acetyl-2-methyl-6-{1-[2-(methylamino)ethyl]-1H-pyrazol-4-yl}-N-2-pyridinyl-1,2,3,4-tetrahydro-4-quinolinamine formate salt

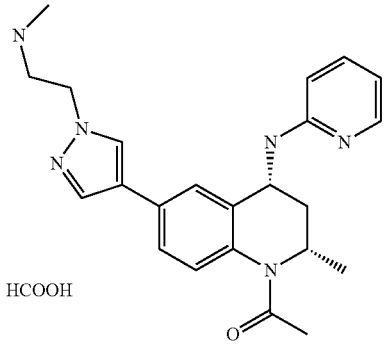 [SMILES: "HCOOH" ; CNCCn1cc(-c2ccc3c(c2)[C@H](Nc2ccccn2)C[C@H](C)N3C(C)=O)cn1]

A solution of 1,1-dimethylethyl (2-{4-[(2S,4R)-1-acetyl-2-methyl-4-(2-pyridinylamino)-1,2,3,4-tetrahydro-6-quinolinyl]-1H-pyrazol-1-yl}ethyl)methylcarbamate (for a preparation see intermediate 60) (126 mg, 0.250 mmol) in dichloromethane (DCM) (2 mL) was treated at room temperature with trifluoroacetic acid (TFA) (500 µl, 6.49 mmol) and the resulting mixture was stirred at this temperature for 1.5 h then concentrated in vacuo. The residue was dissolved in MeOH (1 mL) and purified by MDAP (modifier: formic acid). The desired fractions were combined and the solvent was removed under vacuo to give (2S,4R)-1-acetyl-2-methyl-6-{1-[2-(methylamino)ethyl]-1H-pyrazol-4-yl}-N-2-pyridinyl-1,2,3,4-tetrahydro-4-quinolinamine formate (93 mg, 0.206 mmol, 83% yield) as a cream solid.

LCMS (high pH): Retention time 0.39 min, [M+H]+=405.3

Example 132

(cis)-1-Acetyl-6-(6-amino-3-pyridinyl)-2-methyl-N-phenyl-1,2,3,4-tetrahydro-4-quinolinamine hydrochloride

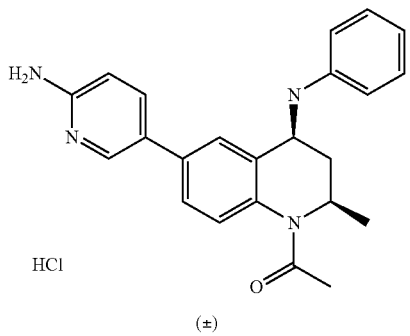 [SMILES: CC(=O)N1c2ccc(-c3ccc(N)nc3)cc2[C@@H](Nc2ccccc2)C[C@H]1C ; Cl]

A flask was charged with (cis)-1-acetyl-6-bromo-2-methyl-N-phenyl-1,2,3,4-tetrahydro-4-quinolinamine (for a preparation see intermediate 39) (72 mg, 0.200 mmol), potassium carbonate (55.4 mg, 0.401 mmol), 5-(4,4,5,5-tetramethyl-1,3,2-dioxaborolan-2-yl)-2-pyridinamine (52.9 mg, 0.240 mmol) then filled with toluene (1 mL) and ethanol (1 mL). Tetrakis(triphenylphosphine)palladium(0) (11.58 mg, 10.02 µmol) was added and the resulting mixture was stirred at 90° C. under nitrogen for 16 h then cooled to room temperature and concentrated in vacuo. Purification of the residue by SP4 using a 12 G silica cartridge (gradient:0 to 35% (10% (0.5M NH$_3$ in MeOH) in DCM) in DCM) gave a residue which was further purified by SP4 using a 12 G silica cartridge (40 to 100% AcOEt in Hexanes then 0 to 100% (20% (0.5M NH$_3$ in MeOH) in DCM) in DCM) to give a second residue. Purification of this residue using MDAP (modifier: ammonium bicarbonate) gave a third residue which was dissolved in MeOH (2 mL) and treated with HCl (1.25M in MeOH, 2 mL, 2.5 mmol). The resulting mixture was concentrated in vacuo and the residue triturated with Et$_2$O to give (cis)-1-acetyl-6-(6-amino-3-pyridinyl)-2-methyl-N-phenyl-1,2,3,4-tetrahydro-4-quinolinamine hydrochloride (24 mg, 0.058 mmol, 29%) as an off white solid.

LCMS (high pH): Retention time 0.97 min, [M+H]+=373.24

Example 133

(cis)-1-Acetyl-2-methyl-6-[4-(1-pipendinylmethyl)phenyl]-N-2-pyridinyl-1,2,3,4-tetrahydro-4-quinolinamine formate salt

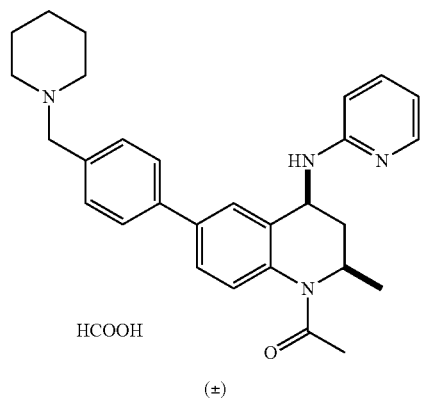 [SMILES: CC(=O)N1c2ccc(-c3ccc(CN4CCCCC4)cc3)cc2[C@@H](Nc2ccccn2)C[C@H]1C ; "HCOOH"]

(cis)-1-Acetyl-2-methyl-6-[4-(1-piperidinylmethyl)phenyl]-1,2,3,4-tetrahydro-4-quinolinamine (for a preparation see intermediate 25) (100 mg, 0.265 mmol), racemic BINAP (8.25 mg, 0.013 mmol), sodium tert-butoxide (30.5 mg, 0.318 mmol), 2-chloropyridine (0.025 ml, 0.265 mmol) and tris (dibenzylideneacetone)dipalladium(0) (12.13 mg, 0.013 mmol) were suspended in toluene (2.5 mL) under nitrogen and the resulting mixture was stirred at 100° C. for 5 h under microwave irradiation then cooled to room temperature and partitioned between AcOEt (20 mL) and 1:1 saturated NaHCO$_3$ aqueous solution:water (5 mL). The layers were separated and the organic phase washed with saturated NaHCO$_3$ aqueous solution:water (5 mL) then brine (5 mL), dried over Na$_2$SO$_4$ and concentrated in vacuo. Purification of the residue by MDAP (modifier: formic acid) gave (cis)-1-acetyl-2-methyl-6-[4-(1-piperidinylmethyl)phenyl]-N-2-pyridinyl-1,2,3,4-tetrahydro-4-quinolinamine formate salt (31.9 mg, 0.062 mmol, 24%) as a white solid.

LCMS (high pH): Retention time 0.57 min, [M+H]+=455.0

Example 134

(cis)-1-Acetyl-2-methyl-6-[4-(1-piperidinylmethyl)phenyl]-N-[5-(trifluoromethyl)-2-pyridinyl]-1,2,3,4-tetrahydro-4-quinolinamine formate salt

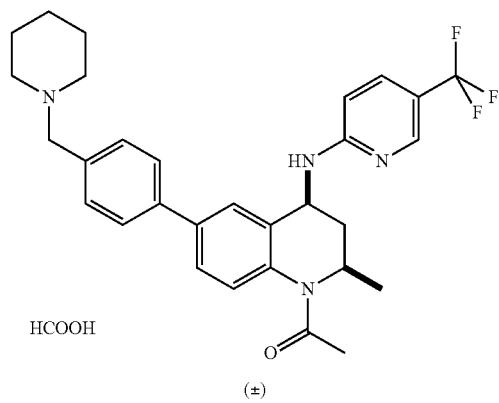 [SMILES: "HCOOH" ; CC(=O)N1c2ccc(-c3ccc(CN4CCCCC4)cc3)cc2[C@@H](Nc2ccc(C(F)(F)F)cn2)C[C@H]1C]

A flask was charged with 2-chloro-5-(trifluoromethyl)pyridine (57.7 mg, 0.318 mmol), (cis)-1-acetyl-2-methyl-6-[4-(1-piperidinylmethyl)phenyl]-1,2,3,4-tetrahydro-4-quinolinamine (for a preparation see Intermediate 25) (100 mg, 0.265 mmol), racemic BINAP (8.25 mg, 0.013 mmol), sodium tert-butoxide (30.5 mg, 0.318 mmol) and tris(dibenzylideneacetone)dipalladium(0) (12.13 mg, 0.013 mmol) then filled with toluene (2.5 mL), and the resulting mixture was stirred at 110° C. under nitrogen for 16 h then cooled to room temperature and loaded on a 5 g SCX cartridge. It was then eluted with MeOH (30 mL) followed by 2M $NH_3$ in MeOH (25 mL). The ammonia fractions were collected and concentrated in vacuo. Purification of the residue by MDAP (modifier: formic acid) gave (cis)-1-acetyl-2-methyl-6-[4-(1-piperidinylmethyl)phenyl]-N-[5-(trifluoromethyl)-2-pyridinyl]-1,2,3,4-tetrahydro-4-quinolinamine formate salt (15 mg, 0.026 mmol, 10%) as an off white solid LCMS (Formic): Retention time 0.79 min, [M+H]+=523.0

Example 135

(cis)-1-Acetyl-2-methyl-N-(5-methyl-2-pyridinyl)-6-[4-(1-piperidinylmethyl)phenyl]-1,2,3,4-tetrahydro-4-quinolinamine formate salt

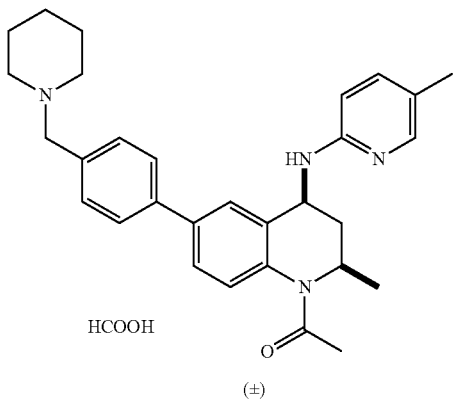 [SMILES: CC(=O)N1c2ccc(-c3ccc(CN4CCCCC4)cc3)cc2[C@@H](Nc2ccc(C)cn2)C[C@H]1C ; "HCOOH"]

A flask was charged with 2-chloro-5-methylpyridine (0.035 ml, 0.318 mmol), (cis)-1-acetyl-2-methyl-6-[4-(1-piperidinylmethyl)phenyl]-1,2,3,4-tetrahydro-4-quinolinamine (for a preparation see Intermediate 25) (100 mg, 0.265 mmol), racemic BINAP (8.25 mg, 0.013 mmol), sodium tert-butoxide (30.5 mg, 0.318 mmol) and tris(dibenzylideneacetone)dipalladium(0) (12.13 mg, 0.013 mmol) then filled with toluene (2.5 mL), and the resulting mixture was stirred at 110° C. under nitrogen for 16 h then cooled to room temperature and loaded on a 5 g SCX cartridge. It was then eluted with MeOH (30 mL) followed by 2M $NH_3$ in MeOH (25 mL). The ammonia fractions were collected and concentrated in vacuo. Purification of the residue by MDAP (modifier: formic acid) gave (cis)-1-acetyl-2-methyl-N-(5-methyl-2-pyridinyl)-6-[4-(1-piperidinylmethyl)phenyl]-1,2,3,4-tetrahydro-4-quinolinamine formate salt (21 mg, 0.04 mmol, 15%) as a white solid LCMS (Formic): Retention time 0.59 min, [M+H]+=469.0

Example 136

(cis)-1-Acetyl-N-(5-chloro-2-pyridinyl)-2-methyl-6-[4-(1-piperidinylmethyl)phenyl]-1,2,3,4-tetrahydro-4-quinolinamine formate salt

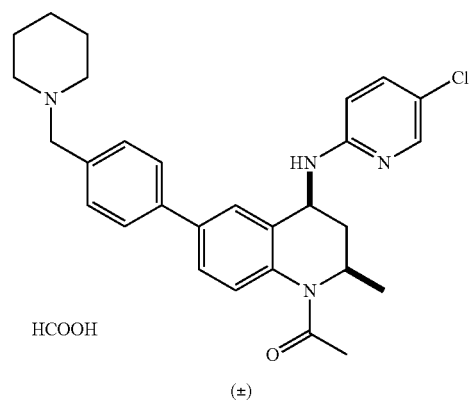 [SMILES: "HCOOH" ; CC(=O)N1c2ccc(-c3ccc(CN4CCCCC4)cc3)cc2[C@@H](Nc2ccc(Cl)cn2)C[C@H]1C]

A flask was charged with 2-chloro-5-chloropyridine (47.0 mg, 0.318 mmol), (cis)-1-acetyl-2-methyl-6-[4-(1-piperidinylmethyl)phenyl]-1,2,3,4-tetrahydro-4-quinolinamine (for a preparation see Intermediate 25) (100 mg, 0.265 mmol), racemic BINAP (8.25 mg, 0.013 mmol), sodium tert-butoxide (30.5 mg, 0.318 mmol) and tris(dibenzylideneacetone)dipalladium(0) (12.13 mg, 0.013 mmol) then filled with toluene (2.5 mL), and the resulting mixture was stirred at 110° C. under nitrogen for 16 h then cooled to room temperature and loaded on a 5 g SCX cartridge. It was then eluted with MeOH (30 mL) followed by 2M $NH_3$ in MeOH (25 mL). The ammonia fractions were collected and concentrated in vacuo. Purification of the residue by MDAP (modifier: formic acid) gave (cis)-1-acetyl-N-(5-chloro-2-pyridinyl)-2-methyl-6-[4-(1-piperidinylmethyl)phenyl]-1,2,3,4-tetrahydro-4-quinolinamine formate salt (23 mg, 0.04 mmol, 15%) as an off white solid.

LCMS (Formic): Retention time 0.68 min, [M+H]+=489.0

Example 137

(cis)-1-Acetyl-N-(5-fluoro-2-pyridinyl)-2-methyl-6-[4-(1-piperidinylmethyl)phenyl]-1,2,3,4-tetrahydro-4-quinolinamine formate salt

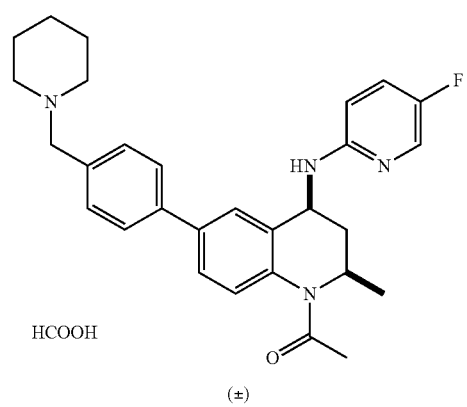 [SMILES: "HCOOH" ; CC(=O)N1c2ccc(-c3ccc(CN4CCCCC4)cc3)cc2[C@@H](Nc2ccc(F)cn2)C[C@H]1C]

A flask was charged with 2-chloro-5-fluoropyridine (0.032 ml, 0.318 mmol), (cis)-1-acetyl-2-methyl-6-[4-(1-piperidinylmethyl)phenyl]-1,2,3,4-tetrahydro-4-quinolinamine (for a preparation see Intermediate 25) (100 mg, 0.265 mmol), racemic BINAP (8.25 mg, 0.013 mmol), sodium tert-butoxide (30.5 mg, 0.318 mmol) and tris(dibenzylideneacetone)dipalladium(0) (12.13 mg, 0.013 mmol) then filled with toluene (2.5 mL), and the resulting mixture was stirred at 110° C. under nitrogen for 16 h then cooled to room temperature and loaded on a 5 g SCX cartridge. It was then eluted with MeOH (30 mL) followed by 2M NH$_3$ in MeOH (25 mL). The ammonia fractions were collected and concentrated in vacuo. Purification of the residue by MDAP (modifier: formic acid) gave (cis)-1-acetyl-N-(5-fluoro-2-pyridinyl)-2-methyl-6-[4-(1-piperidinylmethyl)phenyl]-1,2,3,4-tetrahydro-4-quinolinamine formate salt (35 mg, 0.066 mmol, 25%) as an off white solid LCMS (Formic): Retention time 0.63 min, [M+H]+=473.0

Example 138

(cis)-1-Acetyl-2-methyl-6-[4-(1-piperidinylmethyl)phenyl]-N-4-pyridinyl-1,2,3,4-tetrahydro-4-quinolinamine trifluoroacetate

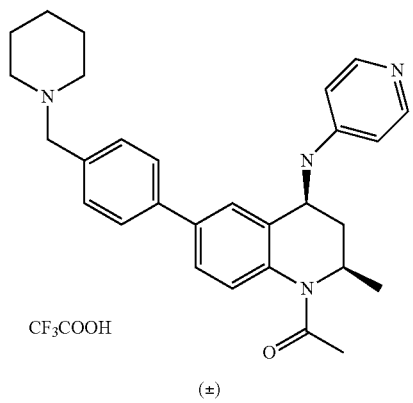 [SMILES: "CF3COOH" ; CC(=O)N1c2ccc(-c3ccc(CN4CCCCC4)cc3)cc2[C@@H](Nc2ccncc2)C[C@H]1C]

(±)

A flask was charged with 4-bromopyridine hydrochloride (61.8 mg, 0.318 mmol), (cis)-1-acetyl-2-methyl-6-[4-(1-piperidinylmethyl)phenyl]-1,2,3,4-tetrahydro-4-quinolinamine (for a preparation see Intermediate 25) (100 mg, 0.265 mmol), racemic BINAP (8.25 mg, 0.013 mmol), sodium tert-butoxide (30.5 mg, 0.318 mmol) and tris(dibenzylideneacetone)dipalladium(0) (12.13 mg, 0.013 mmol) then filled with toluene (2.5 mL). The resulting mixture was stirred at 110° C. under nitrogen for 20 h then cooled to room temperature. An extra 1.2 equivalent of 4-bromopyridine hydrochloride (60 mg) and sodium tert-butoxide (30 mg) were added as well as racemic BINAP (0.05 equivalent, 8 mg) and the resulting mixture was stirred at 110° C. for 5 h. After the mixture was cooled to room temperature, a further 1.2 eq of bromopyridine (62 mg) was added and the reaction mixture stirred at 110° C. for 16 h then cooled to room temperature. An extra 0.05 eq of racemic BINAP (8 mg) and tris(dibenzylideneacetone)dipalladium(0) (12 mg) were added and the resulting mixture stirred at 110° C. for 5 h then cooled to room temperature and loaded onto a 5 g SCX column then eluted with MeOH (2 column volume (CV)) followed by 2M NH$_3$ in MeOH (4 CV). The ammonia fractions were combined and concentrated in vacuo. Purification of the residue by MDAP (modifier: trifluoroacetic acid) gave cis-1-acetyl-2-methyl-6-[4-(1-piperidinylmethyl)phenyl]-N-4-pyridinyl-1,2,3,4-tetrahydro-4-quinolinamine (22 mg, 0.037 mmol, 13.88% yield).

LCMS (TFA): Retention time 0.56 min, [M+H]+=455.0

Example 139

Methyl 4-{[(cis)-1-acetyl-2-methyl-6-(4-methyl-1H-imidazol-1-yl)-1,2,3,4-tetrahydro-4-quinolinyl]amino}benzoate

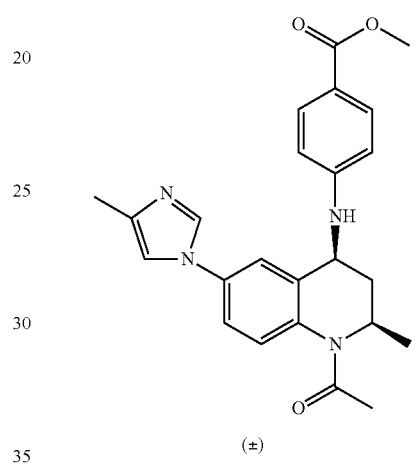

(±)

A flask was charged with (cis)-1-acetyl-2-methyl-6-(4-methyl-1H-imidazol-1-yl)-1,2,3,4-tetrahydro-4-quinolinamine di-hydrochloride (for a preparation see Intermediate 61) (250 mg, 0.700 mmol), methyl 4-iodobenzoate (202 mg, 0.770 mmol), sodium tert-butoxide (235 mg, 2.449 mmol), 2'-(dicyclohexylphosphino)-N,N-dimethylbiphenyl-2-amine (DavePhos) (55.0 mg, 0.140 mmol) and tris(dibenzylideneacetone)dipalladium(0) (64.1 mg, 0.070 mmol) then filled with dried degassed toluene (15 mL) and the resulting mixture was stirred at 70° C. under nitrogen for 5 h then was cooled to room temperature and filtered through celite. The insoluble were rinsed with toluene (3×30 mL) and the combined filtrate and washings were concentrated in vacuo. The residue was partitioned between AcOEt (50 mL) and water (20 mL) and the layers were separated. The organic phase was washed with brine, and the combined aqueous phases were extracted with AcOEt (30 mL). The combined organic phases were dried over MgSO$_4$ and concentrated in vacuo. Purification of the residue by SP4 using a 25 G silica cartridge (gradient:0 to 20% MeOH in DCM) gave methyl 4-{[(cis)-1-acetyl-2-methyl-6-(4-methyl-1H-imidazol-1-yl)-1,2,3,4-tetrahydro-4-quinolinyl]amino}benzoate (37 mg, 0.088 mmol, 13%).

LCMS (high pH): Retention time 0.92 min, [M+H]+=419.14

Example 140

(cis)-1-Acetyl-N-(5-fluoro-2-pyridinyl)-2-methyl-6-(4-methyl-1H-imidazol-1-yl)-1,2,3,4-tetrahydro-4-quinolinamine

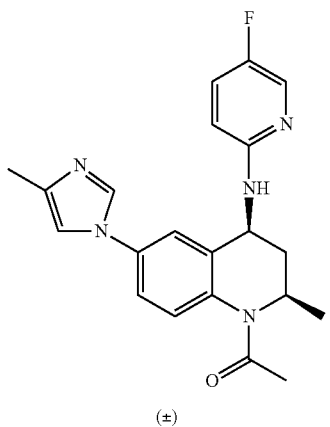

(±)

A mixture of (cis)-1-acetyl-2-methyl-6-(4-methyl-1H-imidazol-1-yl)-1,2,3,4-tetrahydro-4-quinolinamine di-hydrochloride (for a preparation see intermediate 61) (250 mg, 0.700 mmol), sodium tert-butoxide (235 mg, 2.449 mmol), 2-bromo-5-fluoropyridine (123 mg, 0.700 mmol), 2'-(dicyclohexylphosphino)-N,N-dimethylbiphenyl-2-amine (DavePhos) (55.0 mg, 0.140 mmol) and tris(dibenzylideneacetone)dipalladium(0) (64.1 mg, 0.070 mmol) was stirred in toluene (12 mL) at 70° C. under nitrogen for 2 h. An extra portion of 2-bromo-5-fluoropyridine (123 mg, 0.700 mmol), sodium tert-butoxyde (81 mg, 0.84 mmol), Davephos (55.0 mg, 0.140 mmol) and tris(dibenzylideneacetone)dipalladium (0) (64.1 mg, 0.070 mmol) was added after having cooled the mixture down. The resulting mixture was stirred at 70° C. under nitrogen for 12 h then was cooled to room temperature and concentrated in vacuo. The residue was suspended in 10% MeOH in DCM (100 mL) and filtered through celite. The insoluble material was rinsed with 10% MeOH in DCM (2×50 mL) and the combined filtrate and washings were concentrated in vacuo. The residue was partitioned between DCM (50 mL) and a saturated NaHCO₃ aqueous solution and the layers were separated. The aqueous phase was extracted with DCM (50 mL) and AcOEt (50 mL). The combined organic phases were washed with brine (50 mL), dried over MgSO₄ and concentrated in vacuo. Purification of the residue by flash chromatography on silica gel (gradient:0 to 5% MeOH in DCM) gave a residue which was further purified by MDAP (modifier: ammonium formate) to give (cis)-1-acetyl-N-(5-fluoro-2-pyridinyl)-2-methyl-6-(4-methyl-1H-imidazol-1-yl)-1,2,3,4-tetrahydro-4-quinolinamine (36.5 mg, 0.096 mmol, 14%) as a colourless solid.

LCMS (high pH): Retention time 0.87 min, [M+H]+=380.14

Example 141

(cis)-1-Acetyl-2-methyl-6-(4-methyl-1H-imidazol-1-yl)-N-(5-methyl-2-pyridinyl)-1,2,3,4-tetrahydro-4-quinolinamine hydrochloride

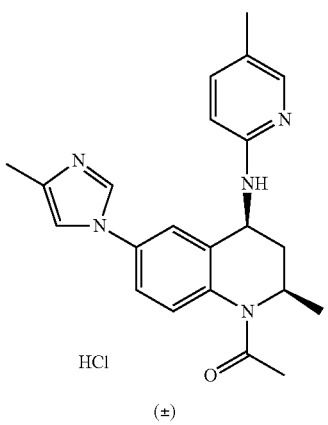

HCl (±)

A mixture of (cis)-1-acetyl-2-methyl-6-(4-methyl-1H-imidazol-1-yl)-1,2,3,4-tetrahydro-4-quinolinamine di-hydrochloride (for a preparation see intermediate 61) (250 mg, 0.700 mmol), sodium tert-butoxide (336 mg, 3.50 mmol), 2-bromo-5-methylpyridine (132 mg, 0.770 mmol), 2'-(dicyclohexylphosphino)-N,N-dimethylbiphenyl-2-amine (DavePhos) (55.0 mg, 0.140 mmol) and tris(dibenzylideneacetone)dipalladium(0) (64.1 mg, 0.070 mmol) was stirred in toluene (12 mL) at 75° C. under nitrogen for 5 h. An extra portion of sodium tert-butoxyde (81 mg, 0.84 mmol), Davephos (55.0 mg, 0.140 mmol) and tris(dibenzylideneacetone)dipalladium(0) (64.1 mg, 0.070 mmol) was added after having cooled the mixture down and the resulting mixture was stirred at 85° C. for 60 h under nitrogen, then cooled to room temperature and filtered through celite. The insoluble material was rinsed with DCM, stirred in 5% MeOH in DCM (100 mL) then filtered off. The combined filtrate and washings were concentrated in vacuo. Purification of the residue by flash chromatography on silica gel using a 20 G silica cartridge (gradient:0 to 3% MeOH in DCM) gave a residue which was dissolved in AcOEt. The resulting solution was treated with HCl (1.0M in Et₂O, 3 mL) then concentrated in vacuo. Trituration of the residue with Et₂O gave (cis)-1-acetyl-2-methyl-6-(4-methyl-1H-imidazol-1-yl)-N-(5-methyl-2-pyridinyl)-1,2,3,4-tetrahydro-4-quinolinamine hydrochloride (143 mg, 0.347 mmol, 50%) as an off white solid.

LCMS (high pH): Retention time 0.88 min, [M+H]+=376.18

Example 142

4-{[(cis)-1-Acetyl-2-methyl-6-(4-methyl-1H-imidazol-1-yl)-1,2,3,4-tetrahydro-4-quinolinyl]amino}benzamide

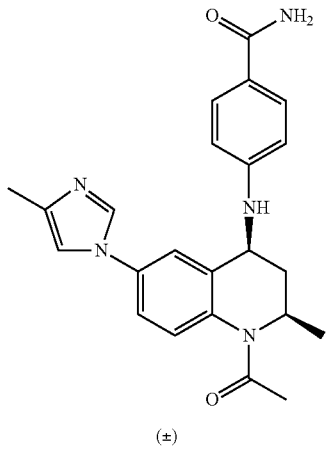

(±)

A mixture of 1-(cis)-1-acetyl-2-methyl-6-(4-methyl-1H-imidazol-1-yl)-1,2,3,4-tetrahydro-4-quinolinamine di-hydrochloride (for a preparation see intermediate 61) (200 mg, 0.560 mmol), sodium tert-butoxide (242 mg, 2.52 mmol), 2'-(dicyclohexylphosphino)-N,N-dimethylbiphenyl-2-amine (DavePhos) (44.0 mg, 0.112 mmol), 4-iodobenzamide (166 mg, 0.672 mmol) and tris(dibenzylideneacetone)dipalladium (0) (51.3 mg, 0.056 mmol) in dry degassed toluene was stirred at 85° C. under nitrogen for 6 h then cooled to room temperature. An extra portion of sodium tert-butoxide (64.5 mg, 0.67 mmol), Davephos (44.0 mg, 0.112 mmol) and tris(dibenzylideneacetone)dipalladium(0) (51.3 mg, 0.056 mmol) was added to the mixture which was then stirred at 85° C. for 24 h before being cooled to room temperature and filtered through celite. The insoluble material was rinsed with DCM, stirred in 5% MeOH in DCM (100 mL) then filtered off. The combined filtrate and washings were concentrated in vacuo. Purification of the residue by flash chromatography on silica gel using a 20 G silica cartridge (gradient:0 to 6% MeOH in DCM) gave a residue which was further purified using MDAP (modifier: ammonium formate) to give 4-{[(cis)-1-acetyl-2-methyl-6-(4-methyl-1H-imidazol-1-yl)-1,2,3,4-tetrahydro-4-quinolinyl]amino}benzamide (2.6 mg, 6.44 μmol, 1.15%) as a white solid.

LCMS (formic): Retention time 0.56 min, [M+H]+=404.3

Example 143

6-{[(cis)-1-acetyl-2-methyl-6-(4-methyl-1H-imidazol-1-yl)-1,2,3,4-tetrahydro-4-quinolinyl]amino}-3-pyridinecarboxylic acid

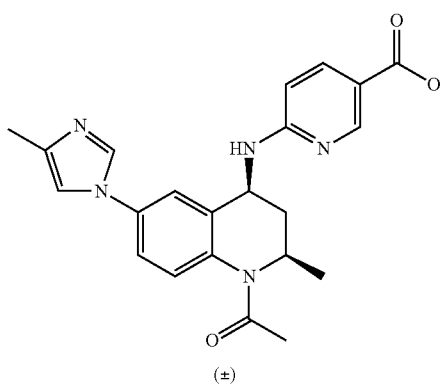 [SMILES: CC(=O)N1c2ccc(-n3cnc(C)c3)cc2[C@@H](Nc2ccc(C(=O)O)cn2)C[C@H]1C]

(±)

A mixture of 1-(cis)-1-acetyl-2-methyl-6-(4-methyl-1H-imidazol-1-yl)-1,2,3,4-tetrahydro-4-quinolinamine di-hydrochloride (for a preparation see intermediate 61) (31 mg, 0.098 mmol), methyl 6-bromo-3-pyridinecarboxylate (63.6 mg, 0.294 mmol), sodium tert-butoxide (94 mg, 0.981 mmol), 2'-(dicyclohexylphosphino)-N,N-dimethylbiphenyl-2-amine (DavePhos) (15.42 mg, 0.039 mmol) and tris(dibenzylideneacetone)dipalladium(0) (17.97 mg, 0.020 mmol) was stirred at 85° C. under nitrogen in dry degassed toluene (1.5 mL) for 10 h then was cooled to room temperature. One spatula of celite and 10% MeOH in DCM (10 mL) were added to the mixture which was stirred for 10 min then was filtered through celite. The insoluble material was rinsed with 10% MeOH in DCM (3×10 mL). The combined filtrate and washings were concentrated in vacuo. The residue was loaded on a 5 g SCX column then eluted with MeOH (50 mL) followed by 2N NH3 in MeOH (50 mL). The ammonia fractions were combined and concentrated in vacuo. The residue obtained was loaded on a 2 g NH2 column then eluted with MeOH (35 mL) and 5% AcOH in MeOH (50 mL). The acetic acid fractions were combined and concentrated in vacuo. The residue was purified by MDAP (modifier: ammonium bicarbonate) to give 6-{[(cis)-1-acetyl-2-methyl-6-(4-methyl-1H-imidazol-1-yl)-1,2,3,4-tetrahydro-4-quinolinyl]amino}-3-pyridinecarboxylic acid (5.2 mg, 0.013 mmol, 13%) as a white solid.

LCMS (high pH): Retention time 0.57 min, [M+H]+=406.32

Example 144

Methyl 6-{[(cis)-1-acetyl-2-methyl-6-(4-methyl-1H-imidazol-1-yl)-1,2,3,4-tetrahydro-4-quinolinyl]amino}-3-pyridinecarboxylate

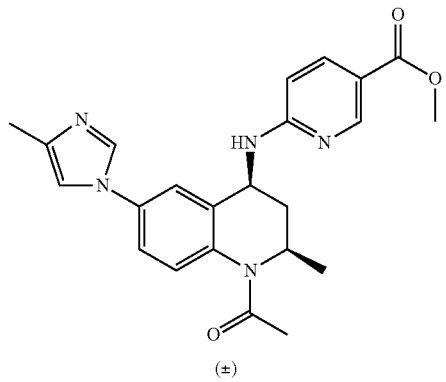

(±)

A solution of 6-{[1-acetyl-2-methyl-6-(4-methyl-1H-imidazol-1-yl)-1,2,3,4-tetrahydro-4-quinolinyl]amino}-3-pyridinecarboxylic acid (for a preparation see example 143) (40 mg, 0.099 mmol) in dry methanol (2 mL) was treated at room temperature with HCl (4M in 1,4-dioxane, 200 μl, 0.800 mmol) and the resulting mixture was stirred at this temperature for one hour. Another portion of HCl (4M in 1,4-dioxane, 200 μl, 0.800 mmol) was added and the mixture was refluxed for 1 hour then cooled to room temperature and concentrated in vacuo. The residue was purified using MDAP (modifier: ammonium formate) to give methyl 6-{[(cis)-1-acetyl-2-methyl-6-(4-methyl-1H-imidazol-1-yl)-1,2,3,4-tetrahydro-4-quinolinyl]amino}-3-pyridinecarboxylate (12 mg, 0.029 mmol, 29%) as a white solid.

LCMS (high pH): Retention time 0.84 min, [M+H]+=420.19

Example 145

(2S,4R)-1-Acetyl-2-methyl-6-(4-methyl-1H-imidazol-1-yl)-N-(5-methyl-2-pyridinyl)-1,2,3,4-tetrahydro-4-quinolinamine

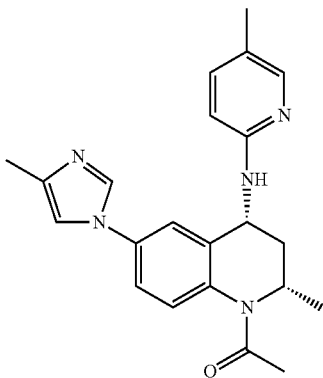

The separation of 69 mg of (cis)-1-acetyl-2-methyl-6-(4-methyl-1H-imidazol-1-yl)-N-(5-methyl-2-pyridinyl)-1,2,3,4-tetrahydro-4-quinolinamine (for a preparation see example 141) using a chiral chromatography column was done as follow: Approximately 20 mg of Example 20 were dissolved in EtOH (2 mL) and Heptane (1 mL) and injected onto the column (10% EtOH/Heptane), f=20 ml/min, wavelength 215 nm, 4. Ref 550,100; Column 2 cm×25 cm Chiralpak AD; Lot No. AD00CJ-JA001) and this operation was repeated 6 times. The fractions corresponding to the faster enantiomer (20-30 min run) were combined and concentrated in vacuo to give (2S,4R)-1-acetyl-2-methyl-6-(4-methyl-1H-imidazol-1-yl)-N-(5-methyl-2-pyridinyl)-1,2,3,4-tetrahydro-4-quinolinamine (20 mg, 58%) as a white solid.

LCMS (high pH): Retention time 0.88 min, [M+H]+=376.25

Example 146

(2S,4R)-1-Acetyl-N-(5-fluoro-2-pyridinyl)-2-methyl-6-[4-(1-piperidinylmethyl)phenyl]-1,2,3,4-tetrahydro-4-quinolinamine

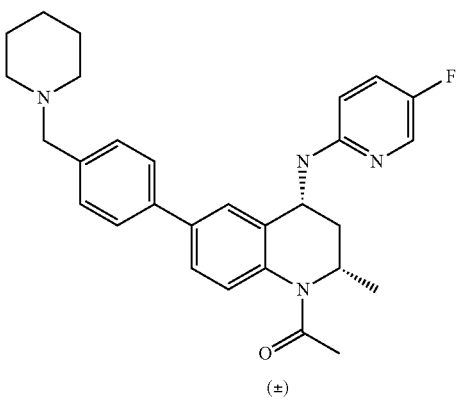 [SMILES: CC(=O)N1c2ccc(-c3ccc(CN4CCCCC4)cc3)cc2[C@H](Nc2ccc(F)cn2)C[C@@H]1C]

A solution of (2S,4R)-1-acetyl-2-methyl-6-[4-(1-piperidinylmethyl)phenyl]-1,2,3,4-tetrahydro-4-quinolinamine (for a preparation see intermediate 66) (150 mg, 0.397 mmol) in toluene (4 mL) was treated under nitrogen with 2-chloro-5-Fluoropyridine (63 mg, 0.479 mmol), sodium tert-butoxide (46 mg, 0.479 mmol), racemic BINAP (12.9 mg, 0.021 mmol) and tris(dibenzylideneacetone)dipalladium(0) (19 mg, 0.021 mmol) and the resulting mixture was stirred under nitrogen at 110° C. for 16 h then cooled to room temperature. The mixture was loaded on a 5 g SCX cartridge and eluted with MeOH (25 mL) then with a 2N NH$_3$ in MeOH (25 mL). The ammonia fractions were combined and concentrated in vacuo. Purification of the residue by flash chromatography on silica gel using a 20 G silica cartridge (gradient:1 to 5% (2N NH$_3$ in MeOH) in DCM) gave (2S,4R)-1-acetyl-N-(5-fluoro-2-pyridinyl)-2-methyl-6-[4-(1-piperidinylmethyl)phenyl]-1,2,3,4-tetrahydro-4-quinolinamine (49.7 mg, 0.098 mmol, 25%) as an orange oil.

LCMS (formic): Retention time 0.70 min, [M+H]+=473.2

Example 147

(2S,4R)-1-Acetyl-2-methyl-6-{1-[2-(methylamino)ethyl]-1H-pyrazol-4-yl}-N-(6-methyl-2-pyridinyl)-1,2,3,4-tetrahydro-4-quinolinamine hydrochloride

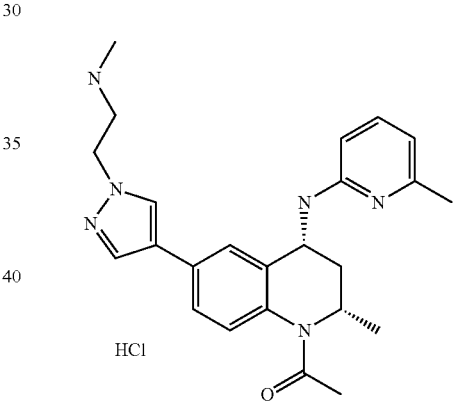

A solution of 1,1-dimethylethyl[2-(4-{(2S,4R)-1-acetyl-2-methyl-4-[(6-methyl-2-pyridinyl)amino]-1,2,3,4-tetrahydro-6-quinolinyl}-1H-pyrazol-1-yl)ethyl]methylcarbamate for a preparation see Intermediate 69) (107.9 mg, 0.208 mmol) in dichloromethane (DCM) (4 mL) was treated with trifluoroacetic acid (TFA) (1 mL, 12.98 mmol) and the resulting mixture was stirred at room temperature for 1.5 h then concentrated in vacuo. The residue was loaded on a 5 g SCX cartridge then eluted with MeOH (20 mL) followed by 2M NH$_3$ in MeOH (20 mL). The ammonia fractions were combined and concentrated in vacuo to give a residue which was dissolved in DCM (5 mL). The resulting solution was treated with HCl (1M in Et$_2$O, 0.22 mL, 0.220 mmol) then concentrated in vacuo. Trituration of the residue with Et$_2$O gave (2S,4R)-1-acetyl-2-methyl-6-{1-[2-(methylamino)ethyl]-1H-pyrazol-4-yl}-N-(6-methyl-2-pyridinyl)-1,2,3,4-tetrahydro-4-quinolinamine hydrochloride (79.5 mg, 0.161 mmol, 77% yield) as a beige solid.

LCMS (high pH): Retention time 0.43 min, [M+H]+=419.23

Example 148

(2S,4R)-1-Acetyl-2-methyl-6-{1-[2-(methylamino)ethyl]-1H-pyrazol-4-yl}-N-(3-methyl-2-pyridinyl)-1,2,3,4-tetrahydro-4-quinolinamine hydrochloride

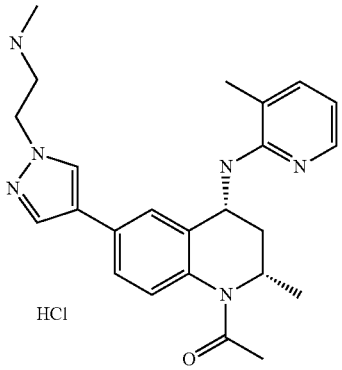 [SMILES: CNCCn1cc(-c2ccc3c(c2)[C@H](Nc2ncccc2C)C[C@H](C)N3C(C)=O)cn1 ; Cl]

A solution of 1,1-dimethylethyl[2-(4-{(2S,4R)-1-acetyl-2-methyl-4-[(3-methyl-2-pyridinyl)amino]-1,2,3,4-tetrahydro-6-quinolinyl}-1H-pyrazol-1-yl)ethyl]methylcarbamate (for a preparation see intermediate 70) (161 mg, 0.310 mmol) in dichloromethane (DCM) (4 mL) was treated with trifluoroacetic acid (TFA) (1 mL, 12.98 mmol) and the resulting mixture was stirred at room temperature for 1.5 h then concentrated in vacuo. The residue was loaded on a 5 g SCX cartridge then eluted with MeOH (20 mL) followed by 2M NH$_3$ in MeOH (20 mL). The ammonia fractions were combined and concentrated in vacuo to give a residue which was dissolved in DCM (5 mL). The resulting solution was treated with HCl (1M in Et$_2$O, 0.22 mL, 0.220 mmol) then concentrated in vacuo. Trituration of the residue with Et$_2$O gave (2S,4R)-1-acetyl-2-methyl-6-{1-[2-(methylamino)ethyl]-1H-pyrazol-4-yl}-N-(3-methyl-2-pyridinyl)-1,2,3,4-tetrahydro-4-quinolinamine hydrochloride (103.3 mg, 0.214 mmol, 68.9% yield) as a light brown solid.

LCMS (high pH): Retention time 0.43 min, [M+H]+=419.23

Example 149

(2S,4R)-1-Acetyl-2-methyl-6-{1-[2-(methylamino)ethyl]-1H-pyrazol-4-yl}-N-(4-methyl-2-pyridinyl)-1,2,3,4-tetrahydro-4-quinolinamine hydrochloride

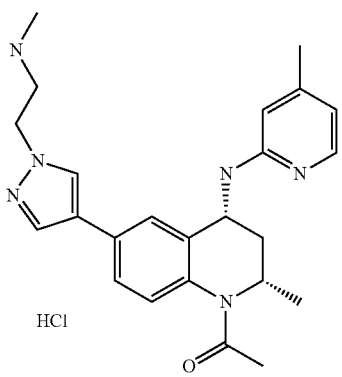 [SMILES: CNCCn1cc(-c2ccc3c(c2)[C@H](Nc2cc(C)ccn2)C[C@H](C)N3C(C)=O)cn1 ; Cl]

A solution of 1,1-dimethylethyl[2-(4-{(2S,4R)-1-acetyl-2-methyl-4-[(4-methyl-2-pyridinyl)amino]-1,2,3,4-tetrahydro-6-quinolinyl}-1H-pyrazol-1-yl)ethyl]methylcarbamate (for a preparation see intermediate 71) (192.2 mg, 0.371 mmol) in dichloromethane (DCM) (4 mL) was treated with trifluoroacetic acid (TFA) (1 mL, 12.98 mmol) and the resulting mixture was stirred at room temperature for 1.5 h then concentrated in vacuo. The residue was loaded on a 5 g SCX cartridge then eluted with MeOH (20 mL) followed by 2M NH$_3$ in MeOH (20 mL). The ammonia fractions were combined and concentrated in vacuo. Purification of the residue on SP4 using a 25 G silica cartridge (gradient:1 to 10% (2M NH$_3$ in MeOH) in DCM) gave a first residue which was purified by MDAP (modifier: formic acid) to give another residue which was dissolved in DCM (5 mL). The resulting solution was treated with HCl (1M in Et$_2$O, 0.22 mL, 0.220 mmol) then concentrated in vacuo. Trituration of the residue with Et$_2$O gave (2S,4R)-1-acetyl-2-methyl-6-{1-[2-(methylamino)ethyl]-1H-pyrazol-4-yl}-N-(4-methyl-2-pyridinyl)-1,2,3,4-tetrahydro-4-quinolinamine hydrochloride (79.7 mg, 0.171 mmol, 46.1% yield) as a white solid.

LCMS (high pH): Retention time 0.43 min, [M+H]+=419.23

Example 150

(2S,4R)-1-Acetyl-N-(3-fluoro-2-pyridinyl)-2-methyl-6-{1-[2-(methylamino)ethyl]-1H-pyrazol-4-yl}-1,2,3,4-tetrahydro-4-quinolinamine hydrochloride

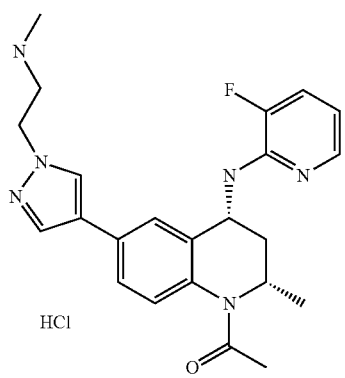 [SMILES: CNCCn1cc(-c2ccc3c(c2)[C@H](Nc2ncccc2F)C[C@H](C)N3C(C)=O)cn1 ; Cl]

A solution of 1,1-dimethylethyl[2-(4-{(2S,4R)-1-acetyl-4-[(3-fluoro-2-pyridinyl)amino]-2-methyl-1,2,3,4-tetrahydro-6-quinolinyl}-1H-pyrazol-1-yl)ethyl]methylcarbamate (for a preparation see intermediate 72) (111.6 mg, 0.214 mmol) in dichloromethane (DCM) (4 mL) was treated with trifluoroacetic acid (TFA) (1 mL, 12.98 mmol) and the resulting mixture was stirred at room temperature for 45 min then concentrated in vacuo. The residue was loaded on a 5 g SCX cartridge then eluted with MeOH (20 mL) followed by 2M NH$_3$ in MeOH (20 mL). The ammonia fractions were combined and concentrated in vacuo to give a residue which was dissolved in DCM (5 mL). The resulting solution was treated with HCl (1M in Et$_2$O, 0.2 mL, 0.2 mmol) then concentrated in vacuo. Trituration of the residue with Et$_2$O gave (2S,4R)-1-acetyl-N-(3-fluoro-2-pyridinyl)-2-methyl-6-{1-[2-(methylamino)ethyl]-1H-pyrazol-4-yl}-1,2,3,4-tetrahydro-4-quinolinamine hydrochloride (67.4 mg, 0.137 mmol, 64.1% yield) as a light orange solid.

LCMS (high pH): Retention time 0.43 min, [M+H]+=423.1

Example 151

(2S,4R)-1-Acetyl-N-(6-fluoro-2-pyridinyl)-2-methyl-6-{1-[2-(methylamino)ethyl]-1H-pyrazol-4-yl}-1,2,3,4-tetrahydro-4-quinolinamine hydrochloride

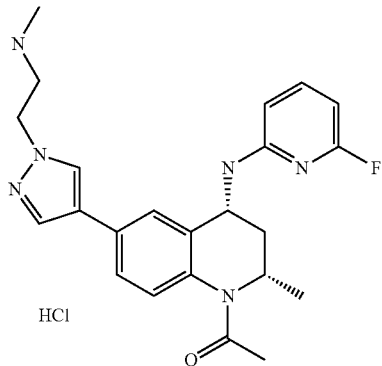 [SMILES: CNCCn1cc(-c2ccc3c(c2)[C@H](Nc2cccc(F)n2)C[C@H](C)N3C(C)=O)cn1 ; Cl]

A solution of 1,1-dimethylethyl[2-(4-{(2S,4R)-1-acetyl-4-[(6-fluoro-2-pyridinyl)amino]-2-methyl-1,2,3,4-tetrahydro-6-quinolinyl}-1H-pyrazol-1-yl)ethyl]methylcarbamate (for a preparation see intermediate 73) (260.2 mg, 0.498 mmol) in dichloromethane (DCM) (4 mL) was treated with trifluoroacetic acid (TFA) (1 mL, 12.98 mmol) and the resulting mixture was stirred at room temperature for 45 min then concentrated in vacuo. The residue was loaded on a 5 g SCX cartridge then eluted with MeOH (20 mL) followed by 2M NH$_3$ in MeOH (20 mL). The ammonia fractions were combined to give a residue which was purified by MDAP (modifier: formic acid) to give a second residue which was dissolved in DCM (5 mL). The resulting solution was treated with HCl (1M in Et$_2$O, 0.24 mL, 0.24 mmol) then concentrated in vacuo. Trituration of the residue with Et$_2$O gave (2S,4R)-1-acetyl-N-(6-fluoro-2-pyridinyl)-2-methyl-6-{1-[2-(methylamino)ethyl]-1H-pyrazol-4-yl}-1,2,3,4-tetrahydro-4-quinolinamine hydrochloride (100.6 mg, 0.201 mmol, 40.4% yield) as a white solid.

LCMS (high pH): Retention time 0.67 min, [M+H]+=423.11

Example 152

(2S,4R)-1-Acetyl-2-methyl-6-{1-[2-(methylamino)ethyl]-1H-pyrazol-4-yl}-N-2-pyrazinyl-1,2,3,4-tetrahydro-4-quinolinamine hydrochloride

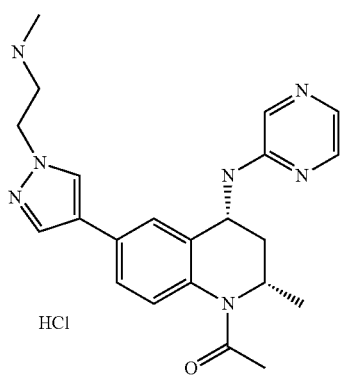 [SMILES: CNCCn1cc(-c2ccc3c(c2)[C@H](Nc2cnccn2)C[C@H](C)N3C(C)=O)cn1 ; Cl]

A solution 1,1-dimethylethyl (2-{4-[(2S,4R)-1-acetyl-2-methyl-4-(2-pyrazinylamino)-1,2,3,4-tetrahydro-6-quinolinyl]-1H-pyrazol-1-yl}ethyl)methylcarbamate (for a preparation see Intermediate 74) (204 mg, 0.403 mmol) in dichloromethane (DCM) (4 mL) was treated with trifluoroacetic acid (TFA) (1 mL, 12.98 mmol) and the resulting mixture was stirred at room temperature for 30 min then concentrated in vacuo. The residue was loaded on a 5 g SCX cartridge then eluted with MeOH (20 mL) followed by 2M NH$_3$ in MeOH (20 mL). The ammonia fractions were combined to give a residue. Purification of this residue on SP4 using a 25 G silica cartridge (gradient:1 to 10% (2M NH$_3$ in MeOH) in DCM) gave a second residue which was purified by MDAP (modifier: formic acid) to give a third residue which was loaded on a 5 g SCX cartridge then eluted with MeOH (20 mL) followed by 2M NH$_3$ in MeOH (20 mL). The ammonia fractions were combined to give a residue which was dissolved in DCM (5 mL). The resulting solution was treated with HCl (1M in Et$_2$O, 0.2 mL, 0.2 mmol) then concentrated in vacuo. Trituration of the residue with Et$_2$O gave (2S,4R)-1-acetyl-2-methyl-6-{1-[2-(methylamino)ethyl]-1H-pyrazol-4-yl}-N-2-pyrazinyl-1,2,3,4-tetrahydro-4-quinolinamine hydrochloride (77 mg, 0.159 mmol, 39.3% yield) as a cream solid.

LCMS (high pH): Retention time 0.53 min, [M+H]+=406.17

Example 153

(2S,4R)-1-Acetyl-2-methyl-6-{1-[2-(methylamino)ethyl]-1H-pyrazol-4-yl}-N-2-pyrimidinyl-1,2,3,4-tetrahydro-4-quinolinamine hydrochloride

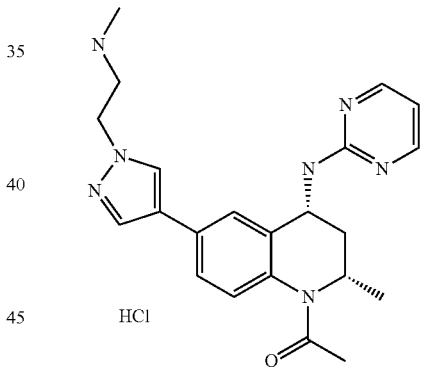

A solution of 1,1-dimethylethyl (2-{4-[(2S,4R)-1-acetyl-2-methyl-4-(2-pyrimidinylamino)-1,2,3,4-tetrahydro-6-quinolinyl]-1H-pyrazol-1-yl}ethyl)methylcarbamate (for a preparation see intermediate 75) (64.8 mg, 0.128 mmol) in dichloromethane (DCM) (4 mL) was treated with trifluoroacetic acid (TFA) (1 mL, 12.98 mmol) and the resulting mixture was stirred at room temperature for 30 min then concentrated in vacuo. The residue was loaded on a 5 g SCX cartridge then eluted with MeOH (20 mL) followed by 2M NH$_3$ in MeOH (20 mL). The ammonia fractions were combined to give a residue which was purified on SP4 using a 25 G silica cartridge (gradient:1 to 10% (2M NH$_3$ in MeOH) in DCM) gave a second residue which was dissolved in DCM (5 mL). The resulting solution was treated with HCl (1M in Et$_2$O, 0.1 mL, 0.1 mmol) then concentrated in vacuo.

Trituration of the residue with Et$_2$O gave (2S,4R)-1-acetyl-2-methyl-6-{-[2-(methylamino)ethyl]-1H-pyrazol-4-yl}-N-2-pyrimidinyl-1,2,3,4-tetrahydro-4-quinolinamine hydrochloride (26.3 mg, 0.059 mmol, 45.8% yield) as an orange solid.

LCMS (formic): Retention time 0.54 min, [M+H]+=406.2

Example 154

(2S,4R)-1-Acetyl-N-(5-fluoro-2-pyridinyl)-2-methyl-6-{1-[2-(methylamino)ethyl]-1H-pyrazol-4-yl}-1,2,3,4-tetrahydro-4-quinolinamine hydrochloride

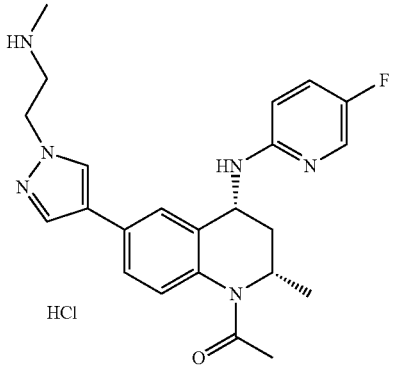 [SMILES: CNCCn1cc(-c2ccc3c(c2)[C@H](Nc2ccc(F)cn2)C[C@H](C)N3C(C)=O)cn1 ; Cl]

A solution of 1,1-dimethylethyl[2-(4-{(2S,4R)-1-acetyl-4-[(5-fluoro-2-pyridinyl)amino]-2-methyl-1,2,3,4-tetrahydro-6-quinolinyl}-1H-pyrazol-1-yl)ethyl]methylcarbamate (for a preparation see intermediate 76) (51 mg, 0.098 mmol) in dichloromethane (DCM) (4 mL) was treated with trifluoroacetic acid (TFA) (1 ml, 12.98 mmol) and the resulting mixture was stirred at room temperature for 1 h then concentrated in vacuo. The residue was loaded onto a 2 g SCX cartridge and eluted with MeOH (45 mL) followed by 2M NH$_3$ in MeOH (45 mL). The ammonia fractions were combined and concentrated in vacuo. The residue was dissolved in MeOH (1 mL) and the solution was treated with HCl (1M in Et$_2$O, 0.11 mmol, 0.11 ml) then was concentrated in vacuo. Trituration of the residue with Et$_2$O gave (2S,4R)-1-acetyl-N-(5-fluoro-2-pyridinyl)-2-methyl-6-{1-[2-(methylamino)ethyl]-1H-pyrazol-4-yl}-1,2,3,4-tetrahydro-4-quinolinamine hydrochloride (52 mg, 0.102 mmol, 104%) as an orange solid.

LCMS (formic): Retention time 0.56 min, [M+H]+=423.2

Example 155

(2S,4R)-1-Acetyl-2-methyl-6-{1-[2-(methylamino)ethyl]-1H-pyrazol-4-yl}-N-(5-methyl-2-pyridinyl)-1,2,3,4-tetrahydro-4-quinolinamine hydrochloride

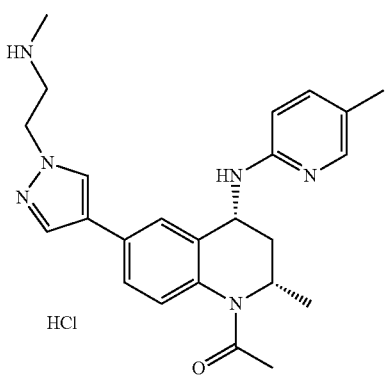 [SMILES: CNCCn1cc(-c2ccc3c(c2)[C@H](Nc2ccc(C)cn2)C[C@H](C)N3C(C)=O)cn1 ; Cl]

A solution of 1,1-dimethylethyl[2-(4-{(2S,4R)-1-acetyl-2-methyl-4-[(5-methyl-2-pyridinyl)amino]-1,2,3,4-tetrahydro-6-quinolinyl}-1H-pyrazol-1-yl)ethyl]methylcarbamate (for a preparation see intermediate 77) (40 mg, 0.077 mmol) in dichloromethane (DCM) (4 mL) was treated with trifluoroacetic acid (1 mL, 12.98 mmol) and the resulting mixture was stirred at room temperature for 3 h then concentrated in vacuo. The residue was loaded onto a 2 g SCX cartridge and eluted with MeOH (45 mL) followed by 2M NH$_3$ in MeOH (45 mL). The ammonia fractions were combined and concentrated in vacuo. The residue was dissolved in MeOH (1 mL) and the solution was treated with HCl (1M in Et$_2$O, 0.09 mmol, 0.09 ml) then was concentrated in vacuo. Trituration of the residue with Et$_2$O gave (2S,4R)-1-acetyl-2-methyl-6-{-1-[2-(methylamino)ethyl]-1H-pyrazol-4-yl}-N-(5-methyl-2-pyridinyl)-1,2,3,4-tetrahydro-4-quinolinamine hydrochloride (39 mg, 0.073 mmol, 94%) as a beige solid.

LCMS (high pH): Retention time 0.43 min, [M+H]+=419.14

Example 156

(2S,4R)-1-Acetyl-N-(4-fluoro-2-pyridinyl)-2-methyl-6-{1-[2-(methylamino)ethyl]-1H-pyrazol-4-yl}-1,2,3,4-tetrahydro-4-quinolinamine hydrochloride

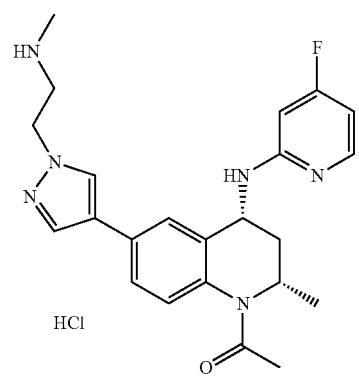 [SMILES: CNCCn1cc(-c2ccc3c(c2)[C@H](Nc2cc(F)ccn2)C[C@H](C)N3C(C)=O)cn1 ; Cl]

A solution of 1,1-dimethylethyl[2-(4-{(2S,4R)-1-acetyl-4-[(4-fluoro-2-pyridinyl)amino]-2-methyl-1,2,3,4-tetrahydro-6-quinolinyl}-1H-pyrazol-1-yl)ethyl]methylcarbamate (for a preparation see intermediate 78) (36 mg, 0.069 mmol) in dichloromethane (DCM) (4 mL) was treated with trifluoroacetic acid (TFA) (1 mL, 12.98 mmol) and the resulting mixture was stirred at room temperature for 2.5 h then concentrated in vacuo. The residue was loaded onto a 2 g SCX cartridge and eluted with MeOH (45 mL) followed by 2M NH$_3$ in MeOH (45 mL). The ammonia fractions were combined and concentrated in vacuo. The residue was dissolved in MeOH (1 mL) and the solution was treated with HCl (1M in Et$_2$O, 0.06 mmol, 0.09 ml) then was concentrated in vacuo. Trituration of the residue with Et$_2$O gave (2S,4R)-1-acetyl-N-(4-fluoro-2-pyridinyl)-2-methyl-6-{1-[2-(methylamino)ethyl]-1H-pyrazol-4-yl}-1,2,3,4-tetrahydro-4-quinolinamine hydrochloride (23 mg, 0.043 mmol, 62%) as a pale brown solid.

LCMS (formic): Retention time 0.46 min, [M+H]+=423.20

Example 157

(2S,4R)-1-Acetyl-N-(5-fluoro-2-pyridinyl)-2-methyl-6-{4-[(methylamino)methyl]phenyl}-1,2,3,4-tetrahydro-4-quinolinamine hydrochloride

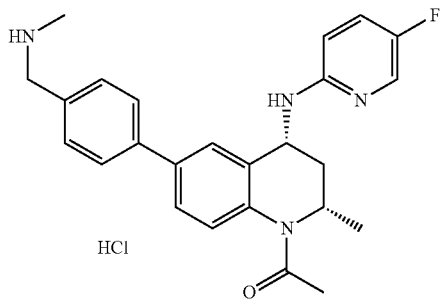 [SMILES: CNCc1ccc(-c2ccc3c(c2)[C@H](Nc2ccc(F)cn2)C[C@H](C)N3C(C)=O)cc1 ; Cl]

A mixture of phenylmethyl[(4-{(2S,4R)-1-acetyl-4-[(5-fluoro-2-pyridinyl)amino]-2-methyl-1,2,3,4-tetrahydro-6-quinolinyl}phenyl)methyl]methylcarbamate (for a preparation see intermediate 79) (55 mg, 0.100 mmol) and palladium (10% w/w on charcoal, 50% wet, 6.35 mg, 0.060 mmol) in ethanol (9 mL) was stirred under hydrogen (1 bar) at room temperature for 17 h then filtered through celite. The insoluble material was rinsed with ethanol (20 mL) and the combined filtrate and washings were concentrated in vacuo. Purification of the residue with MDAP (modifier: ammonium bicarbonate) gave a white solid which was dissolved in MeOH (0.4 mL), then treated with HCl (1.25M in MeOH, 38.3 μL, 0.0478 mmol). The resulting mixture was concentrated in vacuo to give (2S,4R)-1-acetyl-N-(5-fluoro-2-pyridinyl)-2-methyl-6-{4-[(methylamino)methyl]phenyl}-1,2,3,4-tetrahydro-4-quinolinamine hydrochloride (23 mg, 48%) as a pale yellow solid.

LCMS (formic): Retention time 0.57 min, [M+H]+=419.1

Example 158

Ethyl 4-{(2S,4R)-1-acetyl-4-[(4-chlorophenyl)amino]-2-methyl-1,2,3,4-tetrahydro-6-quinolinyl}benzoate

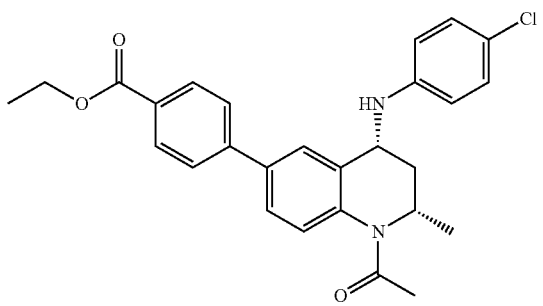 [SMILES: CCOC(=O)c1ccc(-c2ccc3c(c2)[C@H](Nc2ccc(Cl)cc2)C[C@H](C)N3C(C)=O)cc1]

Ethyl 4-[(2S,4R)-1-acetyl-4-amino-2-methyl-1,2,3,4-tetrahydro-6-quinolinyl]benzoate (for a preparation see intermediate 84) (6.6 g, 18.73 mmol), 1-bromo-4-chlorobenzene (3.94 g, 20.60 mmol), bis(dibenzylideneacetone)palladium (0) (690 mg, 1.2 mmol) and [2'-(dicyclohexylphosphanyl)-2-biphenylyl]dimethylamine (Dave-phos) (590 mg, 1.499 mmol)) were mixed in toluene (120 mL) and the resulting mixture was treated with sodium t-butoxide (2.52 g, 26.2 mmol). The reaction was degassed under house vacuum with several quenches with nitrogen, heated at 70° C. under nitrogen for 16 h, then was allowed to cool to room temperature and filtered. The insoluble residue was washed with toluene and then Et₂O. The combined filtrate and washings were washed twice with water then extracted twice with 2N hydrochloric acid solution in water, resulting in the precipitation of an orange oil which was collected with the aqueous acidic phases. The acidic extracts were washed with Et₂O and the combined organic phases were washed with brine, dried using a hydrophobic frit and concentrated in vacuo. Purification of the residue by SP4 using a 330 g silica cartridge (gradient:5 to 45% AcOEt in Hexanes) gave 2.77 g of a pale yellow foam. This foam was dissolved in AcOEt (50 mL) and treated with functional thiourea silica (0.56 g, palladium scavenger). The mixture was stirred at room temperature (air atmosphere) for approximately 20 min and then left at room temperature for 16 h. The mixture was filtered and the insoluble residues washed with AcOEt. The combined filtrate and washings were concentrated in vacuo to give ethyl 4-{(2S,4R)-1-acetyl-4-[(4-chlorophenyl)amino]-2-methyl-1,2,3,4-tetrahydro-6-quinolinyl}benzoate (3.7 g, 8.0 mmol, 32%) as a yellow oil.

LCMS (high pH): Retention time 1.08 min, no mass ion.

Example 159

6-{[(cis)-1-acetyl-2-methyl-6-(4-methyl-1H-imidazol-1-yl)-1,2,3,4-tetrahydro-4-quinolinyl]amino}-3-pyridinecarbonitrile

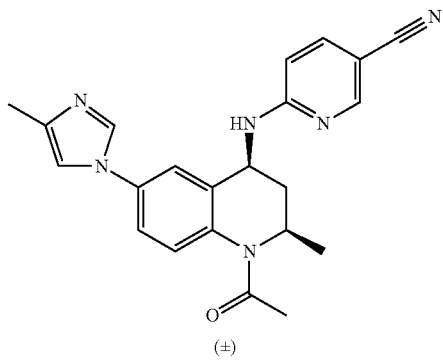 [SMILES: CC(=O)N1c2ccc(-n3cnc(C)c3)cc2[C@@H](Nc2ccc(C#N)cn2)C[C@H]1C]

(±)

A solution of 1-acetyl-2-methyl-6-(4-methyl-1H-imidazol-1-yl)-1,2,3,4-tetrahydro-4-quinolinamine di-hydrochloride (for a preparation see intermediate 61) (85 mg, 0.299 mmol) in NMP (2 mL) was treated with DIPEA (0.209 ml, 1.196 mmol), then 6-chloro-3-pyridinecarbonitrile (49.7 mg, 0.359 mmol) and the resulting mixture was heated at 200° C. for 30 min under microwave irradiation, then cooled to room temperature and the solution purified by MDAP to give 6-{[1-acetyl-2-methyl-6-(4-methyl-1H-imidazol-1-yl)-1,2,3,4-tetrahydro-4-quinolinyl]amino}-3-pyridinecarbonitrile (12.2 mg, 0.032 mmol, 11% yield) as a beige solid.

LCMS (high pH): Retention time 0.56 min, [M+H]+=387.15

Example 160

4-{(2S,4R)-1-Acetyl-4-[(4-chlorophenyl)amino]-2-methyl-1,2,3,4-tetrahydro-6-quinolinyl}benzamide

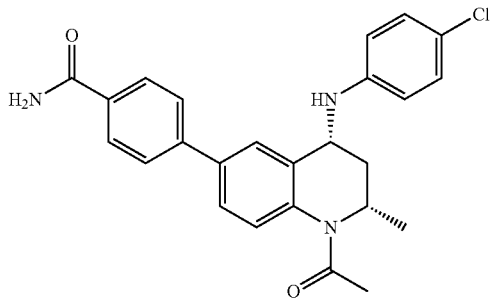 [SMILES: CC(=O)N1c2ccc(-c3ccc(C(N)=O)cc3)cc2[C@H](Nc2ccc(Cl)cc2)C[C@@H]1C]

A flask was charged with 4-{(2S,4R)-1-acetyl-4-[(4-chlorophenyl)amino]-2-methyl-1,2,3,4-tetrahydro-6-quinolinyl}benzoic acid (for a preparation see example 6) (109 mg, 0.251 mmol), HOBT.NH$_3$ (85 mg, 0.501 mmol) and EDC (57.7 mg, 0.301 mmol) then filled with dichloromethane (DCM) (5 mL) and the resulting mixture was treated with N-ethylmorpholine (NEM) (0.095 mL, 0.752 mmol) then stirred a room temperature. After 4 h, 50% of the previous quantities of EDAC, HOBT and NEM were added and the resulting mixture was stirred at room temperature for 16 h. Most of the DCM was removed in vacuo and the residue was partitioned between AcOEt and water. The layers were separated and the aqueous phase was extracted with AcOEt. The combined organic phases were washed twice with a saturated NaHCO$_3$ aqueous solution then brine, dried over MgSO$_4$ and concentrated in vacuo. The residue was triturated with Et$_2$O then filtered off and dried under house vacuum to give 4-{(2S,4R)-1-acetyl-4-[(4-chlorophenyl)amino]-2-methyl-1,2,3,4-tetrahydro-6-quinolinyl}benzamide (75 mg, 0.173 mmol, 69.0% yield) as a very pale yellow solid.

LCMS (high pH): Retention time 1.03 min, [M+H]+=434.05

Example 161

4-[(cis)-1-Acetyl-4-(phenylamino)-2-propyl-1,2,3,4-tetrahydro-6-quinolinyl]benzoic acid

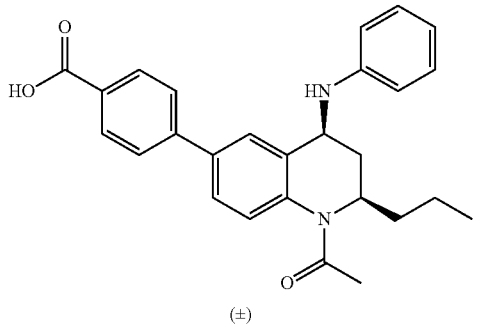 [SMILES: CCC[C@@H]1C[C@H](Nc2ccccc2)c2cc(-c3ccc(C(=O)O)cc3)ccc2N1C(C)=O]
(±)

A mixture of 4-(dihydroxyboranyl)benzoic acid (25.7 mg, 0.155 mmol), (cis)-1-acetyl-6-bromo-N-phenyl-2-propyl-1,2,3,4-tetrahydro-4-quinolinamine (for a preparation see intermediate 86) (40 mg, 0.103 mmol), tetrakis(triphenylphosphine)palladium(0) (11.93 mg, 10.33 µmol) and potassium carbonate (42.8 mg, 0.310 mmol) in 1,4-dioxane (1 mL) and water (0.5 mL) was stirred at 130° C. for 15 min under microwave irradiation then cooled to room temperature and concentrated in vacuo. Purification of the residue by MDAP (modifier:formic acid) gave 4-[(cis)-1-acetyl-4-(phenylamino)-2-propyl-1,2,3,4-tetrahydro-6-quinolinyl]benzoic acid (19 mg, 0.044 mmol, 43%).

LCMS (formic): Retention time 1.16 min, [M−H]−=427.2

Example 162

4-[(cis)-1-Acetyl-2-ethyl-4-(phenylamino)-1,2,3,4-tetrahydro-6-quinolinyl]benzoic acid

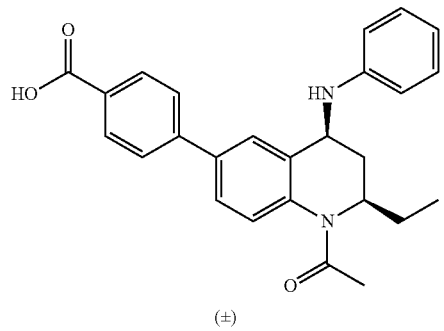 [SMILES: CC[C@@H]1C[C@H](Nc2ccccc2)c2cc(-c3ccc(C(=O)O)cc3)ccc2N1C(C)=O]
(±)

A mixture of 4-(dihydroxyboranyl)benzoic acid (30 mg, 0.181 mmol), (cis)-1-acetyl-6-bromo-2-ethyl-N-phenyl-1,2,3,4-tetrahydro-4-quinolinamine (for a preparation see intermediate 90) (40 mg, 0.107 mmol) and tetrakis(triphenylphosphine)palladium(0) (15 mg, 0.013 mmol) in 1,4-dioxane (1 mL) and water (0.5 mL) was treated with potassium carbonate (45 mg, 0.326 mmol) and the resulting mixture was stirred at 130° C. for 15 min under microwave irradiation then cooled to room temperature and concentrated in vacuo. Purification of the residue by MDAP (modifier: formic acid) gave 4-[(cis)-1-acetyl-2-ethyl-4-(phenylamino)-1,2,3,4-tetrahydro-6-quinolinyl]benzoic acid (20 mg, 0.048 mmol, 45%)

LCMS (formic): Retention time 1.09 min, [M+H]+=415.2

Example 163

(cis)-1-Acetyl-2-ethyl-N-phenyl-6-[4-(1-piperidinylmethyl)phenyl]-1,2,3,4-tetrahydro-4-quinolinamine formate salt

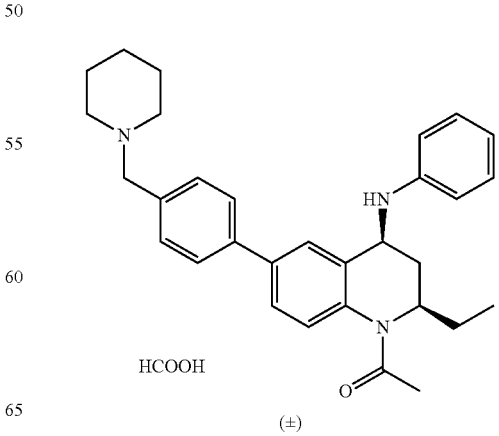
(±)

A solution of 4-[(2R,4S)-1-acetyl-2-ethyl-4-(phenylamino)-1,2,3,4-tetrahydro-6-quinolinyl]benzaldehyde (for a preparation see intermediate 92) (50 mg, 0.125 mmol), piperidine (0.019 mL, 0.188 mmol) and acetic acid (0.014 mL, 0.251 mmol) in dichloromethane (DCM) (4 mL) was stirred at room temperature under nitrogen for 30 min before being treated with sodium triacetoxyborohydride (34.6 mg, 0.163 mmol) portionwise. The resulting mixture was stirred at room temperature for 72 h then was partitioned between DCM (10 mL) and a saturated NaHCO₃ aqueous solution (10 mL). The layers were separated and the organic phase was dried using a hydrophobic frit then concentrated in vacuo. Purification of the residue by MDAP (modifier: formic acid) gave (cis)-1-acetyl-2-ethyl-N-phenyl-6-[4-(1-piperidinylmethyl)phenyl]-1,2,3,4-tetrahydro-4-quinolinamine formate salt (14.8 mg, 0.029 mmol, 23%).

LCMS (formic): Retention time 0.86 min, [M+H]+=468.1

Example 164

(2S,4R)-1-Acetyl-2-methyl-N-phenyl-6-[4-(1-piperidinylmethyl)phenyl]-1,2,3,4-tetrahydro-4-quinolinamine

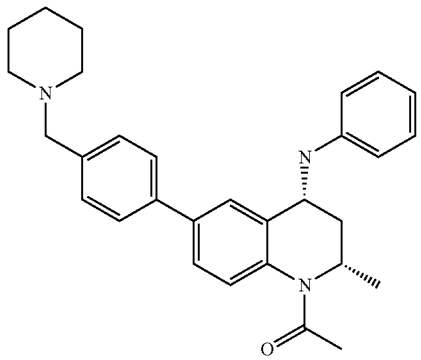 [SMILES: CC(=O)N1c2ccc(-c3ccc(CN4CCCCC4)cc3)cc2[C@H](Nc2ccccc2)C[C@@H]1C]

This example was obtained from Example 17 using chiral chromatographic technique: Column CHIRALPAK AD 250× 4.6 mm 10 μm; eluant: hexane/ethanol 40/60; concentration 1 mg/mL; Injection 10 μL; debit: 1 mL/min. Analysis time: 15 min. Detection UV 254 nm.

Retention time of example in these conditions: 4.7 min

The material can be recrystallised as a yellow powder in DCM/hexanes

[α](D) (c=1.06, MeOH)=+211.93°

Example 165

(2S,4R)-1-Acetyl-6-[3,4-bis(methyloxy)phenyl]-2-methyl-N-3-pyridinyl-1,2,3,4-tetrahydro-4-quinolinamine

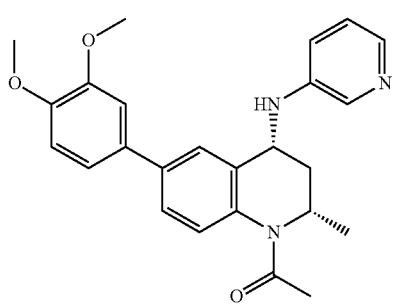 [SMILES: COc1ccc(-c2ccc3c(c2)[C@H](Nc2cccnc2)C[C@H](C)N3C(C)=O)cc1OC]

To a stirred solution of (2S,4R)-1-acetyl-6-[3,4-bis(methyloxy)phenyl]-2-methyl-1,2,3,4-tetrahydro-4-quinolinamine (for a preparation see intermediate 94) (50.1 mg, 0.147 mmol) in dichloromethane (DCM) (2 mL) was added triethylamine (0.061 mL, 0.442 mmol) and copper (II) acetate (41.0 mg, 0.226 mmol) followed after 10 min by 3-pyridinylboronic acid (36.4 mg, 0.296 mmol). The resulting mixture was stirred at room temperature for 3 h. Further 3-pyridinylboronic acid (9.1 mg, 0.074 mmol) was added and the mixture was stirred at room temperature for a further 6 days after which time the solvent had evaporated in vacuo. After standing for 19 days, further dichloromethane (DCM) (2 mL) was added followed by further 3-pyridinylboronic acid (18.6 mg, 0.151 mmol) and copper (II) acetate (42.3 mg, 0.233 mmol). The mixture was stirred at room temperature for a further 24 h, then left to stand for 36 h before further triethyalamine (0.061 mL, 0.443 mmol) and 3-pyridinylboronic acid (19.8 mg, 0.161 mmol) were added. Stirring at room temperature continued for a further 6 h before additional 3-pyridinylboronic acid (19.5 mg, 0.159 mmol) was added. After stirring for a further 65 h a 3:1 mixture of water/0.880 ammonia (1 mL) was added and the mixture was stirred for 15 min then was diluted with a saturated NaHCO₃ aqueous solution (6 mL). The aqueous phase was extracted with dichloromethane (3×6 mL) and the combined organic phases were dried using a phase separator then concentrated using a stream of nitrogen. The residue was dissolved in methanol (1 mL) and was purified by MDAP (modifier: formic acid) to give (2S,4R)-1-acetyl-6-[3,4-bis(methyloxy)phenyl]-2-methyl-N-3-pyridinyl-1,2,3,4-tetrahydro-4-quinolinamine (2.8 mg, 6.71 μmol, 4.56% yield) as a light brown oil.

LCMS (formic): Retention time 0.74 min, [M+H]+=418.32

Example 166

4-[(2S,4R)-1-Acetyl-2-methyl-4-(3-pyridinylamino)-1,2,3,4-tetrahydro-6-quinolinyl]-3-methylbenzoic acid

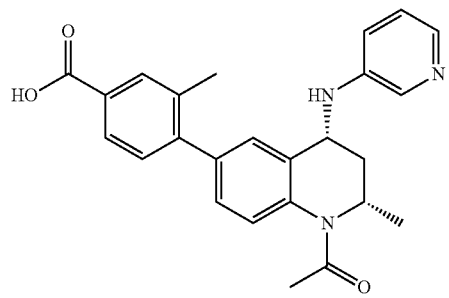 [SMILES: CC(=O)N1c2ccc(-c3ccc(C(=O)O)cc3C)cc2[C@H](Nc2cccnc2)C[C@@H]1C]

Methyl 4-[(2S,4R)-1-acetyl-2-methyl-4-(3-pyridinylamino)-1,2,3,4-tetrahydro-6-quinolinyl]-3-methylbenzoate (for a preparation see Example 173) (25 mg, 0.058 mmol) was dissolved in ethanol (1 mL) and treated with sodium hydroxide (1M in water, 0.291 mL, 0.291 mmol) and the resulting mixture was stirred at room temperature for 4 h then was concentrated in vacuo. Purification of the residue by MDAP (modifier: formic acid) gave 4-[(2S,4R)-1-acetyl-2-methyl-4-(3-pyridinylamino)-1,2,3,4-tetrahydro-6-quinolinyl]-3-methylbenzoic acid (2 mg, 8%) as a brown solid.

LCMS (formic): Retention time 0.67 min, [M+H]+=416.21

Example 167

Methyl-4-[(2S,4R)-1-acetyl-2-methyl-4-(3-pyridinylamino)-1,2,3,4-tetrahydro-6-quinolinyl]-3-methylbenzoate

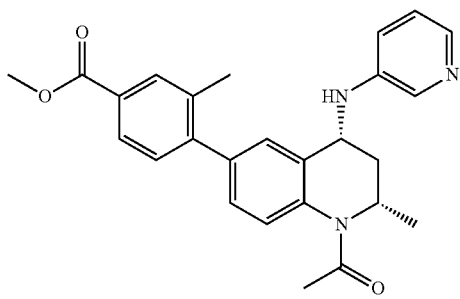 [SMILES: COC(=O)c1ccc(-c2ccc3c(c2)[C@H](Nc2cccnc2)C[C@H](C)N3C(C)=O)c(C)c1]

Methyl-4-[(2S,4R)-1-acetyl-4-amino-2-methyl-1,2,3,4-tetrahydro-6-quinolinyl]-3-methylbenzoate (for a preparation see Intermediate 96) (40 mg, 0.113 mmol) was dissolved in dichloromethane (DCM) (1.5 mL) and treated with copper (II) acetate (30.9 mg, 0.170 mmol) and triethylamine (0.047 mL, 0.340 mmol) The resulting mixture was stirred at room temperature for a few minutes then pyridine-3-boronic acid (41.9 mg, 0.340 mmol) was added. After 5 h, further boronic acid (3.5 mg, 0.028 mmol, 0.25 eq) was added and the mixture stirred at room temperature. The stirring was continued for 7 days with 10 additions of pyridine-3-boronic acid (41.9 mg, 0.340 mmol) at regular intervals (except on day 4 and day 5). The reaction mixture was then treated with a 3:1 water/ammonia 0.88 (1 mL), then was stirred for 10 min before being diluted with DCM (20 mL). The layers were separated and the organic phase was washed with a saturated NaHCO$_3$ aqueous solution. The combined aqueous phases were extracted with DCM (20 mL). The combined organic phases were dried using a hydrophobic frit and then concentrated in vacuo. Purification of the residue on SP4 using a 10 G silica cartridge (gradient:50 to 100% AcOEt in Hexanes then 0 to 10% (2M NH$_3$ in MeOH) in DCM) gave Methyl 4-[(2S,4R)-1-acetyl-2-methyl-4-(3-pyridinylamino)-1,2,3,4-tetrahydro-6-quinolinyl]-3-methylbenzoate (25 mg, 50%) as a yellow oil.

LCMS (formic): Retention time 0.82 min, [M+H]+=430.23

Example 168

3-[(2S,4R)-1-Acetyl-2-methyl-4-(3-pyridinylamino)-1,2,3,4-tetrahydro-6-quinolinyl]benzoic acid

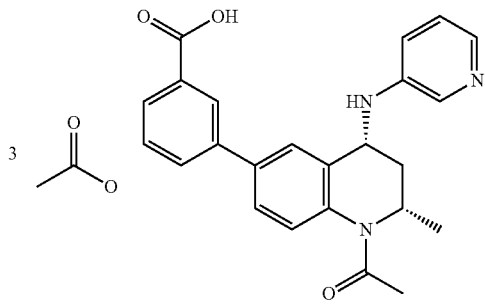

To a stirred solution of methyl 3-[(2S,4R)-1-acetyl-2-methyl-4-(3-pyridinylamino)-1,2,3,4-tetrahydro-6-quinolinyl]benzoate (for a preparation see Example 175) (14.5 mg, 0.035 mmol) in methanol (1 mL) was added NaOH (2M in water, 0.5 mL, 1.000 mmol) and the resulting mixture was stirred at room temperature for 100 min then was concentrated under a stream of nitrogen. The residue was dissolved in water (0.2 mL) and methanol (0.8 mL) before being purified by MDAP (modifier: formic acid) to give 3-[(2S,4R)-1-acetyl-2-methyl-4-(3-pyridinylamino)-1,2,3,4-tetrahydro-6-quinolinyl]benzoic acid:formic acid 1:3 (14.3 mg, 85% yield).

LCMS (formic): Retention time 0.67 min, [M+H]+=402.20

Example 169

Methyl 3-[(2S,4R)-1-acetyl-2-methyl-4-(3-pyridinylamino)-1,2,3,4-tetrahydro-6-quinolinyl]benzoate

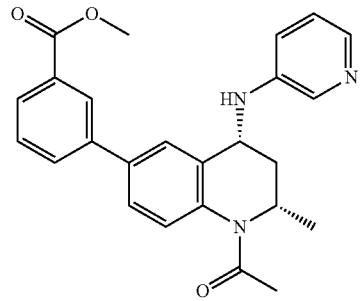 [SMILES: COC(=O)c1cccc(-c2ccc3c(c2)[C@H](Nc2cccnc2)C[C@H](C)N3C(C)=O)c1]

To a stirred solution of methyl 3-[(2S,4R)-1-acetyl-4-amino-2-methyl-1,2,3,4-tetrahydro-6-quinolinyl]benzoate (for a preparation see Intermediate 98) (50.0 mg, 0.148 mmol) in dichloromethane (DCM) (2 mL) were added triethylamine (0.062 mL, 0.443 mmol) and copper (II) acetate (40.2 mg, 0.221 mmol) followed after 10 min by 3-pyridinylboronic acid (36.7 mg, 0.299 mmol). The resulting mixture was stirred at room temperature for 3 h. Further 3-pyridinylboronic acid (9.2 mg, 0.075 mmol) was added and the mixture was stirred at room temperature for a further 6 days after which time the solvent had evaporated in vacuo. After standing for 19 days, further dichloromethane (DCM) (2 mL) was added followed by further 3-pyridinylboronic acid (18.8 mg, 0.153 mmol) and copper (II) acetate (45.0 mg, 0.248 mmol). The mixture was stirred at room temperature for a further 24 h, then left to stand for 36 h before further triethyalamine (0.062 mL, 0.443 mmol) and 3-pyridinylboronic acid (18.2 mg, 0.148 mmol) were added. The mixture was stirred at room temperature for a further 6 hours before additional 3-pyridinylboronic acid (18.5 mg, 0.151 mmol) was added. After stirring for a further 65 h a 3:1 mixture of water/0.880 ammonia (1 mL) was added and the mixture was stirred for 15 min then was diluted with a saturated NaHCO3 aqueous solution (6 mL). The aqueous phase was extracted with dichloromethane (3×6 mL). The combined organic phases were dried using a phase separator and the solvent was evaporated under a stream of nitrogen. Purification of the residue by MDAP (modifier: ammonium bicarbonate) gave methyl 3-[(2S,4R)-1-acetyl-2-methyl-4-(3-pyridinylamino)-1,2,3,4-tetrahydro-6-quinolinyl]benzoate (10.1 mg, 0.024 mmol, 16.45% yield) as a clear gum.

LCMS (formic): Retention time 0.79 min, [M+H]+=416.21

Example 170

3-[(2S,4R)-1-acetyl-2-methyl-4-(3-pyridinylamino)-1,2,3,4-tetrahydro-6-quinolinyl]-N,N-dimethylbenzamide

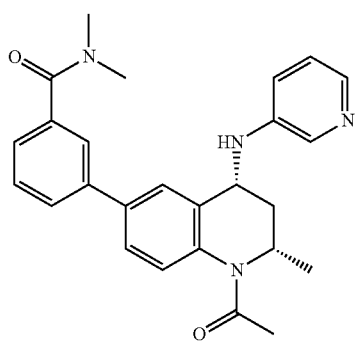 [SMILES: CC(=O)N1c2ccc(-c3cccc(C(=O)N(C)C)c3)cc2[C@H](Nc2cccnc2)C[C@@H]1C]

A solution of 3-[(2S,4R)-1-acetyl-2-methyl-4-(3-pyridinylamino)-1,2,3,4-tetrahydro-6-quinolinyl]benzoic acid (for a preparation see Example 174) (9.0 mg, 0.022 mmol) and O-(7-azabenzotriazol-1-yl)-N,N,N',N'-tetramethyluronium-hexafluorophosphate (HATU) (43.6 mg, 0.115 mmol) in N,N-dimethylformamide (DMF) (0.5 ml) was treated with N,N-diisopropylethylamine (DIPEA) (0.023 ml, 0.135 mmol) and dimethylamine (2.0M solution in THF, 0.112 ml, 0.224 mmol). The resulting mixture was stirred at room temperature for 55 min then was reduced in volume under a stream of nitrogen, diluted with acetonitrile and directly purified by MDAP to give 3-[(2S,4R)-1-acetyl-2-methyl-4-(3-pyridinylamino)-1,2,3,4-tetrahydro-6-quinolinyl]-N,N-dimethylbenzamide (5.7 mg, 0.013 mmol, 59.3% yield) as a orange gum.

LCMS (formic): Retention time 0.67 min, [M+H2]+=429.21

Example 171

(2S,4R)-1-Acetyl-2-methyl-N-(5-methyl-2-pyridinyl)-6-(1H-1,2,3-triazol-4-yl)-1,2,3,4-tetrahydro-4-quinolinamine

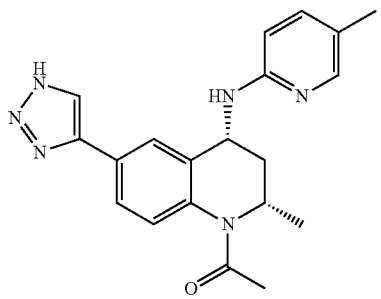

A flask was charged with (2S,4R)-1-acetyl-6-ethynyl-2-methyl-N-(5-methyl-2-pyridinyl)-1,2,3,4-tetrahydro-4-quinolinamine (for a preparation see Intermediate 110) (57 mg, 0.178 mmol) and copper(I) iodide (3.40 mg, 0.018 mmol) then filled with N,N-dimethylformamide (DMF) (1.8 mL) and methanol (0.2 mL) and the resulting mixture was treated with trimethylsilyl azide (0.095 mL, 0.714 mmol). The flask was flushed with nitrogen then the mixture was stirred at 100° C. for 2 h under microwave irradiation then cooled to room temperature. Most of the methanol was removed in vacuo and the residue partitioned between AcOEt and water. The layers were separated and the aqueous layer was extracted with AcOEt. The combined organic phases were washed with water, dried over MgSO₄ and concentrated in vacuo. Purification of the residue by MDAP (modifier: ammonium bicarbonate) gave (2S,4R)-1-acetyl-2-methyl-N-(5-methyl-2-pyridinyl)-6-(1H-1,2,3-triazol-4-yl)-1,2,3,4-tetrahydro-4-quinolinamine (0.6 mg, 1.655 μmol, 0.928% yield) as a colourless solid.

LCMS (Method B): Retention time 0.73 min, [M+H]+=363.16

Example 172

(2S,4R)-1-Acetyl-2-methyl-N-(6-methyl-2-pyridinyl)-6-(1H-1,2,3-triazol-4-yl)-1,2,3,4-tetrahydro-4-quinolinamine

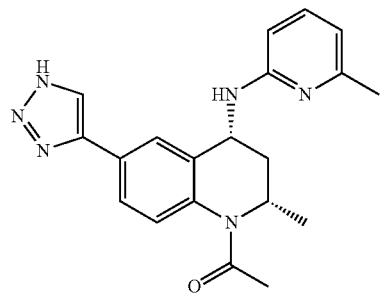 [SMILES: CC(=O)N1c2ccc(-c3c[nH]nn3)cc2[C@H](Nc2cccc(C)n2)C[C@@H]1C]

A flask was charged with (2S,4R)-1-acetyl-6-ethynyl-2-methyl-N-(6-methyl-2-pyridinyl)-1,2,3,4-tetrahydro-4-quinolinamine (for a preparation see Intermediate 112) (90 mg, 0.282 mmol) and copper(I) iodide (5.37 mg, 0.028 mmol) then filled with N,N-dimethylformamide (DMF) (0.9 mL) and methanol (0.100 mL) and the resulting mixture was treated with trimethylsilyl azide (0.150 mL, 1.127 mmol). The flask was flushed with nitrogen then the mixture was stirred at 100° C. for 1 hr under microwave irradiation then cooled to room temperature. Most of the methanol was removed in vacuo and the remaining organic phase was purified by MDAP (modifier: ammonium bicarbonate) to give (2S,4R)-1-acetyl-2-methyl-N-(6-methyl-2-pyridinyl)-6-(1H-1,2,3-triazol-4-yl)-1,2,3,4-tetrahydro-4-quinolinamine (3 mg, 8.28 μmol, 2.94% yield) as a colourless glass.

LCMS (Method B): Retention time 0.72 min, [M+H]+=363.15

Example 173

(2S,4R)-1-Acetyl-2-methyl-N-2-pyrimidinyl-6-(1H-1,2,3-triazol-4-yl)-1,2,3,4-tetrahydro-4-quinolinamine

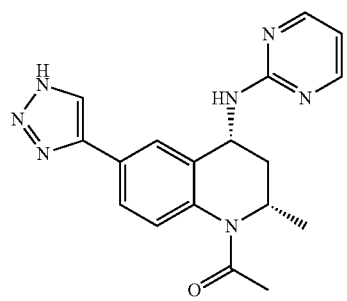 [SMILES: CC(=O)N1c2ccc(-c3c[nH]nn3)cc2[C@H](Nc2ncccn2)C[C@@H]1C]

A flask was charged with (2S,4R)-1-acetyl-6-ethynyl-2-methyl-N-2-pyrimidinyl-1,2,3,4-tetrahydro-4-quinolinamine (for a preparation see Intermediate 114) (45 mg, 0.147 mmol) and copper (I) iodide (2.80 mg, 0.015 mmol) then filled with N,N-dimethylformamide (DMF) (1.8 mL) and methanol (0.200 mL) and the resulting mixture was treated with trimethylsilyl azide (0.078 mL, 0.588 mmol). The flask was flushed with nitrogen then the mixture was stirred at 100° C. for 1 h under microwave irradiation then cooled to room temperature. Most of the methanol was removed in vacuo and the remaining organic phase was purified by MDAP (modifier: ammonium bicarbonate) to give (2S,4R)-1-acetyl-2-methyl-N-2-pyrimidinyl-6-(1H-1,2,3-triazol-4-yl)-1,2,3,4-tetrahydro-4-quinolinamine (3 mg, 8.59 µmol, 5.85% yield) as a colourless film.

LCMS (Method B): Retention time 0.58 min, [M+H]+=350.17

Further compounds of the invention include:

| Ex No. | Structure |
|---|---|
| 174 | 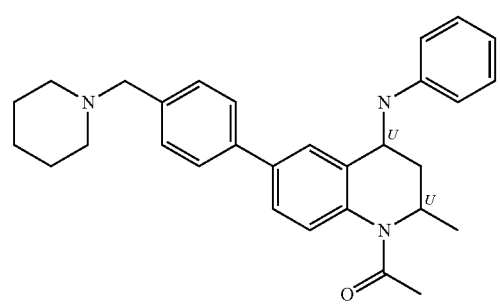 |
| 175 | 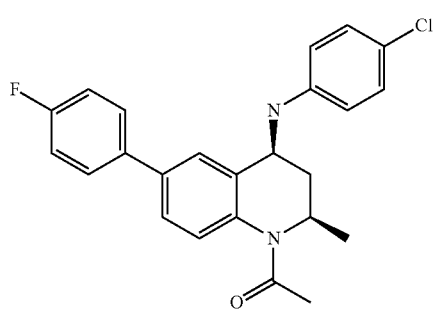 [SMILES: CC(=O)N1c2ccc(-c3ccc(F)cc3)cc2[C@@H](Nc2ccc(Cl)cc2)C[C@H]1C] |
| 176 | 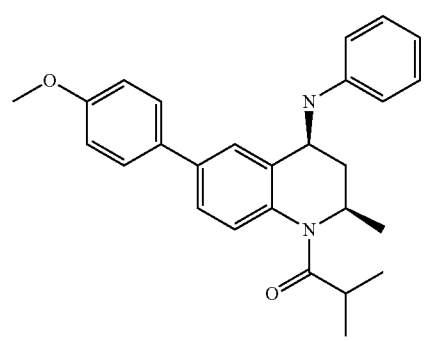 [SMILES: COc1ccc(-c2ccc3c(c2)[C@@H](Nc2ccccc2)C[C@@H](C)N3C(=O)C(C)C)cc1] |
| 177 | 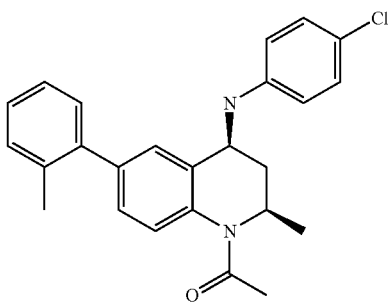 [SMILES: CC(=O)N1c2ccc(-c3ccccc3C)cc2[C@@H](Nc2ccc(Cl)cc2)C[C@H]1C] |
| 178 | 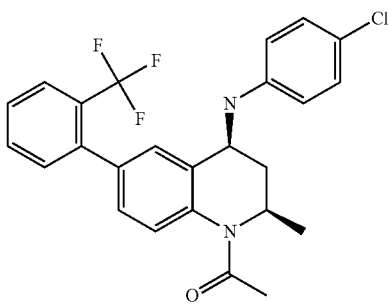 [SMILES: CC(=O)N1c2ccc(-c3ccccc3C(F)(F)F)cc2[C@@H](Nc2ccc(Cl)cc2)C[C@H]1C] |
| 179 | 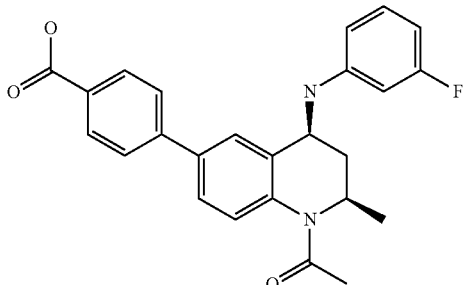 |
| 180 | 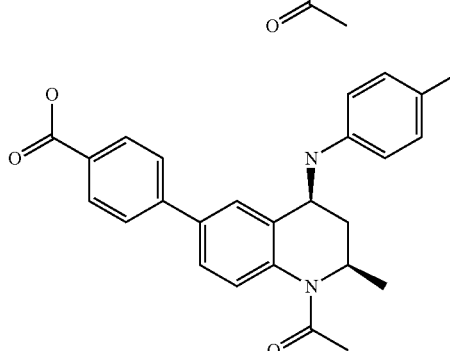 |
| 181 | 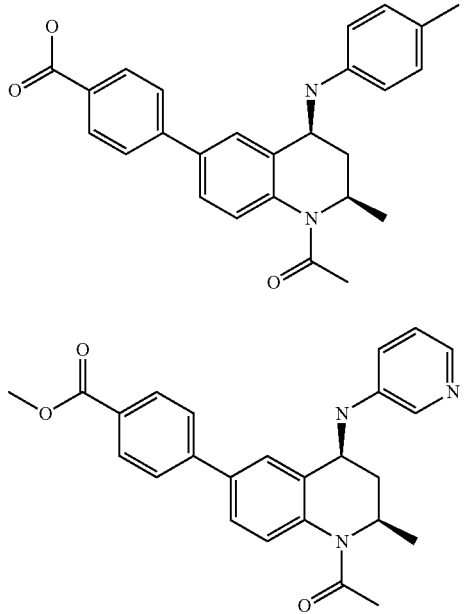 |

| Ex No. | Structure |
|---|---|
| 182 | 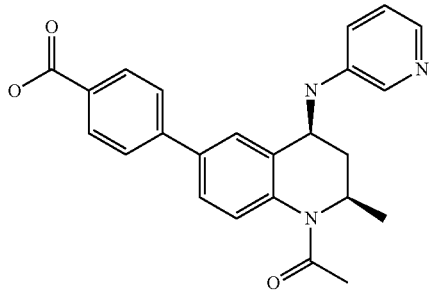 [SMILES: CC(=O)N1c2ccc(-c3ccc(C(=O)O)cc3)cc2[C@@H](Nc2cccnc2)C[C@H]1C] |
| 183 | 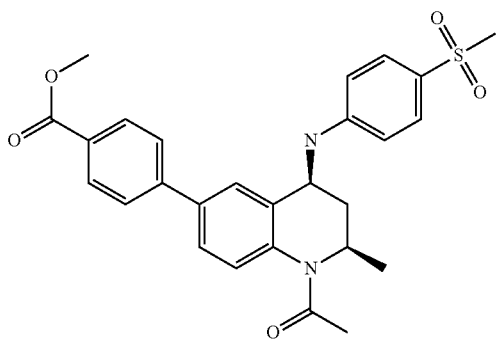 [SMILES: COC(=O)c1ccc(-c2ccc3c(c2)[C@@H](Nc2ccc(S(C)(=O)=O)cc2)C[C@@H](C)N3C(C)=O)cc1] |
| 184 | 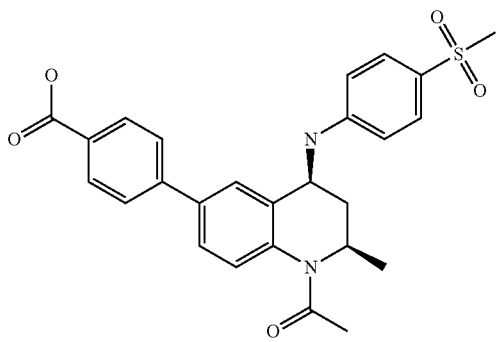 [SMILES: CC(=O)N1c2ccc(-c3ccc(C(=O)O)cc3)cc2[C@@H](Nc2ccc(S(C)(=O)=O)cc2)C[C@H]1C] |
| 185 | 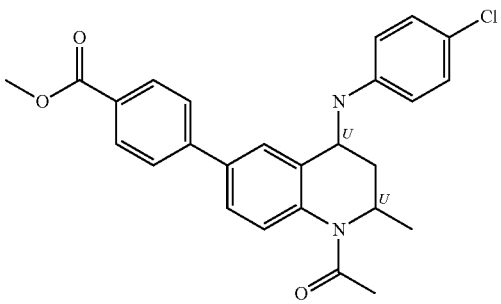<br>(cis) Enantiomer 1 |
| 186 | 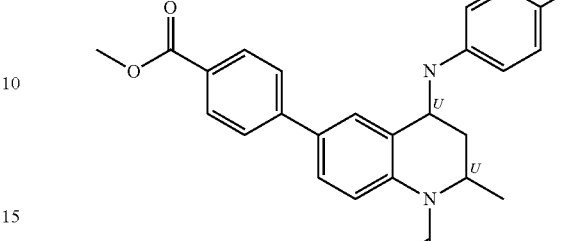<br>(cis) Enantiomer 2 |
| 187 | 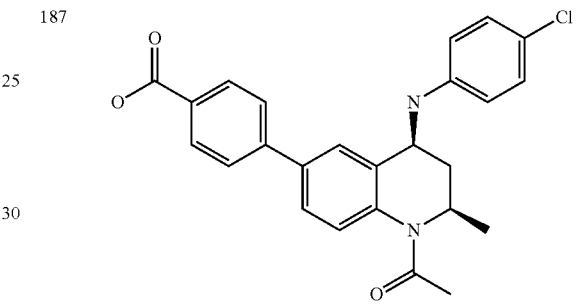 |
| 188 | 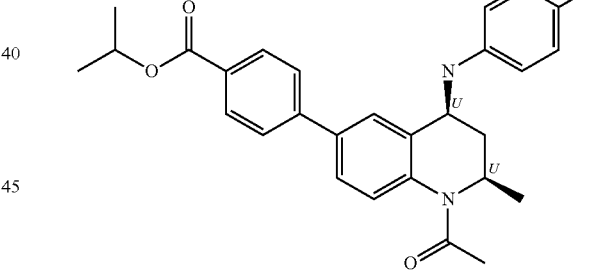 |
| 189 | 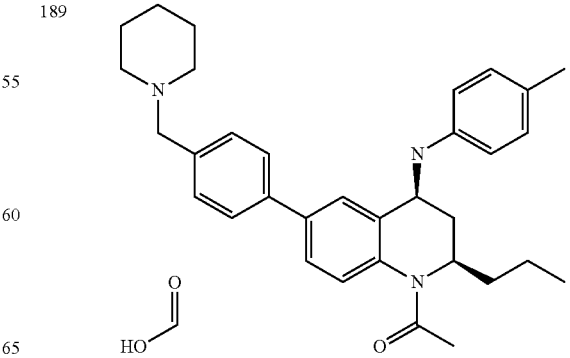 |

| Ex No. | Structure |
|---|---|
| 190 | 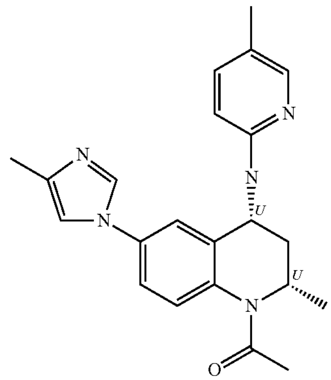 |
| 191 | 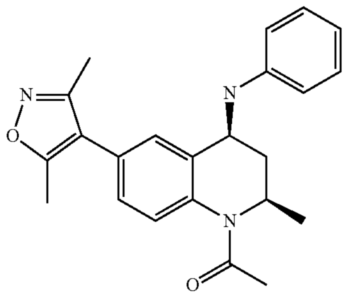 [SMILES: CC(=O)N1c2ccc(-c3c(C)noc3C)cc2[C@@H](Nc2ccccc2)C[C@H]1C] |

It will be understood that in the context of the examples used to illustrate the invention that information about how the compounds were prepared cannot be drawn from the format used to present the information, for example, the intermediates and final products may have been prepared by different individuals, and/or at different timepoints, employing various batches and appropriate techniques.

Reference Compounds

Experimental details of LC/MS methods D and F as referred to herein are as follows:

LC/MS (Method D) was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give $[M+H]^+$ and $[M+NH_4]^+$ molecular ions] or electrospray negative ionisation [(ES−ve to give [M−H]− molecular ion] modes. Analytical data from this apparatus are given with the following format: $[M+H]^+$ or $[M-H]^-$.

LC/MS (Method F) was conducted on an Sunfire C18 column (30 mm×4.6 mm i.d. 3.5 μm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give $MH^+$ molecular ions] or electrospray negative ionisation [ES−ve to give $(M-H)^-$ molecular ions] modes.

TLC (thin layer chromatography) refers to the use of TLC plates sold by Merck coated with silica gel 60 F254.

Silica chromatography techniques include either automated (Flashmaster or Biotage SP4) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Reference Compound A 2-methyl-6-(methyloxy)-4H-3,1-benzoxazin-4-one

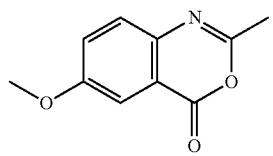

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 $[M+H]^+$, Rt 1.69 min.

Reference Compound B

[2-amino-5-(methyloxy)phenyl](4-chlorophenyl)methanone

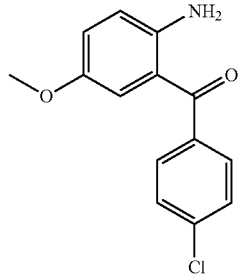 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in $Et_2O$, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield); LC/MS (Method D): m/z 262 [M+H]+, Rt 2.57 min.

Reference Compound C

Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate

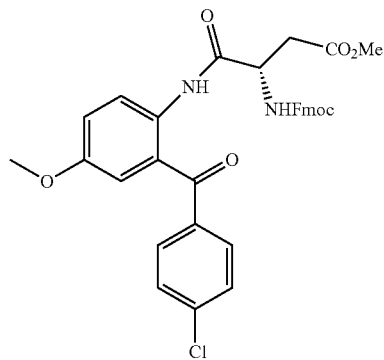

Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl$_3$ (270 mL) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference Compound D

Methyl[(3S)-5-(4-chlorophenyl)-7-(methyloxy)-2-oxo-2,3-dihydro-1H-1,4-benzodiazepin-3-yl]acetate

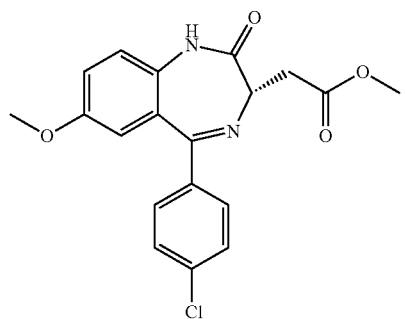

To a solution of Methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product R$_f$=0.34 (DCM/MeOH:95/5).

HRMS (M+H)$^+$ calculated for C$_{19}$H$_{18}$$^{35}$ClN$_2$O$_4$ 373.0955. Found 373.0957.

Reference Compound E

Methyl[(3S)-5-(4-chlorophenyl)-7-(methyloxy)-2-thioxo-2,3-dihydro-1H-1,4-benzodiazepin-3-yl]acetate

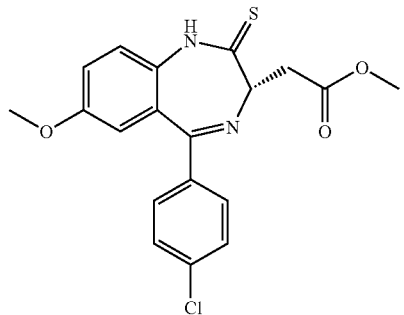

A suspension of P$_4$S$_{10}$ (36.1 g, 81.1 mmol) and Na$_2$CO$_3$ (8.6 g, 81.1 mmol) in 1,2-DCE (700 mL) at room temperature was stirred for 2 h before Methyl[(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. NaHCO$_3$ and brine. The organic layer was dried over Na$_2$SO$_4$, filtered and concentrated under reduced pressure. The crude product was purified by flash-chromatography on silica gel (DCM/MeOH:99/1) to afford the title compound (17.2 g, 98% yield) as a yellowish solid. LC/MS (Method D): m/z 389 [M($^{35}$Cl)+H]$^+$, Rt 2.64 min HRMS (M+H)$^+$ calculated for C$_{19}$H$_{18}$$^{35}$ClN$_2$O$_3$S 389.0727. Found 389.0714.

Reference Compound F

Methyl[(3S)-2-[(1Z)-2-acetylhydrazino]-5-(4-chlorophenyl)-7-(methyloxy)-3H-1,4-benzodiazepin-3-yl]acetate

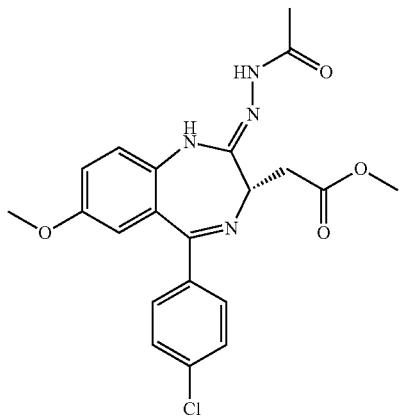

To a suspension of methyl[(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. Et$_3$N (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over Na$_2$SO$_4$, filtered and concentrated in vacuo to give the crude title compound (9.7 g, 98% yield) which was used without further purification. R$_f$=0.49 (DCM/MeOH:90/10).

Reference Compound G

Methyl[(4S)-6-(4-chlorophenyl)-1-methyl-8-(methyloxy)-4H-[1,2,4]triazolo[4,3-a][1,4]benzodiazepin-4-yl]acetate

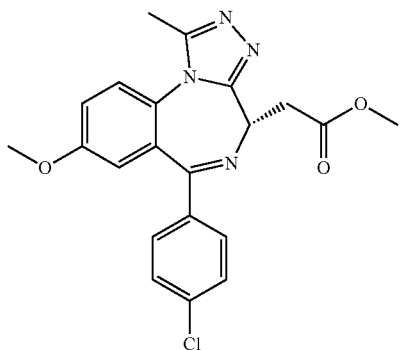

The crude methyl[(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-Pr$_2$O and filtered to give the title compound (8.7 g, 91% over 3 steps) as an off-white solid.

HRMS (M+H)$^+$ calculated for C$_{21}$H$_{20}$ClN$_4$O$_3$ 411.1229. Found 411.1245.

Reference Compound H

[(4S)-6-(4-Chlorophenyl)-1-methyl-8-(methyloxy)-4H-[1,2,4]triazolo[4,3-a][1,4]benzodiazepin-4-yl] acetic acid

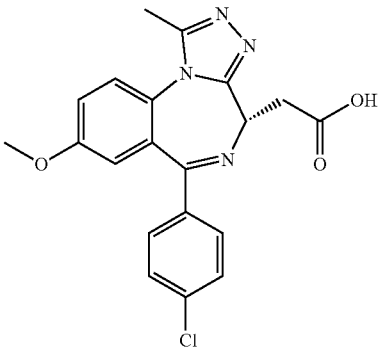 [SMILES: COc1ccc2c(c1)C(c1ccc(Cl)cc1)=N[C@@H](CC(=O)O)c1nnc(C)n1-2]

To a solution of methyl[(4S)-6-(4-chlorophenyl)-1-methyl-8-(methyloxy)-4H-[1,2,4]triazolo[4,3-a][1,4]benzodiazepin-4-yl]acetate (for a preparation see Reference compound G)(7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over Na$_2$SO$_4$, filtered and concentrated under reduced pressure to give the title compound (7 g, 98% yield) as a pale yellow solid.

Reference Compound H 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

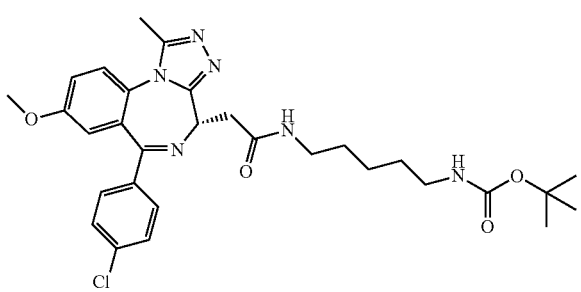 [SMILES: COc1ccc2c(c1)C(c1ccc(Cl)cc1)=N[C@@H](CC(=O)NCCCCCNC(=O)OC(C)(C)C)c1nnc(C)n1-2]

A mixture of [(4S)-6-(4-chlorophenyl)-1-methyl-8-(methyloxy)-4H-[1,2,4]triazolo[4,3-a][1,4]benzodiazepin-4-yl] acetic acid (for a preparation see Reference compound G)

(1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference Compound J

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate To a solution of 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound H) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS (M+H)$^+$ calculated for $C_{25}H_{29}ClN_6O_2$ 481.2119. Found 481.2162.

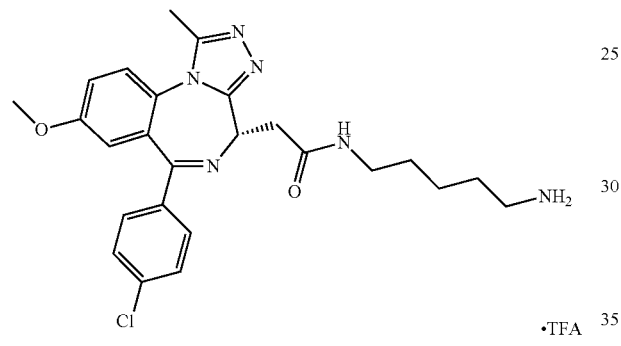

Reference Compound K

Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]-benzodiazepin-4-yl]acetamide

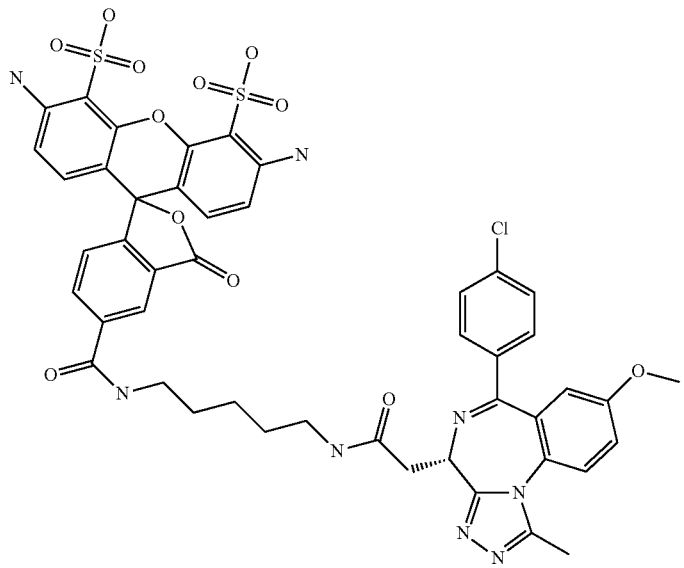

-continued

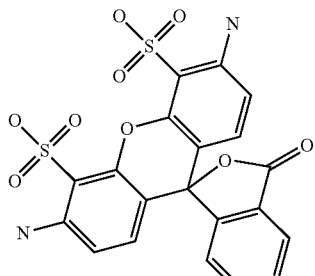
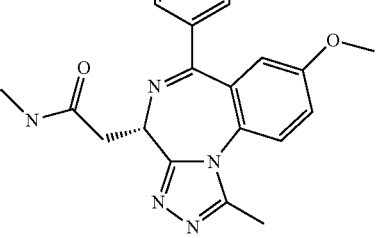

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-Dimethylformamide (DMF) (300 µl) and added to Alexa Fluor 488 carboxylic acid succinimidyl ester (5 mg, 7.77 µmol, mixture of 5 and 6 isomers, available from Invitrogen, product number A-20100) in an Eppendorf centrifuge tube. Hunig's base (7.0 µl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown.

LC/MS (Method F): MH+=999, rt=1.88 min.

BIOLOGICAL TEST METHODS

Fluorescence Anisotropy Binding Assay

The binding of the compounds of formula (I) to Bromodomain 2, 3 and 4 was assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$y = a + ((b-a)/(1 + (10^x/10^c)^d)$

Where 'a' is the minimum, 'b' is the Hill slope, 'c' is the pIC50 and 'd' is the maximum.

Recombinant Human Bromodomains (Bromodomain 2 (1-473), Bromodomain 3 (1-435) and Bromodomain 4 (1-477)) were expressed in $E.\ coli$ cells (in pET15b vector) with a six-His tag at the N-terminal. The His-tagged Bromodomain was extracted from $E.\ coli$ cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80 C in 20 mM HEPES pH 7.5 and 100 mM NaCl.

Protocol for Bromodomain BRD2: All components were dissolved in buffer composition of 50 mM HEPES pH7.4, 150 mm NaCl and 0.5 mM CHAPS with final concentrations of Bromodomain 2, 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic −505 nM).

Protocol for Bromodomain BRD3: All components were dissolved in buffer of composition 50 mM HEPES pH7.4, 150 mm NaCl and 0.5 mM CHAPS with final concentrations of Bromodomain 3, 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic −505 nM).

Protocol for Bromodomain BRD4: All components were dissolved in buffer of composition 50 mM HEPES pH7.4, 150 mm NaCl and 0.5 mM CHAPS with final concentrations of Bromodomain 4, 75 nM, fluorescent ligand 5 nM. 10 µl of this reaction mixture was added using a micro multidrop to wells containing 100 nl of various concentrations of test compound or DMSO vehicle (1% final) in Greiner 384 well Black low volume microtitre plate and equilibrated in the dark for 60 mins at room temperature. Fluorescence anisotropy was read in Envision ($\lambda$ex=485 nm, $\lambda$EM=530 nm; Dichroic −505 nM).

All examples (with the exception of examples 1-5, 11, 17, 32, 35, 52, 60, 68, 85, 89, 93, 119, 120, 146, 158, 160, 165-173, 176, 182, 185, 186 and 190) were tested in the assays described above. All tested compounds, with the exception of examples 174 and 187 had a pIC50 ≥5.0 in one or more of the BRD2, BRD3 and BRD4 assays. Examples 6-10, 31, 82, 96, 109, 118, 122-128, 131-137, 139, 140, 147, 149, 151-157, 164, 180 and 184 had a pIC50 ≥6.5 in one or more of the BRD2, BRD3 and BRD4 assays described above.

LPS Stimulated Whole Blood Measuring TNFα Levels Assay

Activation of monocytic cells by agonists of toll-like receptors such as bacterial lipopolysaccharide (LPS) results in production of key inflammatory mediators including TNFα. Such pathways are widely considered to be central to the pathophysiology of a range of auto-immune and inflammatory disorders.

Compounds to be tested are diluted to give a range of appropriate concentrations and 1 ul of the dilution stocks is added to wells of a 96 plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and TNFα levels assayed by immunoassay (typically by MesoScale Discovery technology) either immediately or following storage at −20 degrees. Dose response curves for each compound was generated from the data and an IC50 value was calculated.

Examples 6-10, 12, 15, 18, 20, 26, 28, 33, 39, 56, 58, 75, 87, 91, 92, 94-96, 99, 102, 106-109, 112-114, 116, 117, 132-138, 157, 162-164, 179 and 189 were tested in the above assay and were found to have a pIC50 ≥5.0.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 ul of the diluted stocks is added to a 96 well plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and IL-6 levels assayed by immunoassay (typically by MesoScale Discovery technology) either immediately or following storage at −20 degrees. Concentration response curves for each compound was generated from the data and an IC50 value was calculated.

Examples 6, 122-131, 137, 139-145, 147-156, 159, 164 and 190 were tested in the above assay and all, with the exception of Examples 126, 130, 143 and 190, were found to have a pIC50 ≥5.0.

These data demonstrate that bromodomain inhibitors tested in the above two whole blood assays inhibited the production of the key inflammatory mediators TNFα and/or IL6.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds of the invention groups of eight Balb/c male mice were given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals was monitored at 4 days.

Numbers of animals surviving at 4 days (summed across multiple repeat experiments)

| | |
|---|---|
| Vehicle | 4/66 (6%) |
| Compound of Example 6 | 14/24 (58%) |

These data demonstrate that the bromodomain inhibitor tested in the above model gave rise to a significant animal survival effect following intravenous administration.

Oncology Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (T0) measurement and compound (20 point titration from 14.7 uM to 7 µM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results were expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin−T0 value is determined by subtracting the T0 value (100%) from the Ymin value (%) determined from the fit of the concentration response curve. Values from the wells with no cells were subtracted from all samples for background correction.

The compound of Example 6 was tested in accordance with the above assay and found to have a $gIC_{50}$ in the range 35-9200 nM across all cell lines, more specifically in the range 35-844 nM for heme cell lines and 40-9200 nM for breast cell lines.

These data demonstrate that the bromodomain inhibitor tested in the above assay inhibited cell growth in a panel of oncology cell lines.

All publications, including but not limited to patents and patent applications, cited in this specification are herein incorporated by reference as if each individual publication were specifically and individually indicated to be incorporated by reference herein as though fully set forth.

What is claimed is:

1. A compound of formula (I) or a salt thereof

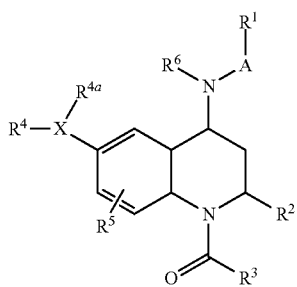

wherein:
A represents a bond or $C_{1-4}$ alkyl;
X represents:
  i) a 6 to 10 membered aromatic group, or
  ii) a 5 to 10 membered heteroaromatic comprising 1, 2 or 3 heteroatoms selected from the group consisting of O, N and S;
$R^1$ represents:
  i) phenyl optionally substituted by 1 or 2 substituents independently selected from halogen, cyano, $C_{1-6}$ alkyl, $C_{1-6}$ haloalkyl, $C_{1-6}$ alkoxy, $SO_2C_{1-6}$ alkyl and —$COR^7$,
  ii) a 5 to 10 membered heteroaromatic comprising 1, 2 or 3 heteroatoms selected from the group consisting of O, N and S optionally substituted by 1 or 2 substituents independently selected from halogen, cyano, $C_{1-6}$ alkyl, $C_{1-6}$ haloalkyl, $C_{1-6}$ alkoxy and —$COR^7$, or
  iii) cyclohexyl;
$R^2$ represents $C_{1-6}$ alkyl;
$R^3$ represents $C_{1-6}$ alkyl;
$R^4$ represents:
  i) H, halogen, cyano, $C_{1-6}$ alkyl, $C_{1-6}$ haloalkyl, $C_{1-6}$ alkoxy, $C_{0-6}$ hydroxyalkyl, $SO_2C_{1-6}$ alkyl, —C(O)$NR^8R^9$, $C(O)R^{10}$, —$C_{0-6}$ alkyl—$NR^{11}R^{12}$, or
  ii) —$O_mC_{0-6}$ alkyl substituted by a 5 or 6 membered heterocyclyl or heteroaromatic each comprising 1, 2, 3 or 4 heteroatoms independently selected from the group consisting of N, O and S and wherein said hetercyclyl or heteroaromatic is optionally substituted by 1, 2 or 3 groups independently selected from halogen, cyano, $C_{1-6}$ alkyl, $C_{1-6}$ haloalkyl and $C_{1-6}$ alkoxy,
  wherein when the heterocyclyl or heteroatomic is linked through a heteroatom and m is 1, then the heteroatom and O are not directly linked if the resultant arrangement would be unstable;
$R^{4a}$ represents H, halogen, $C_{1-6}$ alkyl, $C_{1-6}$ haloalkyl, $C_{1-6}$ alkoxy or $C_{0-6}$ hydroxyalkyl;
$R^5$ represents H, halogen, —$C_{1-6}$ alkyl or —$C_{1-6}$ alkoxy;
$R^6$ represents H, —$C_{1-6}$ alkyl, —$C_{0-6}$ alkylcyano, —$C_{0-6}$ alkyl$C_{1-6}$ alkoxy or $C_{0-2}$ alkyl$COR^7$;
$R^7$ represents hydroxyl, $C_{1-6}$ alkoxy, —$NH_2$, —$NHC_{1-6}$ alkyl or $N(C_{1-6}$ alkyl$)_2$;
$R^8$ and $R^9$ independently represent:
  i) H, $C_{1-6}$ alkyl, —$C_{0-6}$ alkylphenyl, —$C_{0-6}$ alkylheteroaromatic, $C_{3-6}$ cycloalkyl, or
  ii) $R^8$ and $R^9$ together with the N to which they are attached form a 5 or 6 membered heterocyclyl or heteroaromatic wherein said heterocyclyl or heteroaromatic may comprise 1, 2 or 3 further heteroatoms independently selected from O, N and S;
$R^{10}$ represents hydroxyl, $C_{1-6}$ alkoxy or a 5 or 6 membered heterocyclyl or heteroaromatic comprising 1, 2, 3 or 4 heteroatoms selected from O, N and S;
$R^{11}$ and $R^{12}$ independently represent:
  i) H, $C_{1-6}$ alkyl; or
  ii) $R^{11}$ and $R^{12}$ together with the N to which they are attached form a 5 or 6 membered heterocyclyl or heteroaromatic wherein said heterocyclyl or heteroaromatic may comprise 1, 2 or 3 further heteroatoms independently selected from O, N and S; and
m represents 0 or 1.

2. A compound or a salt thereof according to claim 1 wherein $R^1$ represents phenyl optionally substituted by fluoro, chloro, cyano, —$CF_3$, methyl —$COR^7$, or —$SO_2CH_3$.

3. A compound or a salt thereof according to claim 1 wherein $R^1$ represents pyridinyl, pyrazinyl or pyrimidinyl optionally substituted by fluoro, chloro, methyl or —$CF_3$.

4. A compound or a salt thereof according to claim 3 wherein $R^1$ represents unsubstituted pyrazinyl or pyrimidinyl.

5. A compound according to claim 3 wherein $R^1$ represents optionally substituted pyridinyl selected from:

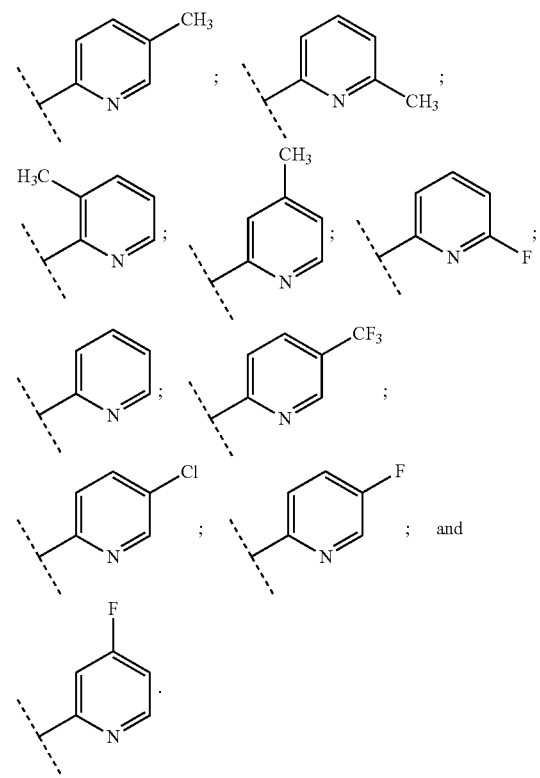

6. A compound or a salt thereof according to claim 1 wherein X is phenyl.

7. A compound or a salt thereof according to claim 1 wherein X is selected from pyridinyl, imidazolyl, pyrazolyl and triazolyl.

8. A compound or a salt thereof according to any claim 1 wherein $R^4$ is selected from methyl, —$C(O)R^{10}$, —$C(O)NR^8R^9$, —$C_{0-6}$alkyl-$NR^{11}R^{12}$ and —$C_{0-6}$hydroxyalkyl.

9. A compound or a salt thereof according to claim 1 wherein $R^8$ and $R^9$ independently represent H or $C_{1-6}$alkyl.

10. A compound or a salt thereof according to claim 1 wherein $R^8$ and $R^9$ together with the N to which they are attached form a 6 membered heterocyclyl comprising 1 further heteroatom independently selected from O and N.

11. A compound or a salt thereof according to claim 1 wherein $R^{10}$ is hydroxyl or methoxy.

12. A compound or a salt thereof according to claim 1 wherein $R^{11}$ and $R^{12}$ independently represent H or $C_{1-6}$ alkyl.

13. A compound or a salt thereof according to claim 1 wherein $R^{11}$ and $R^{12}$ together with the N to which they are attached form a 6-membered heterocyclyl optionally comprising one further heteroatom selected from O and N.

14. A compound or a salt thereof according to claim 1 wherein $R^2$ represents methyl.

15. A compound or a salt thereof according to claim 1 wherein $R^3$ represents methyl.

16. A compound or a salt thereof according to claim 1 wherein $R^7$ represents hydroxyl or methoxy.

17. A compound or a salt thereof according to claim 1 wherein the compound of formula (I) or a salt thereof is the (2S, 4R) enantiomer.

18. A compound which is 4-(2S, 4R)-{-1-acetyl-4-[(4-chlorophenyl)amino]-2-methyl-1,2,3,4-tetrahydro-6-quinolinyl}benzoic acid

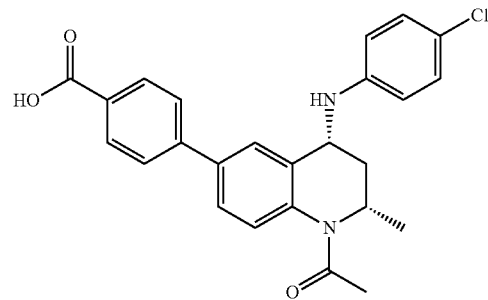 [SMILES: CC(=O)N1c2ccc(-c3ccc(C(=O)O)cc3)cc2[C@H](Nc2ccc(Cl)cc2)C[C@@H]1C]

or a salt thereof.

19. A pharmaceutical composition which comprises a compound or a salt thereof according to claim 1 and one or more pharmaceutically acceptable carriers, diluents or excipients.

* * * * *